(12) United States Patent
Kennes et al.

(10) Patent No.: US 12,137,326 B2
(45) Date of Patent: *Nov. 5, 2024

(54) RETENTION MAGNET SYSTEM FOR MEDICAL DEVICE

(71) Applicant: Cochlear Limited, Macquarie University (AU)

(72) Inventors: Patrik Kennes, Macquarie University (AU); Charles Roger Aaron Leigh, Macquarie University (AU); Paul Michael Carter, Macquarie University (AU); Mark Alan Von Huben, Macquarie University (AU); Jonathan Diolaso, Macquarie University (AU); Scott Matthew Ibbotson, Macquarie University (AU); Irene Tsimos Diolaso, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/072,848

(22) Filed: Dec. 1, 2022

(65) Prior Publication Data

US 2023/0106375 A1 Apr. 6, 2023

Related U.S. Application Data

(63) Continuation of application No. 17/170,585, filed on Feb. 8, 2021, now Pat. No. 11,792,586, which is a
(Continued)

(51) Int. Cl.
*H04R 25/00* (2006.01)

(52) U.S. Cl.
CPC .......... *H04R 25/606* (2013.01); *H04R 25/60* (2013.01); *H04R 2225/67* (2013.01); *H04R 2460/13* (2013.01)

(58) Field of Classification Search
CPC .. A61N 1/36038; A61N 1/3718; A61N 1/372; A61N 1/375; H01F 7/04;
(Continued)

(56) References Cited

U.S. PATENT DOCUMENTS

| 3,043,000 A | 7/1962 | Hatfield |
| 3,487,403 A | 12/1969 | Pihl |

(Continued)

FOREIGN PATENT DOCUMENTS

| AU | 2009101370 A4 | 3/2013 |
| CN | 2411869 Y | 12/2000 |

(Continued)

OTHER PUBLICATIONS

Daniel Rutter, "Comparison: Lightwave 2000, 3000, 4000, Illuminator and Pocket-Bright, and Petzl Tikka" pp. 1-30, Feb. 14, 2002. http://www.dansdata.com/ledlights7.htm.
(Continued)

*Primary Examiner* — Gerald Gauthier
(74) *Attorney, Agent, or Firm* — Pilloff Passino & Cosenza LLP; Martin J. Cosenza

(57) ABSTRACT

An external portion of an auditory prosthesis includes an external magnet that interacts with an implantable magnet to hold the external portion against the skin. Magnetic force generated by the stray field of these magnets can disturb the operation of a vibrating element of the auditory prosthesis. The technologies described herein utilize additional magnets disposed within portions of the auditory prosthesis to redirect the magnetic flux, which allows the vibrating element to be disposed more closely to the magnets, reducing the overall height profile of the prosthesis.

44 Claims, 132 Drawing Sheets

Related U.S. Application Data continuation of application No. 16/376,431, filed on Apr. 5, 2019, now Pat. No. 10,917,730, and a continuation-in-part of application No. 15/919,717, filed on Mar. 13, 2018, now Pat. No. 10,880,662, which is a continuation of application No. PCT/IB2016/001388, filed on Sep. 13, 2016, which is a continuation of application No. 15/158,225, filed on May 18, 2016, now Pat. No. 9,872,115.

(60) Provisional application No. 62/763,203, filed on Jun. 6, 2018, provisional application No. 62/218,339, filed on Sep. 14, 2015.

(58) Field of Classification Search
CPC ....... H01F 7/0278; H01F 41/02; H04R 9/025; H04R 25/00; H04R 25/554; H04R 25/60; H04R 25/606; H04R 2225/67; H04R 2460/13; H04R 15/00; H04S 7/00; H05K 999/99; A61B 17/08; A61M 39/22; H01J 37/345; H01H 36/0073
See application file for complete search history.

(56) References Cited

U.S. PATENT DOCUMENTS

| | | |
|---|---|---|
| 3,573,812 A | 4/1971 | Pihl |
| D227,118 S | 6/1973 | Muraoka |
| 3,771,685 A | 11/1973 | Micallef |
| 3,801,767 A | 4/1974 | Marks |
| 3,987,967 A | 10/1976 | Kuznetsov et al. |
| 4,003,521 A | 1/1977 | Hess |
| 4,038,990 A | 8/1977 | Thompson |
| 4,197,840 A | 4/1980 | Beck et al. |
| 4,199,741 A | 4/1980 | Paulet |
| 4,226,164 A | 10/1980 | Carter |
| 4,240,428 A | 12/1980 | Akhavi |
| 4,257,936 A | 3/1981 | Matsumoto et al. |
| 4,317,969 A | 3/1982 | Riegler et al. |
| 4,352,960 A * | 10/1982 | Dormer ............ A61N 1/372 607/57 |
| D267,541 S | 1/1983 | Kanemitsu |
| 4,414,701 A | 11/1983 | Johnson |
| 4,596,971 A | 6/1986 | Hirabayashi et al. |
| 4,606,329 A | 8/1986 | Hough |
| 4,610,621 A | 9/1986 | Taber et al. |
| 4,628,907 A | 12/1986 | Epley |
| 4,634,191 A | 1/1987 | Studer |
| 4,676,772 A | 6/1987 | Hooven |
| 4,726,378 A | 2/1988 | Kaplan |
| 4,731,718 A | 3/1988 | Sheu |
| 4,736,747 A | 4/1988 | Drake |
| 4,743,264 A | 5/1988 | Sherva-Parker |
| 4,792,368 A | 12/1988 | Sagawa et al. |
| 4,817,607 A | 4/1989 | Tatge |
| RE32,947 E | 6/1989 | Dormer et al. |
| 4,868,530 A | 9/1989 | Ahs |
| 4,917,504 A | 4/1990 | Scott et al. |
| 4,918,745 A | 4/1990 | Hutchison |
| 4,920,679 A | 5/1990 | Sarles et al. |
| 4,957,478 A * | 9/1990 | Maniglia ............ H04R 25/554 623/10 |
| 5,014,592 A | 5/1991 | Zweig et al. |
| 5,015,224 A | 5/1991 | Maniglia |
| 5,096,763 A | 3/1992 | Ogata et al. |
| 5,105,811 A | 4/1992 | Kuzma |
| 5,183,056 A | 2/1993 | Dalen et al. |
| 5,196,710 A | 3/1993 | Kalfaian |
| 5,282,858 A | 2/1994 | Bisch et al. |
| 5,314,453 A | 5/1994 | Jeutter |
| D348,067 S | 6/1994 | Lucey et al. |
| 5,338,287 A * | 8/1994 | Miller ............ H04R 15/00 381/326 |
| 5,360,388 A | 11/1994 | Spindel et al. |
| 5,423,317 A | 6/1995 | Ijima et al. |
| 5,456,654 A | 10/1995 | Ball |
| 5,554,096 A | 9/1996 | Ball |
| 5,603,726 A | 2/1997 | Schulman et al. |
| 5,624,376 A | 4/1997 | Ball et al. |
| 5,630,835 A | 5/1997 | Brownlee |
| 5,716,407 A | 2/1998 | Knapp et al. |
| 5,746,897 A | 5/1998 | Heimanson et al. |
| 5,749,912 A | 5/1998 | Zhang et al. |
| 5,757,183 A | 5/1998 | Smith et al. |
| 5,775,652 A | 7/1998 | Crawshaw et al. |
| 5,785,477 A | 7/1998 | McGuffey et al. |
| 5,800,336 A | 9/1998 | Ball et al. |
| 5,857,958 A | 1/1999 | Ball et al. |
| 5,877,664 A | 3/1999 | Jackson, Jr. |
| 5,897,486 A | 4/1999 | Ball et al. |
| 5,913,815 A | 6/1999 | Ball et al. |
| 5,945,762 A | 8/1999 | Chen et al. |
| 5,965,282 A | 10/1999 | Baermann |
| 5,971,334 A | 10/1999 | Crawshaw et al. |
| 6,040,762 A | 3/2000 | Tompkins |
| 6,073,973 A | 6/2000 | Boscaljon et al. |
| 6,101,417 A | 8/2000 | Vogel et al. |
| 6,138,681 A | 10/2000 | Chen et al. |
| 6,157,278 A * | 12/2000 | Katznelson ........... H01F 7/0278 335/298 |
| 6,157,281 A | 12/2000 | Katznelson et al. |
| 6,175,767 B1 | 1/2001 | Doyle, Sr. |
| 6,178,079 B1 | 1/2001 | Renger |
| 6,178,353 B1 | 1/2001 | Griffith et al. |
| 6,190,305 B1 | 2/2001 | Ball et al. |
| 6,208,235 B1 | 3/2001 | Trontelj |
| 6,208,882 B1 | 3/2001 | Lenarz et al. |
| 6,217,508 B1 | 4/2001 | Ball et al. |
| 6,219,580 B1 | 4/2001 | Faltys et al. |
| 6,244,142 B1 | 6/2001 | Swanson |
| 6,259,951 B1 | 7/2001 | Kuzma et al. |
| 6,263,230 B1 | 7/2001 | Haynor et al. |
| 6,272,382 B1 | 8/2001 | Faltys et al. |
| 6,292,678 B1 | 9/2001 | Hall et al. |
| 6,295,472 B1 | 9/2001 | Rubinstein et al. |
| 6,295,473 B1 | 9/2001 | Rosar |
| 6,308,101 B1 | 10/2001 | Faltys et al. |
| 6,313,551 B1 * | 11/2001 | Hazelton ............ H02K 41/03 310/12.24 |
| 6,348,070 B1 | 2/2002 | Teissl et al. |
| 6,355,998 B1 | 3/2002 | Schöb et al. |
| 6,358,281 B1 | 3/2002 | Berrang et al. |
| 6,401,723 B1 | 6/2002 | Garibaldi et al. |
| 6,475,134 B1 | 11/2002 | Ball et al. |
| 6,505,062 B1 | 1/2003 | Ritter et al. |
| 6,506,987 B1 * | 1/2003 | Woods ............ H01H 36/0073 200/61.7 |
| 6,522,909 B1 | 2/2003 | Garibaldi et al. |
| 6,542,777 B1 | 4/2003 | Griffith et al. |
| 6,571,676 B1 | 6/2003 | Folsom et al. |
| 6,643,378 B2 | 11/2003 | Schumaier |
| 6,668,065 B2 | 12/2003 | Lee et al. |
| 6,838,963 B2 | 1/2005 | Zimmerling et al. |
| 6,857,612 B2 | 2/2005 | Goodbred |
| D512,416 S | 12/2005 | Malaver |
| 6,991,594 B2 | 1/2006 | Holcomb |
| 7,038,565 B1 | 5/2006 | Chell |
| 7,091,806 B2 | 8/2006 | Zimmerling et al. |
| 7,190,247 B2 | 3/2007 | Zimmerling |
| 7,191,007 B2 | 3/2007 | Desai et al. |
| 7,200,504 B1 | 4/2007 | Fister |
| 7,225,028 B2 | 5/2007 | Della Santina et al. |
| 7,231,252 B2 | 6/2007 | Duncan et al. |
| 7,266,208 B2 | 9/2007 | Charvin et al. |
| 7,338,028 B2 * | 3/2008 | Zimmerling ......... A61M 39/22 251/7 |
| 7,386,143 B2 | 6/2008 | Easter et al. |
| 7,532,937 B2 | 5/2009 | Horio et al. |
| 7,566,296 B2 | 7/2009 | Zimmerling et al. |
| 7,610,096 B2 | 10/2009 | McDonald, III |
| 7,642,887 B2 | 1/2010 | Zimmerling |
| 7,647,120 B2 | 1/2010 | Della Santina et al. |
| 7,695,427 B2 | 4/2010 | Kugler et al. |

(56) References Cited

U.S. PATENT DOCUMENTS

| | | |
|---|---|---|
| 7,762,998 B2 | 7/2010 | Birk et al. |
| 7,808,348 B2 * | 10/2010 | Fullerton ............... H01F 41/02 |
| | | 335/306 |
| 7,856,986 B2 | 12/2010 | Darley |
| 7,976,453 B2 | 7/2011 | Zimmerling et al. |
| 7,991,477 B2 | 8/2011 | McDonald, III |
| 8,013,699 B2 | 9/2011 | Zimmerling |
| 8,118,725 B2 | 2/2012 | Zimmerling et al. |
| 8,211,174 B2 | 7/2012 | Park et al. |
| 8,246,533 B2 | 8/2012 | Chang et al. |
| 8,255,058 B2 | 8/2012 | Gibson et al. |
| 8,260,435 B2 | 9/2012 | Johnson et al. |
| 8,270,647 B2 | 9/2012 | Crawford et al. |
| 8,340,774 B2 | 12/2012 | Hochmair et al. |
| 8,400,038 B2 | 3/2013 | Smith et al. |
| 8,406,443 B2 | 3/2013 | Westerkull et al. |
| 8,515,112 B2 | 8/2013 | Crawford et al. |
| 8,515,544 B2 | 8/2013 | Daly et al. |
| 8,532,783 B2 | 9/2013 | Zimmerling et al. |
| 8,634,909 B2 * | 1/2014 | Zimmerling ......... A61N 1/36036 |
| | | 607/116 |
| 8,734,475 B2 * | 5/2014 | Ekvall .................... A61B 17/08 |
| | | 606/157 |
| 8,744,106 B2 | 6/2014 | Ball |
| 8,758,394 B2 | 6/2014 | Zimmerling et al. |
| 8,768,480 B2 | 7/2014 | Charvin |
| 8,811,643 B2 | 8/2014 | Crawford et al. |
| 8,829,462 B2 | 9/2014 | Clarke et al. |
| 8,829,752 B2 | 9/2014 | Chen et al. |
| 8,897,475 B2 * | 11/2014 | Ball ...................... H04R 25/606 |
| | | 381/151 |
| 8,983,102 B2 | 3/2015 | Crawford et al. |
| 8,987,951 B2 | 3/2015 | Park |
| 9,002,469 B2 | 4/2015 | D'Ambrosio |
| 9,014,782 B2 | 4/2015 | Miyoshi |
| 9,022,917 B2 | 5/2015 | Kasic et al. |
| 9,042,995 B2 | 5/2015 | Dinsmoor et al. |
| 9,058,962 B2 * | 6/2015 | Endo ...................... H01J 37/345 |
| 9,113,268 B2 * | 8/2015 | Ball ........................ H04R 9/066 |
| RE45,701 E | 9/2015 | Zimmerling et al. |
| 9,136,728 B2 | 9/2015 | Dinsmoor et al. |
| 9,144,676 B2 | 9/2015 | Gibson et al. |
| 9,179,228 B2 * | 11/2015 | Ruppersberg ......... H04R 25/606 |
| 9,210,521 B2 * | 12/2015 | Kasic .................... H04R 25/606 |
| 9,258,656 B2 * | 2/2016 | Ruppersberg ......... H04R 25/606 |
| 9,392,384 B2 | 7/2016 | Crawford et al. |
| 9,420,388 B2 | 8/2016 | Ball |
| 9,526,810 B2 * | 12/2016 | Ruppersberg ......... H04R 25/606 |
| 9,627,120 B2 | 4/2017 | Scott et al. |
| 9,736,601 B2 * | 8/2017 | Kasic .................... H04R 25/606 |
| 9,739,842 B2 | 8/2017 | Holm et al. |
| 9,788,125 B2 * | 10/2017 | Ruppersberg ......... H04R 25/456 |
| 9,800,982 B2 * | 10/2017 | Andersson ............. H04R 9/025 |
| RE46,624 E | 12/2017 | Zimmerling et al. |
| 9,872,115 B2 | 1/2018 | Kennes |
| 9,872,993 B2 * | 1/2018 | Zimmerling ......... A61N 1/37229 |
| 10,130,807 B2 | 11/2018 | Leigh et al. |
| 10,186,360 B2 | 1/2019 | Shimbo et al. |
| 10,405,891 B2 | 9/2019 | Pool et al. |
| 10,646,712 B2 | 5/2020 | Smith et al. |
| 10,917,730 B2 * | 2/2021 | Kennes ............... A61N 1/36038 |
| 10,942,042 B2 | 3/2021 | Bidaux et al. |
| 11,012,796 B2 | 5/2021 | Andersson et al. |
| 11,097,095 B2 | 8/2021 | Smith et al. |
| 11,792,586 B2 * | 10/2023 | Kennes ............... A61N 1/36038 |
| | | 381/324 |
| 2001/0021805 A1 | 9/2001 | Blume et al. |
| 2002/0076071 A1 | 6/2002 | Single |
| 2002/0103430 A1 | 8/2002 | Hastings |
| 2002/0116033 A1 | 8/2002 | Greatbatch et al. |
| 2002/0116034 A1 | 8/2002 | Miller et al. |
| 2002/0120332 A1 | 8/2002 | Law et al. |
| 2003/0034039 A1 | 2/2003 | Schmid et al. |
| 2003/0034705 A1 | 2/2003 | Hakansson |
| 2003/0089933 A1 | 5/2003 | Janesky et al. |
| 2003/0120202 A1 | 6/2003 | Gordon |
| 2003/0139782 A1 | 7/2003 | Duncan |
| 2003/0161481 A1 | 8/2003 | Miller et al. |
| 2003/0161482 A1 | 8/2003 | Miller et al. |
| 2003/0163021 A1 | 8/2003 | Miller et al. |
| 2003/0163022 A1 | 8/2003 | Miller et al. |
| 2003/0171787 A1 | 9/2003 | Money et al. |
| 2003/0171792 A1 | 9/2003 | Zarinetchi et al. |
| 2003/0181956 A1 | 9/2003 | Duncan et al. |
| 2004/0012470 A1 | 1/2004 | Zimmerling et al. |
| 2004/0032962 A1 | 2/2004 | Westerkull |
| 2004/0059423 A1 | 3/2004 | Barnes et al. |
| 2004/0136558 A1 | 7/2004 | Usuki et al. |
| 2004/0147804 A1 | 7/2004 | Schneider et al. |
| 2004/0148025 A1 | 7/2004 | Schneider et al. |
| 2004/0260361 A1 | 12/2004 | Gibson |
| 2004/0260362 A1 | 12/2004 | Darley |
| 2005/0001703 A1 | 1/2005 | Zimmerling |
| 2005/0004629 A1 * | 1/2005 | Gibson ................. A61N 1/375 |
| | | 607/57 |
| 2005/0062567 A1 | 3/2005 | Zimmerling et al. |
| 2005/0070346 A1 | 3/2005 | Pan |
| 2005/0101830 A1 | 5/2005 | Easter et al. |
| 2005/0159791 A1 | 7/2005 | Daly et al. |
| 2005/0165471 A1 | 7/2005 | Wang et al. |
| 2005/0171579 A1 | 8/2005 | Tasche et al. |
| 2005/0197715 A1 | 9/2005 | Kugler et al. |
| 2005/0216075 A1 | 9/2005 | Wang et al. |
| 2005/0228214 A1 | 10/2005 | Schneider et al. |
| 2005/0228215 A1 | 10/2005 | Schneider et al. |
| 2005/0240098 A1 | 10/2005 | Zhong et al. |
| 2006/0030905 A1 | 2/2006 | Malaver |
| 2006/0045298 A1 | 3/2006 | Westerkull |
| 2006/0056649 A1 | 3/2006 | Schumaier |
| 2006/0084857 A1 | 4/2006 | Massengill et al. |
| 2006/0119356 A1 | 6/2006 | Rabe et al. |
| 2006/0184212 A1 | 8/2006 | Faltys et al. |
| 2006/0217792 A1 | 9/2006 | Hussein et al. |
| 2006/0241746 A1 | 10/2006 | Shaoulian et al. |
| 2006/0244560 A1 | 11/2006 | Zimmerling et al. |
| 2006/0247488 A1 | 11/2006 | Waldmann |
| 2007/0053536 A1 | 3/2007 | Westerkull |
| 2007/0083078 A1 | 4/2007 | Easter et al. |
| 2007/0100197 A1 | 5/2007 | Perkins et al. |
| 2007/0126540 A1 | 6/2007 | Zimmerling |
| 2007/0170533 A1 | 7/2007 | Doogue et al. |
| 2007/0179333 A1 | 8/2007 | Bove |
| 2007/0208403 A1 | 9/2007 | Della Santina et al. |
| 2008/0009920 A1 | 1/2008 | Gibson et al. |
| 2008/0044049 A1 | 2/2008 | Ho et al. |
| 2008/0071353 A1 | 3/2008 | Weber et al. |
| 2008/0221641 A1 | 9/2008 | Hochmair |
| 2008/0293998 A1 | 11/2008 | Andrews |
| 2008/0304686 A1 | 12/2008 | Meskens et al. |
| 2009/0030529 A1 | 1/2009 | Berrang et al. |
| 2009/0043149 A1 | 2/2009 | Abel |
| 2009/0069869 A1 | 3/2009 | Stouffer et al. |
| 2009/0138062 A1 | 5/2009 | Balslev |
| 2009/0237080 A1 | 9/2009 | Kato et al. |
| 2009/0248155 A1 | 10/2009 | Parker |
| 2009/0251264 A1 | 10/2009 | Fullerton et al. |
| 2009/0281367 A1 | 11/2009 | Cho et al. |
| 2009/0287036 A1 | 11/2009 | Shapiro et al. |
| 2009/0287278 A1 | 11/2009 | Charvin |
| 2009/0295521 A1 | 12/2009 | Fullerton et al. |
| 2010/0145135 A1 | 6/2010 | Ball et al. |
| 2010/0219712 A1 | 9/2010 | Kogure et al. |
| 2010/0237969 A1 | 9/2010 | Crawshaw |
| 2010/0272299 A1 | 10/2010 | Van Schuylenbergh et al. |
| 2010/0292759 A1 * | 11/2010 | Hahn ................. A61N 1/36038 |
| | | 607/57 |
| 2011/0004278 A1 | 1/2011 | Aghassian |
| 2011/0022120 A1 | 1/2011 | Ball et al. |
| 2011/0031839 A1 | 2/2011 | Fullerton et al. |
| 2011/0054237 A1 | 3/2011 | Shapiro et al. |
| 2011/0077502 A1 | 3/2011 | Rofougaran |
| 2011/0106210 A1 | 5/2011 | Meskens |
| 2011/0112607 A1 | 5/2011 | Zierhofer |

(56) References Cited

U.S. PATENT DOCUMENTS

| | | |
|---|---|---|
| 2011/0130622 A1 | 6/2011 | Ilberg |
| 2011/0144414 A1* | 6/2011 | Spearman ............ H04R 25/606 600/25 |
| 2011/0152603 A1 | 6/2011 | Perkins et al. |
| 2011/0224789 A1 | 9/2011 | Griffith |
| 2011/0264172 A1* | 10/2011 | Zimmerling ......... A61N 1/3718 607/60 |
| 2011/0268303 A1 | 11/2011 | Ahsani |
| 2011/0285488 A1 | 11/2011 | Scott et al. |
| 2011/0291507 A1 | 12/2011 | Post |
| 2011/0295053 A1 | 12/2011 | Ball |
| 2012/0022616 A1 | 1/2012 | Garnham et al. |
| 2012/0022647 A1 | 1/2012 | Leigh et al. |
| 2012/0029267 A1 | 2/2012 | Ball |
| 2012/0062992 A1 | 3/2012 | Kimoto |
| 2012/0078035 A1 | 3/2012 | Andersson et al. |
| 2012/0080039 A1 | 4/2012 | Siegert |
| 2012/0088956 A1 | 4/2012 | Asnes et al. |
| 2012/0095283 A1 | 4/2012 | Andersson et al. |
| 2012/0104875 A1 | 5/2012 | Park |
| 2012/0108887 A1 | 5/2012 | Vermeiren |
| 2012/0172659 A1 | 7/2012 | Ball et al. |
| 2012/0237067 A1 | 9/2012 | Asnes |
| 2012/0238799 A1 | 9/2012 | Ball et al. |
| 2012/0256715 A1 | 10/2012 | Fullerton et al. |
| 2012/0262019 A1 | 10/2012 | Smith et al. |
| 2012/0262020 A1 | 10/2012 | Smith et al. |
| 2012/0284969 A1 | 11/2012 | Fullerton et al. |
| 2012/0296155 A1* | 11/2012 | Ball ..................... A61N 1/3718 607/57 |
| 2012/0313473 A1 | 12/2012 | Chen et al. |
| 2012/0319809 A1 | 12/2012 | Fullerton |
| 2012/0323066 A1 | 12/2012 | Cho et al. |
| 2012/0330378 A1 | 12/2012 | Crawford et al. |
| 2013/0004003 A1 | 1/2013 | Tada |
| 2013/0006044 A1 | 1/2013 | Menzl |
| 2013/0018218 A1* | 1/2013 | Haller .................. H04R 25/60 600/25 |
| 2013/0023954 A1 | 1/2013 | Meskens |
| 2013/0046131 A1 | 2/2013 | Ball et al. |
| 2013/0046360 A1 | 2/2013 | Gibson et al. |
| 2013/0053874 A1 | 2/2013 | Ekvall et al. |
| 2013/0096366 A1 | 4/2013 | Bervoets et al. |
| 2013/0099703 A1 | 4/2013 | Epstein et al. |
| 2013/0110198 A1 | 5/2013 | Stoffaneller |
| 2013/0114834 A1 | 5/2013 | Bern |
| 2013/0165738 A1 | 6/2013 | Ball et al. |
| 2013/0190552 A1 | 7/2013 | Leblans |
| 2013/0195304 A1 | 8/2013 | Andersson |
| 2013/0199031 A1 | 8/2013 | Fullerton et al. |
| 2013/0202140 A1 | 8/2013 | Asnes |
| 2013/0207760 A1 | 8/2013 | Clarke et al. |
| 2013/0214631 A1 | 8/2013 | Smith et al. |
| 2013/0261701 A1 | 10/2013 | Kuratle et al. |
| 2013/0268012 A1 | 10/2013 | Sison |
| 2013/0278254 A1 | 10/2013 | Reeder et al. |
| 2013/0281764 A1 | 10/2013 | Björn et al. |
| 2013/0289384 A1 | 10/2013 | Jenison et al. |
| 2013/0305522 A1 | 11/2013 | Fullerton et al. |
| 2014/0005522 A1 | 1/2014 | Zurovcik |
| 2014/0012069 A1 | 1/2014 | Ball |
| 2014/0012070 A1 | 1/2014 | Nagl et al. |
| 2014/0012071 A1 | 1/2014 | Nagl et al. |
| 2014/0012349 A1* | 1/2014 | Zimmerling ......... A61N 1/3718 607/57 |
| 2014/0064531 A1 | 3/2014 | Andersson et al. |
| 2014/0094876 A1 | 4/2014 | Wingeier et al. |
| 2014/0121447 A1 | 5/2014 | Kasic et al. |
| 2014/0121450 A1 | 5/2014 | Kasic et al. |
| 2014/0121451 A1 | 5/2014 | Kasic et al. |
| 2014/0163308 A1 | 6/2014 | Miller et al. |
| 2014/0163309 A1 | 6/2014 | Bernhard et al. |
| 2014/0213139 A1 | 7/2014 | Ferguson |
| 2014/0242140 A1 | 8/2014 | Neu et al. |
| 2014/0257081 A1 | 9/2014 | Rapoport |
| 2014/0270297 A1 | 9/2014 | Gustafsson et al. |
| 2014/0275731 A1 | 9/2014 | Andersson et al. |
| 2014/0275736 A1 | 9/2014 | Ruppersberg et al. |
| 2014/0292321 A1 | 10/2014 | Yamazaki et al. |
| 2014/0293073 A1 | 10/2014 | Okamura et al. |
| 2014/0300437 A1 | 10/2014 | Fullerton et al. |
| 2014/0302741 A1 | 10/2014 | Whittaker |
| 2014/0321681 A1* | 10/2014 | Ball ..................... H04R 25/00 600/25 |
| 2014/0336447 A1 | 11/2014 | Björn et al. |
| 2014/0343626 A1 | 11/2014 | Thenuwara et al. |
| 2014/0364681 A1 | 12/2014 | Hillbratt et al. |
| 2014/0364682 A1 | 12/2014 | Hillbratt et al. |
| 2014/0364922 A1 | 12/2014 | Garnham et al. |
| 2014/0375829 A1 | 12/2014 | Nishihara et al. |
| 2014/0379103 A1 | 12/2014 | Ishikawa et al. |
| 2015/0022298 A1 | 1/2015 | Fullerton |
| 2015/0032186 A1 | 1/2015 | Cushing et al. |
| 2015/0045607 A1 | 2/2015 | Håkansson |
| 2015/0045855 A1 | 2/2015 | Griffith |
| 2015/0087892 A1 | 3/2015 | Tourrel et al. |
| 2015/0092969 A1 | 4/2015 | Meskens et al. |
| 2015/0104052 A1 | 4/2015 | Gustafsson et al. |
| 2015/0117689 A1 | 4/2015 | Bergs et al. |
| 2015/0156595 A1 | 6/2015 | Zhong et al. |
| 2015/0157778 A1 | 6/2015 | Ishiyama et al. |
| 2015/0160426 A1 | 6/2015 | Chao et al. |
| 2015/0160470 A1 | 6/2015 | Terajima |
| 2015/0173468 A1 | 6/2015 | Stevenson |
| 2015/0192432 A1 | 7/2015 | Noguchi et al. |
| 2015/0201290 A1 | 7/2015 | Nikles et al. |
| 2015/0215708 A1 | 7/2015 | Meskens et al. |
| 2015/0265842 A1 | 9/2015 | Ridler et al. |
| 2015/0281860 A1 | 10/2015 | Johansson et al. |
| 2015/0312686 A1 | 10/2015 | Gustafsson et al. |
| 2015/0382114 A1 | 12/2015 | Andersson et al. |
| 2016/0021470 A1 | 1/2016 | Gustafsson |
| 2016/0037273 A1* | 2/2016 | Gustafsson .......... H04R 25/606 381/326 |
| 2016/0058555 A1 | 3/2016 | Andersson et al. |
| 2016/0084920 A1 | 3/2016 | Liu et al. |
| 2016/0100260 A1 | 4/2016 | Ruppersberg et al. |
| 2016/0112813 A1 | 4/2016 | Hillbratt et al. |
| 2016/0161288 A1 | 6/2016 | Lu |
| 2016/0198270 A9 | 7/2016 | Nagl et al. |
| 2016/0205484 A1 | 7/2016 | Nagl et al. |
| 2016/0234613 A1 | 8/2016 | Westerkull |
| 2016/0247616 A1 | 8/2016 | Smith et al. |
| 2016/0361537 A1 | 12/2016 | Leigh et al. |
| 2016/0381473 A1* | 12/2016 | Gustafsson ............... H01F 7/04 600/25 |
| 2016/0381474 A1* | 12/2016 | Gustafsson ............... H04S 7/00 600/25 |
| 2017/0078808 A1* | 3/2017 | Kennes ................. H05K 999/99 |
| 2017/0111728 A1 | 4/2017 | Kim et al. |
| 2017/0162311 A1 | 6/2017 | Shmbo et al. |
| 2017/0162367 A1 | 6/2017 | Yokota et al. |
| 2017/0216523 A1 | 8/2017 | Neftel et al. |
| 2017/0251313 A1 | 8/2017 | Gustafsson |
| 2018/0160241 A1 | 6/2018 | Gustafsson et al. |
| 2018/0252228 A1 | 9/2018 | Henseler et al. |
| 2018/0270591 A1 | 9/2018 | Kennes |
| 2018/0288538 A1 | 10/2018 | Andersson et al. |
| 2018/0352349 A1 | 12/2018 | Fung et al. |
| 2018/0369586 A1 | 12/2018 | Lee et al. |
| 2019/0046797 A1 | 2/2019 | Calixto et al. |
| 2019/0076649 A1 | 3/2019 | Lee et al. |
| 2019/0151653 A1 | 5/2019 | Leigh et al. |
| 2019/0215623 A1 | 7/2019 | Bodvarsson |
| 2019/0239007 A1* | 8/2019 | Kennes ................. H04R 25/60 |
| 2019/0293454 A1 | 9/2019 | Bidaux et al. |
| 2020/0114151 A1 | 4/2020 | Smith et al. |
| 2020/0197702 A1 | 6/2020 | Eigentler |
| 2021/0046318 A1 | 2/2021 | Gibson et al. |
| 2021/0106815 A1 | 4/2021 | Smith et al. |
| 2021/0235209 A1* | 7/2021 | Kennes ................. H04R 25/606 |
| 2021/0257139 A1 | 8/2021 | Nellessen |

(56) References Cited

U.S. PATENT DOCUMENTS

| | | | |
|---|---|---|---|
| 2021/0316136 A1 | 10/2021 | Smith et al. | |
| 2022/0072302 A1 | 3/2022 | Zimmerling | |
| 2023/0106375 A1* | 4/2023 | Kennes | H04R 25/606 |
| | | | 381/324 |

FOREIGN PATENT DOCUMENTS

| | | |
|---|---|---|
| EP | 2720480 A2 | 4/2014 |
| EP | 3307383 B1 | 3/2020 |
| GB | 414579 A | 8/1934 |
| GB | 2196855 A | 5/1988 |
| GB | 2205999 A | 12/1988 |
| GB | 2266045 A | 10/1993 |
| JP | 2010075394 A | 4/2010 |
| JP | 2012191448 A | 10/2012 |
| JP | 2013232860 A | 11/2013 |
| KR | 101743793 A | 5/2013 |
| KR | 101297828 B1 | 8/2013 |
| KR | 101537380 B1 | 7/2015 |
| WO | 9716835 A1 | 5/1997 |
| WO | 9939769 A1 | 8/1999 |
| WO | 2007024657 A1 | 3/2007 |
| WO | 2014008169 A1 | 1/2014 |
| WO | 2014011582 A2 | 1/2014 |
| WO | 2015065442 A2 | 5/2015 |
| WO | 2016207856 A1 | 12/2016 |
| WO | 2016207860 A1 | 12/2016 |
| WO | 2017046650 A1 | 3/2017 |
| WO | 2017105510 A1 | 6/2017 |
| WO | 2017105511 A1 | 6/2017 |
| WO | 2018200347 A1 | 11/2018 |
| WO | 2021059163 A1 | 4/2021 |

OTHER PUBLICATIONS

Med-El, "FDA Hands MED-EL Approval for MRI Compatible Cochlear Implant (VIDEO)," believed to be available in Jan. 2015.

\* cited by examiner

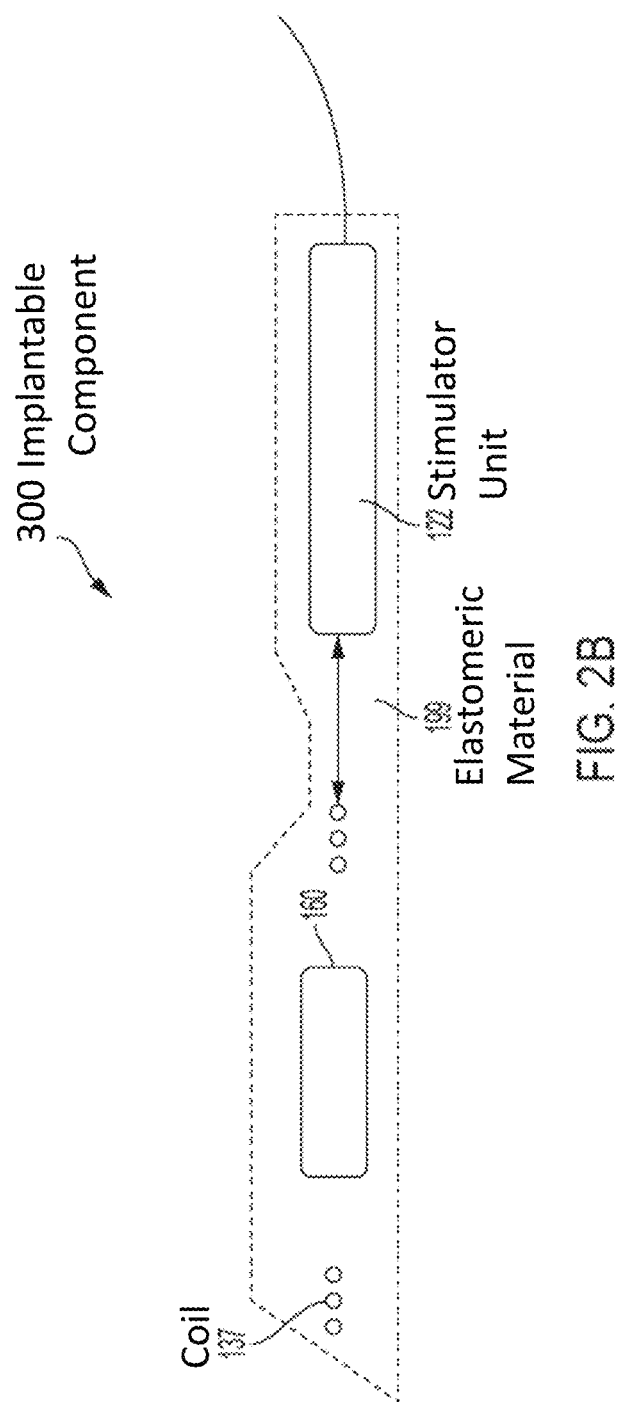

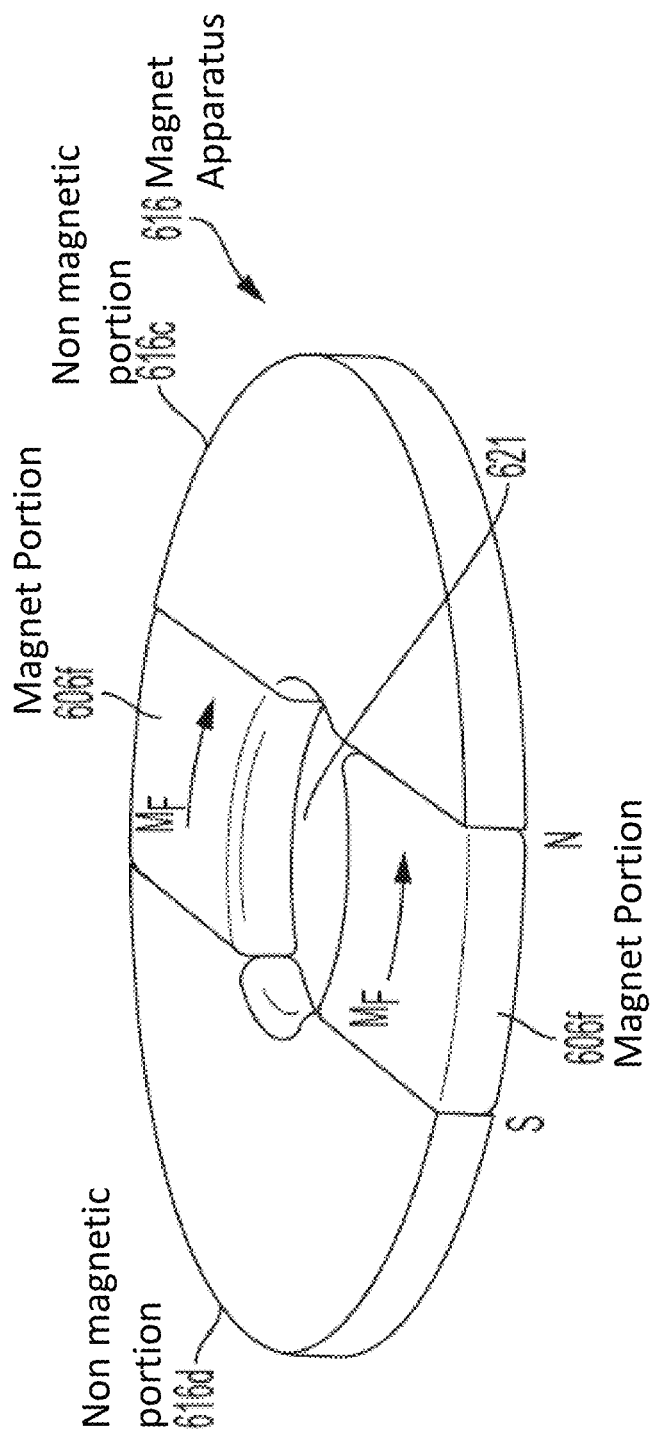

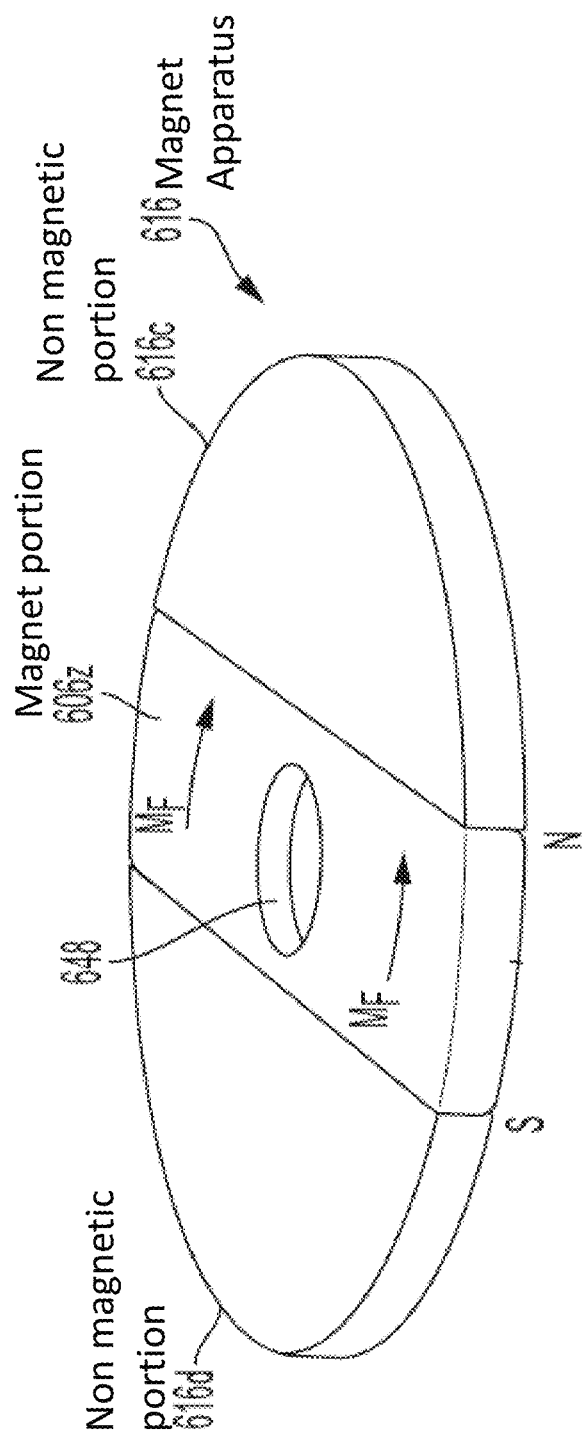
FIG. 6R2

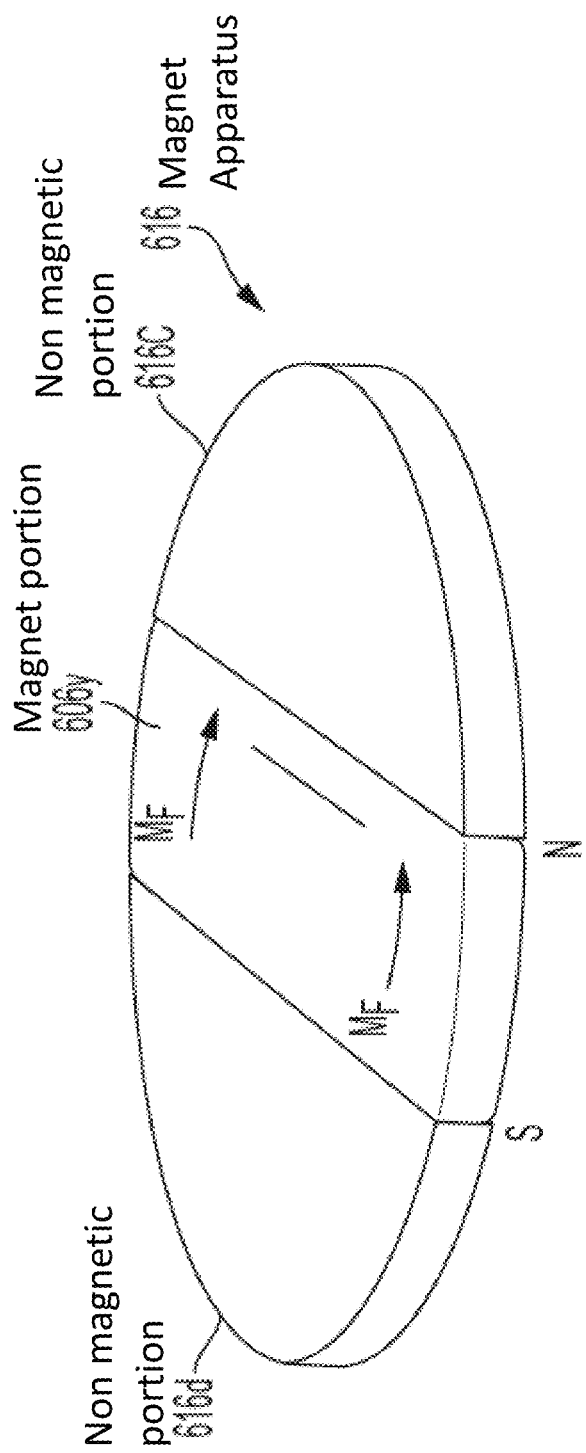
FIG. 6R3

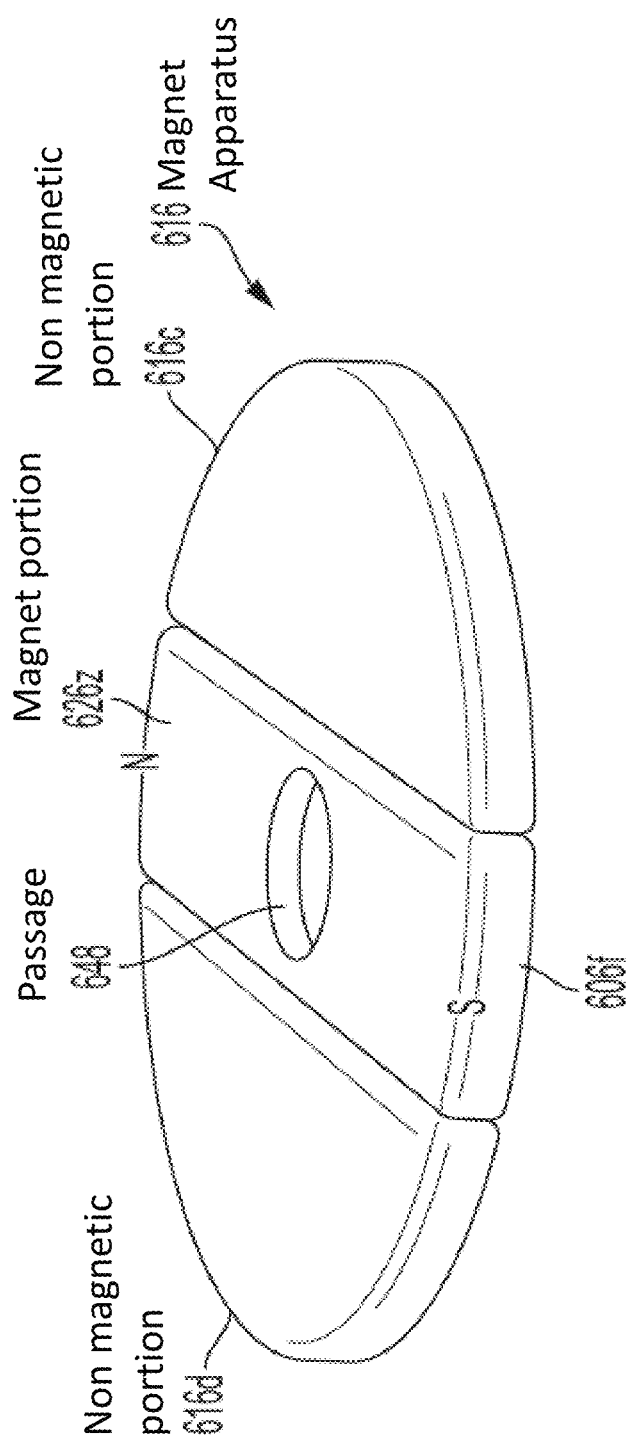
FIG. 6R4

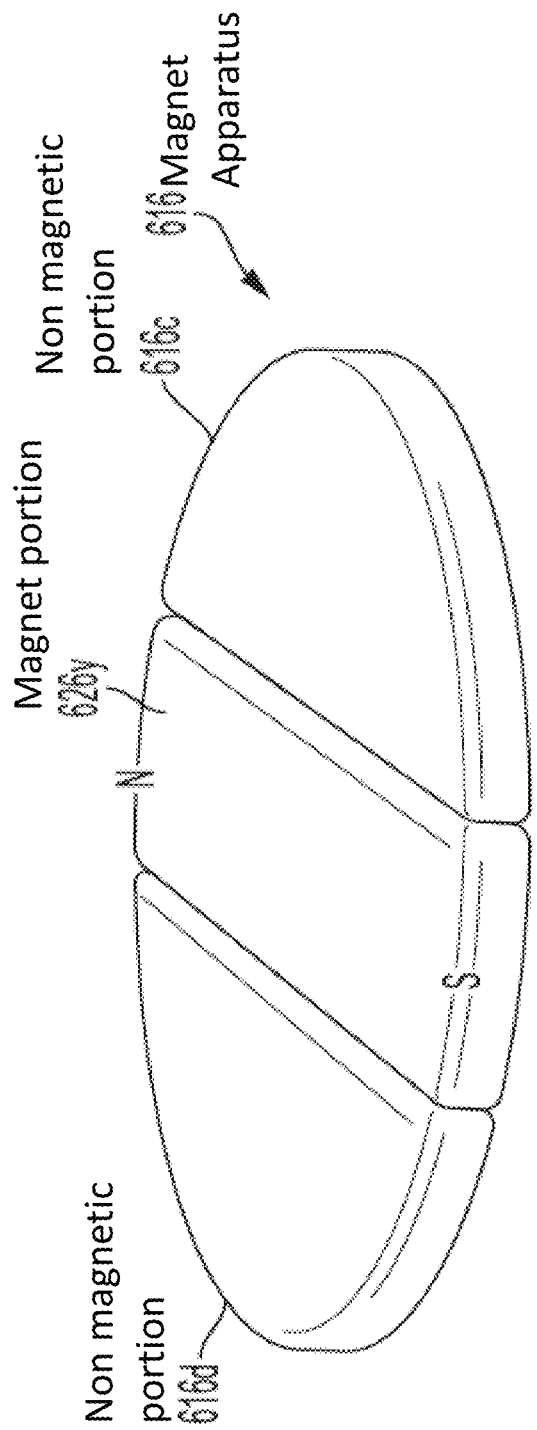
FIG. 6R5

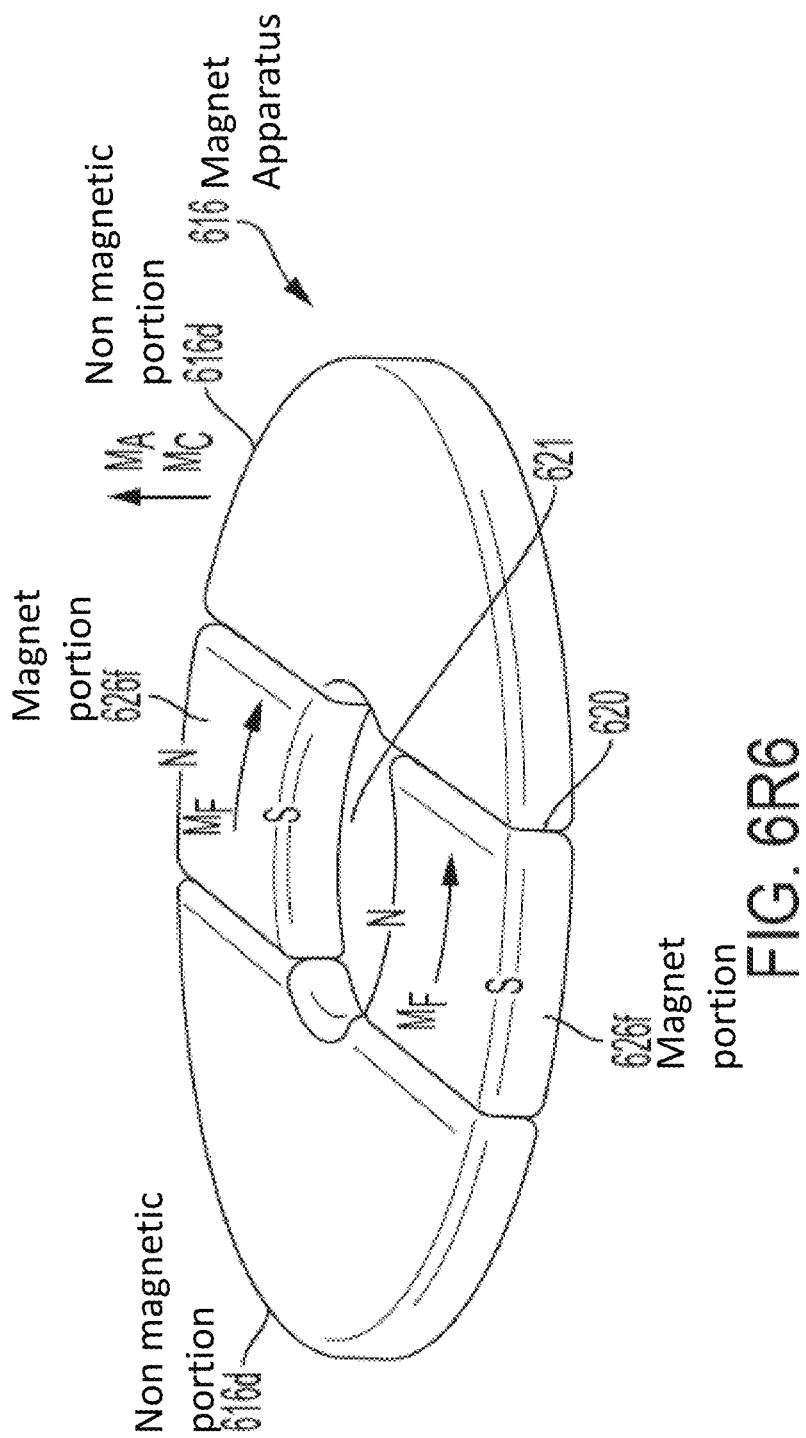
FIG. 6R6

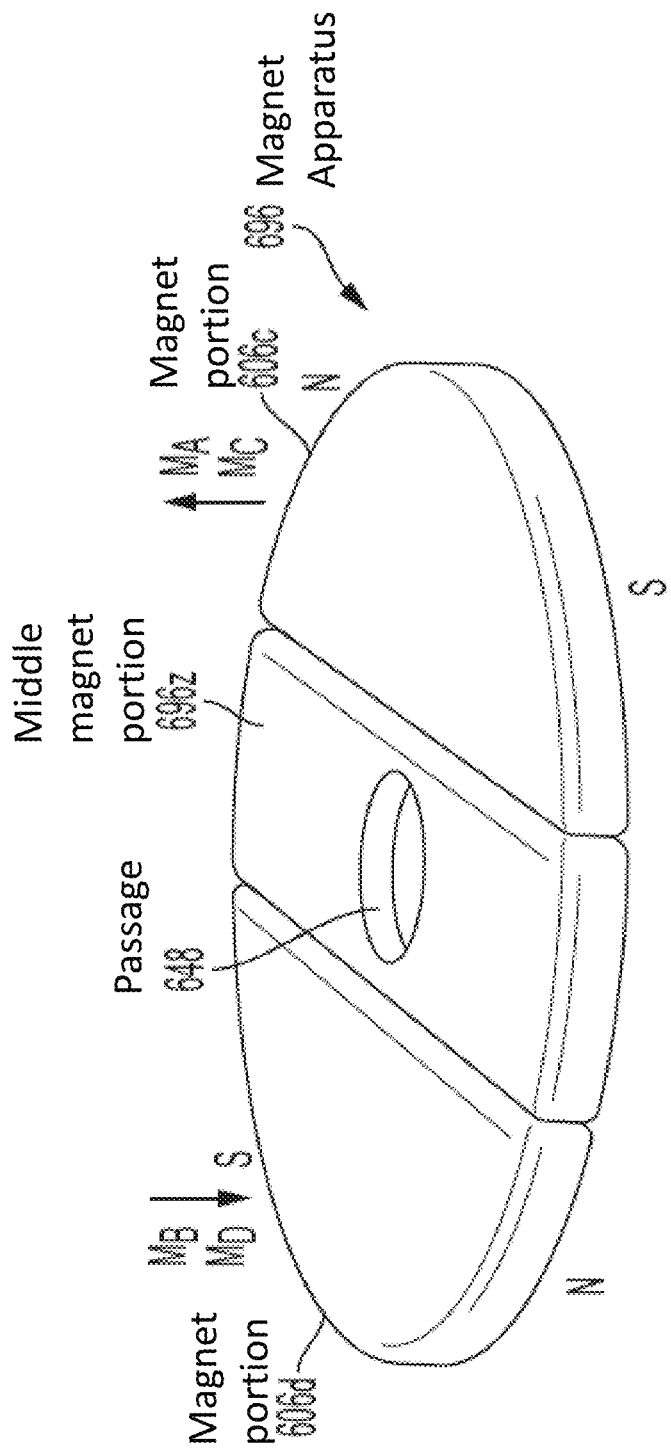
FIG. 6R7

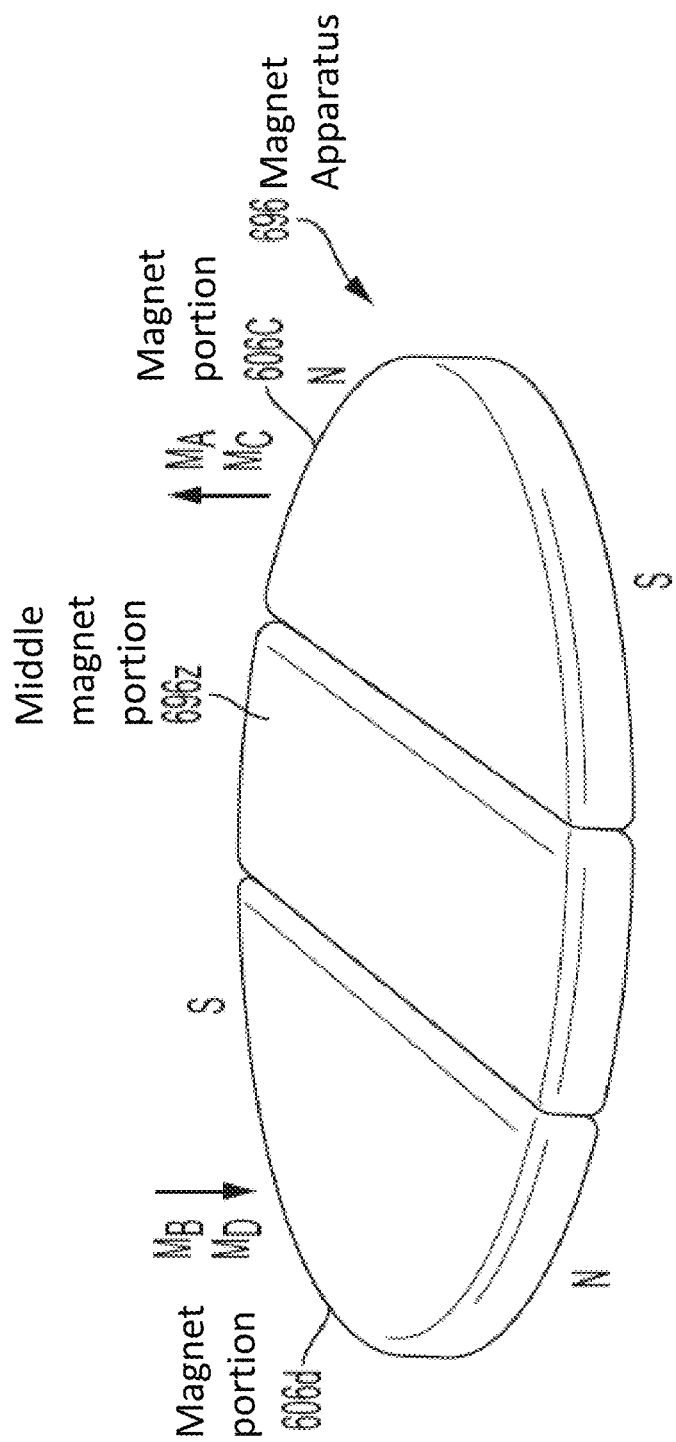
FIG. 6R8

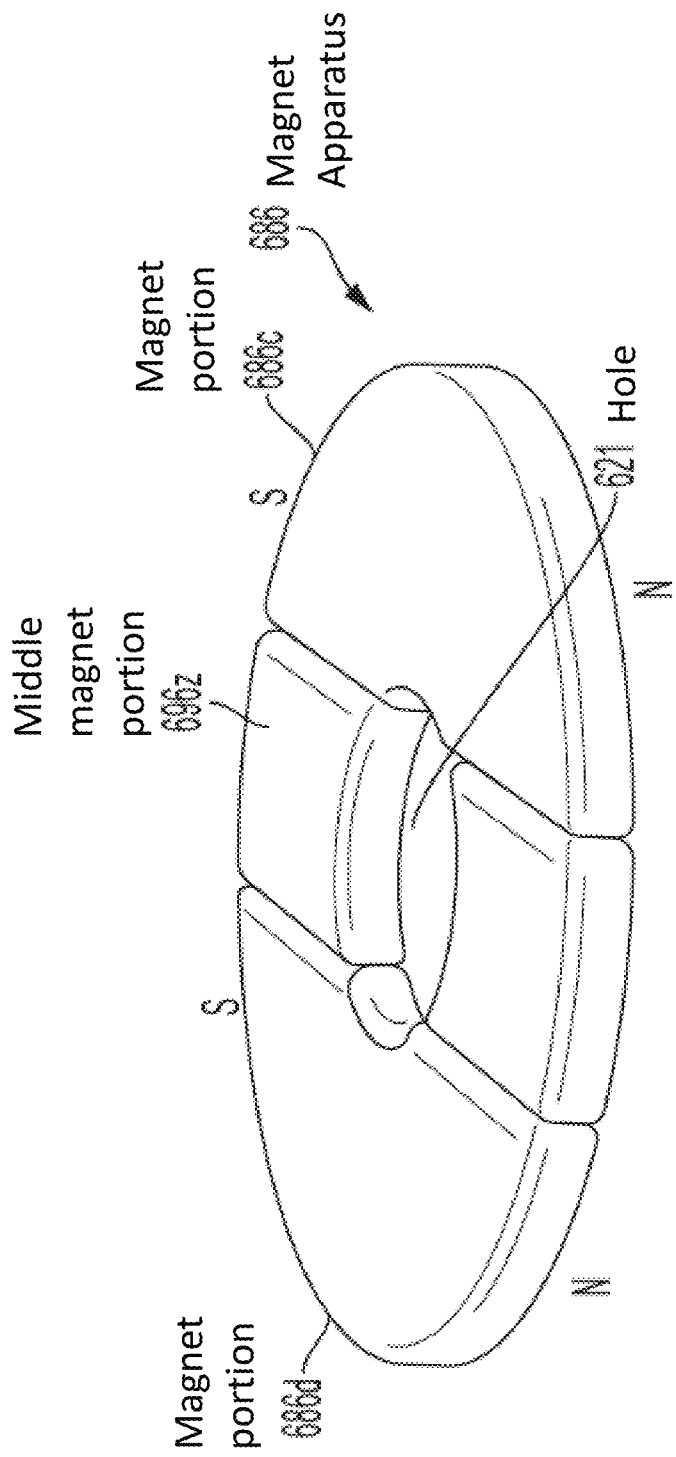

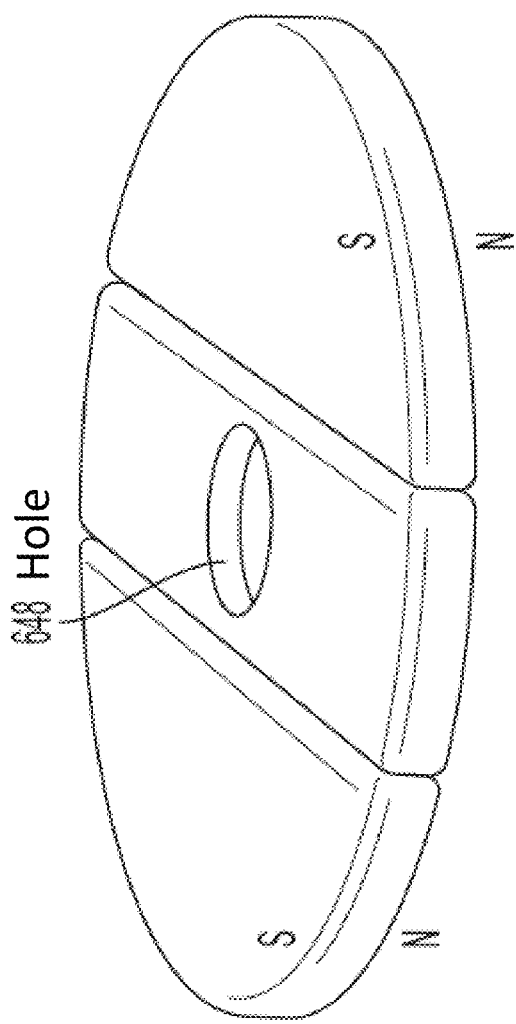
FIG. 6R9A

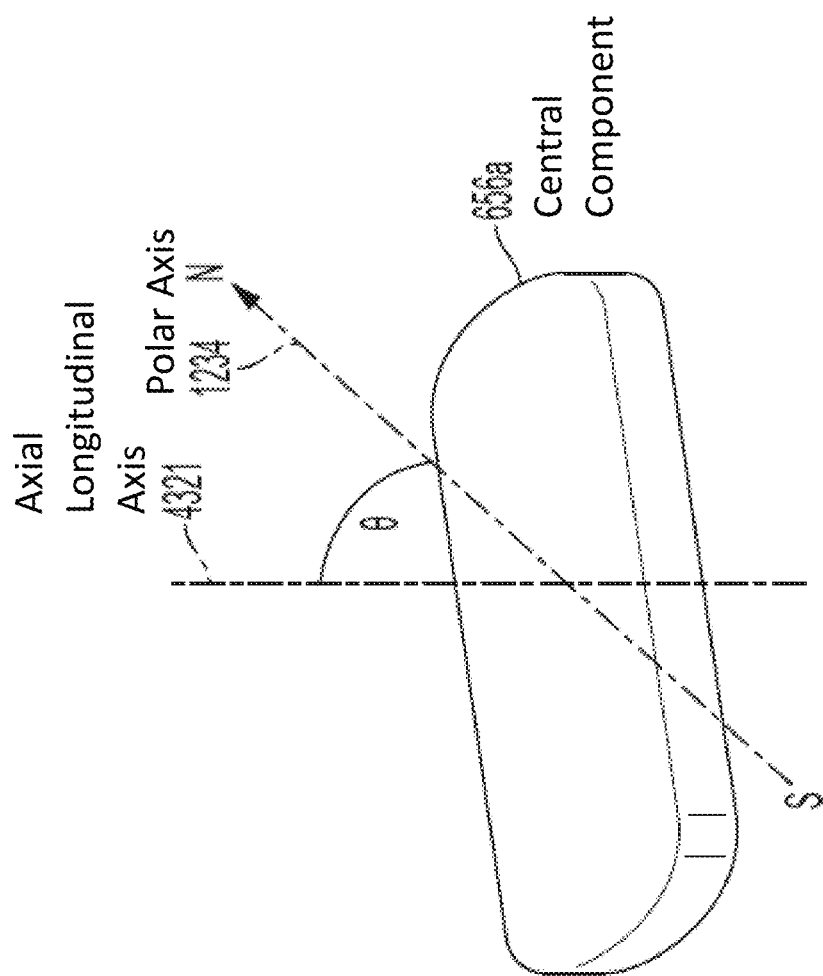

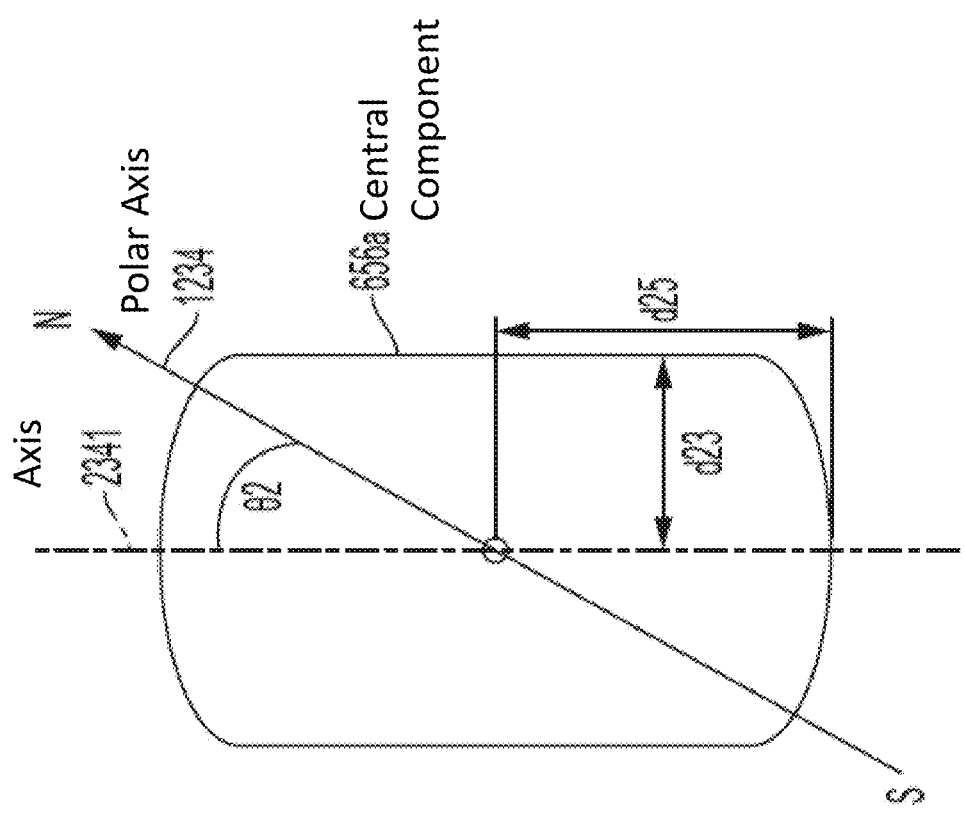
FIG. 6R9C

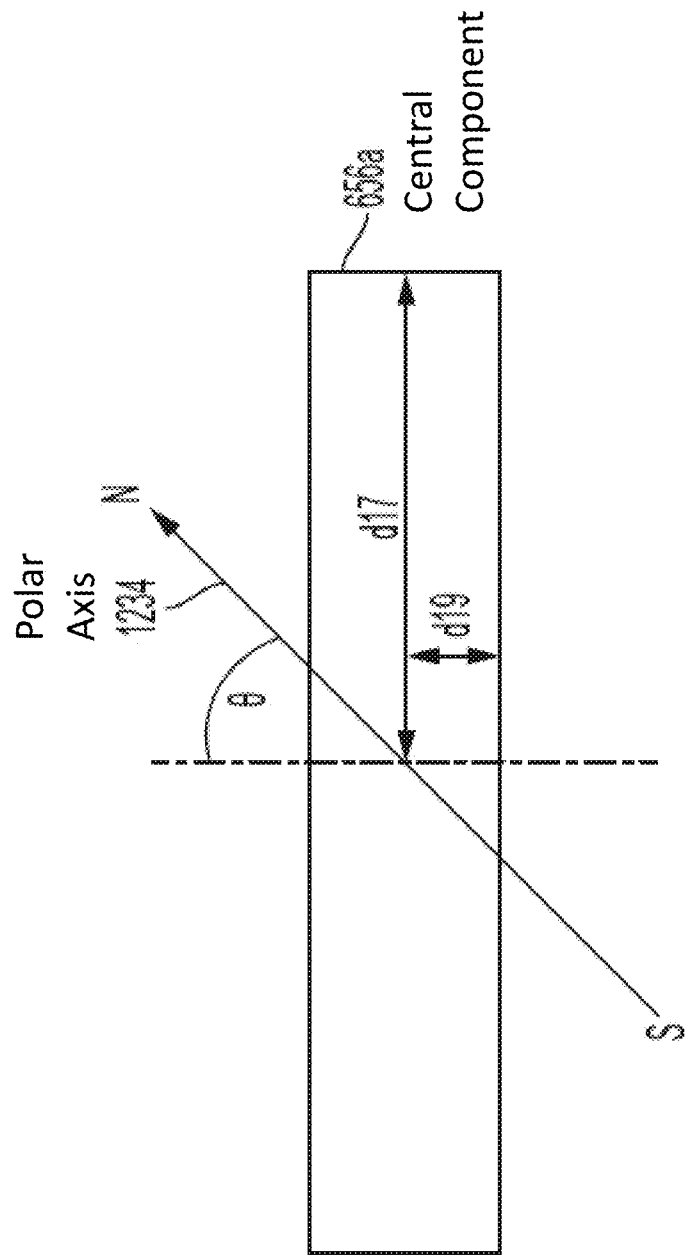

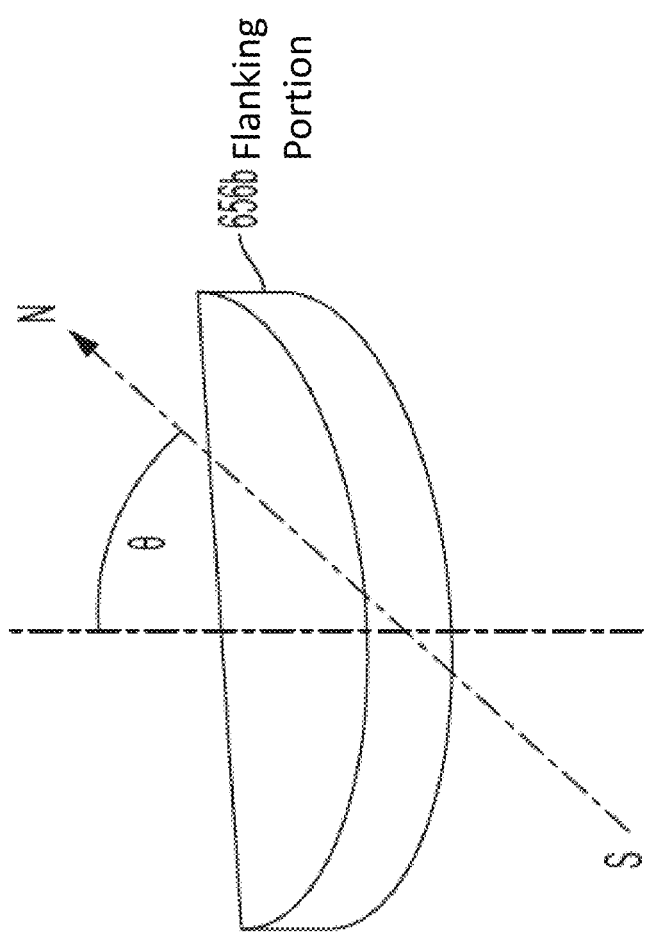
FIG. 6R9E

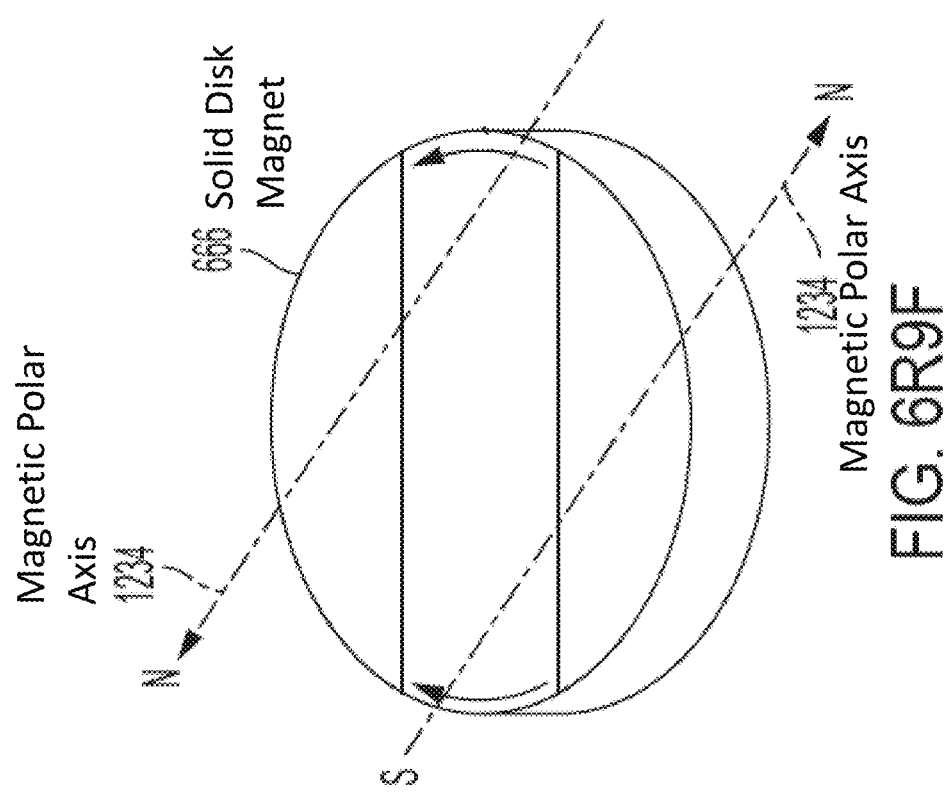

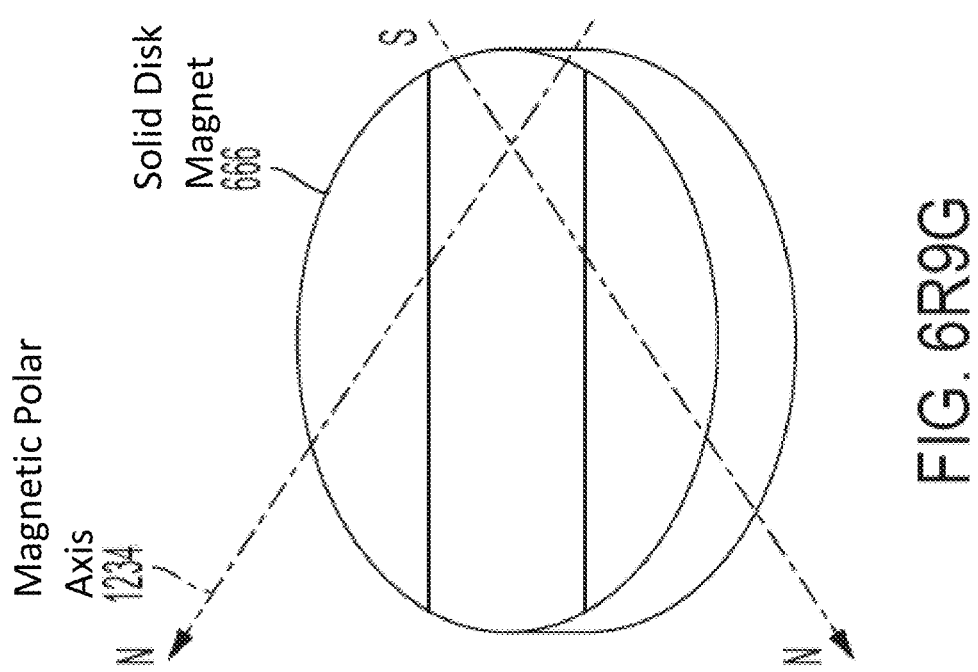
FIG. 6R9G

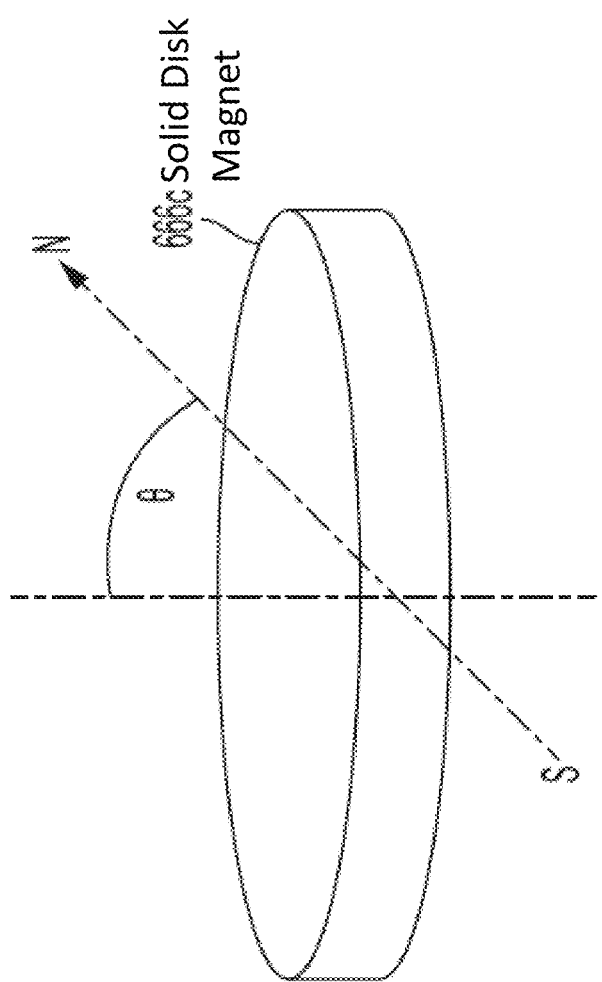
FIG. 6R9H

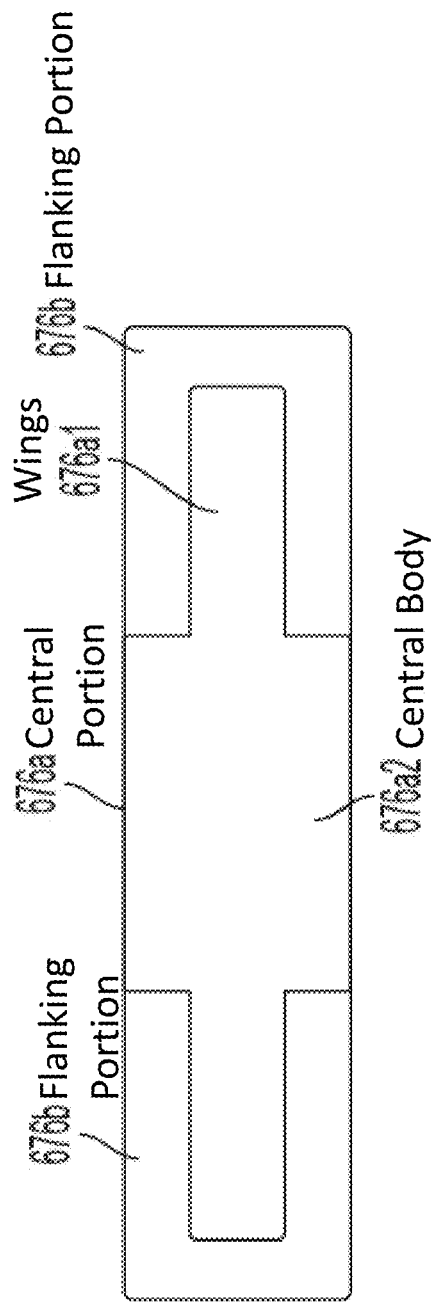
FIG. 6R9I

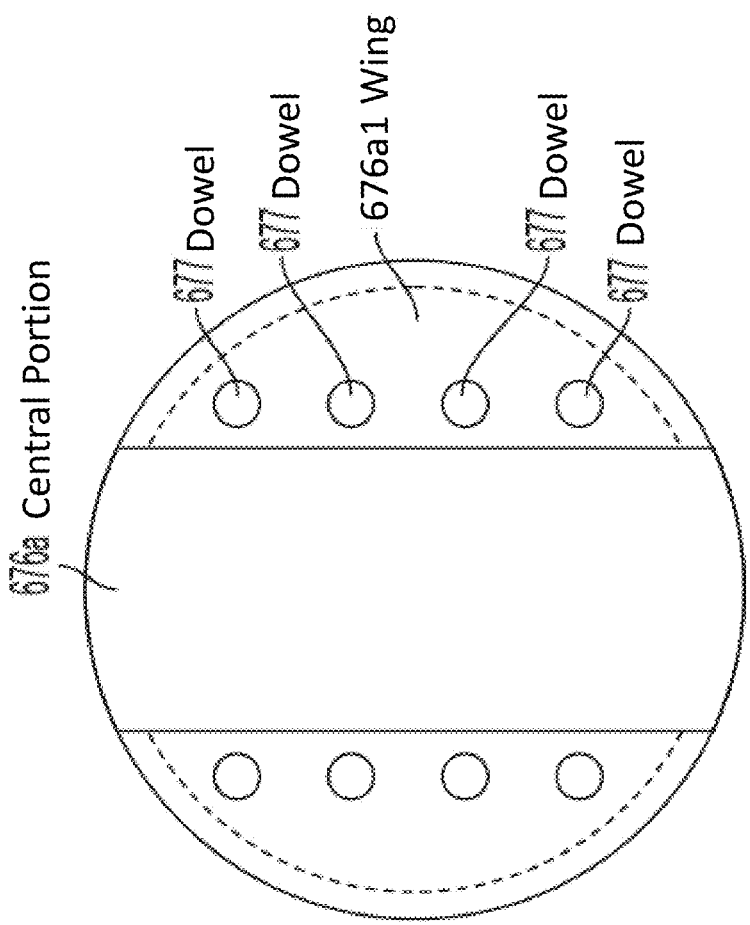

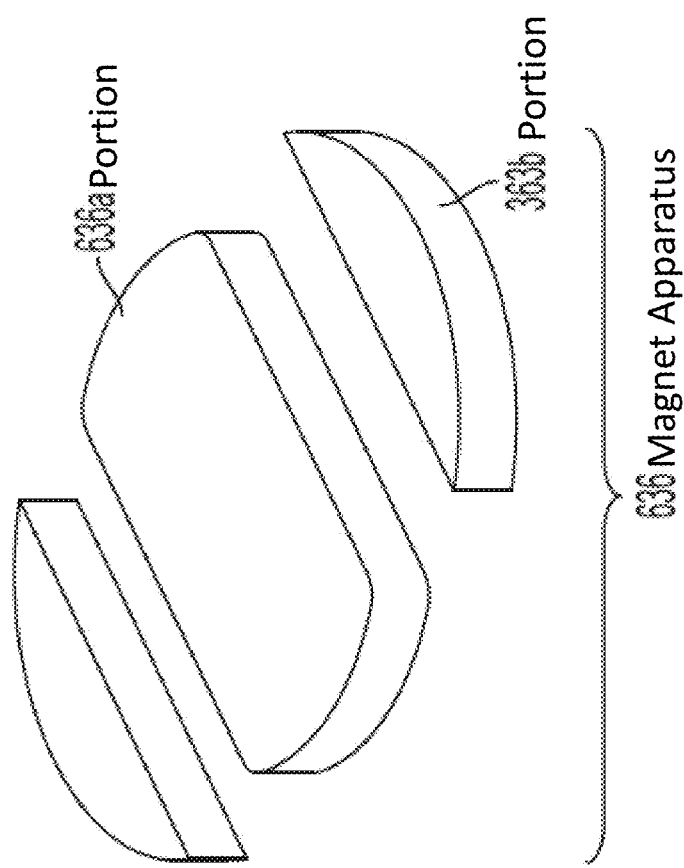
FIG. 6R10

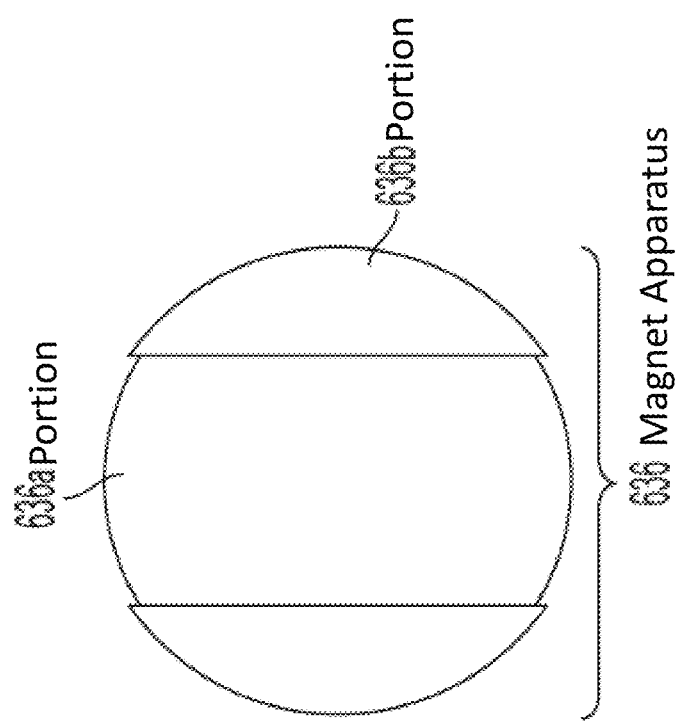
FIG. 6R11

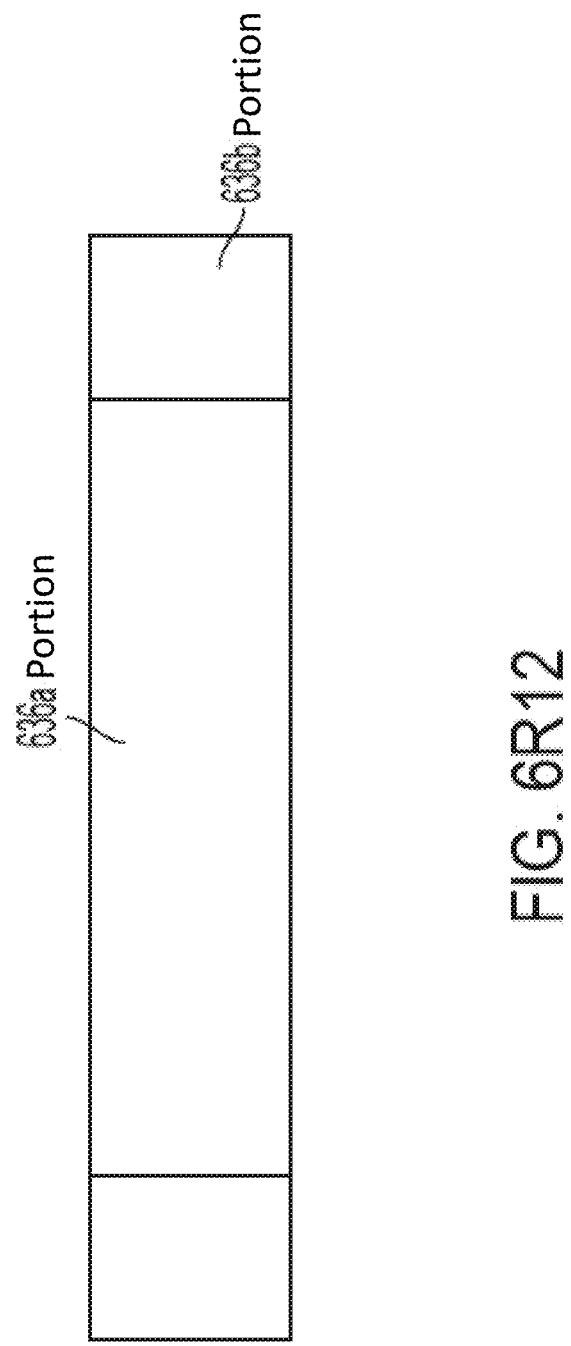
FIG. 6R12

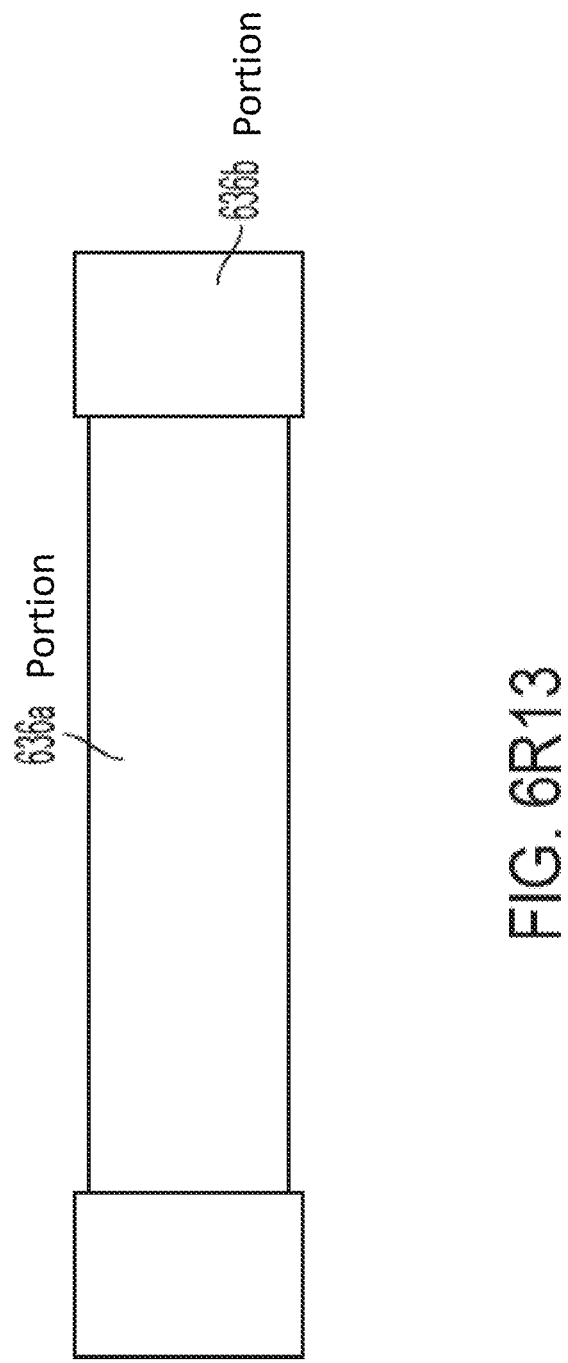
FIG. 6R13

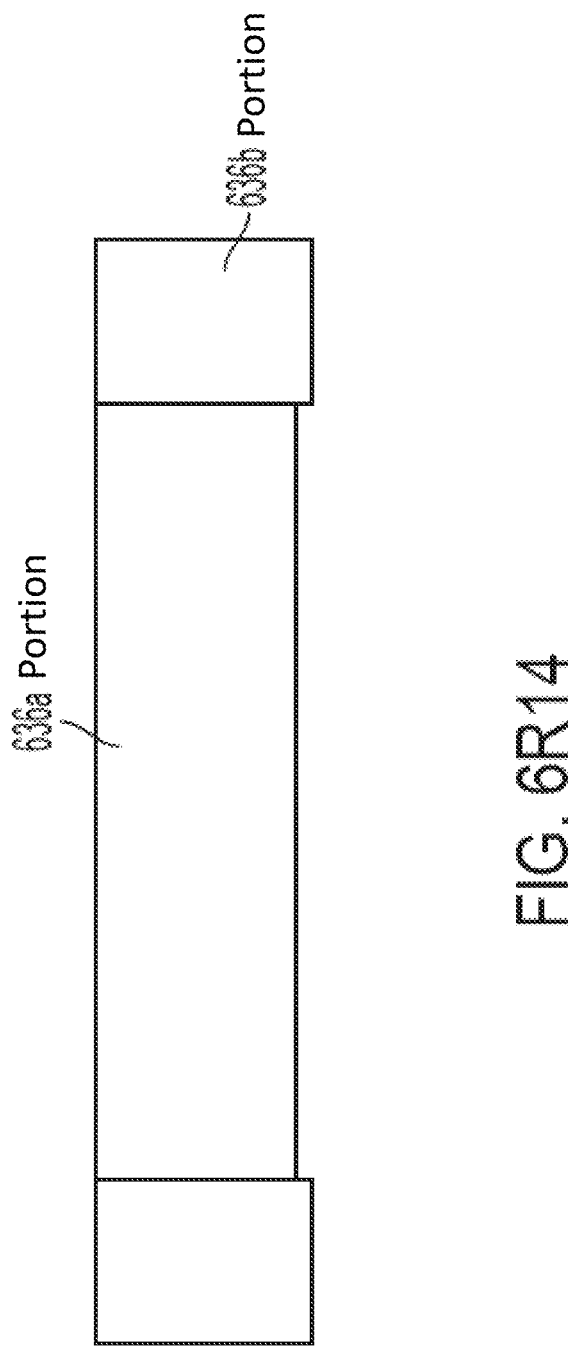

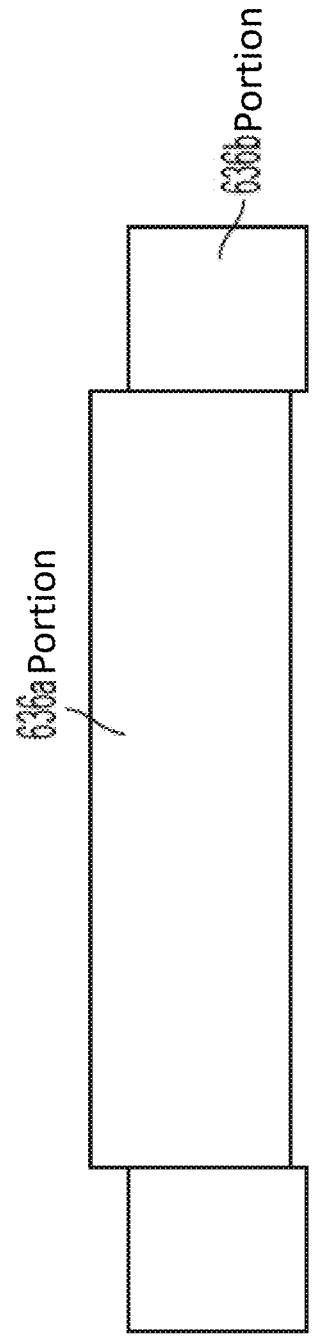
FIG. 6R15

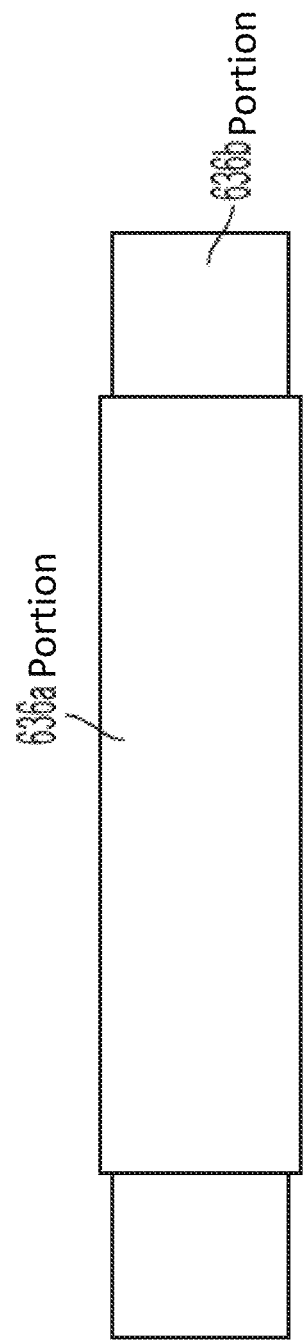
FIG. 6R16

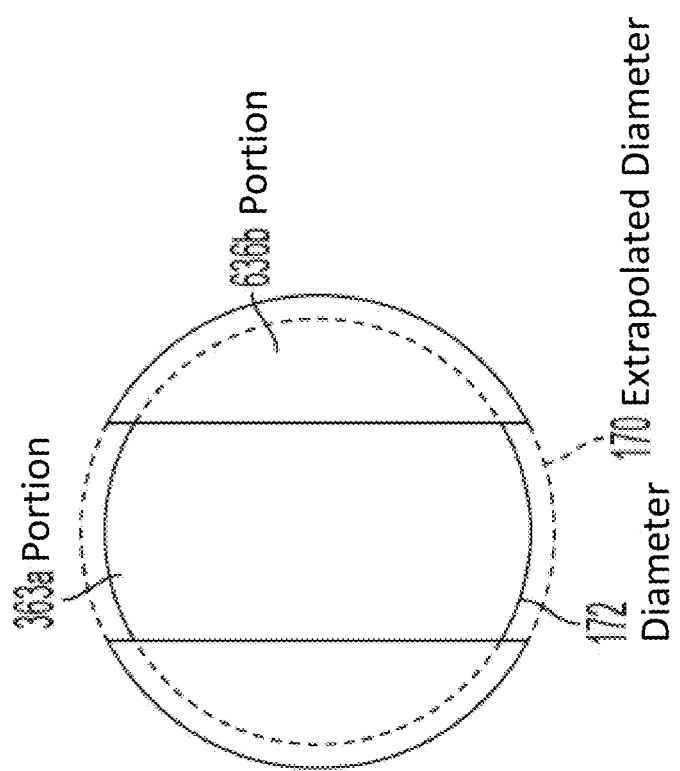
FIG. 6R17

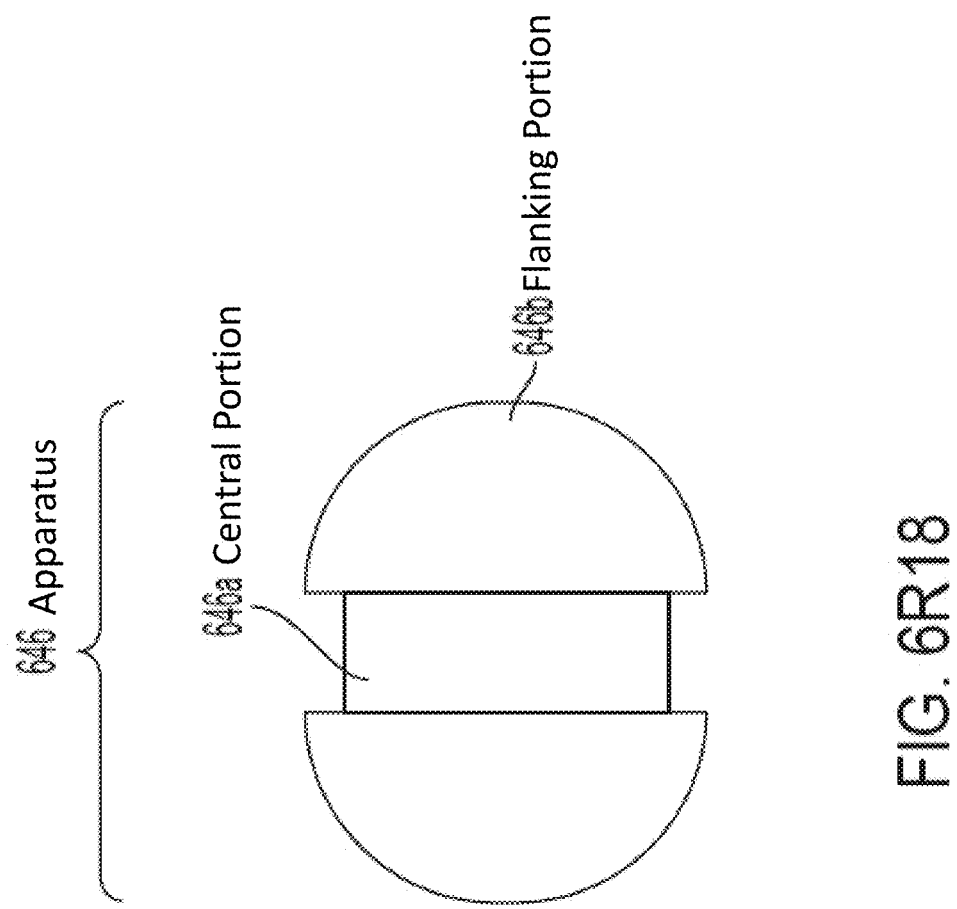
FIG. 6R18

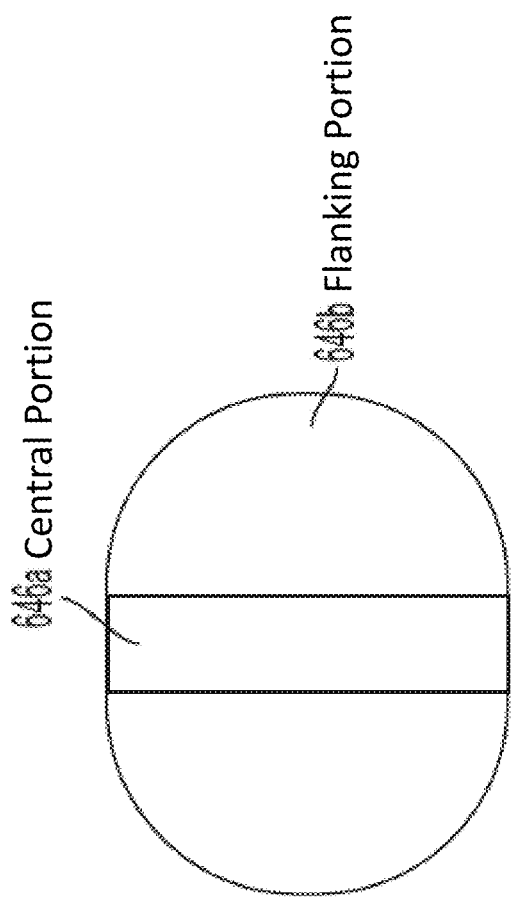
FIG. 6R19

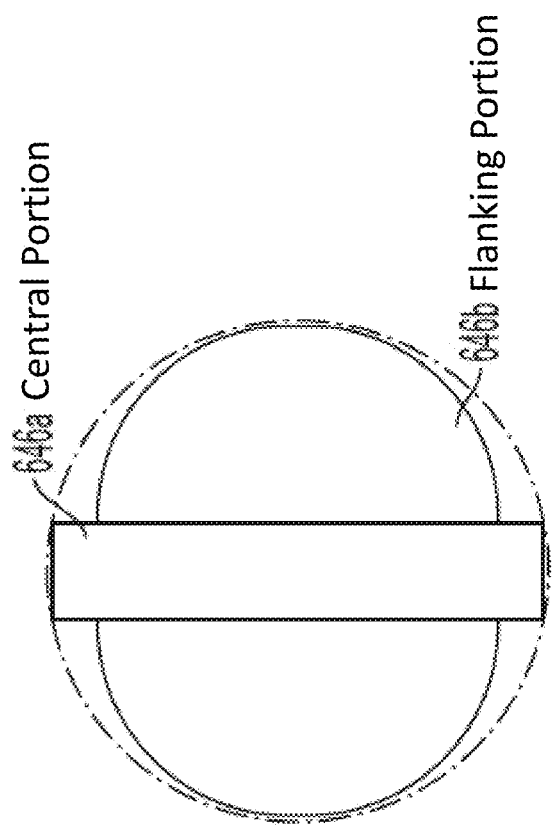
FIG. 6R20

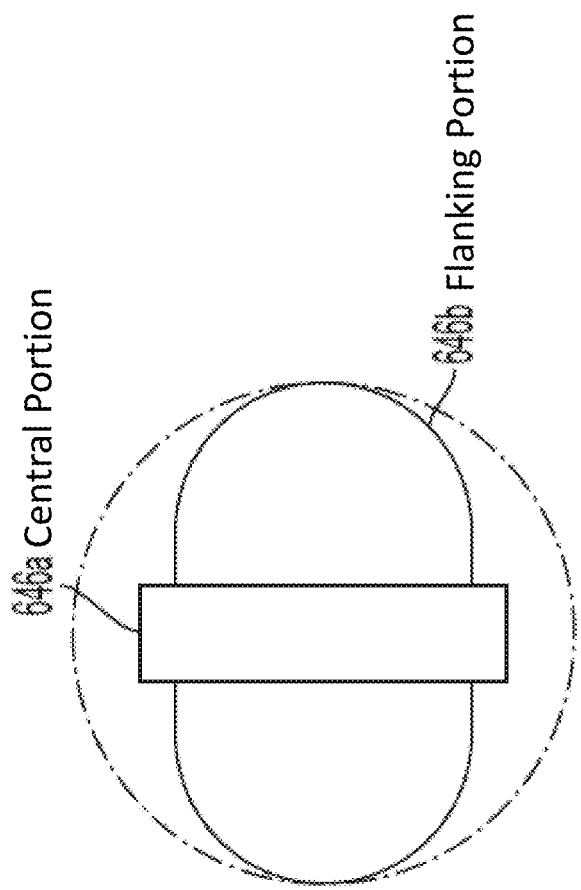
FIG. 6R21

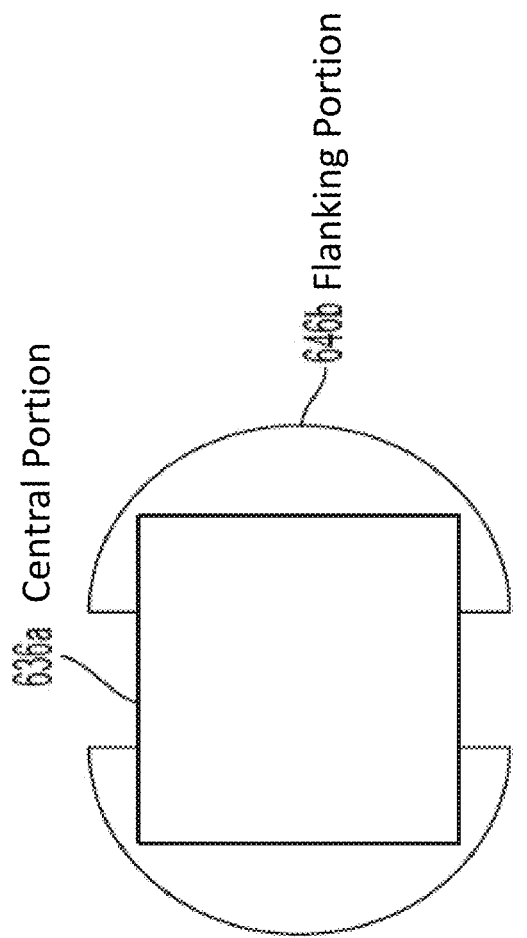

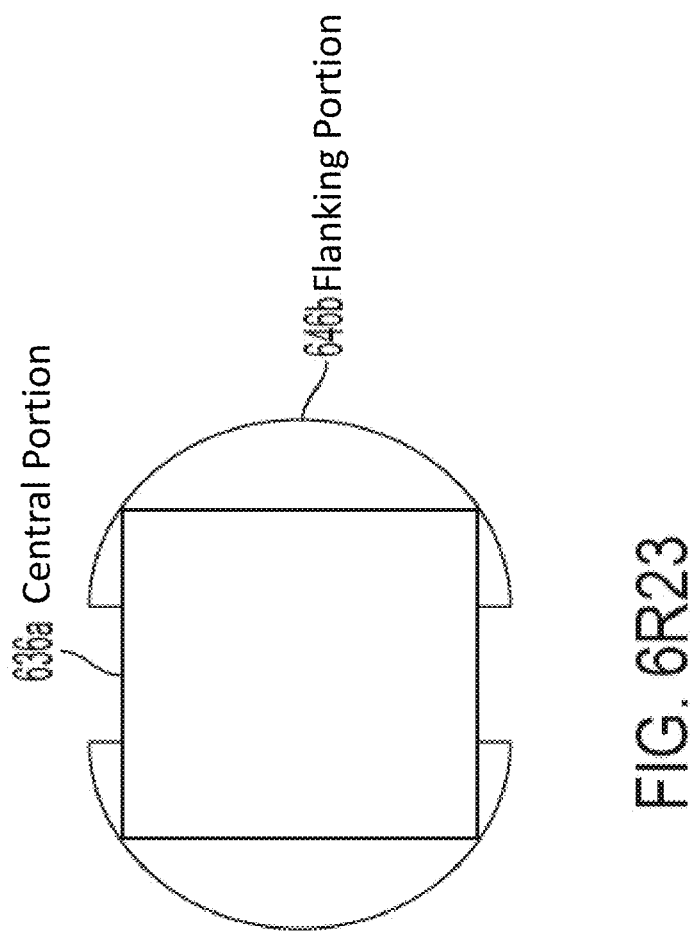
FIG. 6R23

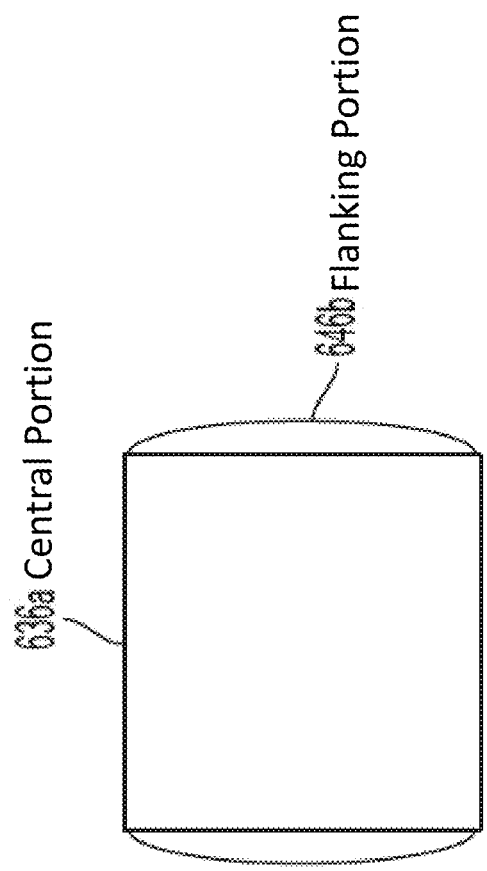
FIG. 6R24

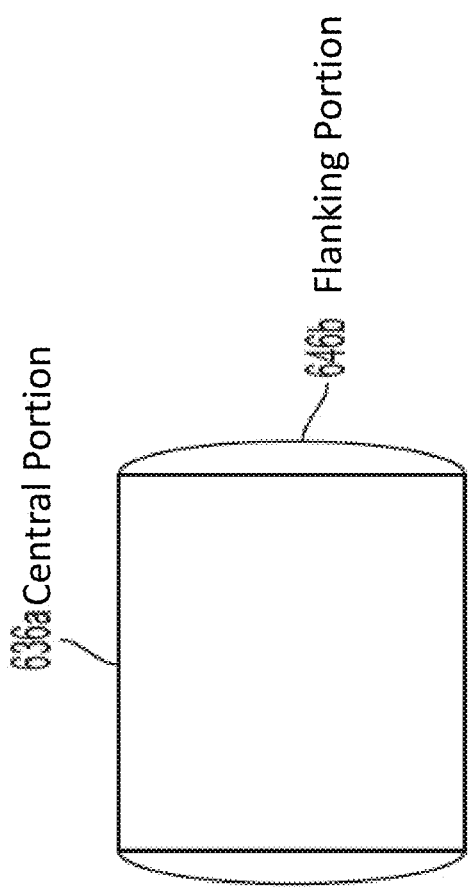
FIG. 6R25

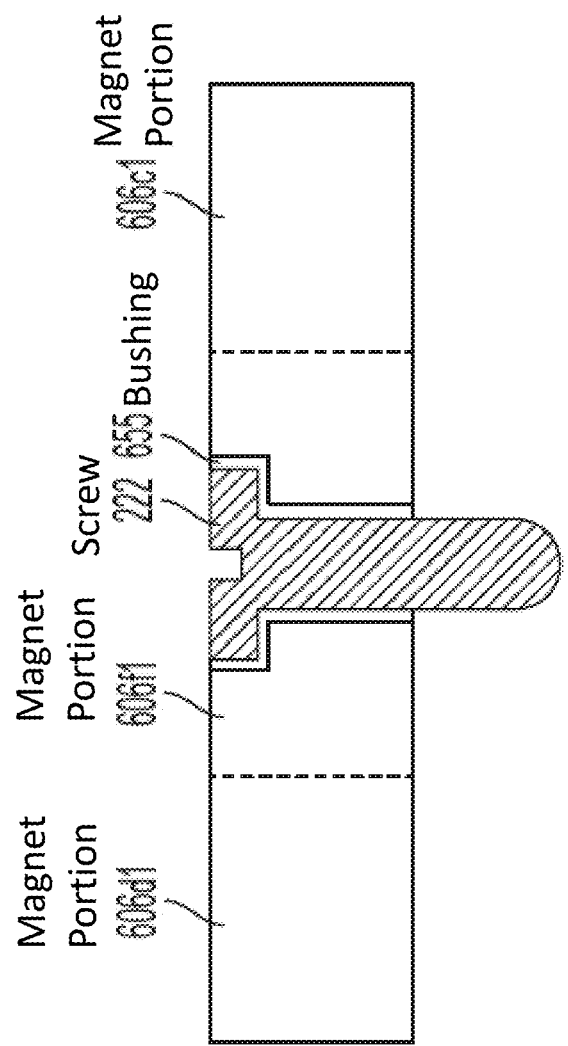
FIG. 6T1

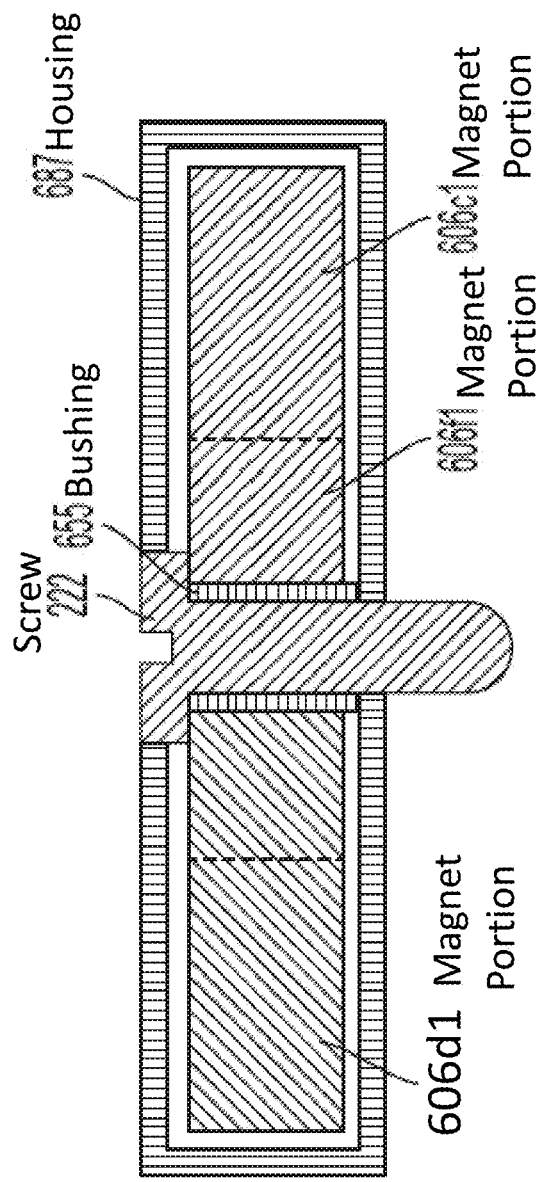
FIG. 6T2

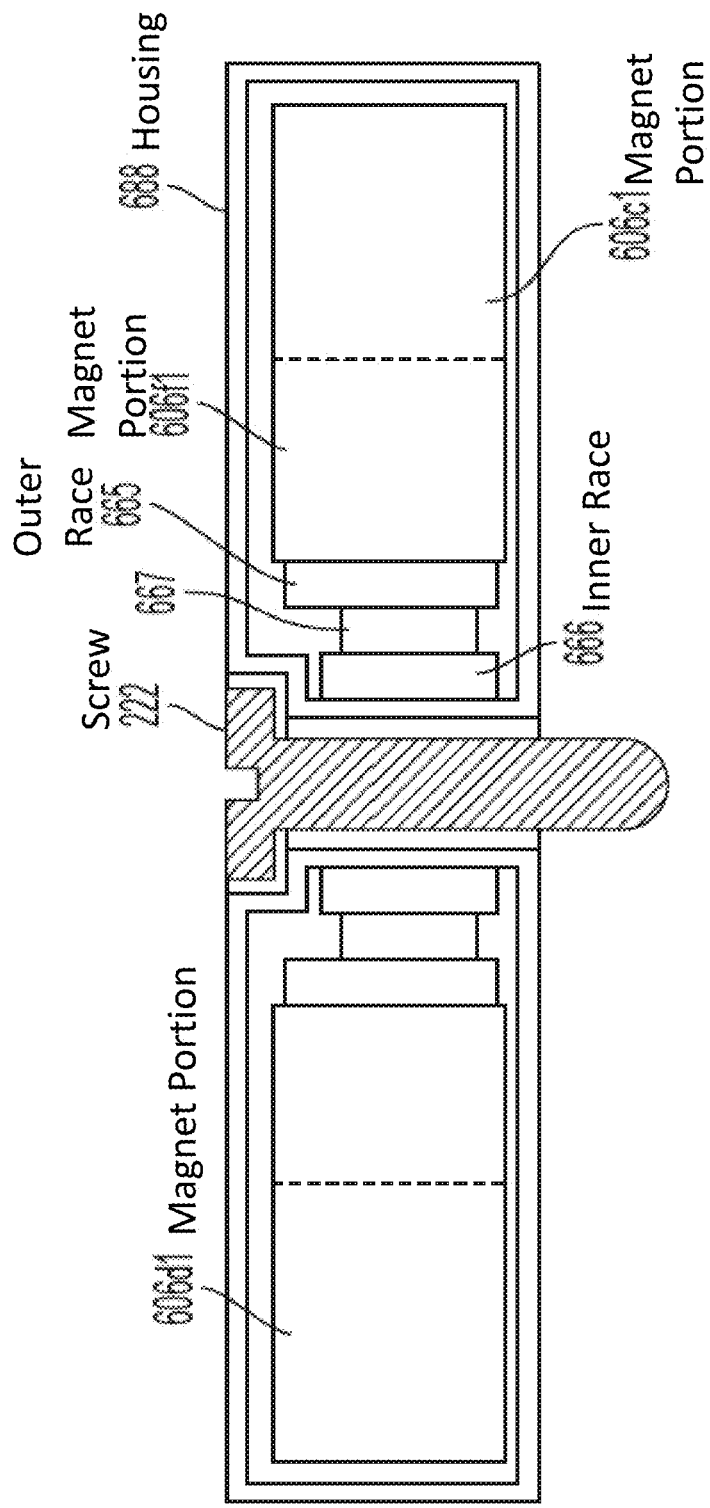
FIG. 6T3

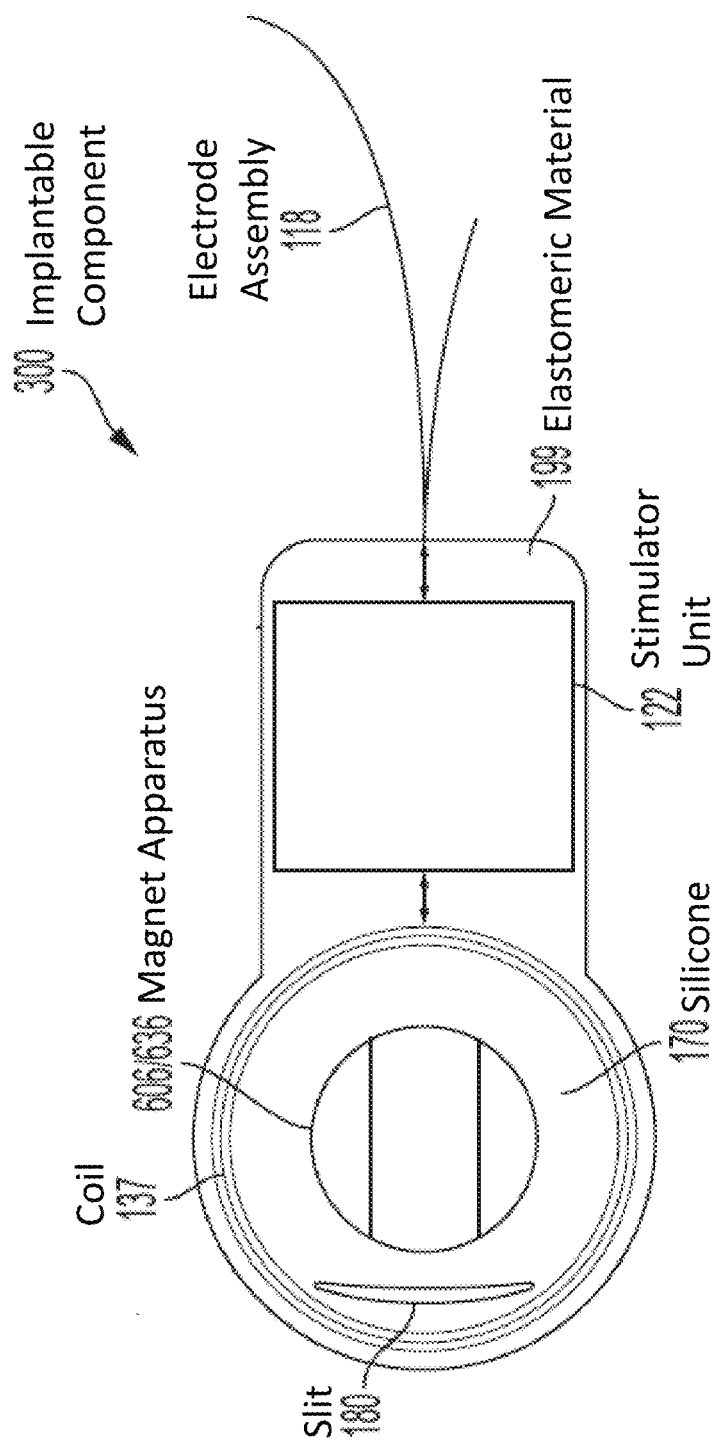
FIG. 6U1

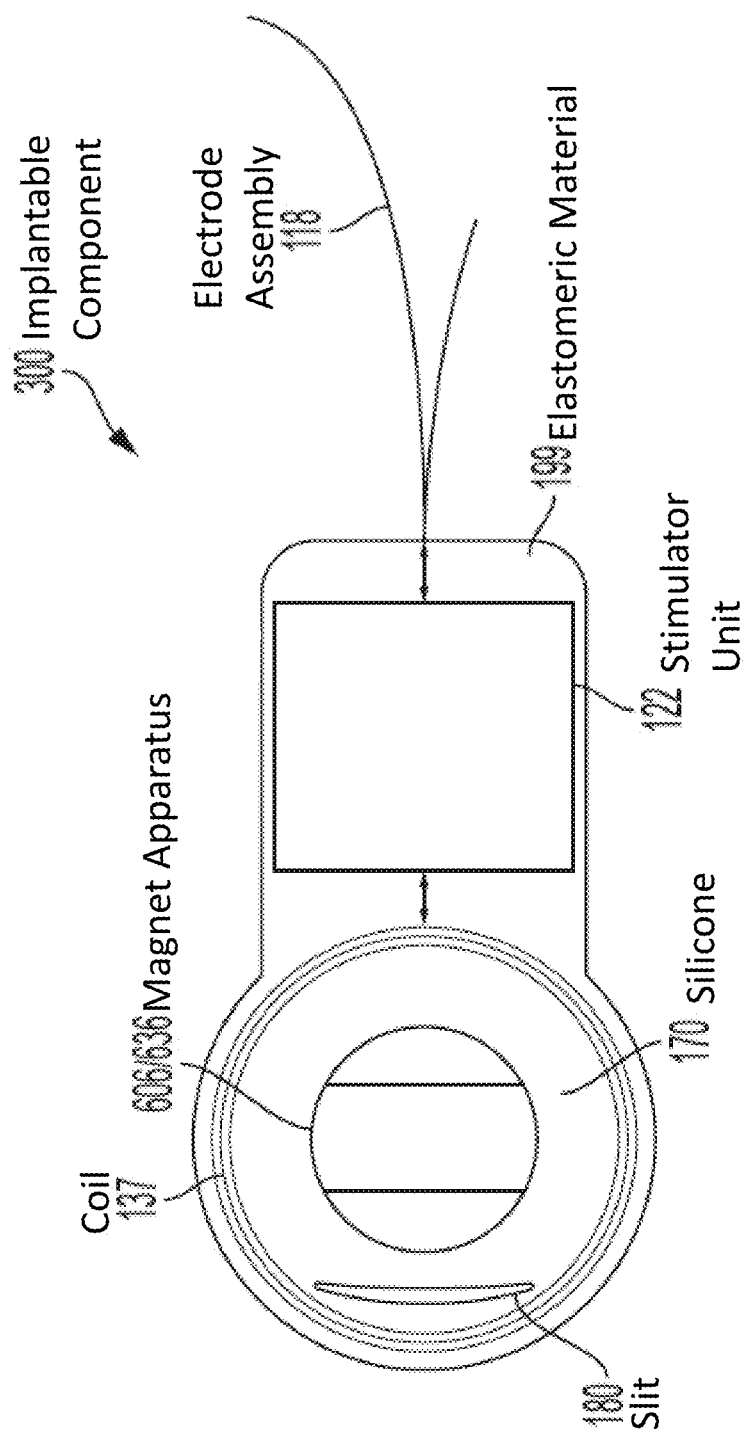
FIG. 6U2

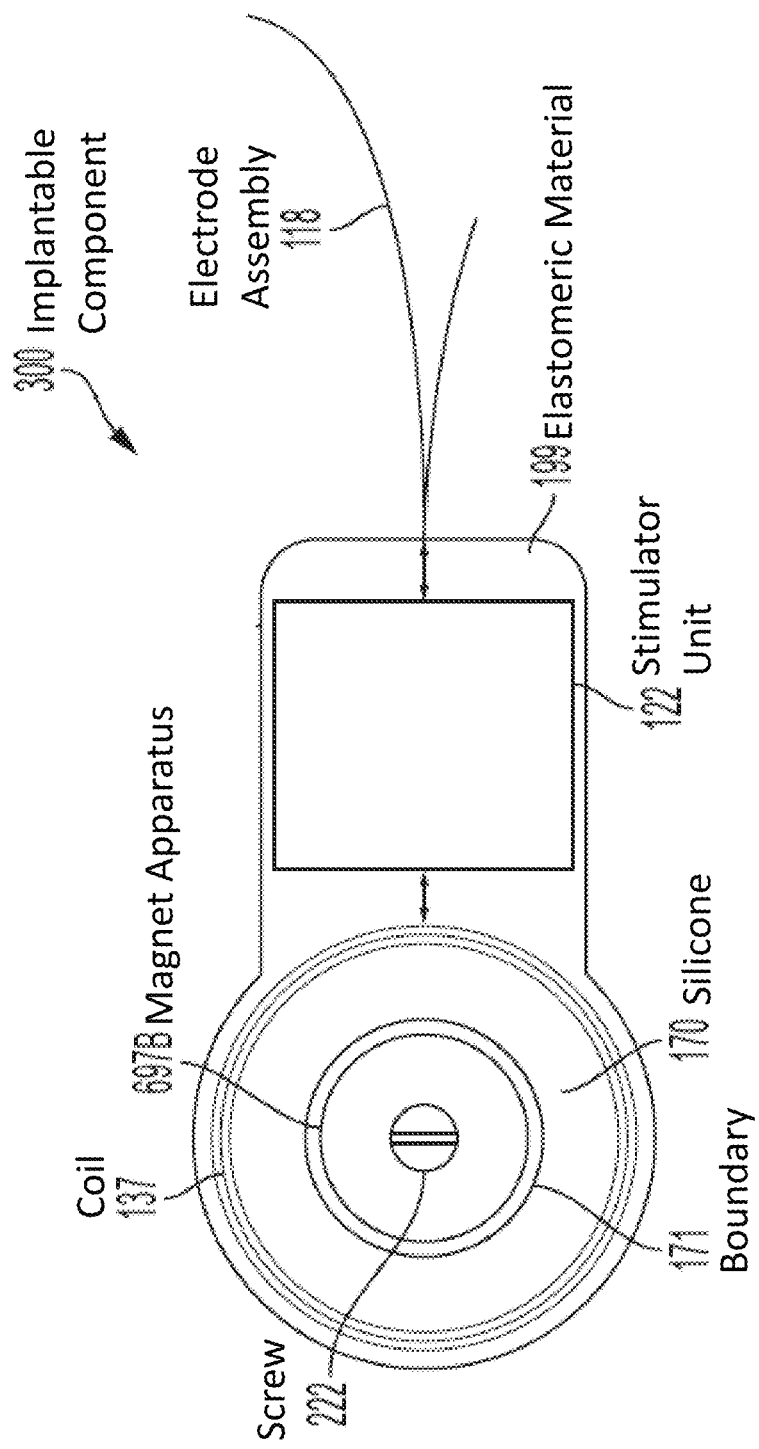
FIG. 6U3

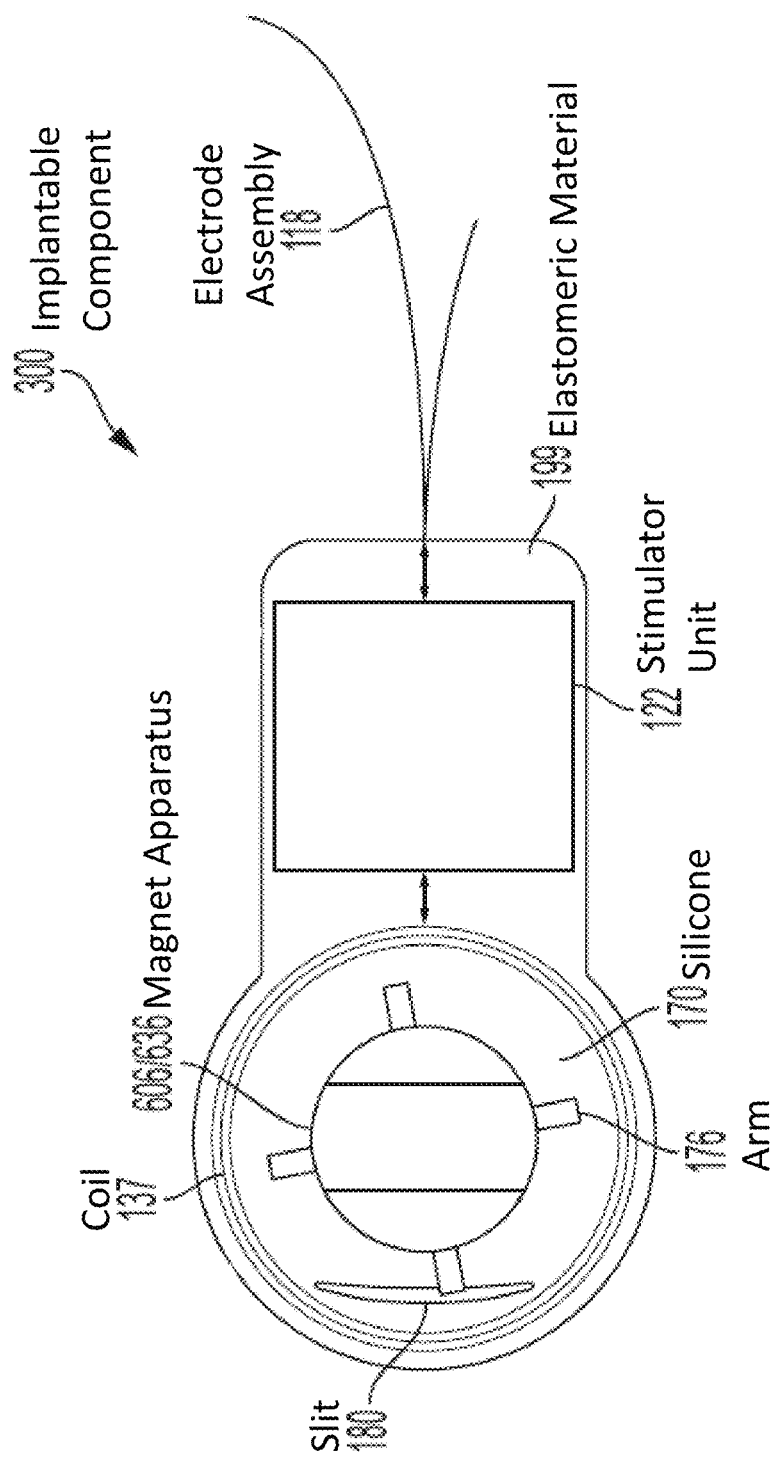
FIG. 6U4

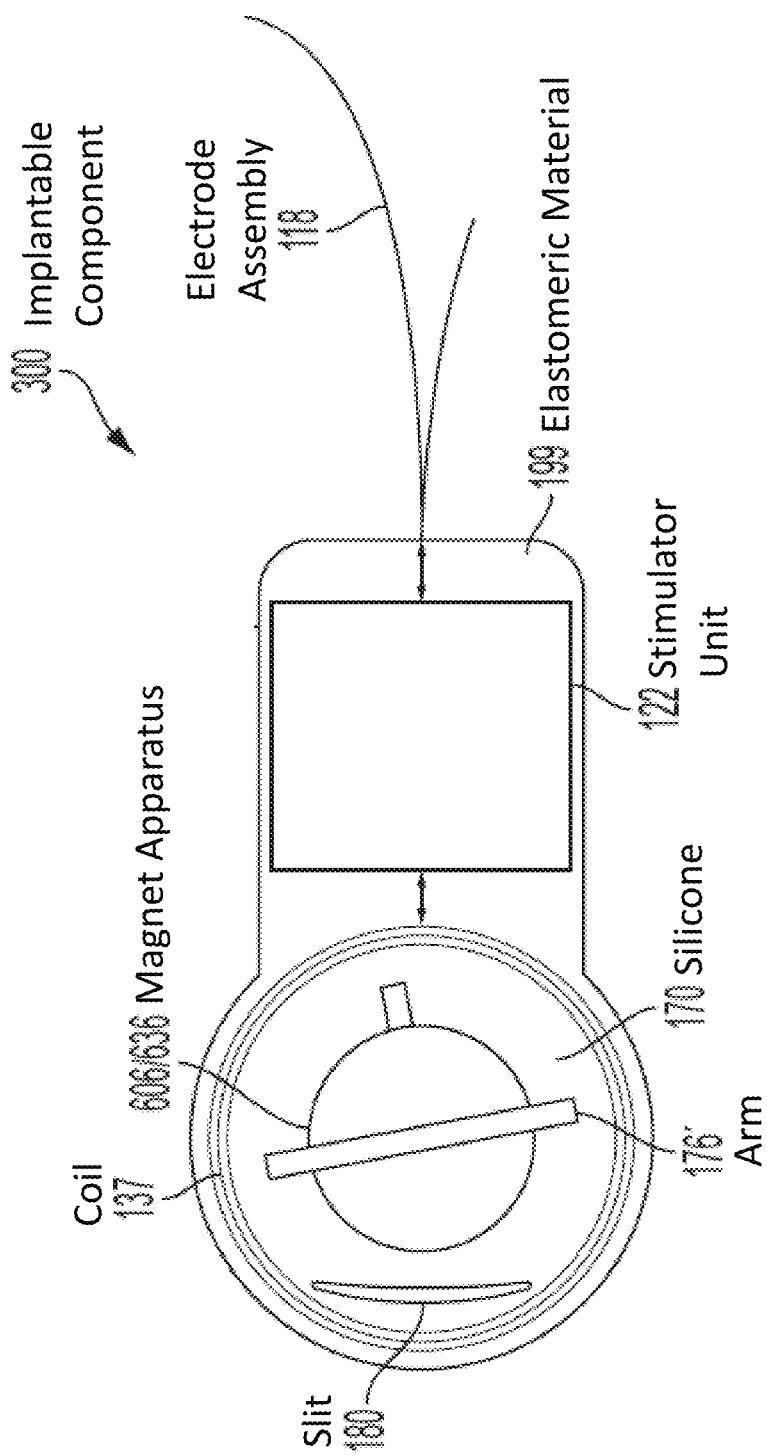
FIG. 6U5

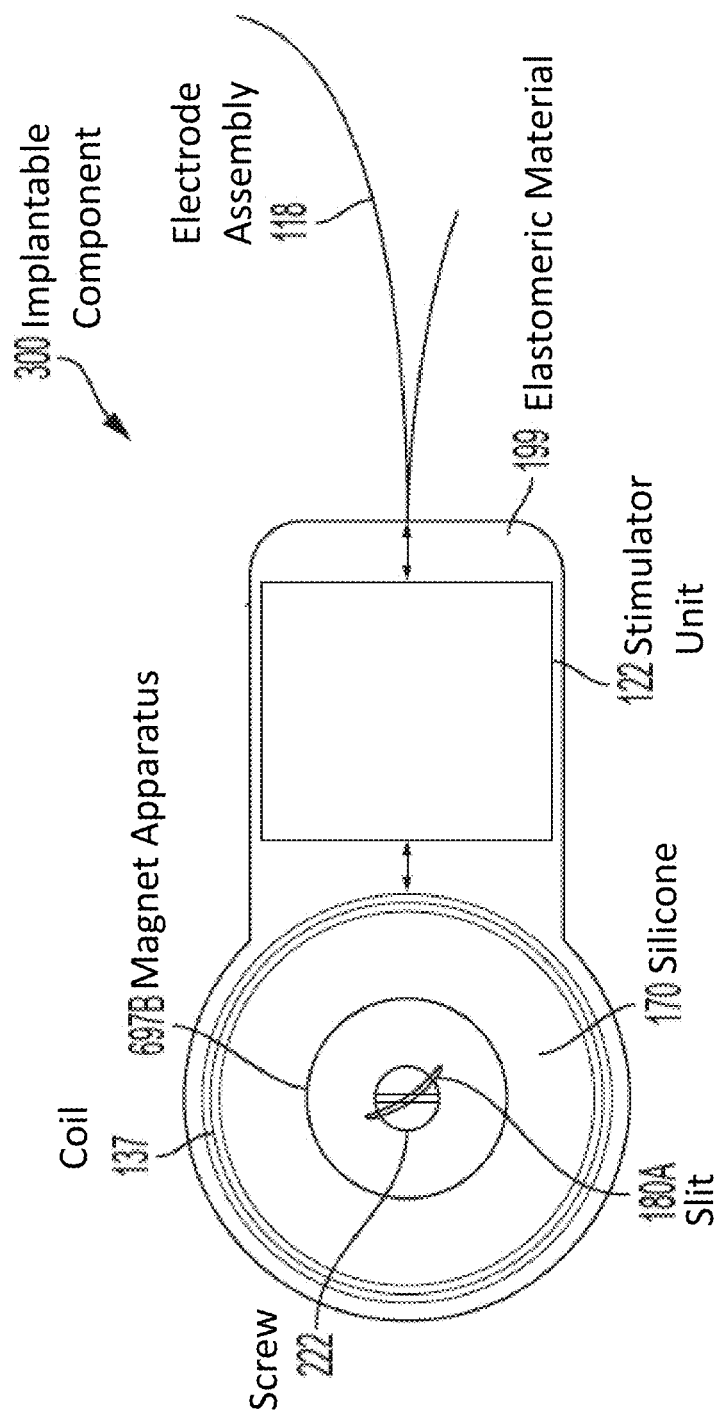
FIG. 6W1

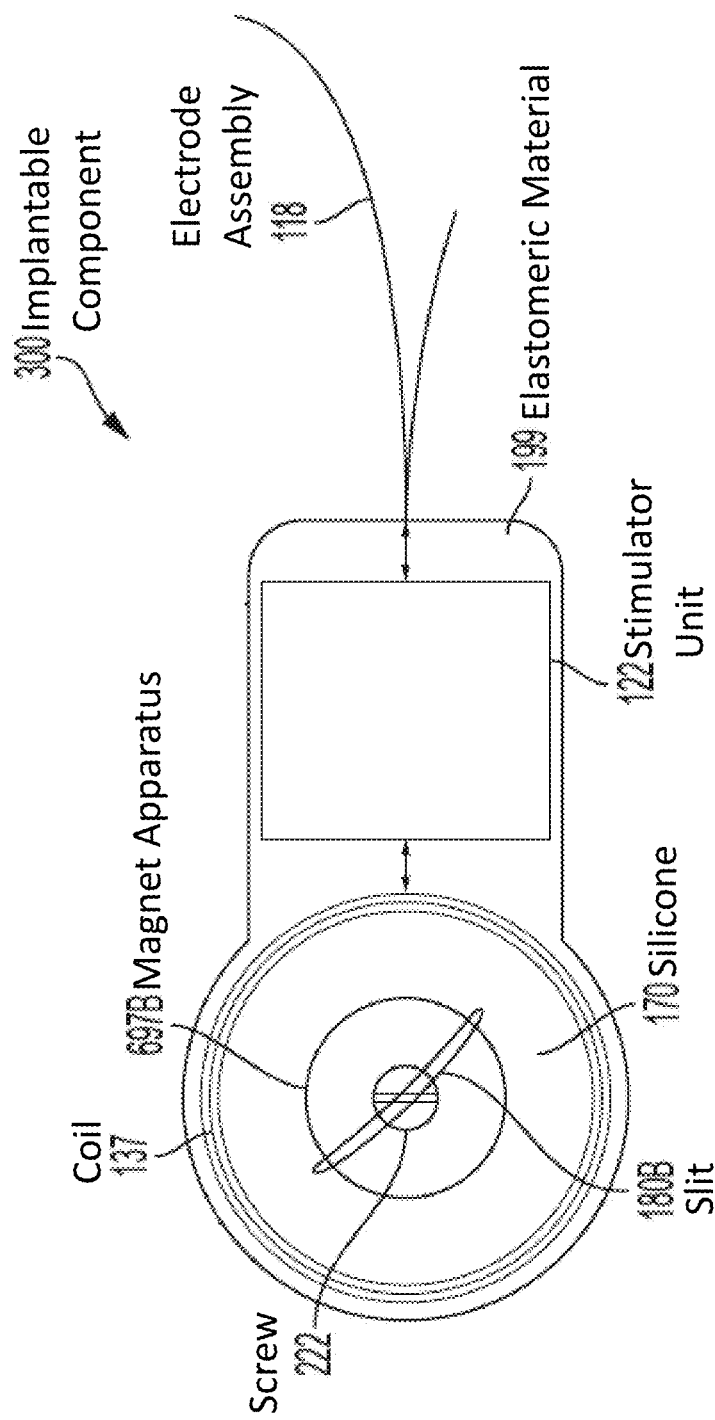
FIG. 6W2

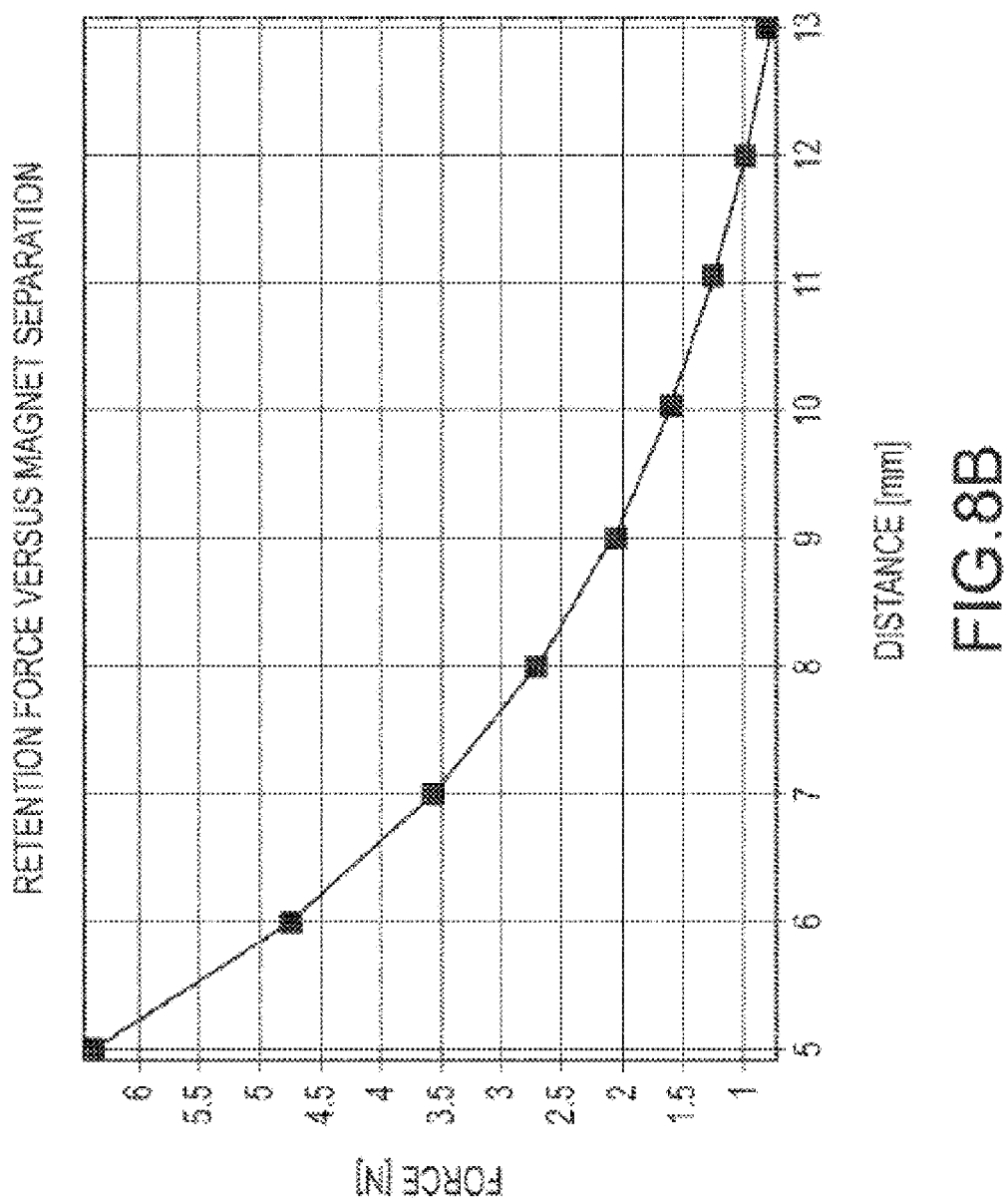

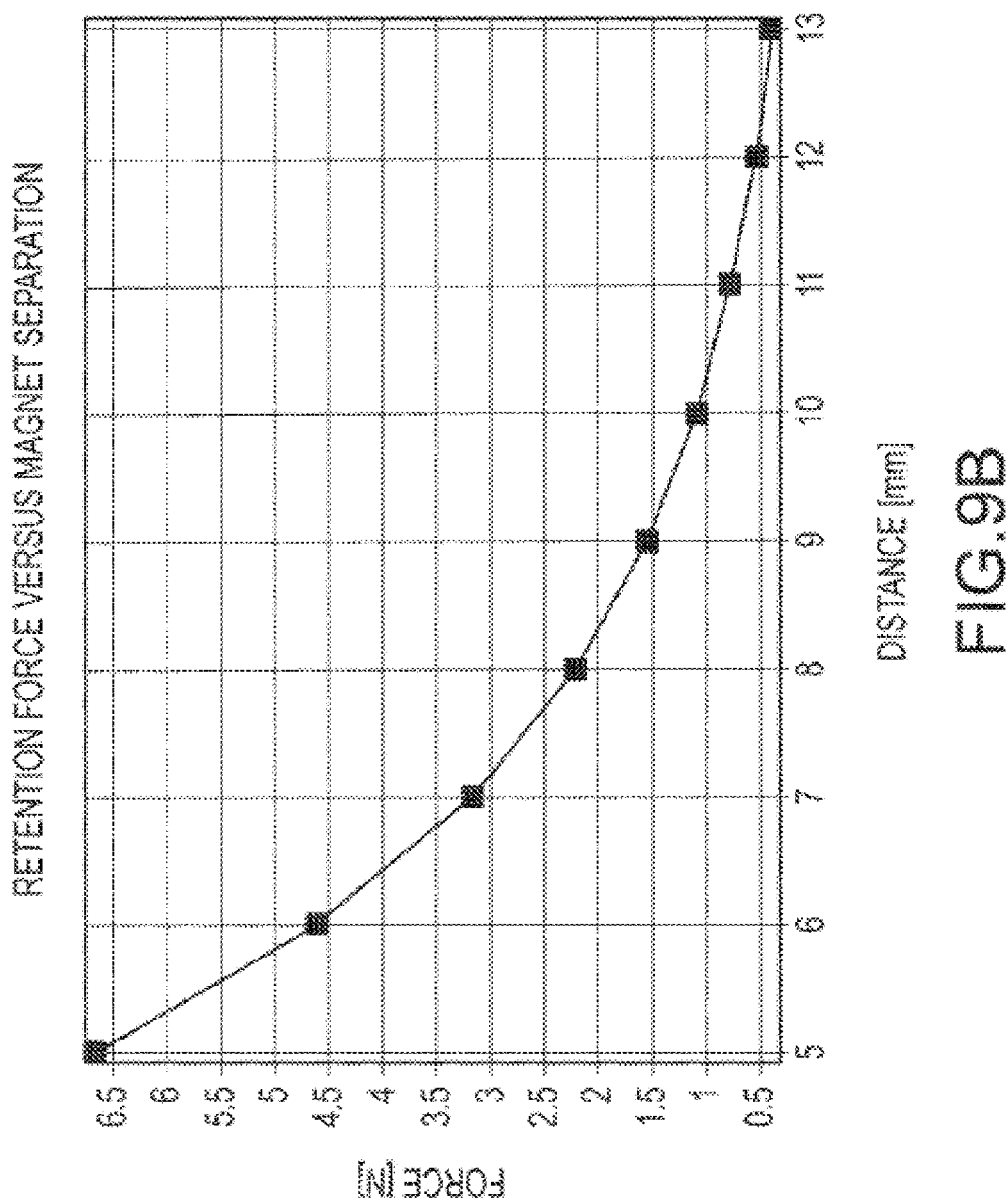

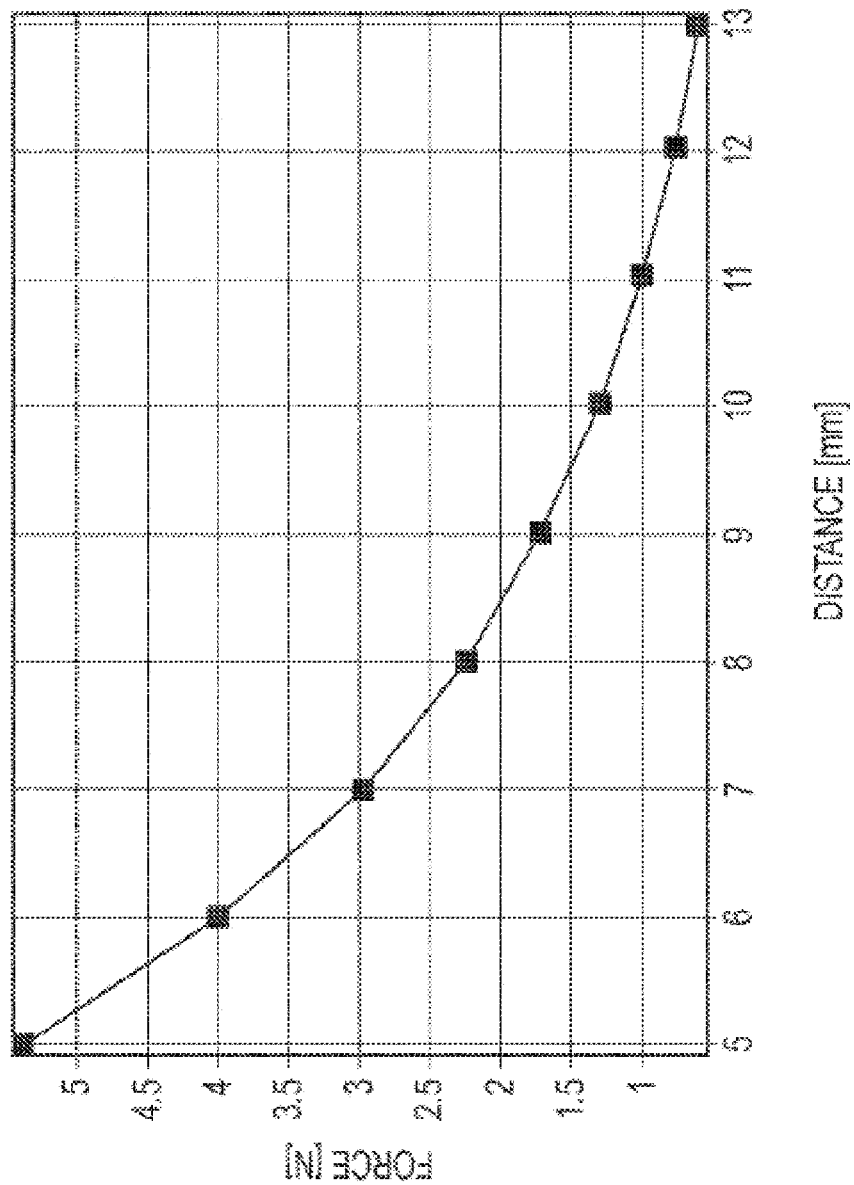

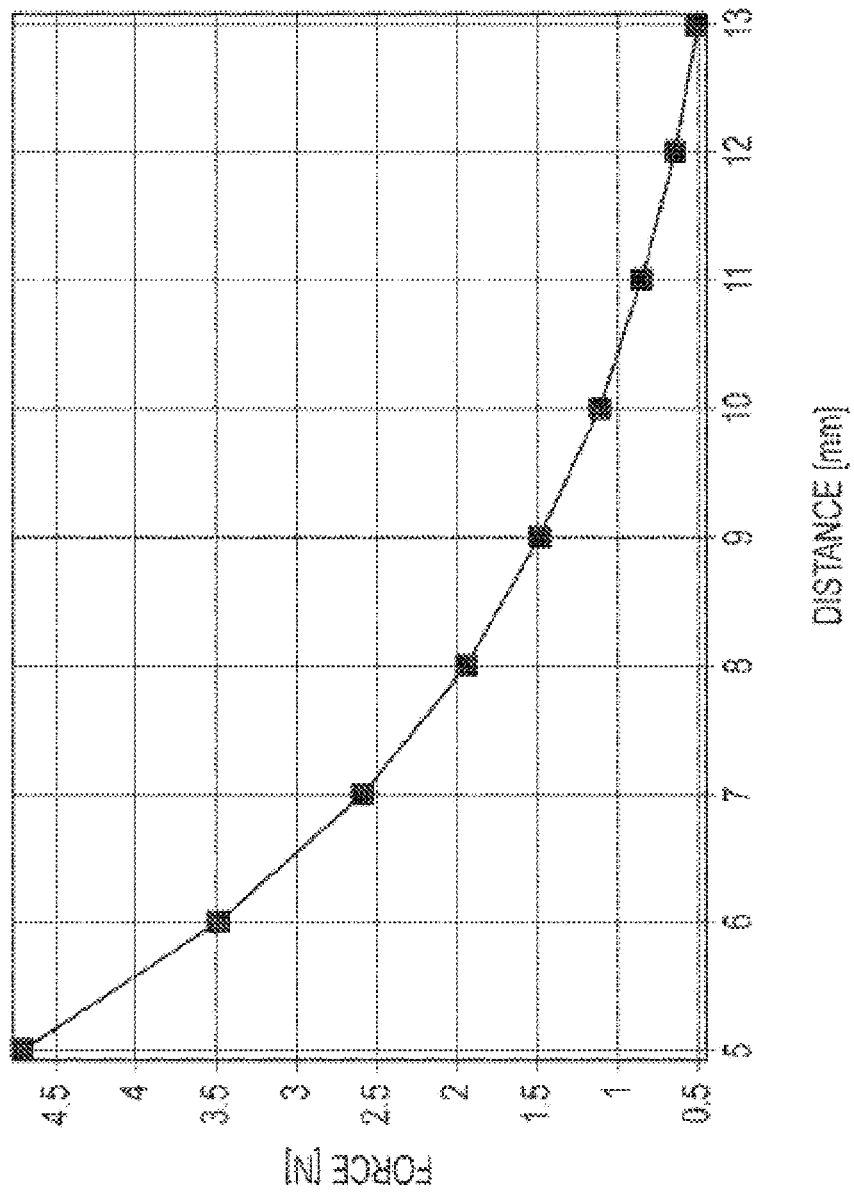

RETENTION MAGNET SYSTEM FOR MEDICAL DEVICE

CROSS-REFERENCE TO RELATED APPLICATIONS

This application is a Continuation application of U.S. patent application Ser. No. 17/170,585, filed Feb. 8, 2021, which is a Continuation application of U.S. patent application Ser. No. 16/376,431, filed Apr. 5, 2019, now U.S. Pat. No. 10,917,730, which claims priority from U.S. Provisional Application No. 62/763,203, filed Jun. 6, 2018, and is also a Continuation-in-part of U.S. Utility patent application Ser. No. 15/919,717, filed on Mar. 13, 2018, which claims priority to PCT/IB2016/001388, filed Sep. 13, 2016, which claims priority to U.S. Utility patent application Ser. No. 15/158,225, filed May 18, 2016, now U.S. Pat. No. 9,872,115, which claims priority to U.S. Provisional patent application Ser. No. 62/218,339, filed Sep. 14, 2015, the entire contents of all of these applications being incorporated herein by reference in their entirety.

BACKGROUND

Hearing loss, which can be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. For example, cochlear implants use an electrode array implanted in the cochlea of a recipient (i.e., the inner ear of the recipient) to bypass the mechanisms of the middle and outer ear. More specifically, an electrical stimulus is provided via the electrode array to the auditory nerve, thereby causing a hearing percept.

Conductive hearing loss occurs when the normal mechanical pathways that provide sound to hair cells in the cochlea are impeded, for example, by damage to the ossicular chain, the ear drum or the ear canal. Individuals suffering from conductive hearing loss can retain some form of residual hearing because some or all of the hair cells in the cochlea function normally.

Individuals suffering from conductive hearing loss often receive a conventional hearing aid. Such hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to conventional hearing aids, which rely primarily on the principles of air conduction, certain types of hearing prostheses commonly referred to as bone conduction devices, convert a received sound into vibrations. The vibrations are transferred through the skull to the cochlea causing motion of the perilymph and stimulation of the auditory nerve, which results in the perception of the received sound. Bone conduction devices are suitable to treat a variety of types of hearing loss and can be suitable for individuals who cannot derive sufficient benefit from conventional hearing aids.

SUMMARY

An external portion of an auditory prosthesis includes an external magnet that interacts with an implantable magnet to hold the external portion against the skin. The stray magnetic field generated by these magnets can disturb the operation of a vibrating element of the auditory prosthesis. The technologies described herein utilize additional magnets disposed within portions of the auditory prosthesis to redirect the magnetic flux, which allows the vibrating element to be disposed more closely to the magnets, reducing the overall height profile of the prosthesis. Additionally, this can result in greater magnetic retention forces, which can allow smaller magnets to be utilized.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

FIG. 1B is a schematic diagram of a percutaneous bone conduction device.

FIG. 2B depicts a side view of an exemplary embodiment.

FIG. 2C depicts a side view of an exemplary embodiment.

FIG. 5B is a plot showing retention force for the magnet group with the deflector of FIG. 4, as compared to the magnet group without deflector of FIG. 5A.

FIG. 5C is a plot showing battery force for the magnet group with the deflector of FIG. 4, as compared to the magnet group without deflector of FIG. 5A.

FIG. 6C is a plot showing retention force for the magnet group with the deflector of FIG. 4, as compared to the magnet groups of FIGS. 6A and 6B.

FIG. 6D is a plot showing battery force for the magnet group with the deflector of FIG. 4, as compared to the magnet groups of FIGS. 6A and 6B.

FIG. 6E to FIG. 6M variously depict exemplary magnet apparatuses.

FIG. 6N to FIG. 6S variously depict additional exemplary magnet apparatuses.

FIGS. 6T1 to 6T3 depict cross-sections of exemplary apparatuses.

FIGS. 6U to 6W2 depict exemplary implantable components.

FIG. 7B is a plot showing retention force versus magnet separation for the magnet group of FIG. 7A.

FIG. 7C is a plot showing battery force versus magnet separation for the magnet group of FIG. 7A.

FIG. 8B is a plot showing retention force versus magnet separation for the magnet group of FIG. 8A.

FIG. 9B is a plot showing retention force versus magnet separation for the magnet group of FIG. 9A.

FIG. 10B is a plot showing retention force versus magnet separation for the magnet group of FIG. 10A.

FIG. 11B is a plot showing retention force versus magnet separation for the magnet group of FIG. 11A.

DETAILED DESCRIPTION

Figure 1A:
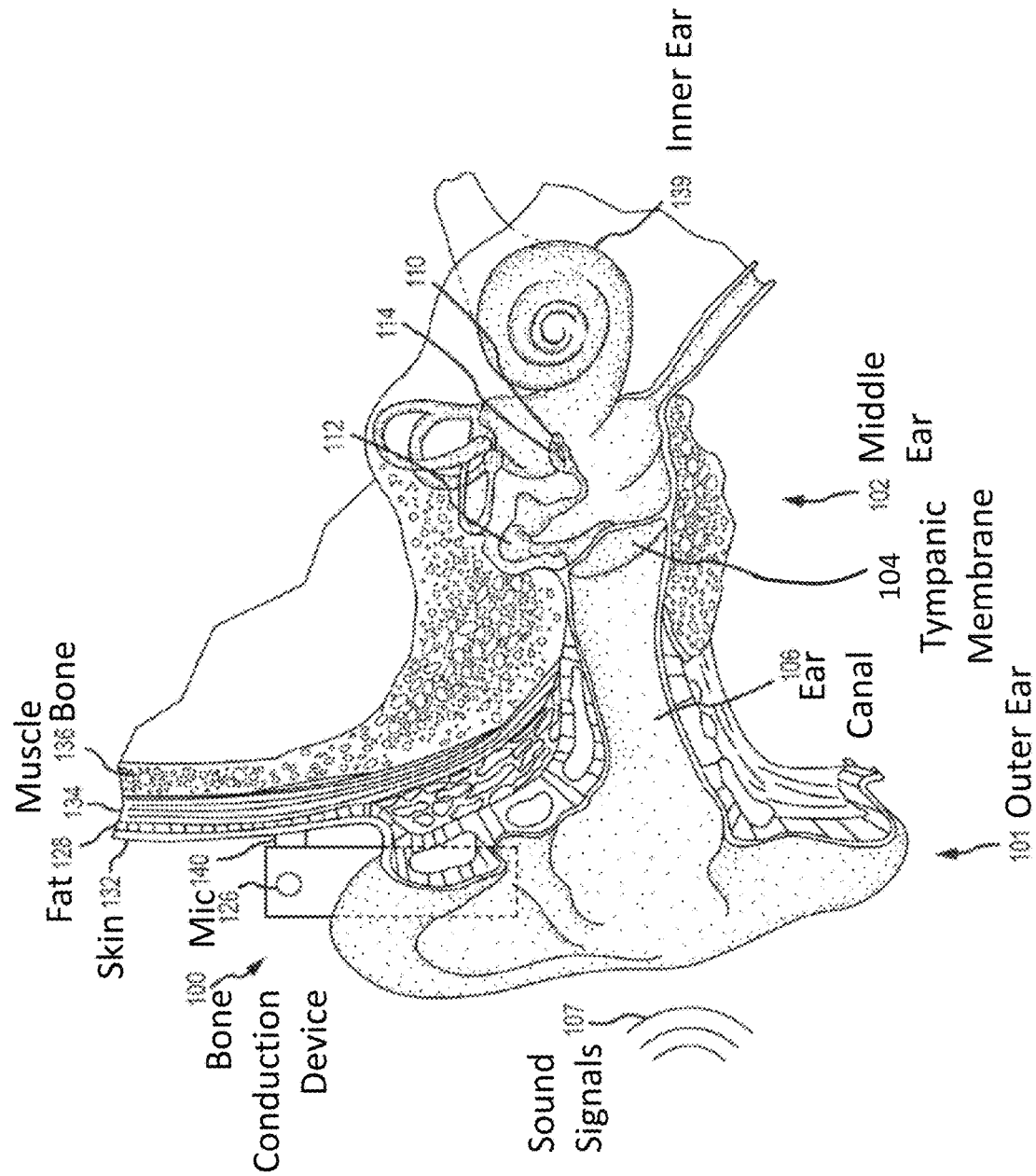
FIG. 1A depicts a partial perspective view of a percutaneous bone conduction device worn on a recipient.

The technologies described herein can be utilized in auditory prostheses such as passive transcutaneous bone conduction devices, active transcutaneous bone conduction devices, cochlear implants, or direct acoustic stimulators. There are typically one or two magnets disposed in an external portion and/or implantable portion of the auditory prosthesis. The magnetic field of the external magnet(s) interacts with a magnetic field of the magnet(s) disposed in an implantable portion of the prosthesis. Other types of auditory prostheses, such as middle ear prostheses, and direct acoustic stimulators utilize a similar configuration where an external magnet mates with an implantable magnet to hold the external portion to the skin. In another example, a percutaneous bone conduction prosthesis utilizes an anchor that penetrates the skin of the head. An external portion of the auditory prosthesis is secured to the anchor with a snap connection. By utilizing the technologies described herein, the anchor can be manufactured in whole or in part of a magnetic material, and a mating magnet group can be disposed in the external portion to mate with the anchor, either alone, or also in conjunction with a snap connection. Moreover, the technologies disclosed herein can be utilized with any type of multi-component medical device where one portion of the device is implanted in a recipient, and the other portion is secured to the skin of a patient via a force generated by a magnetic field. For clarity, however, the technologies will be described generally in the context of auditory prostheses that are bone conduction devices, and more specifically transcutaneous bone conduction devices.

Additionally, many of the magnet groups depicted herein are depicted as substantially arc-shaped. Arc-shaped magnets are depicted and described herein so as to enable valid comparisons between magnet groups having different configurations. Regardless, the magnets can be of virtually any form factor or shape, as required or desired for a particular application. Contemplated shapes include rectangular, crescent, triangular, trapezoidal, circle segments, and so on. Additionally, substantially plate-like or flat magnets are disclosed in several embodiments, but magnets having variable thicknesses are also contemplated. Additionally, the magnet groups can be in the form on a single element that has multiple polarities. Different examples of external and implantable magnet groups, as well as performance characteristics thereof, are described in more detail below. The magnets described in the examples herein have shape that can be defined as similar to at least part of a disk (e.g., in whole or in part, having a round outer perimeter with generally flat upper and lower surfaces). In general, for such disk-like magnets, an axially magnetized magnet has one pole on one of the flat surfaces and a second pole disposed on the opposite flat surface. For such disk-like magnets, a diametrically magnetized magnet has one pole on one hemisphere of the disk, and a second pole disposed on the other hemisphere of the disk. A person of skill in the art would recognize other magnet configurations that would fall within the scope of the described technology.

FIG. 1A depicts a partial perspective view of a percutaneous bone conduction device 100 positioned behind outer ear 101 of the recipient and includes a sound input element 126 to receive sound signals 107. The sound input element 126 can be a microphone, telecoil, or similar. In the present example, sound input element 126 can be located, for example, on or in bone conduction device 100, or on a cable extending from bone conduction device 100. Also, bone conduction device 100 includes a sound processor (not shown), a vibrating electromagnetic actuator and/or various other operational components. Also shown is ear canal 106, tympanic membrane 104, middle ear 102 and inner ear 139. In the middle ear 102 is located the malleus 112 and the stapes 110 which is connected to oval window 114.

More particularly, sound input device 126 converts received sound signals into electrical signals. These electrical signals are processed by the sound processor. The sound processor generates control signals that cause the actuator to vibrate. In other words, the actuator converts the electrical signals into mechanical force to impart vibrations to skull bone 136 of the recipient.

Bone conduction device 100 further includes coupling apparatus 140 to attach bone conduction device 100 to the recipient. In the example of FIG. 1A, coupling apparatus 140 is attached to an anchor system (not shown) implanted in the recipient. An exemplary anchor system (also referred to as a fixation system) can include a percutaneous abutment fixed to the recipient's skull bone 136. The abutment extends from skull bone 136 through muscle 134, fat 128, and skin 132 so that coupling apparatus 140 can be attached thereto. Such a percutaneous abutment provides an attachment location for coupling apparatus 140 that facilitates efficient transmission of mechanical force.

It is noted that sound input element 126 can include devices other than a microphone, such as, for example, a telecoil, etc. In an exemplary embodiment, sound input element 126 can be located remote in a BTE device (not shown) supported by the ear and in communication with the bone conduction device 100 via a cable. Alternatively, sound input element 126 can be subcutaneously implanted in the recipient, or positioned in the recipient's ear canal or positioned within the pinna. Sound input element 126 can also be a component that receives an electronic signal indicative of sound, such as, from an external audio device. For example, sound input element 126 can receive a sound signal in the form of an electrical signal from an MP3 player or a smartphone electronically connected to sound input element 126.

The sound processing unit of the auditory prosthesis processes the output of the sound input element 126, which is typically in the form of an electrical signal. The processing unit generates control signals that cause an associated actuator to vibrate. These mechanical vibrations are delivered by an external portion of the auditory prosthesis 100, as described below.

FIG. 1B is a schematic diagram of a percutaneous bone conduction device 100. Sound 107 is received by sound input element 152. In some arrangements, sound input element 152 is a microphone configured to receive sound 107, and to convert sound 107 into electrical signal 154. Alternatively, sound 107 is received by sound input element 152 as an electrical signal. As shown in FIG. 1B, electrical signal 154 is output by sound input element 152 to electronics module 156. Electronics module 156 is configured to convert electrical signal 154 into adjusted electrical signal 158. As described below in more detail, electronics module 156 can include a sound processor, control electronics, transducer drive components, and a variety of other elements.

As shown in FIG. 1B, transducer 160 receives adjusted electrical signal 158 and generates a mechanical output force in the form of vibrations that is delivered to the skull of the recipient via anchor system 162, which is coupled to bone conduction device 100. Delivery of this output force causes motion or vibration of the recipient's skull, thereby activating the hair cells in the recipient's cochlea (not shown) via cochlea fluid motion.

FIG. 1B also illustrates power module 170. Power module 170 provides electrical power to one or more components of bone conduction device 100. For ease of illustration, power module 170 has been shown connected only to user interface module 168 and electronics module 156. However, it should be appreciated that power module 170 can be used to supply power to any electrically powered circuits/components of bone conduction device 100.

User interface module 168, which is included in bone conduction device 100, allows the recipient to interact with bone conduction device 100. For example, user interface module 168 can allow the recipient to adjust the volume, alter the speech processing strategies, power on/off the device, etc. In the example of FIG. 1B, user interface module 168 communicates with electronics module 156 via signal line 164.

Bone conduction device 100 can further include an external interface module 166 that can be used to connect electronics module 156 to an external device, such as a fitting system. Using external interface module 166, the external device, can obtain information from the bone conduction device 100 (e.g., the current parameters, data, alarms, etc.) and/or modify the parameters of the bone conduction device 100 used in processing received sounds and/or performing other functions.

In the example of FIG. 1B, sound input element 152, electronics module 156, transducer 160, power module 170, user interface module 168, and external interface module have been shown as integrated in a single housing, referred to as an auditory prosthesis housing or an external portion housing 150. However, it should be appreciated that in certain examples, one or more of the illustrated components can be housed in separate or different housings. Similarly, it should also be appreciated that in such embodiments, direct connections between the various modules and devices are not necessary and that the components can communicate, for example, via wireless connections.

Figure 2:
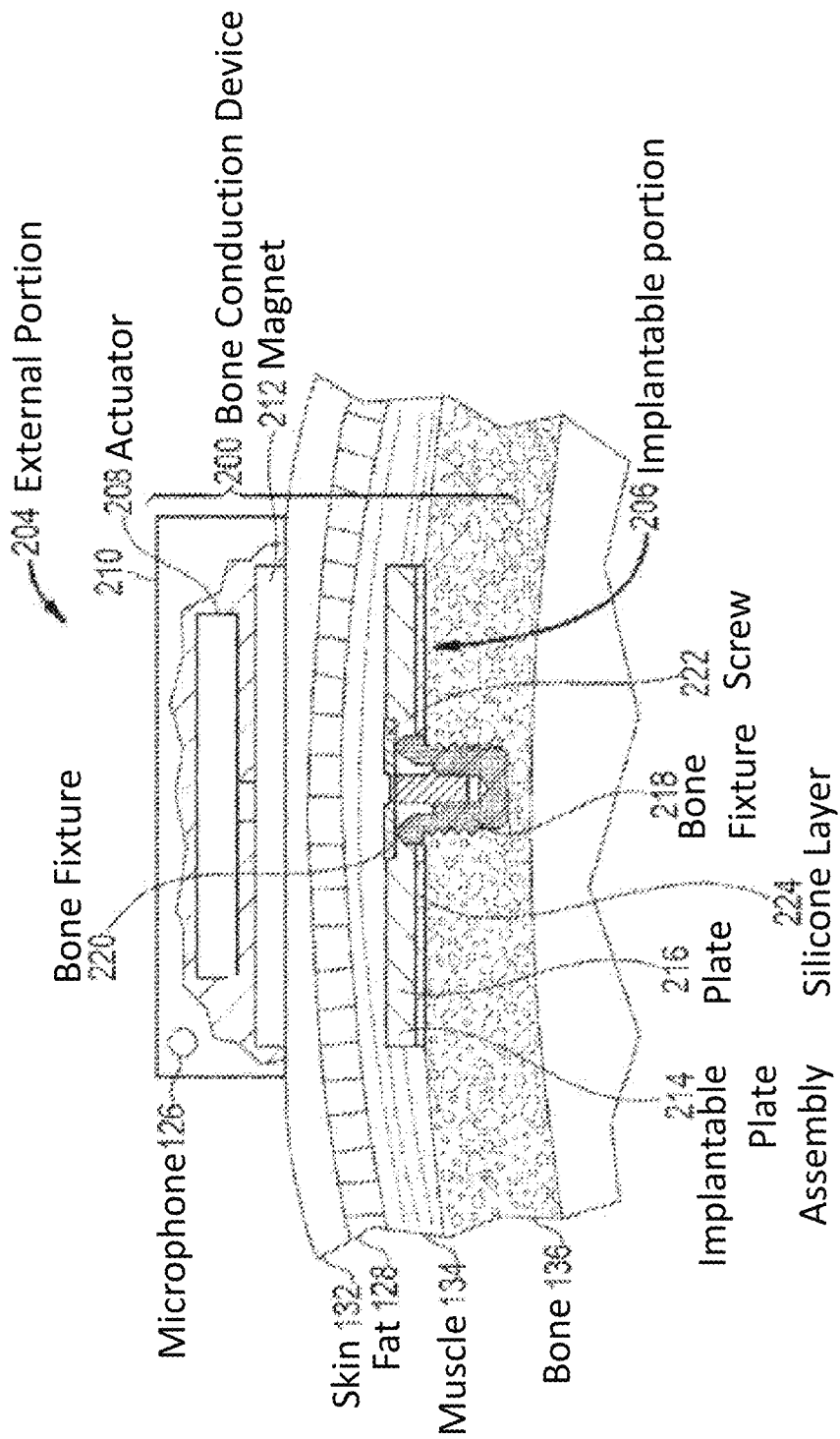
FIG. 2 depicts a cross-sectional schematic view of a passive transcutaneous bone conduction device worn on a recipient.

FIG. 2 depicts an example of a transcutaneous bone conduction device 200 that includes an external portion 204 and an implantable portion 206. The transcutaneous bone conduction device 200 of FIG. 2 is a passive transcutaneous bone conduction device in that a vibrating actuator 208 is located in the external portion 204. Vibrating actuator 208 is located in housing 210 of the external component, and is coupled to plate 212. Plate 212 can be in the form of a permanent magnet, a group of magnets, and/or in another form that generates and/or is reactive to a magnetic field, or otherwise permits the establishment of magnetic attraction between the external portion 204 and the implantable portion 206 sufficient to hold the external portion 204 against the skin of the recipient. Magnetic attraction can be further enhanced by utilization of a magnetic implantable plate 216. A single external magnet 212 of a first polarity and a single implantable magnet 216 of a second polarity, are depicted in FIG. 2. In alternative embodiments, two magnets in both the external portion 204 and implantable portion 206 can be utilized. In a further alternative embodiment, the plate 212 can include an additional plastic or biocompatible housing (not shown) that encapsulates plate 212 and contacts the skin of the recipient.

The vibrating actuator 208 is a device that converts electrical signals into vibration. In operation, sound input element 126 converts sound into electrical signals. Specifically, the transcutaneous bone conduction device 200 provides these electrical signals to vibrating actuator 208, or to a sound processor (not shown) that processes the electrical signals, and then provides those processed signals to vibrating actuator 208. The vibrating actuator 208 converts the electrical signals into vibrations. Because vibrating actuator 208 is mechanically coupled to plate 212, the vibrations are transferred from the vibrating actuator 208 to plate 212. Implantable plate assembly 214 is part of the implantable portion 206, and is made of a ferromagnetic material that can be in the form of a permanent magnet, that generates and/or is reactive to a magnetic field, or otherwise permits the establishment of a magnetic attraction between the external portion 204 and the implantable portion 206 sufficient to hold the external portion 204 against the skin 132 of the recipient. Additional details regarding the magnet groups that can be utilized in both the external portion 204 and the implantable portion 206 are described in more detail herein. Accordingly, vibrations produced by the vibrating actuator 208 of the external portion 204 are transferred from plate 212 across the skin 132 to implantable plate 216 of implantable plate assembly 214. This can be accomplished as a result of mechanical conduction of the vibrations through the skin 132, resulting from the external portion 204 being in direct contact with the skin 132 and/or from the magnetic field between the two plates 212, 216. These vibrations are transferred without a component penetrating the skin 132, fat 128, or muscular 134 layers on the head.

As can be seen, the implantable plate assembly 214 is substantially rigidly attached to bone fixture 220 in this embodiment. Implantable plate assembly 214 includes through hole 220 that is contoured to the outer contours of the bone fixture 218, in this case, a bone screw that is secured to the bone 136 of the skull. This through hole 220 thus forms a bone fixture interface section that is contoured to the exposed section of the bone fixture 218. In an exemplary embodiment, the sections are sized and dimensioned such that at least a slip fit or an interference fit exists with respect to the sections. Plate screw 222 is used to secure implantable plate assembly 214 to bone fixture 218. As can be seen in FIG. 2, the head of the plate screw 222 is larger than the hole through the implantable plate assembly 214, and thus the plate screw 222 positively retains the implantable plate assembly 214 to the bone fixture 218. In certain embodiments, a silicon layer 224 is located between the implantable plate 216 and bone 136 of the skull.

Figure 2A:
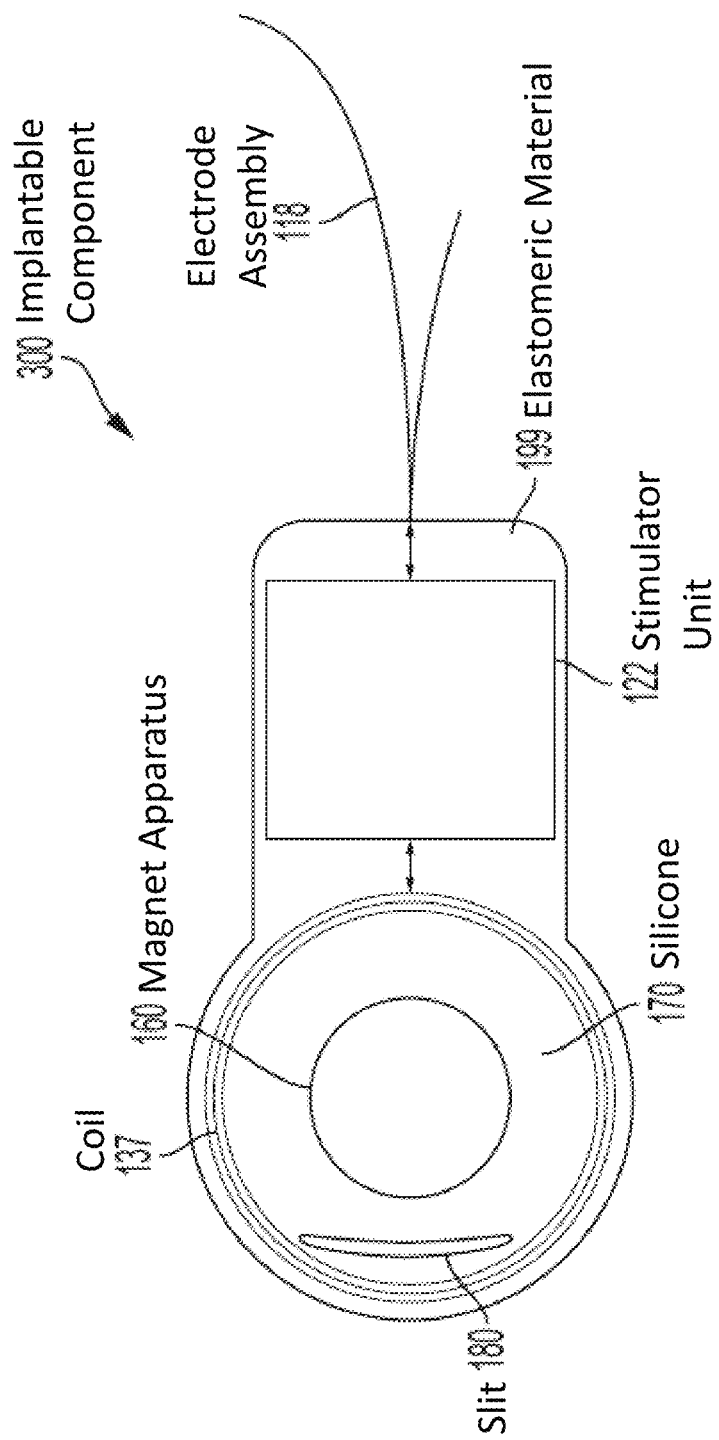
FIG. 2A depicts a top view of an exemplary embodiment.

FIG. 2A depicts an exemplary high-level diagram of another exemplary prosthesis including an implantable component 300 of a so-called cochlear implant system, which can be a totally implantable system or a system with an external component (sound processor, RF antenna, microphone, etc.—more on this below) and the implantable component 300, looking downward from outside the skull towards the skull. As can be seen, implantable component 300 includes a magnet 160 that is surrounded by a coil 137 that is in two-way communication (although in some instances, the communication is one-way) with a stimulator unit 122, which in turn is in communication with the electrode assembly 118. This is basically a classic implantable component of a so-called cochlear implant.

Still with reference to FIG. 2A, it is noted that the stimulator unit 122, and the magnet apparatus 160 are located in a body made of an elastomeric material 199, such as by way of example only and not by way of limitation, silicone. Hereinafter, the elastomeric material 199 of the body will be often referred to as silicone. However, it is noted that any reference to silicone herein also corresponds to a reference to any other type of component that will enable the teachings detailed herein and/or variations thereof, such as, by way of example and not by way of limitation only, bio-compatible rubber, etc.

As can be seen in FIG. 2A, the housing made of elastomeric material 199 includes a slit 180 (not shown in FIG. 2B, as, in some instances, the slit is not utilized, and in other instances, the slit is located elsewhere—more on this below). In some variations, the slit 180 has utilitarian value in that it can enable insertion and/or removal of the magnet apparatus 160 from the body made of elastomeric material 199, such as for MRI treatment. Magnet apparatus is surrounded by silicone 170 of the silicone body 199, and the silicone holds the magnet apparatus in place, and also supports the coil.

It is noted that magnet apparatus 160 is presented in a conceptual manner. In this regard, it is noted that in at least some instances, the magnet apparatus 160 is an assembly that includes a magnet surrounded by a biocompatible coating. Still further by way of example, magnet apparatus 160 is an assembly where the magnet is located within a container having interior dimensions generally corresponding to the exterior dimensions of the magnet, although in other embodiments, this is not the case. This container can be hermetically sealed, thus isolating the magnet in the container from body fluids of the recipient that penetrate the housing (the same principle of operation occurs with respect to the aforementioned coated magnet). In an exemplary embodiment, this container permits the magnet to revolve or otherwise move relative to the container, as is known in the art. Additional details of the container will be described below. In this regard, it is noted that while sometimes the term magnet is used as shorthand for the phrase magnet apparatus, and thus any disclosure herein with respect to a magnet also corresponds to a disclosure of a magnet apparatus according to the aforementioned embodiments and/or variations thereof and/or any other configuration that can have utilitarian value according to the teachings detailed herein.

With reference now to FIG. 2B it is noted that the outlines of the silicone body made from elastomeric material 199 are presented in dashed line format for ease of discussion. In an exemplary embodiment, silicone or some other elastomeric material fills the interior within the dashed line, other than the other components of the implantable device (e.g., plates, magnet, stimulator, etc.). That said, in an alternative embodiment, silicone or some other elastomeric material substantially fills the interior within the dashed lines other than the components of the implantable device (e.g., there can be pockets within the dashed line in which no components and no silicone are located).

It is noted that FIGS. 2A and 2B are conceptual figures presented for purposes of discussion. Commercial embodiments corresponding to these FIGs. can be different from that depicted in the figures.

FIG. 2C depicts an exemplary embodiment of a transcutaneous bone conduction device 499 according to another embodiment that includes an external device 440 and an implantable component 450. The transcutaneous bone conduction device 499 of FIG. 2C is an active transcutaneous bone conduction device in that the vibrating actuator 452 (which can be an electromagnetic actuator, or a piezoelectric actuator, etc.) is located in the implantable component 450. Specifically, a vibratory element in the form of vibrating actuator 452 is located in housing 454 of the implantable component 450. In an exemplary embodiment, much like the vibrating actuator 342 described above with respect to transcutaneous bone conduction device 300, the vibrating actuator 452 is a device that converts electrical signals into vibration.

External component 440 includes a sound input element 126 that converts sound into electrical signals. Specifically, the transcutaneous bone conduction device 499 provides these electrical signals to vibrating actuator 452, or to a sound processor (not shown) that processes the electrical signals, and then provides those processed signals to the implantable component 450 through the skin of the recipient via a magnetic inductance link. In this regard, a transmitter coil 442 of the external component 440 transmits these signals to implanted receiver coil 456 located in housing 458 of the implantable component 450. Components (not shown) in the housing 458, such as, for example, a signal generator or an implanted sound processor, then generate electrical signals to be delivered to vibrating actuator 452 via electrical lead assembly 460. The vibrating actuator 452 converts the electrical signals into vibrations.

The vibrating actuator 452 is mechanically coupled to the housing 454. Housing 454 and vibrating actuator 452 collectively form a vibratory apparatus 453. The housing 454 is substantially rigidly attached to bone fixture 341.

As with the embodiments above, the external device 440 is held against the skin via magnetic attraction between a ferromagnetic body in the external device 440 and the implantable component 450, such as in the implanted receiver coil apparatus 456.

The teachings detailed herein can be used in any of the embodiments disclosed above and/or in other medical devices.

Figure 3A:
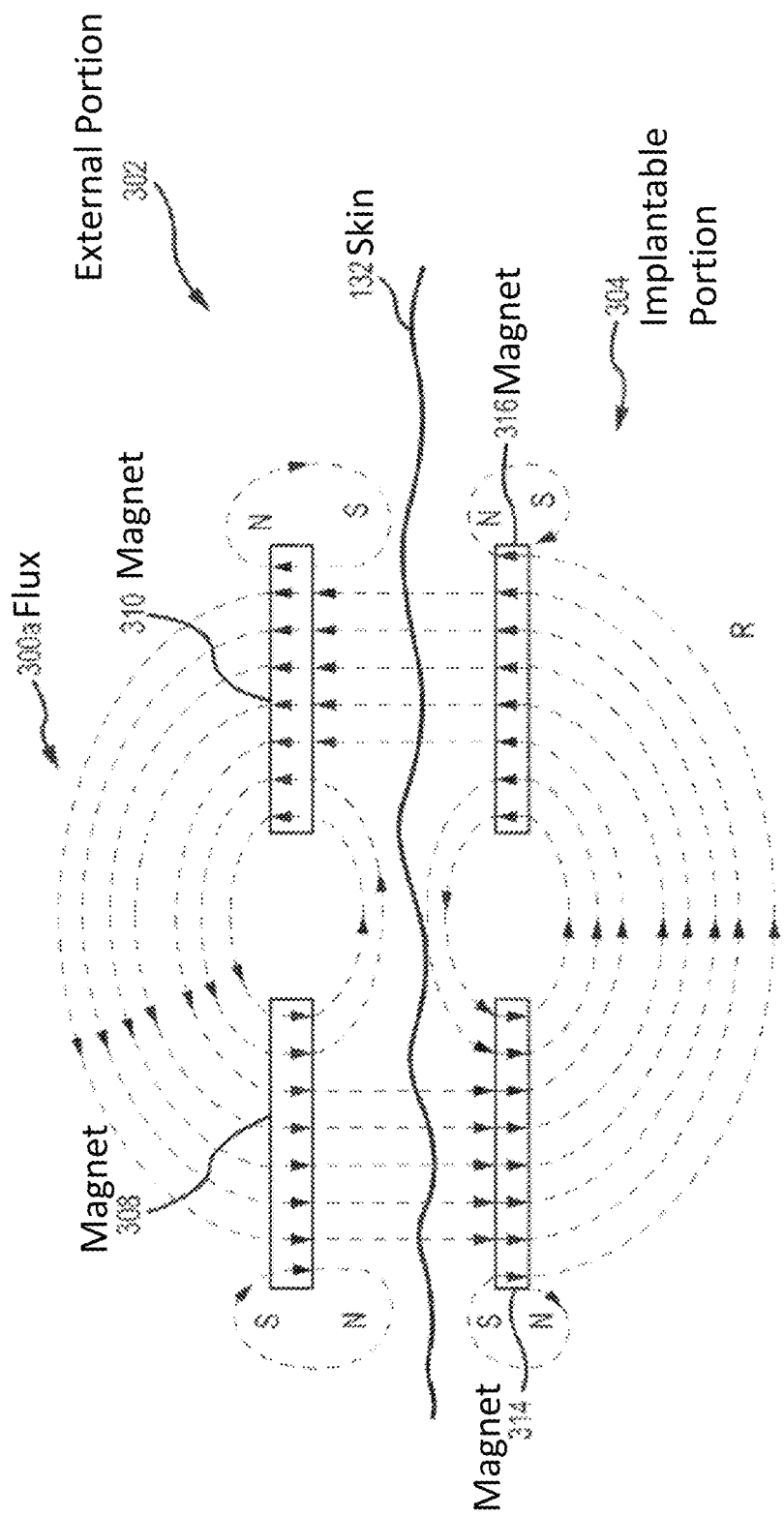
FIG. 3A depicts a partial cross-sectional schematic view of a passive transcutaneous bone conduction device worn on a recipient.

FIG. 3A depicts a partial cross-sectional schematic view of a passive transcutaneous bone conduction device 300a for a recipient R. Only skin 132 of the recipient R is depicted for clarity. The bone conduction device 300a includes an external portion 302 and an implantable portion 304. For clarity, only certain components of each of the external portion 302 and the implantable portion 304 are depicted. Each of the external portion 302 and the implantable portion 304 include reciprocal groups of magnets that form a transcutaneous coupling between those portions 302, 304, via a closed magnetic circuit. Other components in the external portion 302 and the implantable portion 304, e.g., housings, sound processing components, batteries, microphones, actuators, anchors, etc., are described above, but not depicted in FIG. 3A. The external portion 302 includes a plurality of external magnets 308, 310. In this embodiment, magnet 308 has a magnetization direction (e.g., as defined by the north and south poles thereof) that extends into the skin 132 of the recipient R, while magnet 310 has a magnetization direction that extends away from the skin 132. As such, these magnetization directions are substantially parallel and opposed to each other. In the illustrated example, the implantable portion 304 also includes two magnets 314, 316. Magnet 314 has a magnetization direction that is both substantially parallel to and harmonized with the magnetization direction of magnet 308, while magnet 316 has a magnetization direction that is both substantially parallel to and harmonized with the magnetization direction of magnet 310. The magnets 314, 316 can be disposed in a housing.

Magnetic flux generated by the magnets 308, 310, 314, 316 is also depicted in FIG. 3A. The magnetic field, and especially stray portions thereof, can interfere with the operation of the sound processor or other components disposed in the external portion 302. Stray portions are generally not depicted in FIG. 3A. Forces and/or torques are generated on components disposed in the external portion 302, which can compromise the functionality of the actuator, by affecting the functionality of the actuator suspension, thus leading to worsened feedback performance of the device 300. The performance of the vibrating actuator (if electromagnetic) can also be worsened by stray magnetic fields penetrating the actuator, thus reducing sensitivity and causing distortion.

Figure 3B:
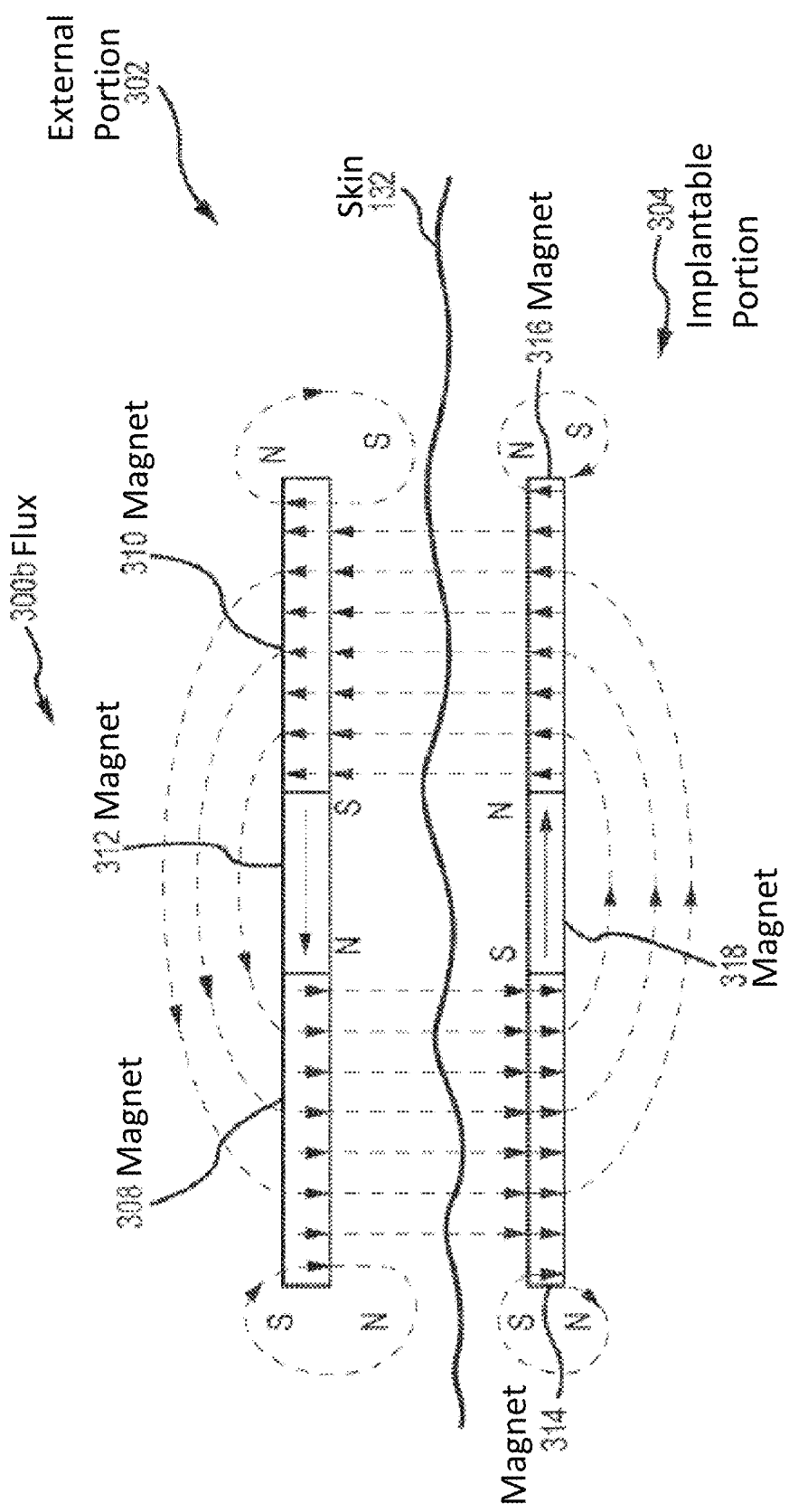
FIG. 3B depicts a partial cross-sectional schematic view of a passive transcutaneous bone conduction device utilizing magnet groups, worn on a recipient.

FIG. 3B depicts a partial cross-sectional schematic view of a passive transcutaneous bone conduction device 300b for a recipient R. This device 300b utilizes additional magnets 312, 318 to reduce stray magnetic fields and otherwise improve performance. Utilization of magnets 312 and 318 can reduce interferences and further improve functionality of the auditory prosthesis 300b. The magnetization direction of magnet 312 is substantially parallel and opposed to magnetization direction of magnet 318. Both of these magnetization directions are substantially parallel to the skin 132. The magnetic components 312, 318 divert the magnetic flux as depicted in FIG. 3B, to reduce the stray magnetic fields, thus correcting or minimizing the above-identified and other problems. Regardless of the number of magnets used, arranging the magnets 312, 318 such that the magnetization directions are in a circuit that defines a substantially continuous magnetic flux path in the medical device. In other words, the magnets 312, 318 create a shortcut for flux on that side of the medical device. As such, each of magnets 308, 310, 312, 314, 316, and 318 define a localized section of the flux path. By creating the circuit of magnetization direction, the magnetic flux is distributed asymmetrically on opposing sides of the medical device. This asymmetrical distribution, in practical terms, results in the retention force on one side of the magnets (e.g., 308 and 310) being increased and the magnetic interference on the other being reduced. Retention force is increased because the depicted arrangement of the magnets produces a flux concentration proximate the skin 132. In the depicted example, magnetic retention force proximate the skin 132 is increased, while magnetic interference away from the skin (e.g., where the sound processor, vibrating actuator, and other components are located) is decreased.

Each magnet in each magnet group generates its own magnetic field. Together, magnets 308, 310, 312, 314, 316, and 318 form a magnet group (and generate a group magnetic field), although subsets of these magnets (e.g., magnets 308, 310, 312 in the external portion 302; and magnets 314, 316, 318 in the implantable portion 304) can also form magnet groups (and their own group magnetic fields). Moreover, the magnets in each magnet group need not be physically separate components, but can be a unitary part having different magnetization directions, which can be accomplished by the magnetization process. The effect on the magnetic field is depicted in FIG. 3B, where the field is channeled through the magnet 312, so as to reduce stray magnetic flux. Of course, magnet 318 channels the field so the stray flux generated by the implantable magnets 314, 316 is also reduced.

Magnets having differing form factors and magnetization directions are contemplated. For example, magnets that are diametrically magnetized and magnets that are axially magnetized are contemplated for applications such as bone conduction devices, to maintain a low profile of the auditory prosthesis. In the depicted embodiment, magnets 308, 310, 314, and 316 are axially magnetized so as to have a magnetization direction normal to a transcutaneous interface (i.e., the interface between the external portion 302 and the implantable portion 304). The magnets 312, 318 are magnetized through the width so as to have a magnetization direction transverse to the magnetization direction of magnets 308, 310, 314, and 316. In examples where a unitary magnet is used, the unitary magnet can be magnetized such that portions thereof are diametrically magnetized, while other portions thereof are axially magnetized. Moreover, each magnet of a given magnet group can physically contact magnets proximate thereto so as to form a continuous flux path within the medical device (or the implanted component), if desired. Other configurations are contemplated and described in more detail below.

Figure 4:
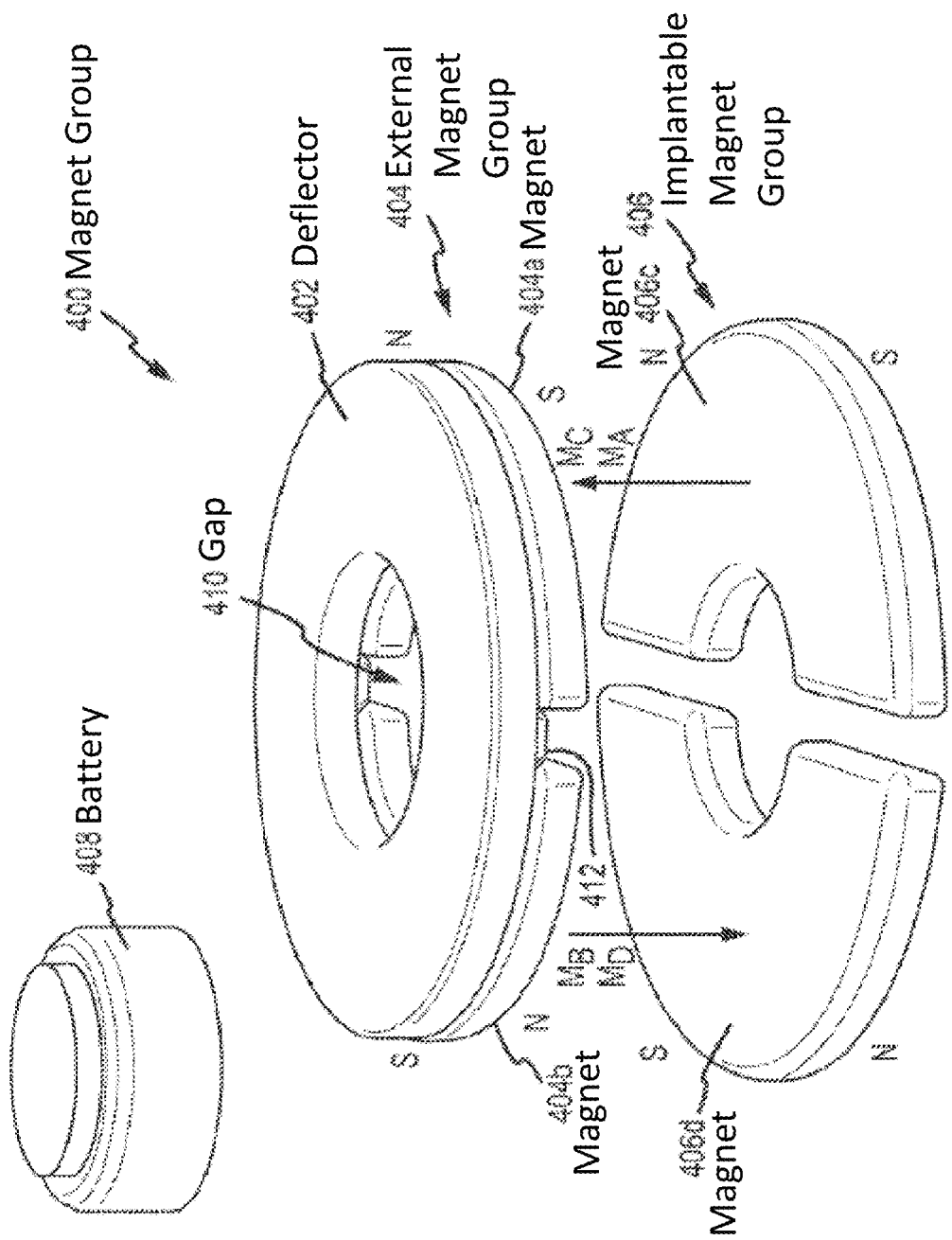
FIG. 4 is perspective view of a reference magnet group incorporating a deflector.

FIG. 4 is perspective view of a reference magnet group 400 incorporating a deflector 402. This configuration of the reference magnet group 400 can be utilized in a transcutaneous bone conduction device having both external and implantable portions. In that regard, external magnet group 404 includes two magnets 404a, 404b that would be disposed in a housing of an external portion. Implantable magnet group 406 includes two magnets 406c, 406d that would be disposed in a housing of an implantable portion. In this and other examples of magnet groups depicted herein, the housings and other components of the auditory prosthesis are not depicted for clarity. A battery 408 is generally above the external magnets 404a, 404b where it is typically located in an auditory prosthesis. The location and orientation of the battery, relative to various magnet groups as described herein is also discussed further below. The deflector 402 in this case, is a soft magnetic component such as soft iron or Permalloy, which is utilized to channel magnetic flux between the two external magnets 404a, 404b. Utilization of a deflector 402 also helps reduce the stray magnetic flux which can cause interference to components. In the depicted embodiment, the deflector 402 bridges a gap 410 between the external magnets 404a, 404b. Ribs 412 can extend from the deflector 402 so as to extend into the gap 410 therebetween. Also seen is gap 410.

In this and subsequent figures, magnetization directions are depicted as single arrows for clarity. Magnetization direction is an indication of the direction of the magnetic field which is, of course, not limited to a single vector extending from a discrete point on a magnet, but instead extends generally through the body of a magnet, dispersed along the entire area thereof. Here, the magnetization directions $M_A$, $M_C$ of magnets 404 a, 406 c are substantially aligned with each other, indicating that the north poles N of both magnets 404 a, 406 c are disposed proximate upper portions thereof, while the south poles S are disposed proximate lower portions thereof. As such, the magnetization directions $M_A$ $M_C$ of magnets 404 a, 406 c can be described as substantially parallel and harmonized with each other. Similarly, the magnetization directions $M_B$, $M_D$ of magnets 404 b, 406 d are substantially aligned with each other, indicating that the north poles N of both magnets 404 b, 406 d are disposed proximate lower portions thereof, while the south poles S are disposed proximate upper portions thereof. As such, the magnetization directions $M_B$, $M_D$ of magnets 404 b, 406 d can be described as substantially parallel and harmonized with each other. The magnetization directions $M_A$, $M_C$, and $M_B$, $M_D$, however, can be characterized as being substantially parallel and opposed.

The configuration and performance characteristics of the magnet group 400 depicted herein, is a reference against which to compare the characteristics of other magnet groups depicted herein and those not necessarily described, but consistent with the disclosures herein. These performance characteristics include retention force, which is an indication of the mutual attraction force between external and implantable magnets, and battery force, which is an indication of the force exerted on the metal casing of a battery by the magnets. Too weak of a retention force can cause the external portion to fall off undesirably, while too strong of a retention force can cause discomfort or skin necrosis. With regard to battery force, a low battery force is described since high loads will preload a suspension spring upon which the battery and sound processor are mounted. This makes for a less effective vibration isolator. Other performance characteristics, such as interference of the stray field with electronic components in the sound processor, can also be improved with utilization of magnet groups such as those described herein, but are not necessarily discussed in detail.

Figure 5A:
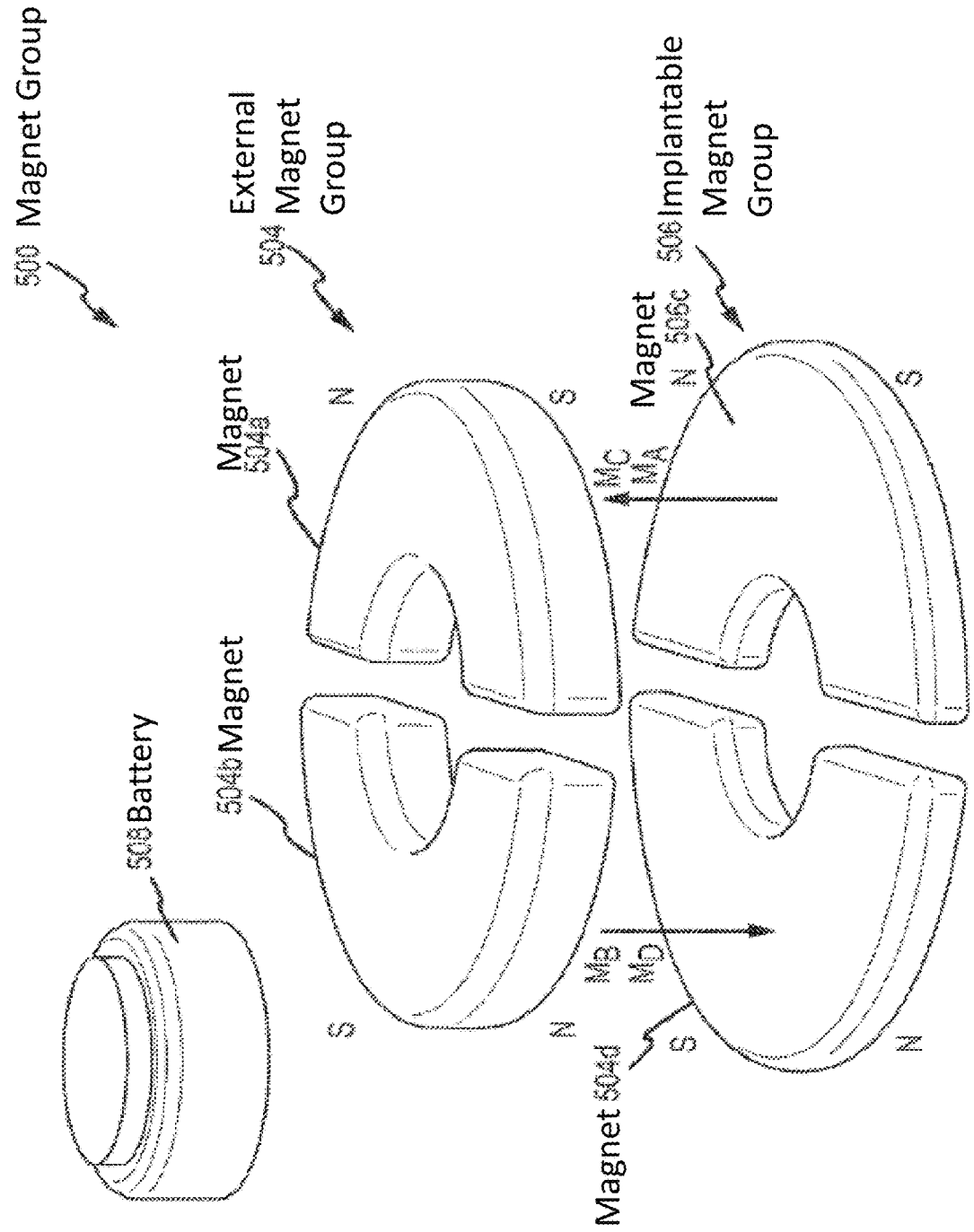
FIG. 5A is a perspective view of the reference magnet group of FIG. 4 without utilizing the deflector.

FIG. 5A is a perspective view of the reference magnet group 400 of FIG. 4, but without the presence of the deflector 402. The heights of magnet 504a and 504b are the same as the overall heights of magnets 404a or 404b and deflector plate 402 (depicted in FIG. 4). Thus, when comparing different magnet configurations, this is done for the same characteristic dimensions of height and diameter. In that case, the magnet group of FIG. 5A is depicted as magnet group 500 and not all elements thereof are necessarily described further. Moreover, the components are generally numbered consistently with the components of FIG. 4, beginning with 500. FIG. 5B is a plot showing retention force for the magnet group 400 (with the deflector 402) of FIG. 4, as compared to the magnet group 500 of FIG. 5A (without a deflector). On the horizontal scale, the distance between an external magnet group (e.g., magnet group 404) and an implantable magnet group (e.g., magnet group 406) is depicted. This distance can vary from recipient to recipient based on the thickness of the skin flap on the head, implantation depth, etc. As can be seen, the retention force of magnet group 400 is comparable to that of magnet group 500, across a range of separation distances. As such, it can be confirmed that the deflector 402 has little effect on retention force. FIG. 5C is a plot showing battery force for the magnet group 400 (with the deflector 402) of FIG. 4, as compared to the magnet group 500 of FIG. 5A (without a deflector). Across a range of separation distances between the external magnet group and implantable magnet group, however, the difference in battery force is marked, which indicates that utilization of a deflector has a significant effect on battery force. In case of a magnet group without deflector, there is a significant preload on a suspension spring.

Figure 6A:
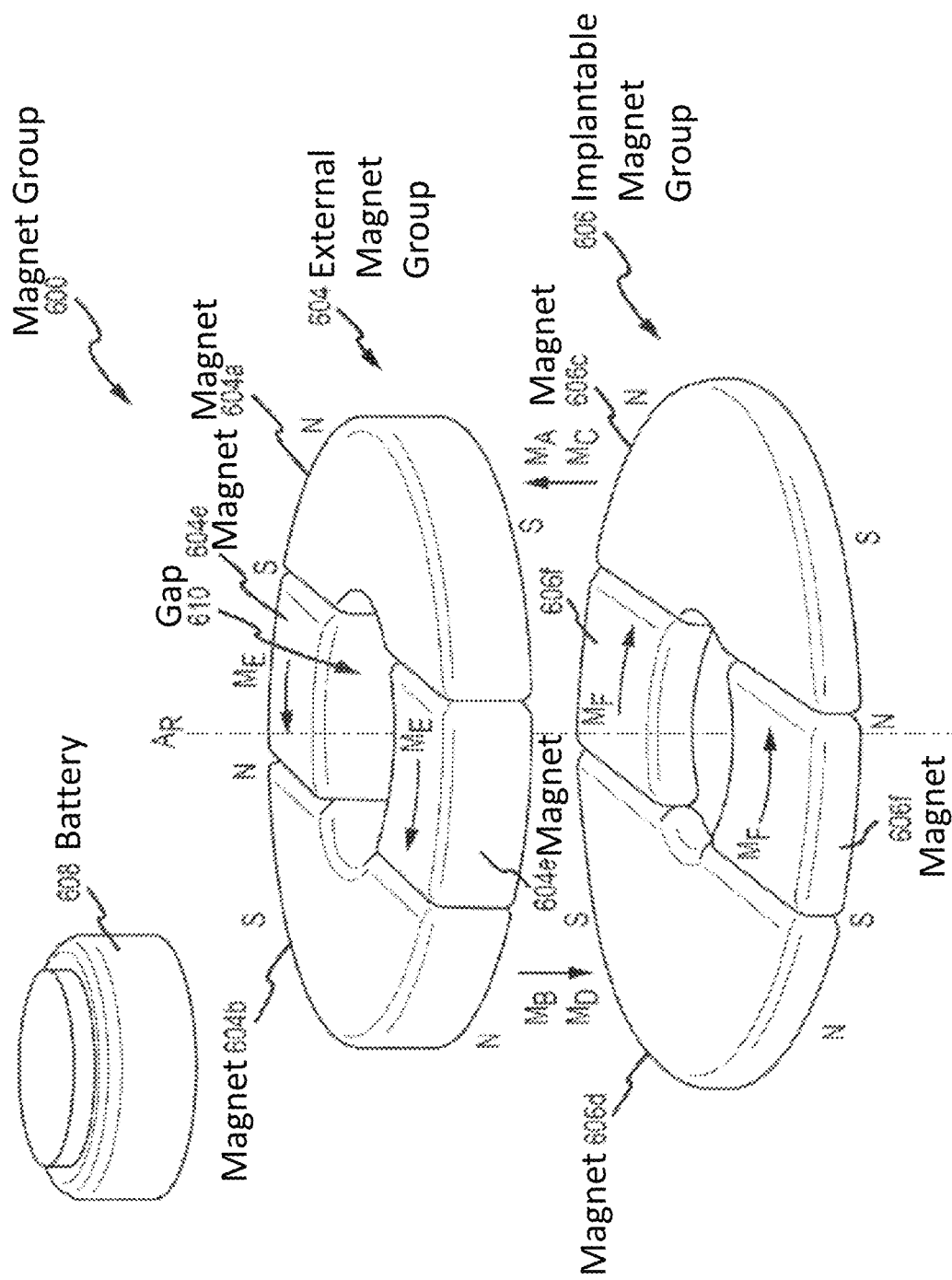
FIG. 6A is a perspective view of a magnet group in accordance with one example of the technology.

FIG. 6A is a perspective view of a magnet group 600 in accordance with one example of the technology. Many of the components are generally numbered consistently with the components of FIG. 4, beginning with 600, and not all elements thereof are necessarily described further. External magnet group includes magnets 604 a and 604 b, each having an arced form factor with two straight ends or edges. External magnet group 604 also includes a third magnet 604 e, disposed between the ends of magnets 604 a and 604 b. In the depicted example, the third magnet 604 e is in two parts, and, in that regard, can be considered to be two discrete magnets, disposed between different ends of magnets 604 a and 604 b. In other examples, magnet 604 e can be configured as a single part, typically defining a gap 610 therein for receipt of a fixation screw 222 (as depicted in FIG. 2). Magnetization direction $M_E$ is depicted, again, in a simplified form as a single vector substantially orthogonal to magnetization directions $M_A$, $M_B$. This magnetization direction $M_E$ indicates that the north pole N of magnet 604 e is disposed proximate magnet 604 b, while the south pole S is disposed proximate magnet 604 a. By orienting the poles as such, magnetic flux of the first magnet 604 a is diverted more directly to the second magnet 604 b, via the third magnet 604 e. Similarly, magnet group 606 also includes a third magnet 606 f, disposed between magnets 606 c and 606 d. In the depicted example, magnet 606 f is in two parts, but in other examples, magnet 606 f can be configured as a single part. Magnetization direction $M_F$ is depicted, again, in a simplified form as a single vector substantially orthogonal to magnetization directions $M_C$, $M_D$. This magnetization direction $M_F$ indicates that the north pole N of magnet 606 f is disposed proximate magnet 606 c, while the south pole S is disposed proximate magnet 606 d. By orienting the poles as such, magnetic flux of the first magnet 606 d is diverted more directly to the second magnet 606 c, via the third magnet 606 f. It should be noted that the magnetization directions $M_E$ and $M_F$ are both substantially parallel and opposed to each other.

Figure 6B:
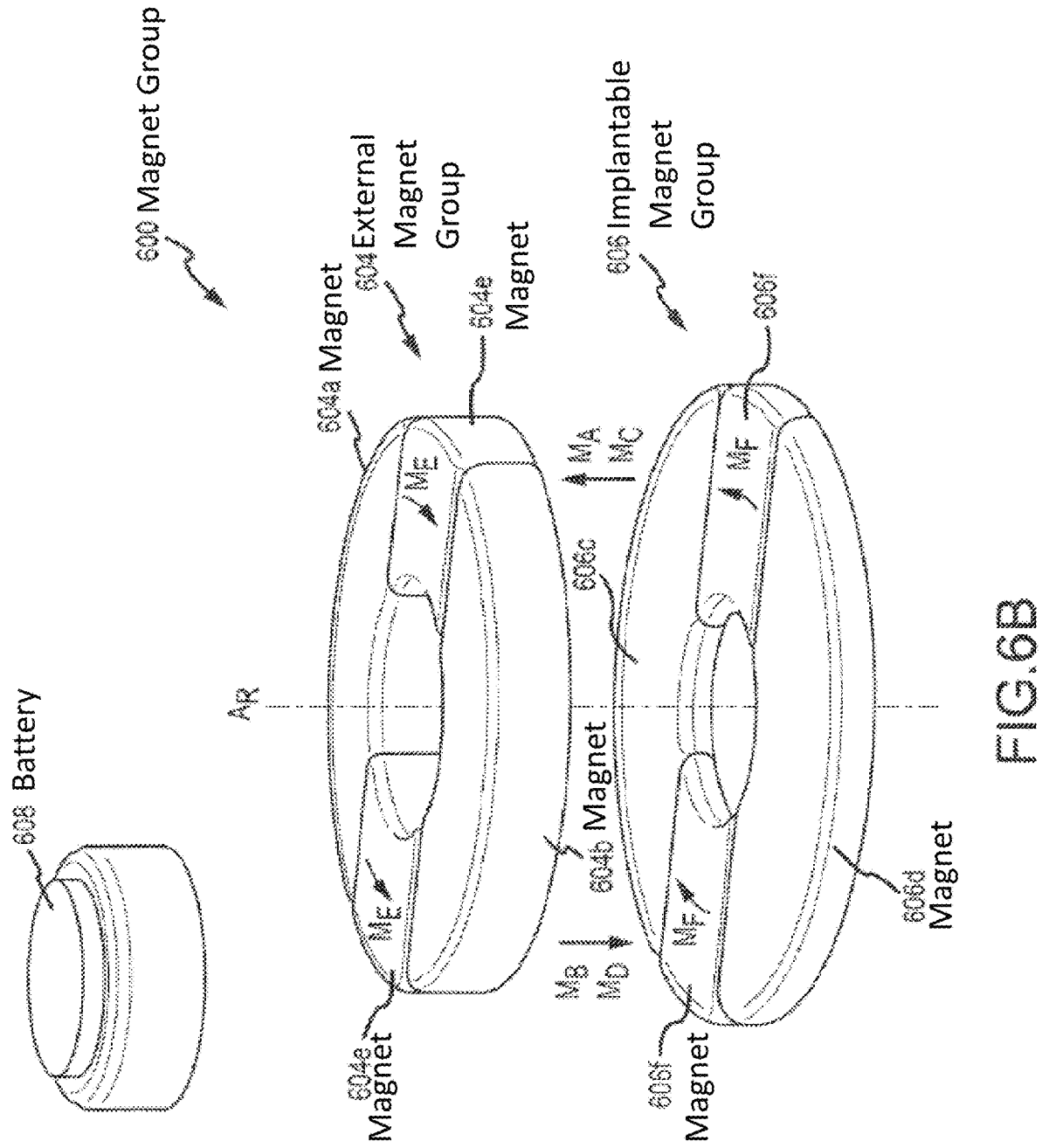
FIG. 6B is a perspective view of the magnet group of FIG. 6A with an altered battery configuration.

FIG. 6B is a perspective view of the magnet group 600' of FIG. 6A with a different battery 608 configuration. The components are generally numbered consistently with the components of FIG. 6A, and not all elements thereof are necessarily described further. Notably, the relative position of the battery 608 and magnet group 600' has changed, although the absolute separation between the battery 608 and the magnet group (determined from the axis of rotational symmetry $A_R$) remains the same. The battery 608 shown in FIG. 6B is disposed adjacent the third magnet 604e. This battery position is beneficial to achieve a low battery force.

The magnets 604a, 604b, 604e of the external magnet group are disposed in a circuit that defines a substantially continuous flux path through the external component. Magnetic flux is channeled along the flux path following the magnetization direction of the respective magnets: from the first end magnet 604a, through the intermediate third magnet 604e, to the second end magnet 604b. This reduces the incidence of stray magnetic flux adjacent the intermediate magnet 604e where the battery 608 is positioned in FIG. 6B.

FIG. 6C is a plot showing retention force for the magnet group 400 with the deflector of FIG. 4, as compared to the magnet groups 600, 600' of FIGS. 6A and 6B, respectively. From this graph, the increase on magnet retention force resulting from the use of additional magnets (e.g., magnets 604e, 606f) is clear, regardless of the orientation of the battery. As such, this increase in retention force can allow comparatively smaller magnets to be used which can reduce the overall size of the external and implantable portion of the auditory prosthesis. FIG. 6D is a plot showing battery force for the magnet group 400 (with the deflector) of FIG. 4, as compared to the magnet groups 600, 600' of FIGS. 6A and 6B, respectively. Noticeably here, battery force of the magnet group 600' of FIG. 6B is consistent with that of the reference magnet group 400 of FIG. 4, while the battery force of magnet group 600 of FIG. 6A differs significantly. This indicates that the configuration of magnet group 600 (and the associated battery) is less desirable.

In view of the above, it can be seen that in an exemplary embodiment there is an apparatus, such as an implantable component of a medical device, such as a hearing prosthesis, or any other device, or an external component of a medical device, for that matter, comprising a housing and a magnet group disposed in the housing. In an exemplary embodiment, the magnet group includes a first magnet portion that generates a first magnetic field, such as by way of example only and not by way of limitation, 606d, a second magnetic portion that generates a second magnetic field, such as by way of example only and not by way of limitation, 606c, and a third magnetic portion that generates a third magnetic field, such as by way of example only and not by way of limitation, 606f. In an exemplary embodiment, each of the first magnet the second magnet are arranged so as to reduce a stray magnetic field of the magnet group. The first magnetic field, the second magnetic field, and the third magnetic field define the group magnetic field.

In an exemplary embodiment of the embodiment just described, the first magnet portion and second magnet portion are axially magnetized, and the third magnet portion is diametrically magnetized. Consistent with the teachings detailed herein, in an exemplary embodiment, the third magnet portion is disposed so as to divert a magnetic flux of the first magnet portion to the second magnet portion.

Further, consistent with the teachings detailed herein, in an exemplary embodiment, the aforementioned first magnet portion is a first end magnet with a magnetization direction that extends normal to a transcutaneous interface of the apparatus and the second magnet portion is a second end magnet with a magnetization direction extending parallel to the magnetization direction of the first end magnet in an opposite direction. In this embodiment the third magnet portion is an intermediate magnet that is disposed between the first and second end magnets, the intermediate magnet having a magnetization direction that is transverse to magnetization direction of the first and second end magnets.

Figure 6E:
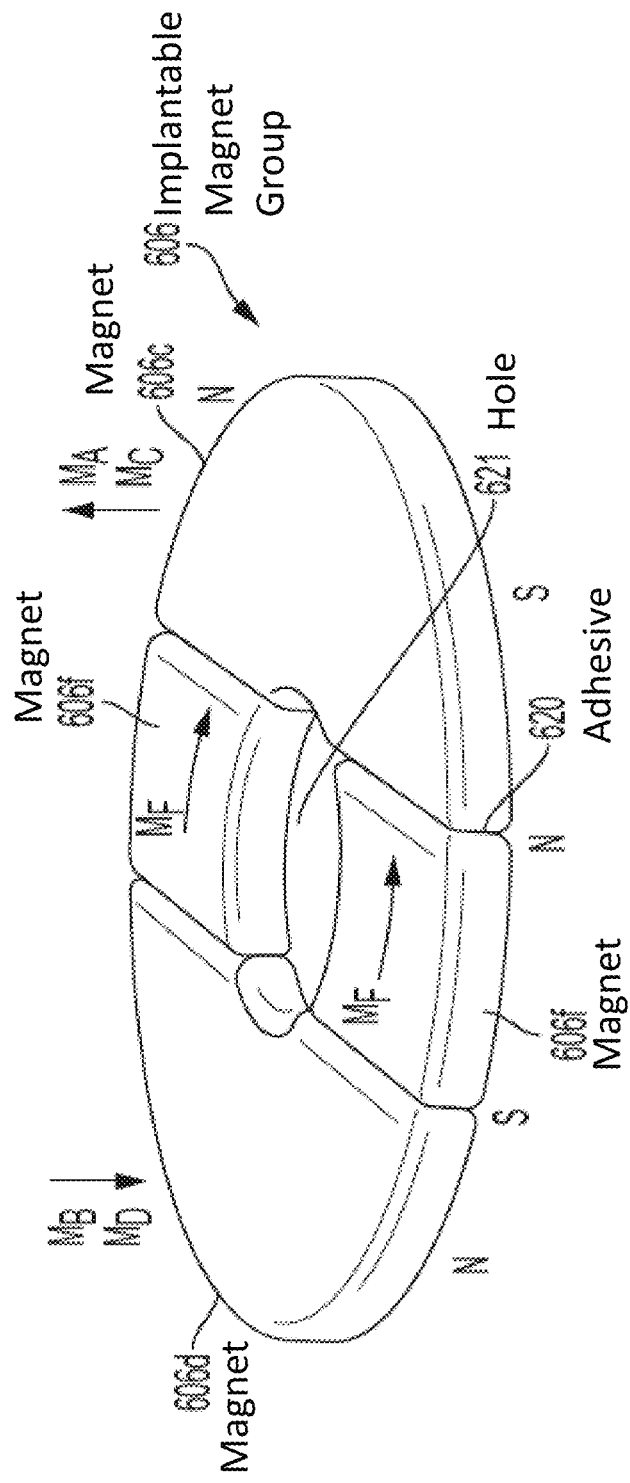
Figure 6F:
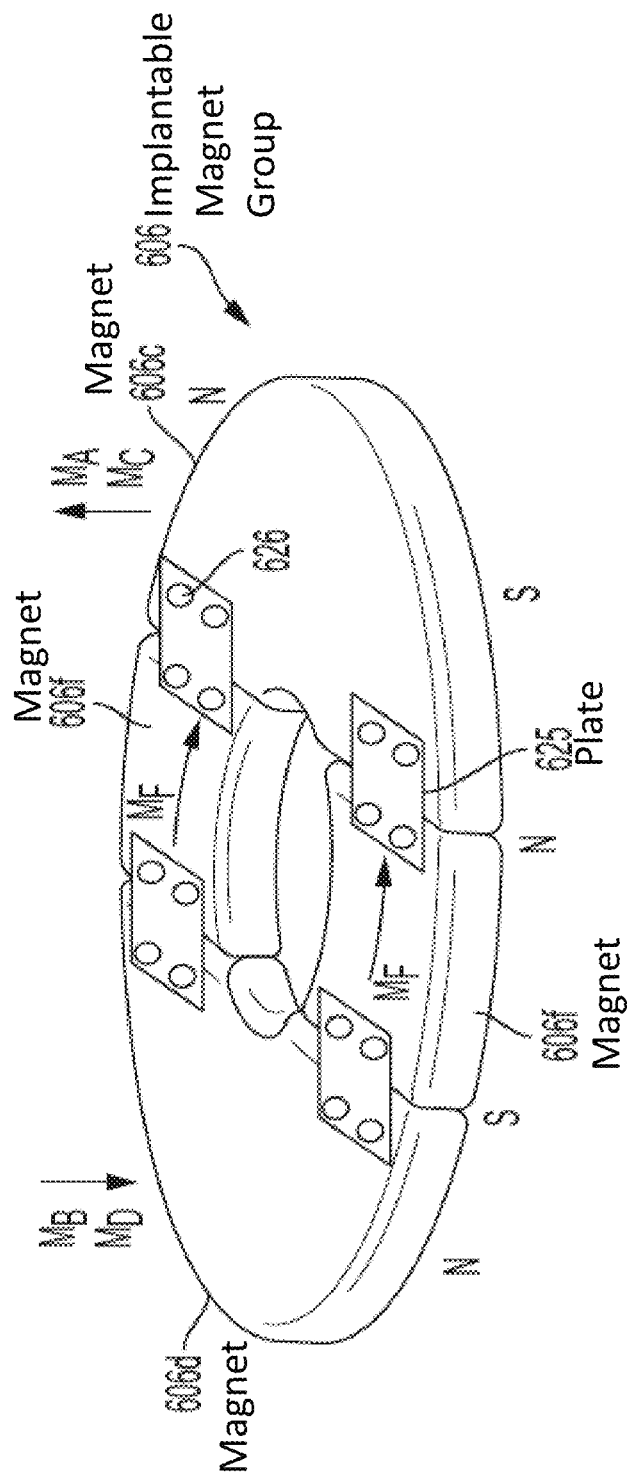

FIG. 6A presents to separate elements 606f that are separated by a space. In an exemplary embodiment, the two separate elements are connected to one another by the magnet portions 606d and 606c, consistent with the embodiment of FIG. 6A. In an exemplary embodiment, adhesive or the like is utilized between the interfacing surfaces of the magnet portions 606d and 606c, and the respective corresponding portions of 606f. FIG. 6E presents an exemplary location where adhesive 620 can be located at the facing surfaces of the respective magnet portions. FIG. 6F depicts another exemplary embodiment that utilizes plates 625 to hold the magnet elements 606f to the magnet portions 606c and 606d. In an exemplary embodiment, these can be plastic plates while in other embodiments these can be metallic plates. In an exemplary embodiment, the plates are bolted or screwed to the respective magnets utilizing bolts/screws 626, while in other embodiments, adhesive is utilized to glue the plates to the magnets. In an exemplary embodiment, there can be plates 625 located on the opposite sides (not shown). The bolts can extend all the way through to the opposite side plates connecting everything together. Any arrangement that can secure the plates to the magnet elements can be utilized in at least some exemplary embodiments.

In an exemplary embodiment, the magnet group is configured such that the first magnetic portion, the second magnetic portion and the third magnetic portion establish a device such that the first portion and the third portion are contiguous, and the second portion and the third portion are contiguous. In an exemplary embodiment, a cross-section of the magnet group lying on a plane perpendicular to a longitudinal axis of the magnet group contains only the gap for the hole 621, while, with respect to other embodiments that will be described below, there are no gaps. In some embodiments, the magnet group is configured such that the first magnetic portion, the second magnetic portion and the third magnetic portion are portions that are solid portions In an exemplary embodiment, the magnet group is configured such that the first magnetic portion, the second magnetic portion and the third magnetic portion are portions that have solid cross-sections when taken on a plane perpendicular to a longitudinal axis of the magnet group, and the second magnetic field extends normal to the first and third magnetic fields, and the second magnetic portion extends from one side of the group to an opposite side of the group.

In an exemplary embodiment, there are only the three portions that make up the magnet group. In an exemplary embodiment, there are only 2, 3, 4, 5, or 6 portions that make up the magnet group.

Other types of arrangements can be utilized to hold the elements 606f together without the utilization of the magnet portions 606d and 606c. FIG. 6F shows an example of the utilization of non-metallic braces 630 that extend between the two magnet portions 606f and also extend into the two magnet portion 606f, whereas in other exemplary embodiments, the braces are adhesively glued or otherwise adhered (welded, soldered, etc.) to the surfaces of the magnet portions 606f. Here, the braces 630 are in the form of plastic rods that extend from cylindrical holes drilled into the inner side walls of the magnet portions 606f. The rods are interference fitted into the holes, while in other embodiments, and adhesive can be utilized to hold them into the holes. Again, as noted above, instead, the rods could be glued against the surfaces of the inner walls facing each other with respect to the element 606f.

Figure 6G:
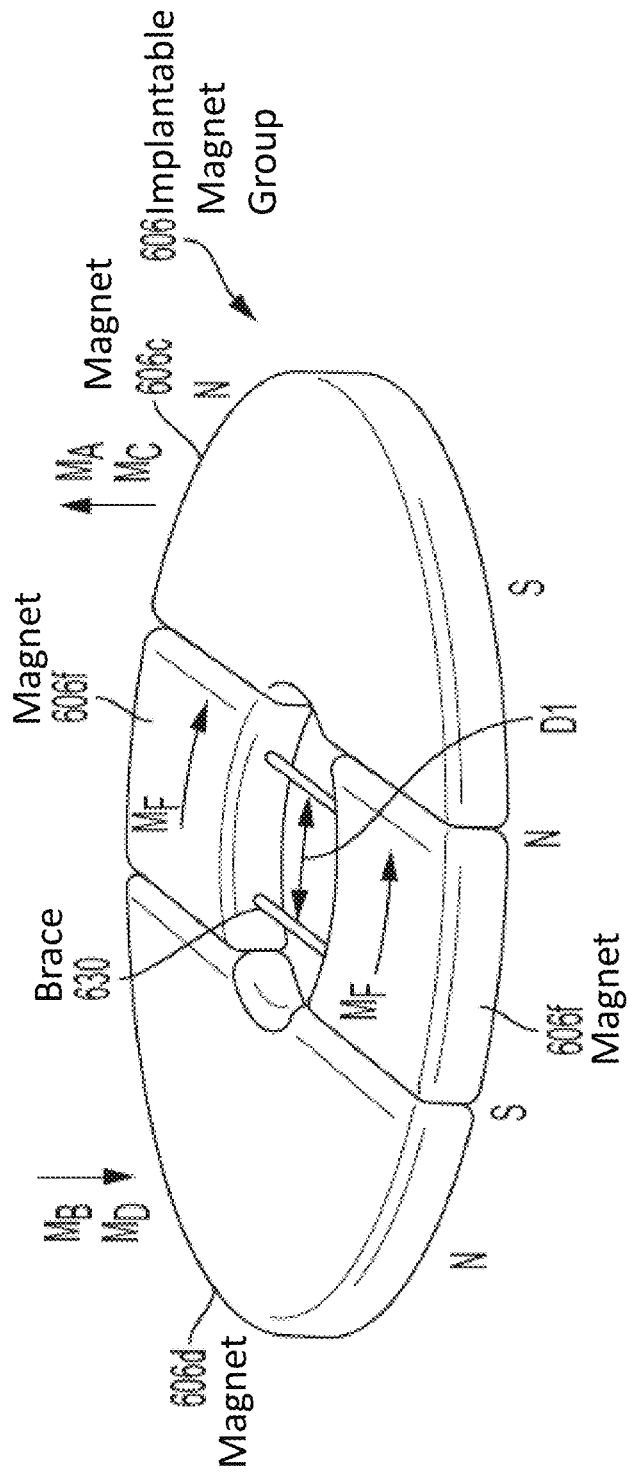

While the embodiment seen in FIG. 6G shows two separate braces 630, in some other embodiments, 1 or 3 or 4 or 5 or 6 or more braces could be utilized to all the magnets together. Any number of braces can be utilized in at least some exemplary embodiments. While the embodiments depicted round rods being utilized, and other embodiments, rectangular cross-sections beams can be utilized. Any configuration of braces that can be utilized to implement the teachings detailed herein can be utilized at least some exemplary embodiments.

Figure 6H:
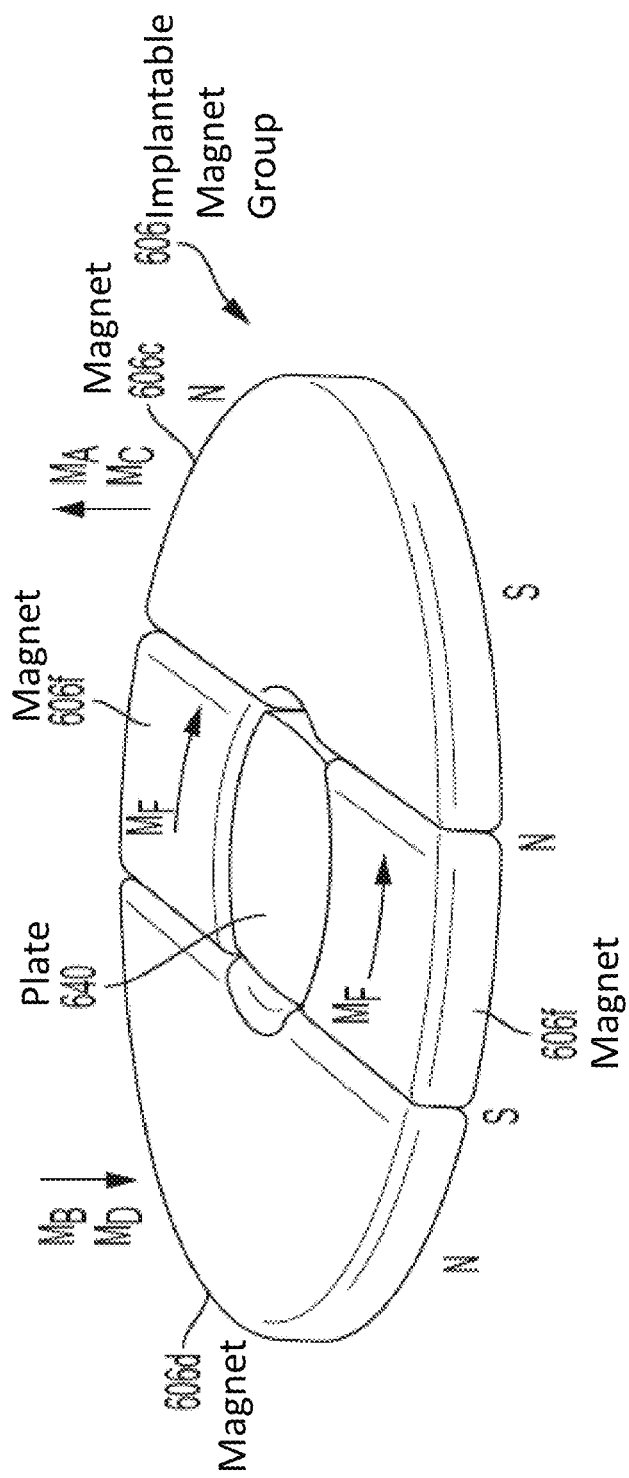
Figure 61:
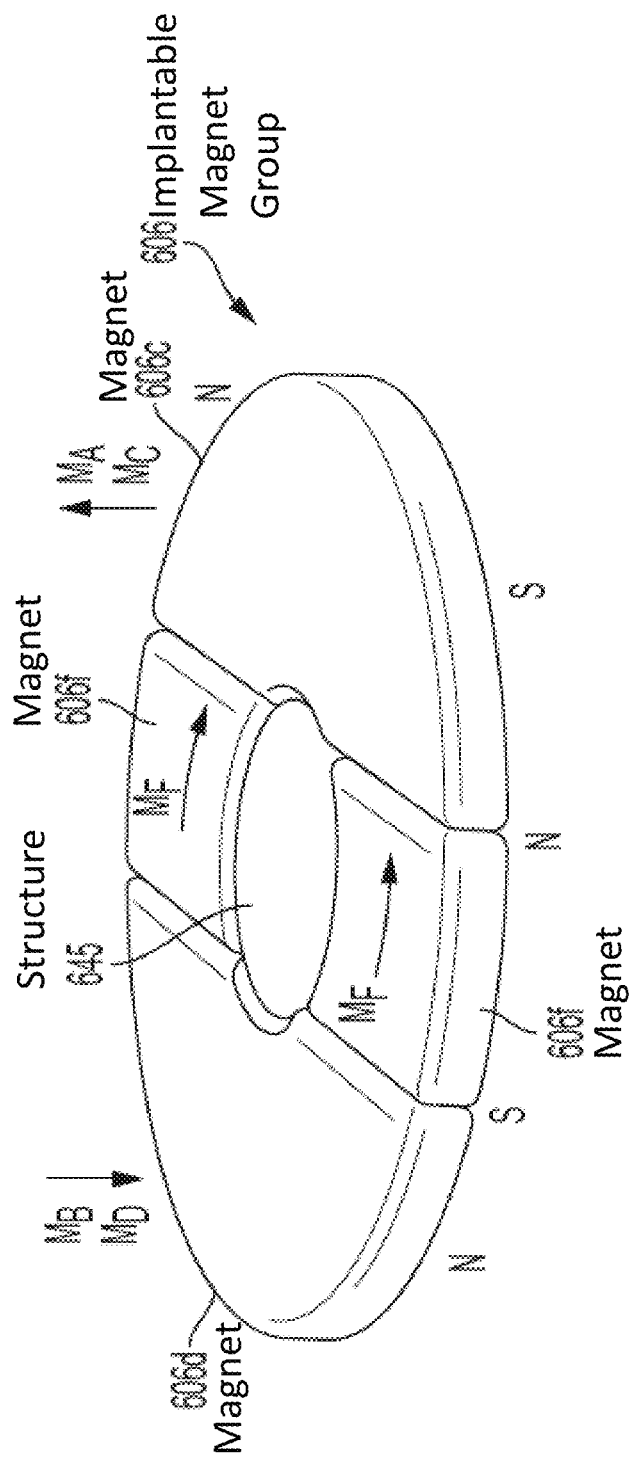

FIG. 6H presents yet another exemplary embodiment of a structure 640 that connects the two separate elements of 606f together. Here, element 640 can be a plate with curved ends that correspond to the curvature of the faces of elements 606f. In an exemplary embodiment, the height of plate 640 can correspond to that of the elements 606f, while in other embodiments, the height can be less than or greater than such. This is also the case with respect to at least some of the embodiments of the braces 630 presented above.

In the embodiments of FIGS. 6H, 6G, and 6F the structure that holds the two elements together is not in contact with the elements 606d and/or 606c. That said, FIG. 6I presents an alternate embodiment where the structure is also in contact with the elements 606d and 606c. In this exemplary embodiment, structure 645 fills the whole between the magnet elements. In an exemplary embodiment, structure 640 and 645 can be glued to the respective magnet elements to hold the magnets in place. In an exemplary embodiment, only elements 606f are glued to the structure 645, while in other embodiments, all of the magnet elements are so glued to the structure 645.

Figure 6J:
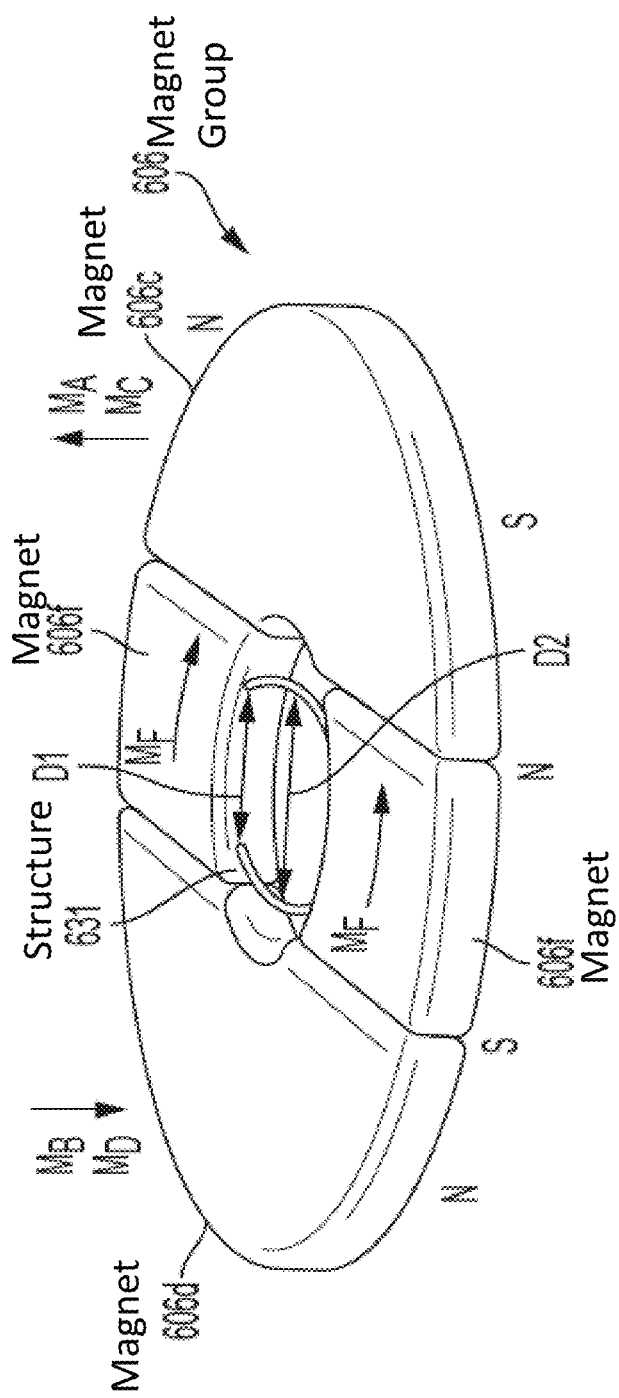

Consistent with the teachings detailed herein, in an exemplary embodiment, the structure that is utilized to hold the magnet elements 606f together can include a space that permits the screw, such as screw 222, to pass through from one side to the other, consistent with the teachings detailed herein vis-a-vis the space between the two separate elements 606f. In an exemplary embodiment, the spaces between beams 640 is such that the screw can pass therethrough. In an exemplary embodiment, distance D1 is less than, equal to and/or greater than 0.5, 1.0, 1.5, 2, 2.5, 3, 3.5, 4, 4.5, 5, 5.5, 6, 6.5, 7, 7.5, 8, 8.5, 9, 9.5, 10, 11, 12, 13, or 14 mm or any value or range of values therebetween or any value that can enable the screw with the threads to pass therethrough. Note also that in an exemplary embodiment, the beams can be curved, as seen in FIG. 6J. Here, beams 631 are presented, and the beams are curved so as to provide room for the threads of the screw while also curving back to interface with the portions of the magnet elements 606f. In an exemplary embodiment, the beams 631 can be configured as having to parallel portions at the ends (in fact, in some embodiments, the portions are coaxial with one another), and a curved portion connecting those two parallel portions together. The end portions can be inserted into the holes that are located in the respective magnet portions as detailed above, thus permitting a straight drill bores to be drilled into the magnet elements 606F.

In an exemplary embodiment, during construction/assembly, the beams can be oversized in length, and originally straight/parallel to one another, and then the beams can be bent or otherwise deformed away from one another to establish the clearance for the screw. In an exemplary embodiment, this will draw the magnet portions 606f towards each other. In an exemplary embodiment, the beams can be oversized in a manner taking into account this drawing action so that when the beams are deformed, proper alignment with the magnet elements of the magnet group are achieved. In an exemplary embodiment, the maximum distance between the two beams is D2, where D2 is less than, equal to and/or greater than 0.5, 1.0, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18 or more mm or any value or range of values therebetween or any value that can enable the screw with the threads to pass therethrough. It is also noted that D2/2 can be a radius of curvature of the beams.

Figure 6K:
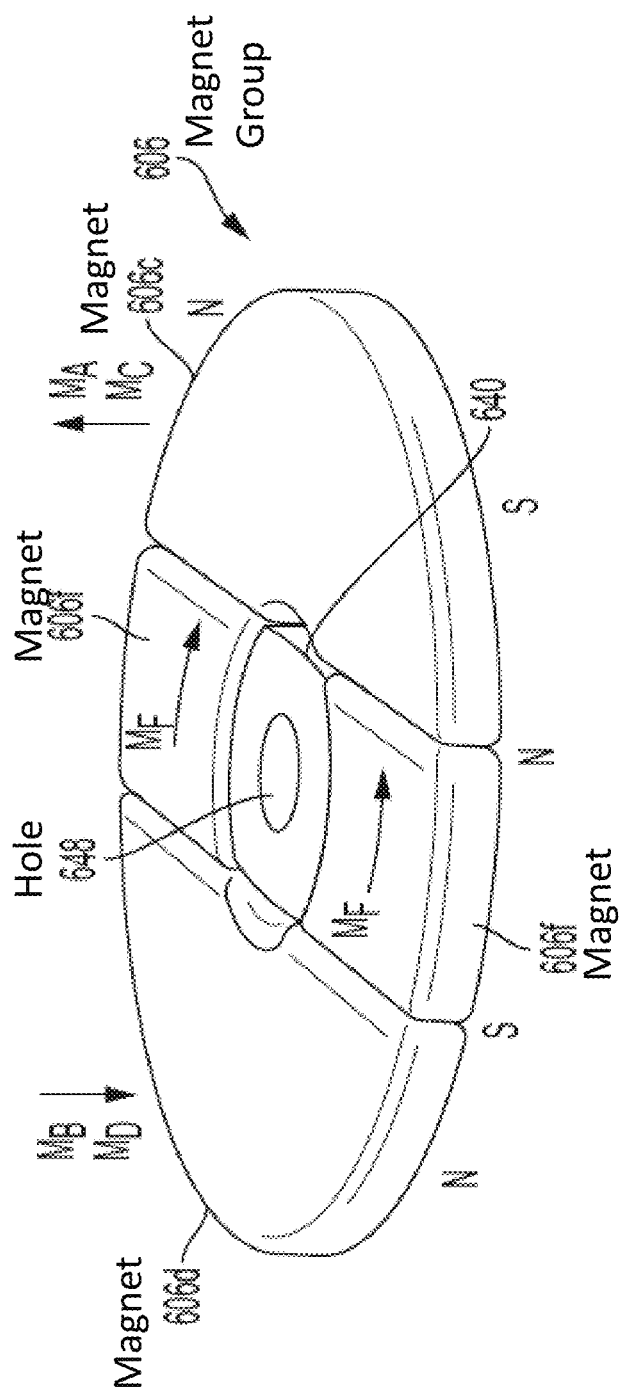

With respect to the embodiments where the structure that connects the two elements 606f together is more beefy, such as a plate configuration, FIG. 6K presents an exemplary embodiment where a hole 648 extends through the center of plate 640. In an exemplary embodiment, the diameter of hole 648 can be greater than, less than or equal to any of D1 or D2. Any size that will enable the screw to pass through the plate 640 can be utilized at least some exemplary embodiments. Note also that the hole can be utilized with element 645 as well.

In an exemplary embodiment, the braces collectively and/or individually are configured to withstand a tensile and/or a compressive force of 1, 1.5, 2, 2.5, 3, 3.5, 4, 5, 6, 7, 8, 9, 10, 11, 12, 13, 14, or 15 or more pounds applied at the peripheries of the magnet portions 606f.

Figure 6L:
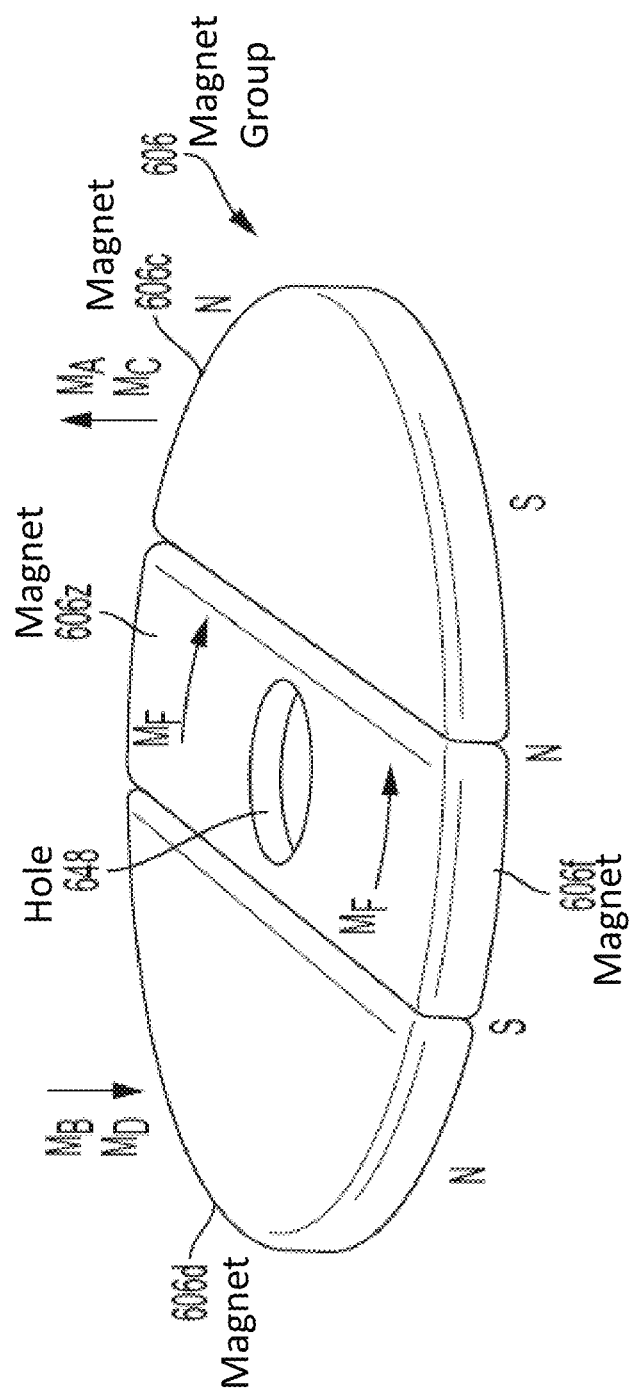

The above said, in some alternate embodiments, the central magnet element is a monolithic component and otherwise is a single piece arrangement. FIG. 6L shows an exemplary embodiment of a magnet group with magnet portion 606z. Here a hole 648 extends through magnet portion 606z, to provide the aforementioned clearance for the screw. In an exemplary embodiment, hole 648 is around and has a diameter that is greater than, less than and/or equal to D1 or D2 or any value or range of values therebetween. In an exemplary embodiment, the hole 648 is as large as possible without reducing the structural integrity of the monolithic magnet portion 606z. While the hole 648 is depicted as being round, in an alternate embodiment, it can be rectangular or any shape that will enable the teachings detailed herein.

Figure 6M:
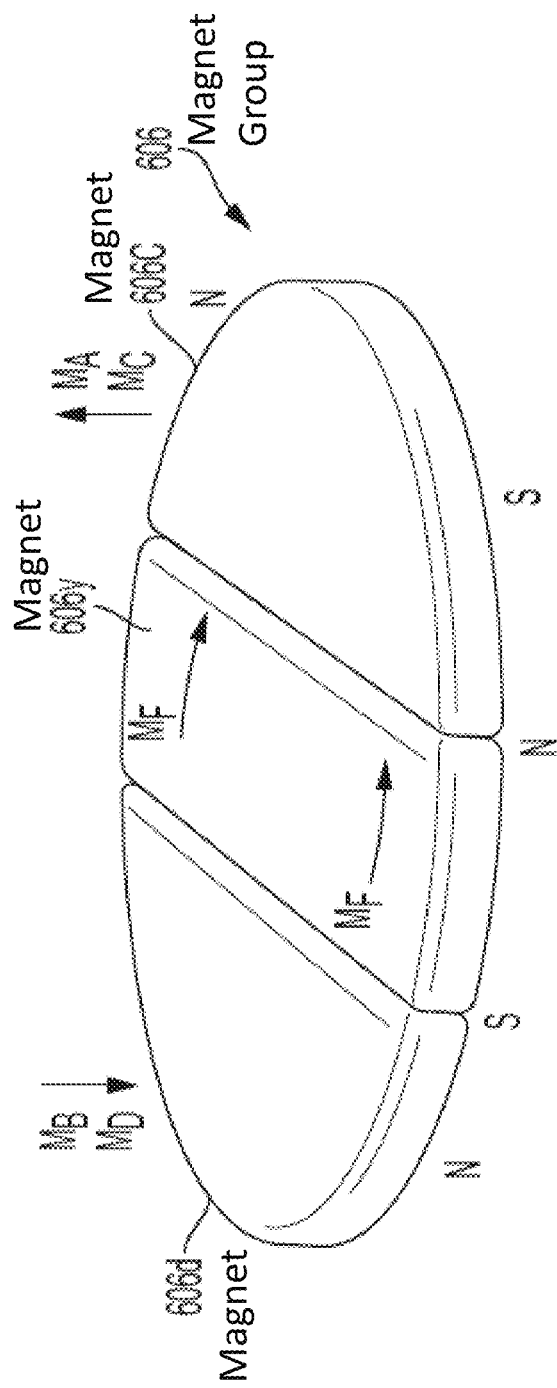

The above said, in some embodiments, there is no hole through the magnet(s). FIG. 6M shows an exemplary embodiment of the magnet group where the third magnet portion 606y is a solid body without any through holes. Such an embodiment can be utilized with, for example, the implantable components where the devices that are utilized to fix the implantable component to the recipient in general, and to bone in particular, are located away from the magnet. Indeed, in an exemplary embodiment, the embodiment of FIG. 6M could be utilized in a device where there is no component per se that fixes the apparatus to the recipient. By way of example only and not by way of limitation, an implantable portion of a cochlear implant could be located in a recipient in a manner without any true positive retention of the implantable portion to the skull. Instead, in an exemplary embodiment, the pressure between the skin in the skull can be utilized to hold the implantable component in place, or at least the receiver stimulator thereof. In an exemplary embodiment, an excavation of the like in the skull can be utilized to hold the receiver stimulator in the lateral plane and the skin over the receiver stimulator can be utilized to hold the receiver stimulator into that excavation.

Figure 6N:
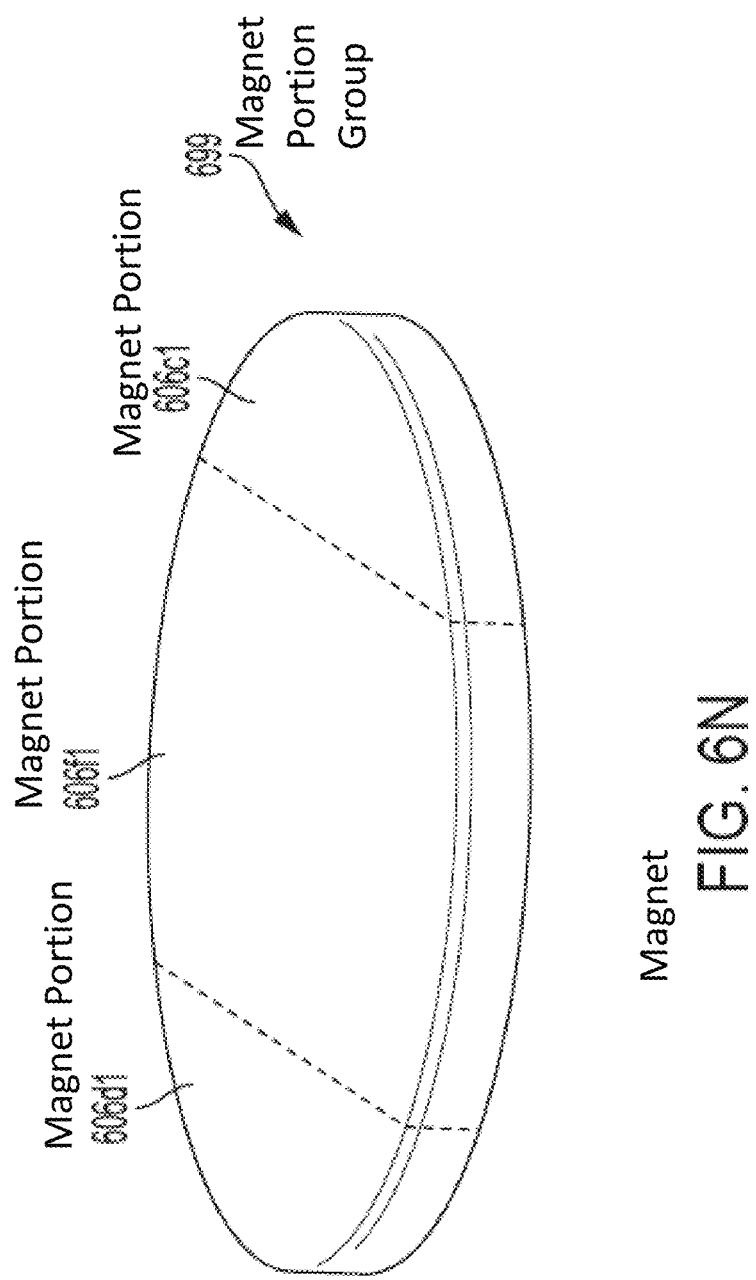
Figure 60:
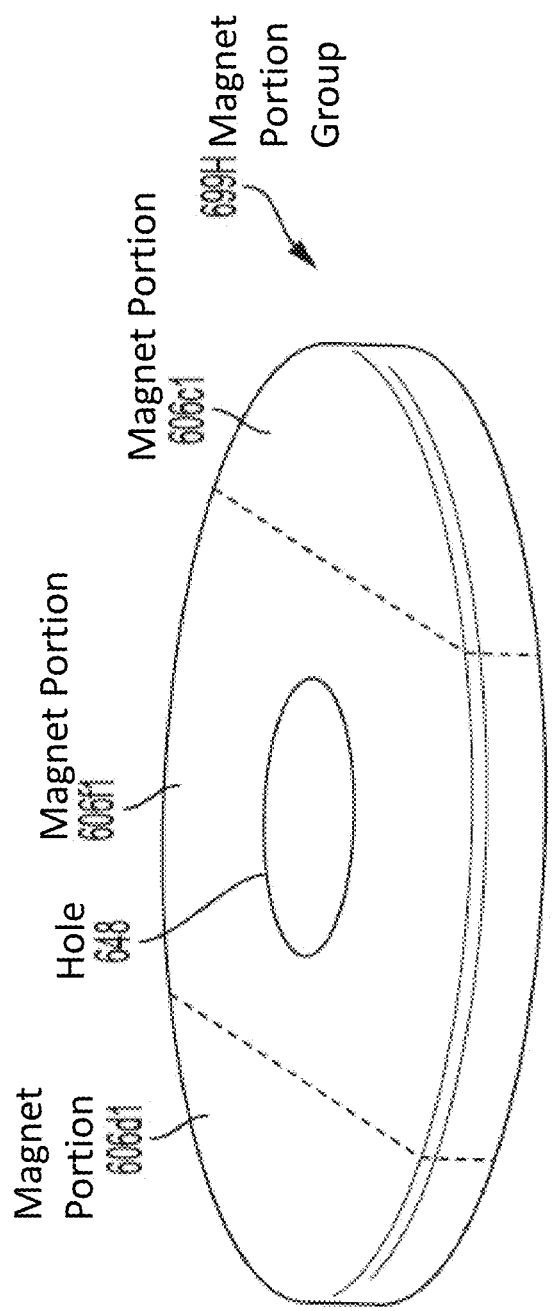

While the embodiments associated with FIGS. 6A, 6B, and FIGS. 6E-6N have been described in terms of three separate magnet portions establishing the magnet group, other embodiments utilize a monolithic single magnet and/or a magnet that combines at least two of the portions into a monolithic component. In this regard, FIG. 6N depicts an exemplary alternate embodiment of a magnet portion group that comprises magnet portion 606*d*1, which corresponds to the first magnet portion detailed above and otherwise has the functionality of magnet 606*d*. The magnet group also comprises magnet portion 606*c*1, which corresponds to the second magnet portion detailed above and otherwise has the functionality of magnet 606*c*. In the middle is the magnet portion 606/1, which corresponds to the third magnet portion detailed above and otherwise has the functionality of magnet 606*f*. In an exemplary embodiment, the magnet portion group 699 is a monolithic disk that has a circular outer circumference and a height of less than, more than or equal to 0.1, 0.2, 0.3, 0.4, 0.5, 0.6, 0.7, 0.8, 0.9, 1.0, 1.1, 1.2, 1.3, 1.4, 1.5. 1.6. 1.7, 1.8. 1.9, 2.0, 2.1, 2.2, 2.3, 2.4, 2.5, 2.6. 2.7, 2.8, 2.9, 3.0, 3.5, 4, 4.5, 5, 5.5, 6, 7, 8, 9, or 10 or 11 or 12 or more mm or any value or range of values therebetween in 0.01 mm increments. The diameter can less than greater than or equal to 0.5, 1.0, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, or 30 mm or any value or range of values therebetween in 0.1 mm increments.

While the embodiment of FIG. 6N is presented as a monolithic disk without any through hole for the screw 222, in an alternate embodiment, such as depicted in FIG. 6O, through hole 648 is present in the monolithic body of the magnet portion group 699H.

Figure 6P:
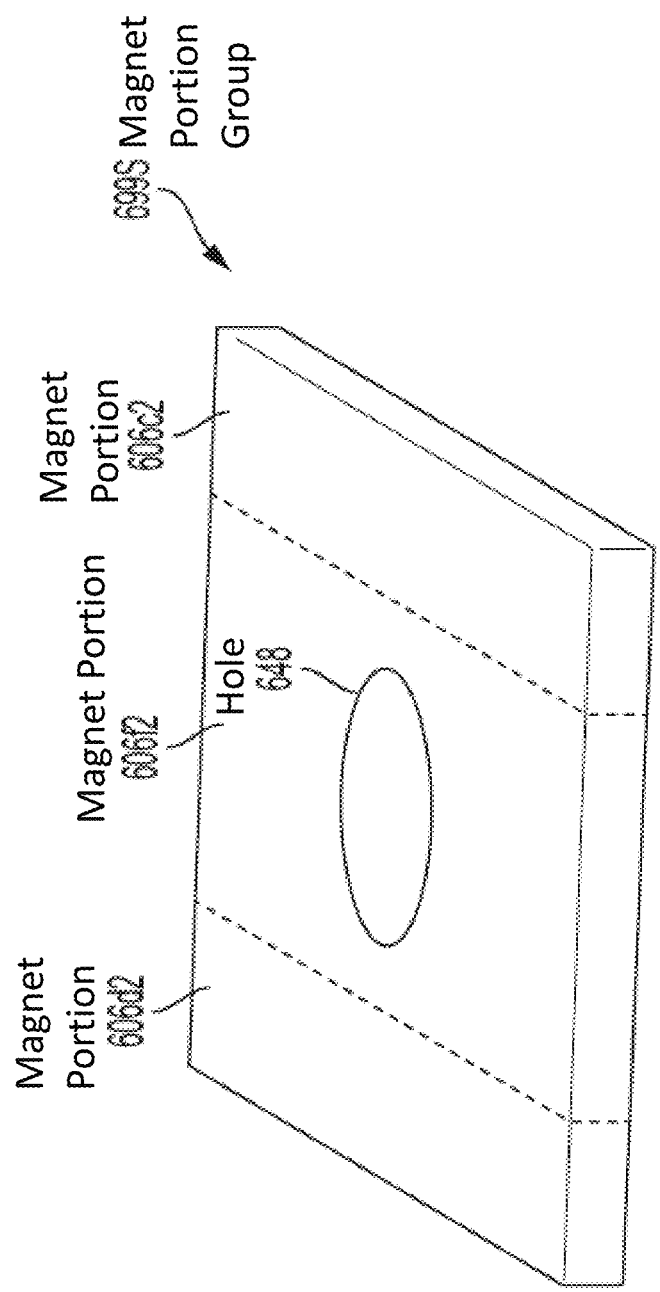
Figure 6Q:
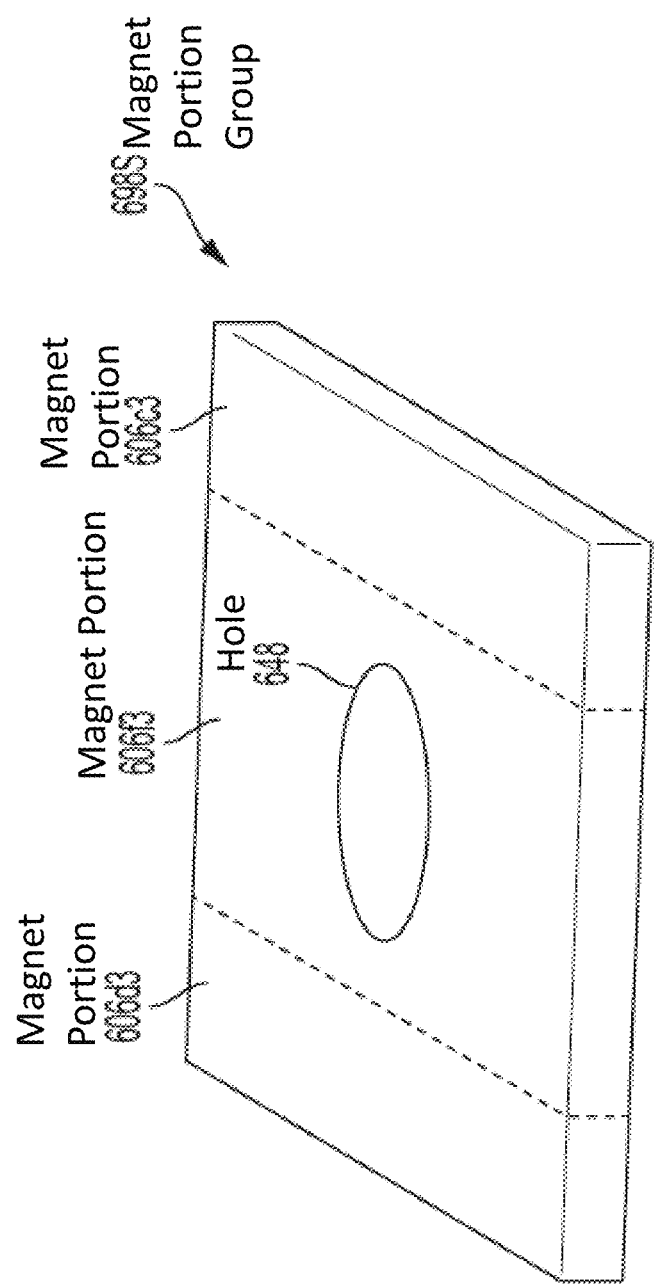

While the embodiments above have focused upon a magnet with a circular outer profile, other embodiments utilize other shaped magnets, such as, for example, rectangular and square-shaped magnets. In this regard. FIG. 6P depicts an exemplary embodiment of a magnet portion group 699S, that includes magnet portions 606D2, 606/2 and 606*c*2, all of which are rectangular in shape as can be seen. The length and/or widths of the magnet group 699S can be any of the above-noted diameters for magnet portion group 699H. It is noted that the monolithic feature of the magnet portions is not limited to the circular cross-section/outer periphery embodiments. FIG. 6Q presents an exemplary embodiment of a monolithic magnet group 698S that includes a first magnet portion 606*d*3, a second magnet portion 606*c* and a third magnet portion 606/3, respectively corresponding to the portions detailed above in functionality. As with the embodiments above, the hole 648 is optional.

Figure 6R:
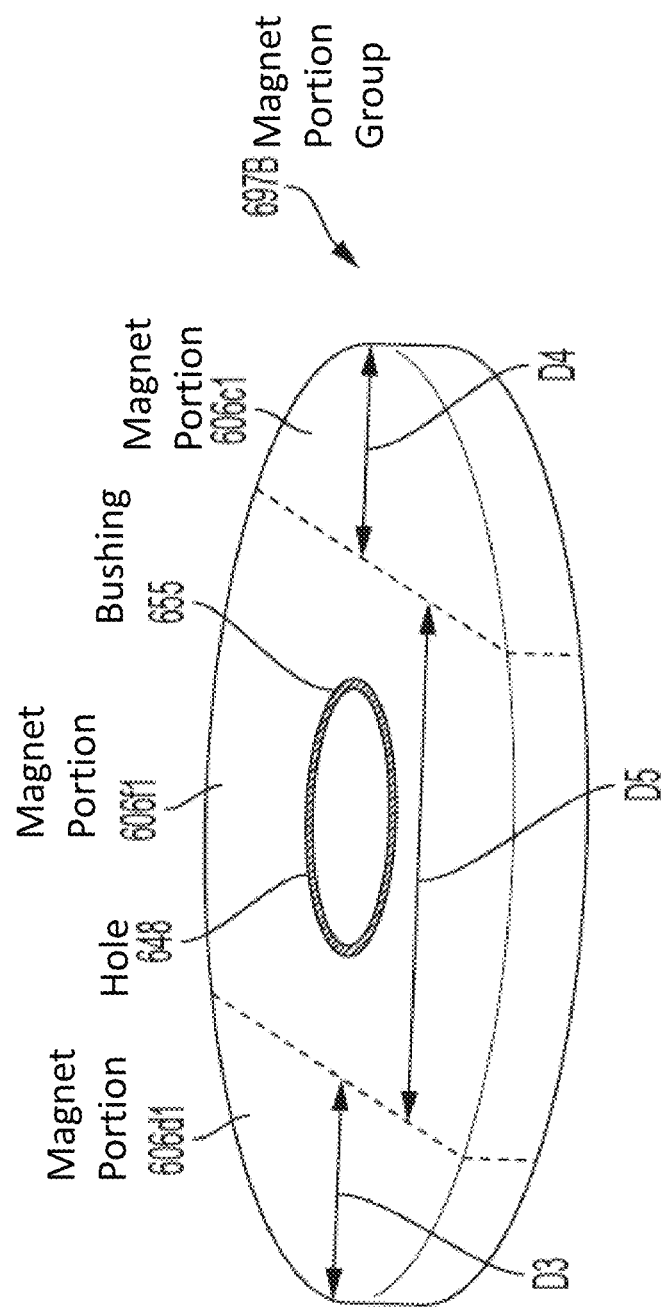

In an exemplary embodiment, a bushing is located in hole 648 to act as a barrier between the screw 222 and the magnet. This is seen in FIG. 6R, where bushing 655 is located in the hole 648. In an exemplary embodiment bushing 655 is interference fitted into the hole 648. In an alternative embodiment, it slipped fitted into the hole 648. In some embodiments, the bushing 655 is adhesively retained in the hole or otherwise welded within the hole the bushing can be made of magnetic and/or nonmagnetic material.

In at least some exemplary embodiments, the bushing 655 is configured to serve as a barrier between the threads of the screw 222 and the magnetic material of the magnet portion group 697B. In an exemplary embodiment, the bushing 655 can be a barrier to magnetic field flow and otherwise serve as a guide for the diametrically aligned magnetic field that flows through portion 606/1. The bushing 655 can be made of PEEK or can be made of steel or titanium or any material that can have utilitarian value (plastic for example). That said, in an exemplary embodiment, the bushing 655 can be its own magnetic body/portion. The bushing 655 can simply be a sacrificial magnetic body relative to the rest of the magnet portion group 697B.

In an exemplary embodiment, there is a magnet group that includes magnets and non-magnets, where only the center portion is a magnet. In this regard, FIG. 6R1 depicts a magnet apparatus 616 that includes magnet portions 606*f* and nonmagnetic portions 616*c* and 616*d*. In an exemplary embodiment, these components are identical to the light components detailed above, while in other embodiments, there are at least slight differences, such as the nonmagnetic portions 616*c* and 616*d* having sharper edges than magnet portions 606*c* and 606*d*. In other embodiments, the sizes can be different. Some additional details will be provided below, but is noted that any configuration that can enable the teachings detailed herein can be utilized at least some exemplary embodiments.

As will be described in greater detail below, in an exemplary embodiment, the nonmagnetic portions are made of material that is not metallic, and, as will be described in greater detail below, because the magnet apparatus 616 can be located in a housing that is made of an metallic material, such as a titanium housing, by utilizing a nonmetallic material, rattling or otherwise contact between metal and metal (metal of the magnet portion and metal of the housing) can be reduced and/or eliminated completely (with respect to the latter, the size of the flanking components (606*d* and 606*c*) can be oversized relative to the central portion and thus support the central portion away from the housing—in an alternate embodiment, again as will be described below, it is the flanking portions that are metallic and the central portion can be oversized to lift up the flanking portions away from the housing).

In an exemplary embodiment, nonmagnetic portions 616*c* and 616*d* can be made of plastic or of aluminum or of any other material that can enable the teachings detailed herein. In an exemplary embodiment, 616*c* and 616*d* can be made of PDFE. Collectively, with the magnet portions, this creates a magnet sub-assembly 616 (or magnet apparatus, as is sometimes referred to herein), which can replace any of the magnets/magnet groups/magnet subassemblies detailed herein (e.g., 606), and thus has the operational/functional features thereof, minus the fact that portions 616*c* and 616*d* are not magnetic/not magnets.

In an exemplary embodiment, there can be utilitarian value with respect to using magnet apparatus 616 instead of the magnet groups 606 detailed above and/or below. Accordingly, any disclosure herein of an embodiment associated with the magnet group 606 corresponds to a disclosure of an embodiment that utilizes magnet apparatus 616.

Moreover, in an exemplary embodiment, these can be substituted for existing magnet(s) in existing implants that are of a traditional design (e.g., a magnetic disk having a north-south alignment that is normal to the direction of the skin). In this regard, in an exemplary embodiment includes retrofitting existing implanted devices that are implanted in the recipient with the magnet apparatus 616. Such can be done, by way of example only and not by way limitation, before and/or after an MRI procedure, via a minor surgery that may or may not include explanting the implant to swap out the magnets.

FIG. 6R2 presents an alternate exemplary embodiment that utilizes magnet portion 606*z*, and nonmagnetic portions 616*c* and 616*d*. The embodiments of FIGS. 6R1 and 6R2 include passage 621 and 648, respectively, for a bolt or the like for attachment to a bone fixture, concomitant with the embodiments detailed above that have this feature as well.

That said, in an alternate embodiment, there is no passage. In this regard, FIG. 6R3 presents an exemplary magnet apparatus 616 that has a magnet portion 606y that does not have a passage.

It is noted that the embodiments of FIGS. 6R3, 6R4, and 6R5 can utilize any device, system, and/or method to connect the portions together. In an exemplary embodiment, any of the connection methods detailed above, such as adhesive, plates, etc., can be used to connect the portions together. This is the case with respect to all of the embodiments detailed herein unless otherwise noted The embodiments described above have been presented in terms of having a magnetic polarity alignment with respect to the magnet portion in the middle that extends across the short axis (at least with respect to the embodiments of FIGS. 6R2 and 6R3). In an alternate embodiment, the magnetic polarity is aligned with respect to the magnet portion in the middle that extends across the long axis. In this regard, FIG. 6R5 depicts an exemplary magnet apparatus 616 that utilizes the nonmagnetic components 616c and 616d, and magnet 626y, which has a magnetic alignment as shown, which is 90° from the magnetic alignment of the embodiments detailed above with respect to the middle portion. In this exemplary embodiment, the magnet alignment is in the plane that is normal to the longitudinal axis of the magnet apparatus (parallel to the skin of the recipient of implanted). FIG. 6R4 presents an alternate embodiment of this concept, except utilizing the magnet portion 626z having the passage 648 therethrough. This concept can be further extended to other embodiments, such as seen in FIG. 6R6, where magnet apparatus 616 includes magnet portions 626f, where the magnetic poles of the magnet portions are aligned 90° from that which was the case in the embodiment of FIG. 6R1.

FIGS. 6R7-6R9 depict exemplary embodiments where the middle portion 696z of the magnet apparatus 696/686 is made of the nonmagnetic material and the flanking portions are magnets. With respect to the magnet apparatus 696, magnet portions 606d and 606c of the polarity alignments detailed above with respect to these magnets. However, magnet portion 686 of FIG. 6R9 has the magnet portions 686d and 686c aligned in a plane normal to the longitudinal axis of the apparatus/parallel to the skin of the recipient when implanted therein. For brevity, the various ways to implement these embodiments is not shown with respect to some of the various configurations detailed herein, but it is noted that any of these features can be combined with any of the other features detailed herein as is consistent with all of the embodiments herein, unless otherwise noted. That is, in an exemplary embodiment, the polarity alignments of the embodiment of FIG. 6R9 can be utilized with the embodiments of FIGS. 6R8 and 6R7, and vice versa. 6R9A has an embodiment where all of the magnets have the same polar alignment. It can be understood that the magnetic alignment can be opposite from that depicted, such as reversed.

FIG. 6R9B presents yet an alternate embodiment where the magnetic polar alignment is different than any of the embodiments described above. Here, there is central component 656a, which in this case is a magnetic component in the form of a permanent magnet, and the magnetic polar alignment of the magnetic polar axis 1234 is neither diametrically aligned nor axially aligned (where 4321 is the axial longitudinal axis). Instead, the alignment of the poles is obliquely angled relative to the two.

More particularly, the magnetic polar axis 1234 is angled by angle theta away from the longitudinal axis 4321. In this exemplary embodiment, the magnetic polar axis lies on a plane that is located on the longitudinal axis 4321 and bisects the central component 656a at the center thereof. Briefly, it is noted that in at least some exemplary embodiments, there can be a $2^{nd}$ degree of orientation from this plane, which will be referred to as theta2. This is seen in FIG. 6F9C, with respect to the axis 2341, where the plane of symmetry extends through the axis 2341 in and out of the page, and the magnetic polar axis 1234 is angled therefrom at theta2. For completeness, FIG. 6R9D presents a side view of the embodiment of FIG. 6R9B. It is noted that in the embodiment of FIG. 6R9B, the magnetic where axis passes through the geometric center and/or the mass center of the central component 656a. That said, in an alternate embodiment, the magnetic polar axis 1234 can extend to a location that is offset from that center. In this regard, the figures depict Cartesian coordinate dimensions d17, which extends from the side (establishing the major axis) of the center component 656a, d19, which extends from the bottom of the center component 656a, d23, which extends from the side (establishing the minor axis) of the center component 656a, and d25, which extends from the side (establishing the major axis) of the center component 656a. The location of the point established by these dimensions can be utilized as the center portion of the polar axis 1234/can be used to establish a Cartesian coordinate system from which the polar coordinates theta and theta2 can be measured.

The values of d17, d19, d23, and d25 can be any value or range of values between and including and/or less than or greater than 0, 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100 percent of the total distance from one side to the other or from the bottom to the top, as appropriate, or any value or range of values therebetween in 0.1% increments, with respect to the component (e.g., if component is 3 mm thick, and d19 is 50% of the total distance from the bottom to the top (min, max, median, mode, etc.), then d19 would be 1.5 mm).

In an exemplary embodiment, the magnetic polar axis can be approximately 30, 45, or 60° offset of the angle that is normal to the tangential plane of the surface of the skin. In this regard, as some embodiments have utilitarian value with respect to a racetrack shaped magnet or a pill or propeller shaped magnet, in that it reduces the friction and hence the torque required to cause a magnet to rotate, this can be an embodiment that enables the magnet axis to be pointed more perpendicular to the skin (and towards the external coil), relative to that which would be the case in the absence of the teachings herein. By way of example only and not by way of limitation, the magnet axis is pointed at least 20, 21, 22, 23, 24, 25, 26, 27, 28, 29, 30, 31, 32, 33, 34, 35, 40, 45, 50, 55, 60, 65, 70, 75, 80, 81, 82, 83, 84, 85, 86, 87, 88, 89, 90, 91, 92, 93, 94, 95, 96, 97, 98, 99, or 100%, or any value or range of values therebetween in 0.1% increments of a direction perpendicular to the skin relative to that which would otherwise be the case, where the percentage is calculated by taking the direction parallel to be 90 degrees and using that as the denominator and using the angle away from 90 degrees that the axis points minus 90 degrees as the numerator. (90-angle)/90, all multiplied by 100 to get the percentage. With respect to FIGS. 6R9C and 6R9D, the angle theta and theta 2 can be (and the two can be different), in an exemplary embodiment, equal to, less than, or greater than 10, 11, 12, 13, 14, 15, 16, 17, 19, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 degrees, or any value or range of values therebetween in 0.1 degree increments.

In an exemplary embodiment, the torque applied to/experienced by the magnet (magnet apparatus/assembly using such) as a result of a 1, 1.5, 2, 2.5, 3, 3.5, 4, 4.5, 5, 6, 7, 8, 9, or 10 T magnetic field from an MRI machine aligned at a direction that is in the plane of FIGS. 6R9c and/or 6R9d, or aligned as detailed below, can be reduced by at least 5, 10, 15, 20, 25, 30, 35, 40, 45, 50, 55, 60, 65, 70, 75, 80, 85, 90, or 95%, or any value or range of values therebetween in 0.1% increments (12.2%, 55.5%, 33.3 to 66.6 percent, etc.) relative to that which would be the case if the angle theta and/or theta2 was zero (parallel to a direction perpendicular/normal to the tangent surface of the skin right above the magnet). Other angles of the aforementioned MRI magnetic field can correspond to any of the values of theta and theta2 based on the coordinates detailed above, where those values can be related to the aforementioned center component or the flanking component (more on this below) and/or can be related to angles off of the overall orientation of the implant (e.g., the longitudinal axis (coil to electrode with respect to the CI, for example) would be the equivalent of axis 2341, and the axis 90 degrees away from that and extending basically normal through the skin would be the equivalent of axis 4321.)

FIG. 6R9E depicts an example of where a flanking portion 656b has the angled polar alignment. Any of the aforementioned features for the central portion 656a can be applicable to this as well, and will not be repeated, but incorporated by reference as applicable to this embodiment.

Moreover, while the embodiments depicted in the figures have the North pole extending upwards, it is noted that in alternate embodiments, the reverse can be the case. Moreover, it is noted that consistent with the teachings detailed above, the orientations of the various components can be different from each other. For example, one side of the flanking component can have the orientation seen in FIG. 6R9E, and the other side of the flanking component can have the opposite orientation with respect to the North pole being on the bottom. Moreover, the angles can be different for the various components. Indeed, in an exemplary embodiment, if one was looking at a side view of the magnet apparatus, there could be two or three different polar axes. FIG. 6R9F presents an exemplary embodiment of a hybrid device where the angled polar concept is used on the flanking magnets and the central magnet is aligned according to the teachings at the beginning of the specification (horizontally). FIG. 6R9G presents an alternate embodiment, where there is a "criss-cross" polar axis alignment (the angles are opposite one another—it is noted that in an exemplary embodiment, the angles can be different in magnitude).

FIG. 6R9H depicts an exemplary embodiment of the angled pole concept applied to a solid disk magnet 666c where the entirety of the magnet apparatus has the depicted polar axis alignment. It is noted that this can be a monolithic embodiment or a divided embodiment, etc. Also, the embodiments of FIGS. 6R9F and 6R9G can be monolithic, where the separate portions are magnetized differently.

Some of the embodiments detailed above can result in a higher external component retention force compared to a magnetic polarity axis that is parallel to the skin. In this regard, all other things being equal (e.g., for a given magnet volume magnetized in similar manner other than the direction of magnetization, the same external component held the same distance away, the same implant other than the different magnet, etc.) the aforementioned oblique angling of the magnetic pole axis can increase the retention force by less than, greater than or equal to 10, 15, 20, 25, 30, 35, 40, 45, 50, 55, 60, 65, 70, 75, 80, 85, 90, 95, 100, 110, 120, 130, 140, 150, 160, 170 percent or more, or any value or range of values therebetween in 1% increments.

It is noted that in at least some exemplary embodiments, there can be utilitarian value with respect to bonding or attaching the flanking portions to the central portion and/or attaching the central portion to the flanking portions, depending on whether or not one or more of these are magnetized, or even if they are all magnetized for that matter, so as to provide support to reduce and/or eliminate the likelihood of the magnet kicking over due to, for example, and unbalanced force and/or torque. In this regard, there could be utilitarian value with respect to providing the central portion without the flanking portions and some embodiments. Indeed, to be clear, in at least some exemplary embodiments, there are implementations where there is only a central portion and/or only the flanking portions detailed herein or variations thereof. However, such implementations could, potentially, result in a scenario where the magnet is more likely to rotate about the axis 2341, for example, relative to that which would otherwise be the case if the magnet apparatus was a full circle, for example. Accordingly, there can be utilitarian value with respect to adding flanking portions to act as something analogous to outriggers or the like on a boat to better balance the magnet as compared to that which would be the case in the absence of the flanking portions. Alternatively, and/or in addition to this, the same can be said for the flanking portions—the presence of a central portion, whether magnetized or not, will provide stability with respect to that which would otherwise be the case if the flanking portions were located individually in the implant. In this regard, it is noted that at least some embodiments include the central portion and/or one or more the flanking portions located in the implant/held in the implant due to being surrounded by the silicone that establishes the body of the implant. It will be understood that because of the relatively narrow nature of the various individual components of the magnet groups/magnet apparatuses relative to that which would be the case if the magnet was a complete circle, these components will be more likely to rotate about the long axis thereof (or even about the short axis thereof—the overall space of a circular magnet provides more resistance to rotation about the short axis relative to that which is the case with a more narrow magnet). Accordingly, by utilizing the flanking components and/or the central components where otherwise such may not necessarily be needed, with respect to establishing a magnetic body, increased stability can be achieved.

Also, in an exemplary embodiment, the flanking portions can reduce friction relative to the housing that might otherwise exist vis-a-vis the magnet of the magnet apparatus contacting the housing with a moment that is unique to the fact that the magnetization axis is out of the plane of rotation and/or out of the axis of rotation. In this regard, in an exemplary embodiment, the magnet apparatus could cant within the housing, when exposed to a magnetic field, such as an MRI field, in a manner that is unique because of the oblique angle of the magnetization. By utilizing the flanking portions, such can stabilize the magnet apparatus so as to reduce the amount of canting (owing to the fact that the flanking portions can serve as outriggers), or otherwise change the location of contact between the magnet apparatus in the housing that would otherwise exist, or at least reduce the friction between the magnet apparatus in the housing because the flanking portions are made of material that has a lower friction coefficient than the magnet apparatus.

Accordingly, in an exemplary embodiments, the utilization of the flanking portions and/or the central portions as opposed to not using them, all other things being equal, can result in a reduction of the total amount of rotation that would be experienced with respect to exposure to a given magnetic field (whether that is from the MRI or from the external component) by at least 10, 15, 20, 25, 30, 35, 40, 45, 50, 55, 60, 65, 70, 75, 80, 85, 86, 87, 88, 89, 90, 91, 92, 93, 94, 95, 96, 97, 98, 99, or 100%, or any value or range of values therebetween in 1% increments as opposed to that which would exist without the utilization of the flanking portions and/or the central portions (to establish the circular body).

It is briefly noted that while the embodiments depicted above have contemplated the utilization of an adhesive or a plate-like structure, etc., to attach the flanking portions to the central portion, in at least some embodiments, a tongue and groove like arrangement can be utilized between the central portion and the flanking portions. By way of example only and not by way of limitation, the flanking portions can be attached to the central portion in a manner analogous to how cabinet furniture can be attached. By way of example only and not by way of limitation, the central portion can have a male tongue on either or both of the flat sides, and the flanking portions can have a groove that mates with the respective male tongs, and/or vice versa. Any arrangement that can enable the teachings detailed herein vis-à-vis attachments of the flanking portions of the central portions can be utilized at least some exemplary embodiments. In an exemplary embodiment where the central portion is the magnetic portion, there can be utilitarian value with respect to making the male tongs part of the central portion as that increases the amount of the magnetic material and the magnet apparatus.

In fact, FIG. 6R9I presents yet an alternate embodiment where the central portion has components that are more like wings than tongues, which wings that extend outward and into the flanking portions in a manner analogous to the tongue. Here, center portion 676a is a magnet, and has wings 676a1 extending from the center body 676a2, into hollows in the flanking portions 676b. This increases the amount of magnetic material relative to that which would be the case (where the center portion is a magnetic body) with a more traditional tongue in groove arrangement. FIG. 6R9J depicts a top view of the embodiment of FIG. 6R9H. It is noted that in an exemplary embodiment, magnetic bolts/dowels 677 can be utilized to secure the flanking portions to the central portion, as can be seen. The dowels can be interference fitted into holes that extend through the flanking portions and the wings of the central portion. An exemplary embodiment, the dowels can be below grade with respect to tops and bottoms of the flanking portions so as to avoid contact with the housing as will be detailed in greater detail below. In an exemplary embodiment, the dowels can be made of magnetic material/permanent magnets, thus increasing the amount of magnet material. The alignment of the polarities of these dowels can be any direction they can have utilitarian value.

In view of the above, there is an implantable medical device, comprising a magnet apparatus and a body encompassing the magnet apparatus, wherein the implantable medical device is MRI compatible owing to a magnetic axis of a magnet located in/that is part of the magnet apparatus being offset from an axis that is normal to a surface of the skin immediately above the magnet apparatus when the implantable medical devices implanted in a recipient. In an exemplary embodiment, the offset between 10 to 80 degrees. In an exemplary embodiment, the offset is between 20 to 70 degrees, between 40 to 70 degrees or between 50 to 70 degrees, etc. In an exemplary embodiment, the offset is 45, 46, 47, 48, 49, 50, 51, 52, 53, 54, 55, 56, 57, 58, 59, 60, 61, 62, 63, 64, 65, 66, 67, 68, 69 or 70 degrees. As will be described below, in an exemplary embodiment, the magnet apparatus/magnet is dome shaped.

Figure 12:
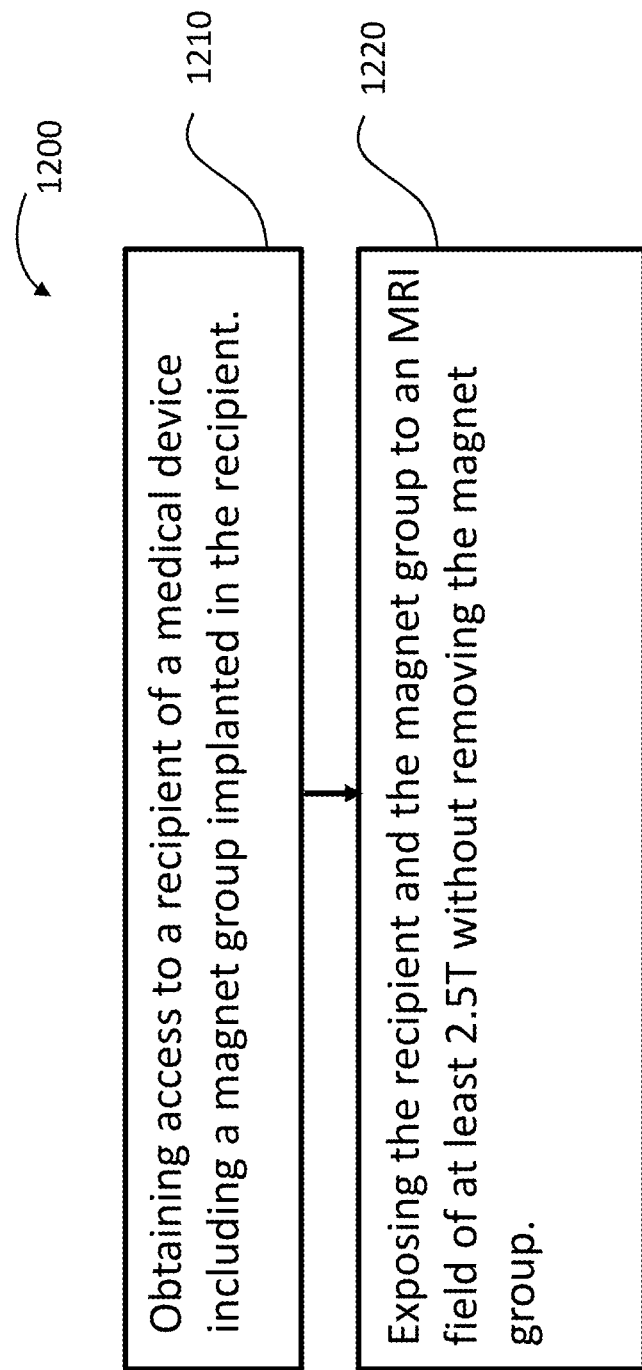
FIGS. 12-19 present exemplary flowcharts for exemplary methods.
Figure 13:
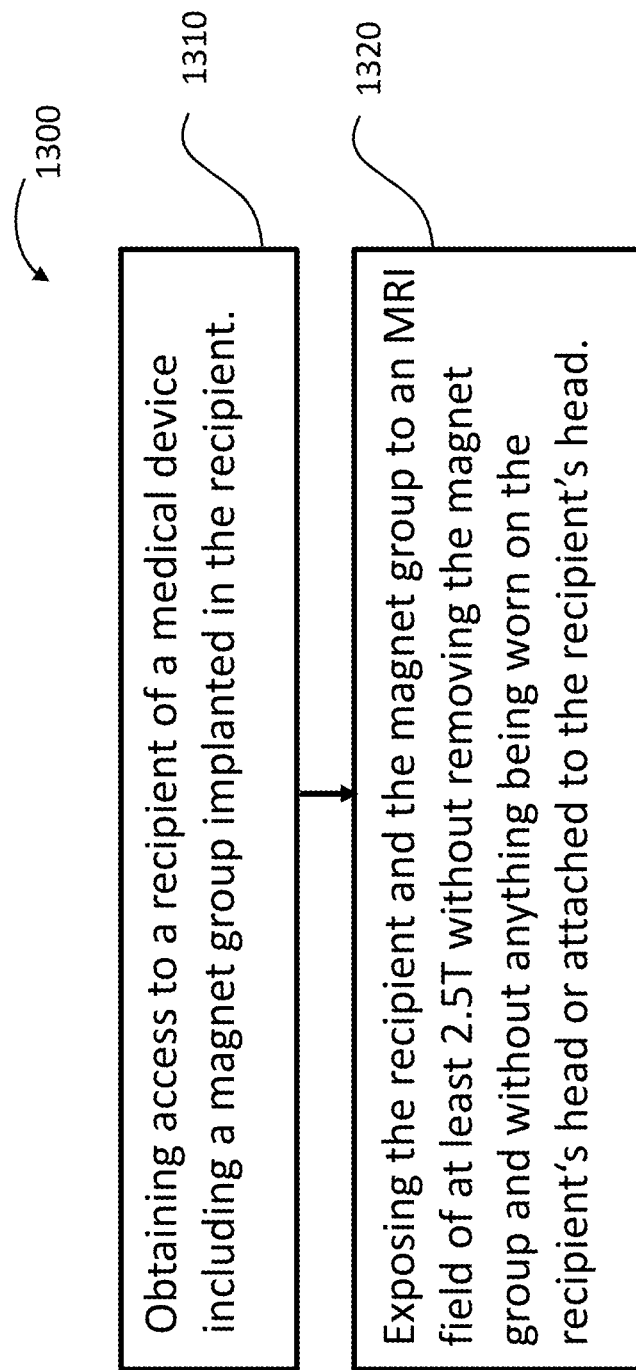
Figure 14:
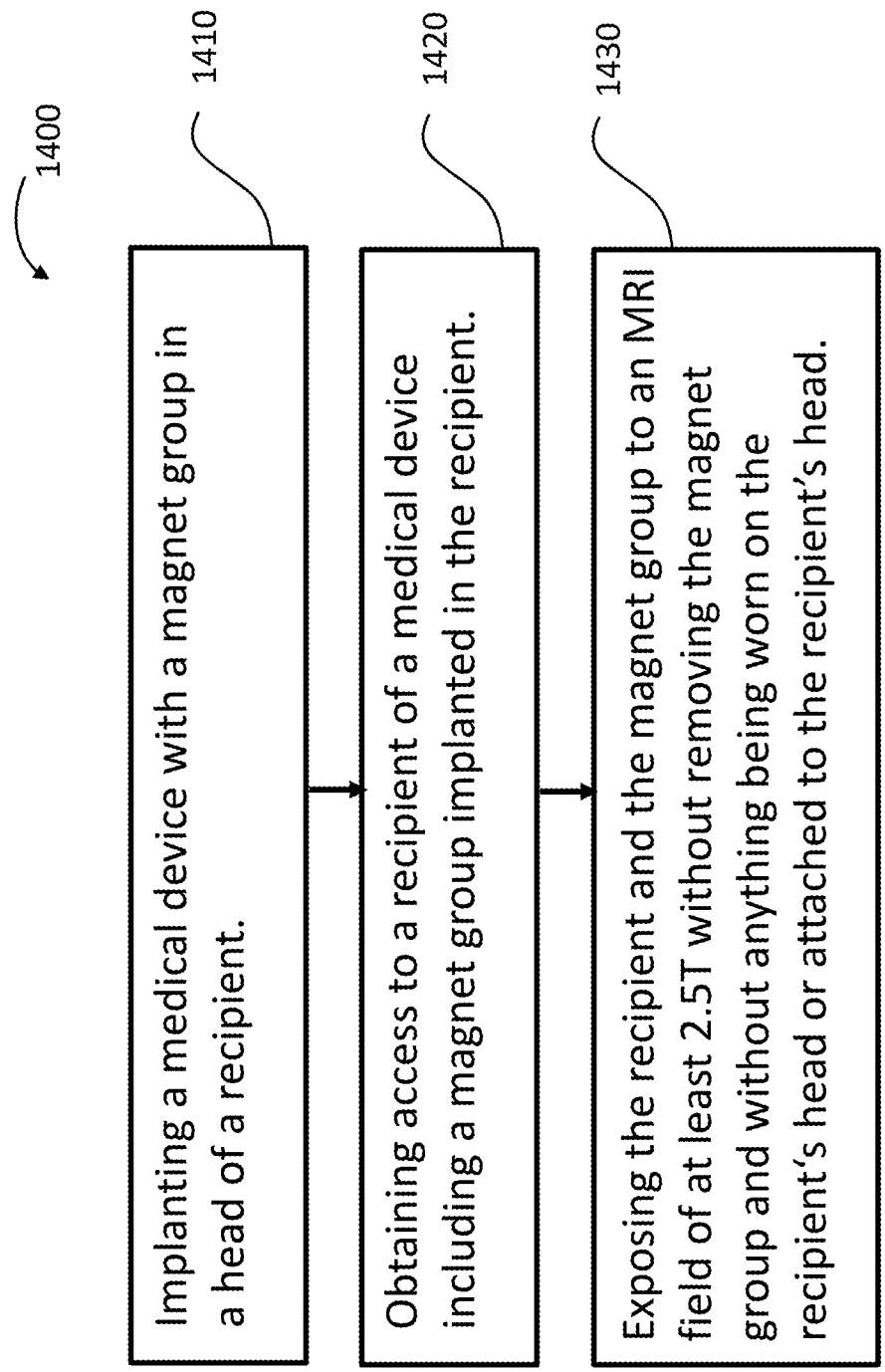
Figure 15:
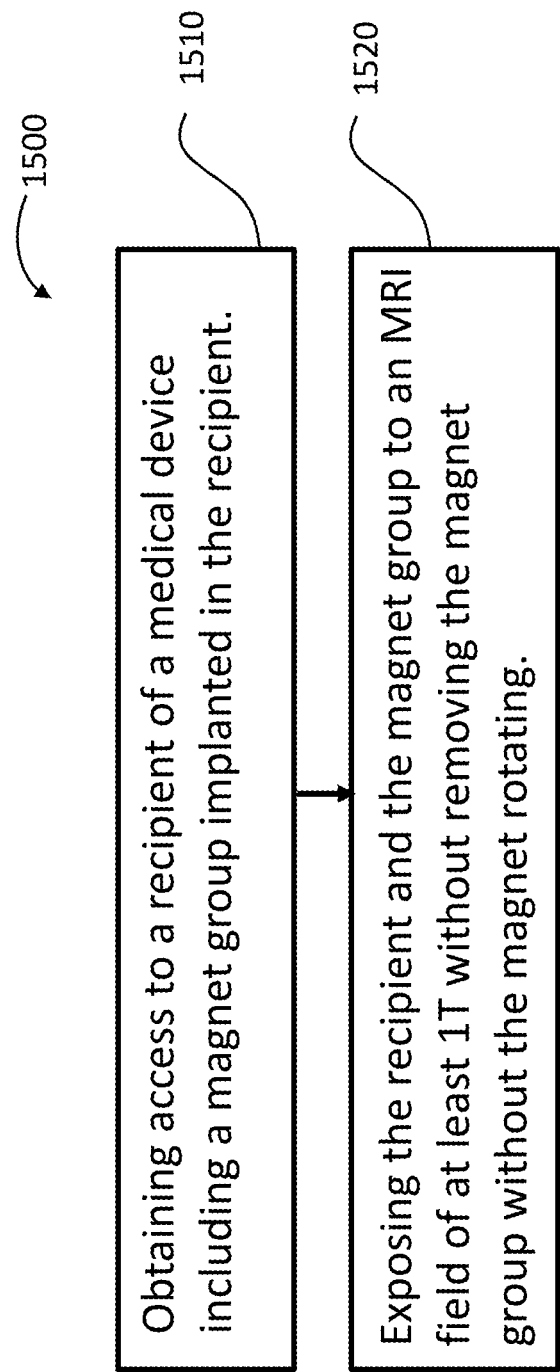
Figure 16:
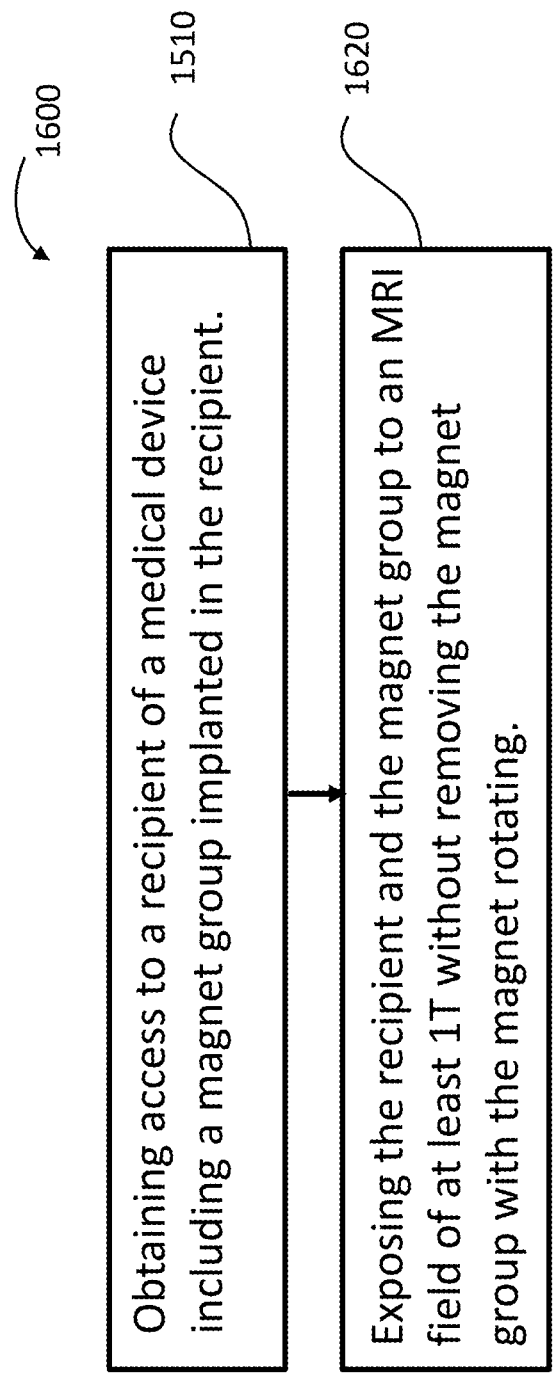

The embodiments detailed above have presented examples of the magnet apparatus of the implant where the structure of the portions that make up the apparatus establishes outer circumference of the overall apparatus that is generally uniform. In an alternate embodiment, the shapes of the portions can be different from that detailed above that results in a different outer periphery. In this regard, FIG. 6R10 depicts a portion 636a (which can be a magnet portion or a non-magnetic portion), in accordance with the teachings above—this disclosure is generically presented, and represents an exemplary concept in which to implement at least some of the teachings detailed herein where the various sub component can be filled in with the "like" structural components presented in the application), that is race track shaped such that the outer periphery of portions that are curved have a different radius of curvature than the portions 636b (which can correspond to any of the flanking magnets detailed herein and variations thereof, and can also can correspond to any of the flanking nonmagnetic portions detailed herein and variations thereof—again, any of the embodiments can be used). In an exemplary embodiment, the radius of curvature of the portion 636a with respect to the ends thereof, and the radius of curvature of the portions 636b with respect to the outer periphery's thereof can have a ratio of 0.1, 0.2, 0.3, 0.4, 0.5, 0.6, 0.7, 0.8, 0.9, 1.0, 1.1, 1.2, 1.3, 1.4, 1.5, 1.75, 2, 2.25, 2.5, 2.75, 3, 3.5, 4, 4.5, 5, 6, 7, 8, 9, or 10 or any value or range of values therebetween in 0.01 increments (0.23, 3.22, 0.55 to 1.77, etc.). FIG. 6R11 depicts an exemplary magnet apparatus 636, with a center magnet 636a flanked by flanking magnet/not-magnet portions 636b. Here, the flanking magnets have a non-exact non non-full moon shape (there would be a crescent to the shape, if it was exact or the shape would be half a circle)—that said in some embodiments, the flanking portions can be crescent-shaped and/or half circle shaped—any arrangement that can be utilized to practice the teachings detailed herein and/or variations thereof can be utilized at least some exemplary embodiments. In this embodiment, the moons have a slightly larger dimensioned relative to the racetrack shaped center portion. FIG. 6R12 depicts a side view of the embodiment of FIG. 6R11. As seen, the portions are all aligned at the top and bottom. In an alternate embodiment, as seen in FIG. 6R13, which can be an alternate embodiment of FIG. 6R11, the flanking portions extend beyond the tops and bottoms of the middle portion. FIG. 6R14 depicts an alternate embodiment, where the flanking portions only extend past the bottom (in an alternate embodiment, they only extend past the top). FIG. 6R15 depicts an alternate embodiment where the bottom portions of the flanking portions extend out past the bottom portions of the center portion, but the top portions of the flanking portions are below the top portions of the center portion (or vice versa in an alternate embodiment). FIG. 6R16 depicts an alternate embodiment where the bottom portions of the flanking portions and the top portions of the flanking portions are above and below, respectively, the portions of the center portion.

Figure 17:
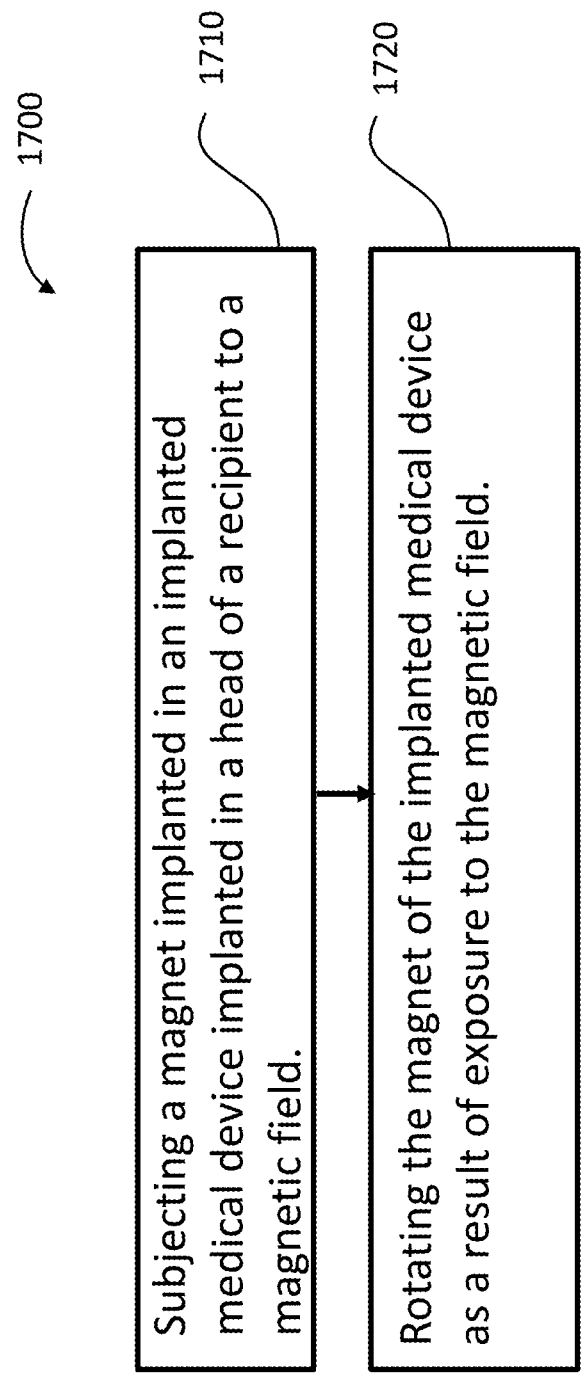

In an exemplary embodiment, referring to FIG. 6R17, the collective extrapolated outer diameter 170 (which should be quasi perfectly circular, but can instead be oval, etc., in other embodiments, in which case it is the maximum extrapolated outer diameter) of the flanking portions is at least X % larger than the maximum and/or extrapolated diameter 172 of the center portion 363a and/or at most X % larger or smaller than the maximum and/or extrapolated diameter 172 of the center portion 363a. X can be 0.1, 0.2, 0.3, 0.4, 0.5, 0.6. 0.7, 0.8. 0.9, 1.0, 1.25, 1.5, 1.75, 2.0, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, or 60, or any value or range of values therebetween in 0.01 increments. Thus, the diameter can be, for example, at least 1.5 percent larger and at most 2.5 percent larger than the center portion. As can be seen above the flanking portions can also extend above and/or below the top and/or bottom of the center portion, and/or can be located below the top or above the bottom of the center portion, and can do so such that the total extension and/or the specific extension above and/or below and/or the "retraction" can be at least X % of the thickness of the center portion. The distances can also be at most X % of the thickness of the center portion, such as, for example, no more than 0.4% of the thickness, and no more than 0.7% of the thickness. The magnet apparatus can be symmetrical about any plane, and/or can be asymmetrical about any plane. The aforementioned heights can be different for the top or the bottom.

By making these partially circular segment flanking portions slightly larger in height and/or effective radius, relative to the central portions, the partially circular segment material will always be in contact with the housing (this can ensure or increase the likelihood of a smooth rotation and/or securement of the magnet apparatus, as will be detailed below). Alternatively, or in addition to this, by making the discorectangular central portion slightly larger in height and/or in effective radius, relative to the flanking portions, the disco rectangular central portion will always be in contact with the housing (and this too can ensure increase the likelihood of a smooth rotation and/or securement of the magnet apparatus, as will be detailed below).

Figure 18:
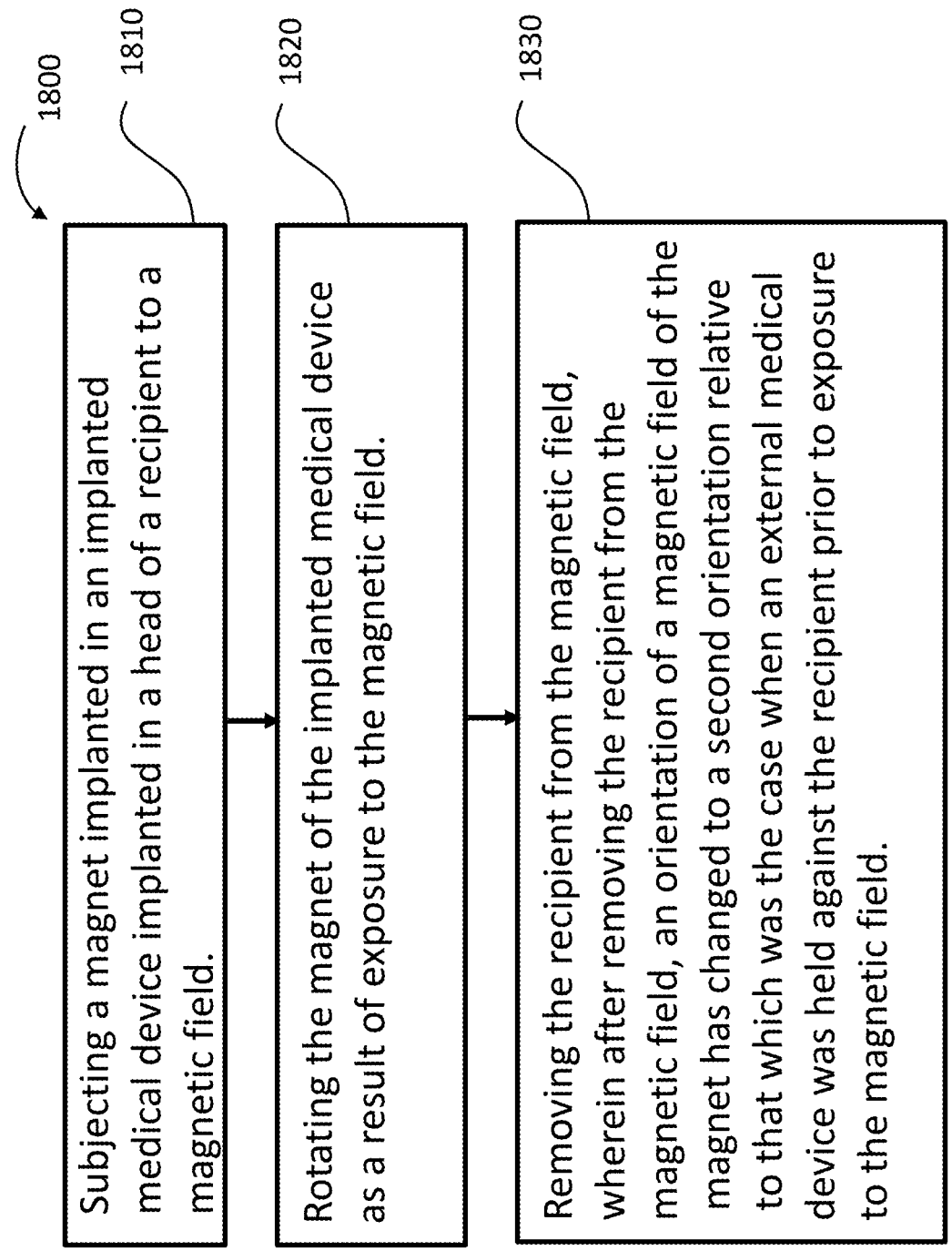

FIG. 6R18 presents an alternate embodiment of an apparatus 646 where a bar central portion 646a is utilized instead of a racetrack shaped portion, and the flanking portions 646b are attached to the lateral sides of the bar shaped portion. As with the embodiments above, the central portion 646a can be a magnet and/or magnetic material and in other embodiments it is not a magnet, such as embodiments where the material is PEEK or PDFE, etc., or a generic plastic. Also, in some embodiments, the flanking portions 646b can be magnet/magnetic material, while in other embodiments it is not a magnet or a magnetic material.

In the embodiment of 6R18, the bar shaped portion is recessed with respect to the extrapolated outer periphery established by the flanking portions. However, FIG. R19 presents an alternate embodiment where such is not the case. In this regard, the bar shaped portion 646a is a maximum diameter that corresponds to the diameter of the flanking portions immediately proximate the bar shaped central portion. That said, FIG. 6R20 depicts another exemplary embodiment where the bar shaped central portion 646a extends past the diameter of the flanking portions immediately proximate the bar shaped portion. In an exemplary embodiment, the bar shaped portion can establish the maximum outer diameter, as shown in FIG. 6R20, where the dashed line represents an extrapolated outer profile of the magnet apparatus. Conversely, as seen in FIG. 6R21, a bar shaped central portion which extends past the flanking portions can still be within the extrapolated outer profile of the apparatus, which outer profile is established by the maximum diameter established by the flanking portion.

In an exemplary embodiment, both the central portion and the outer portion can be flush with the extrapolated outer profile, even if the central portion is a bar shaped central portion.

In an exemplary embodiment, the maximum diameter of the central portion can be X % greater or less than the maximum diameter that corresponds to the distance from one side of flanking portion to the other side of the opposite flanking portion.

Figure 22:
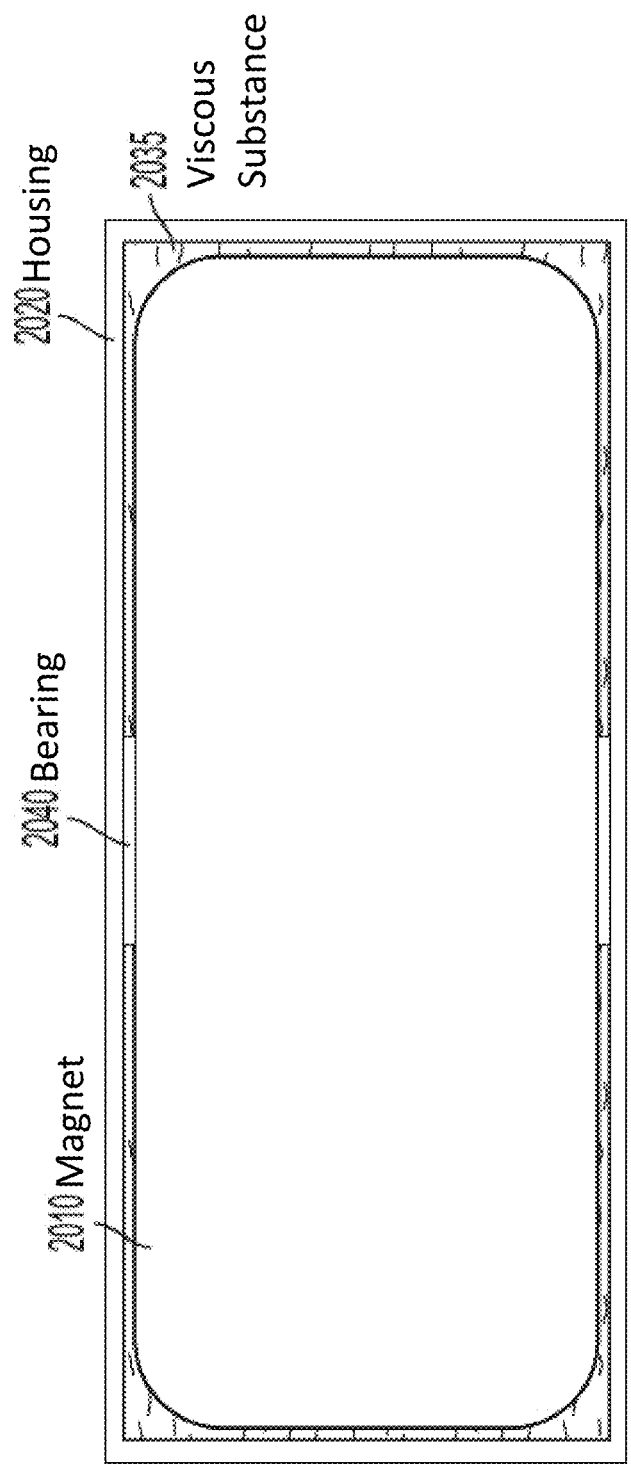
Figure 23:
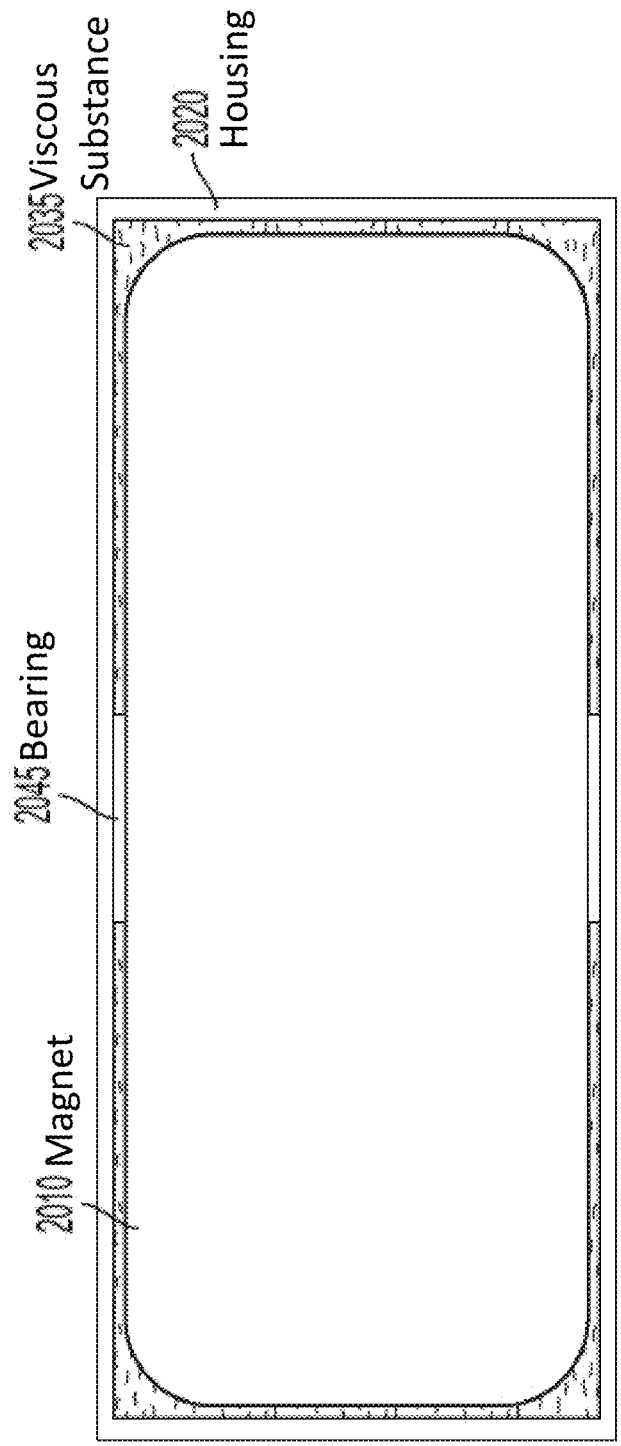
Figure 24:
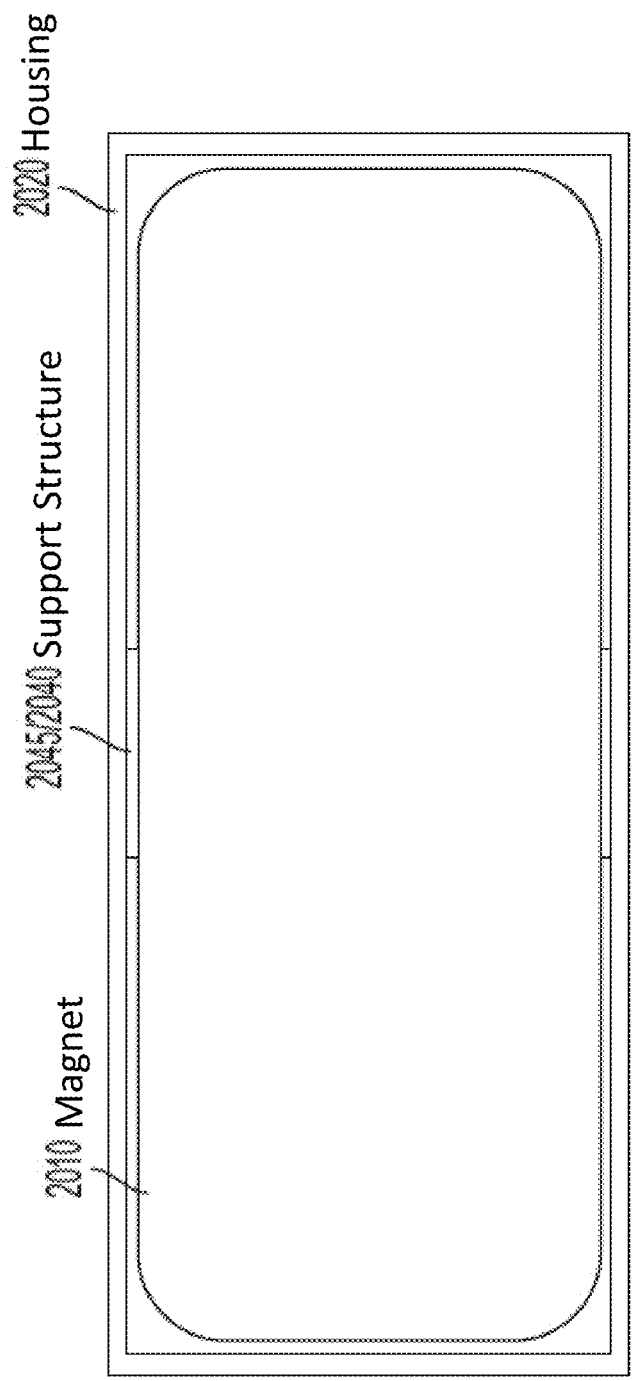
Figure 25:
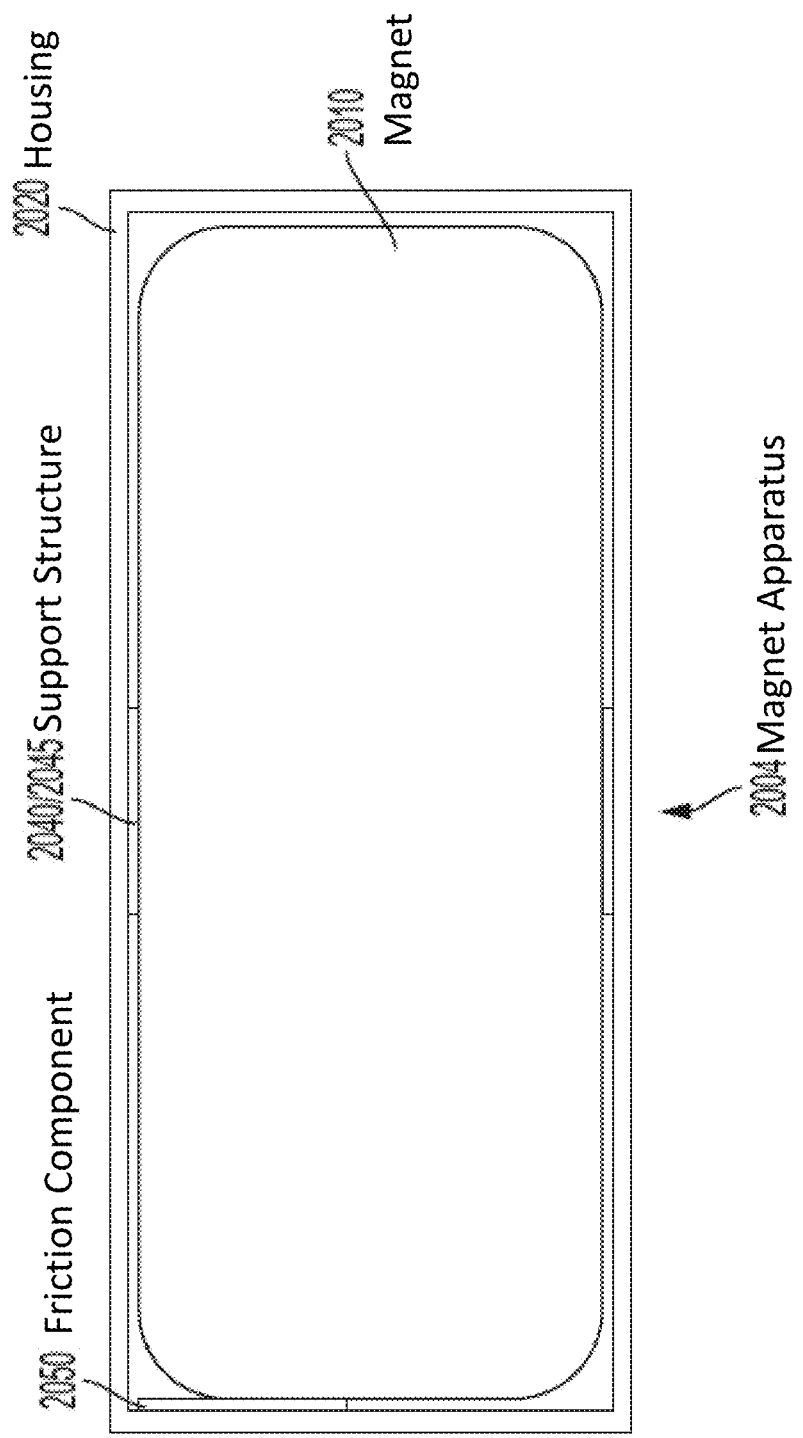

FIG. 6R22 presents an exemplary embodiment of a laterally larger center portion 636a that can be utilized, where the center portion 636a extends into the flanking portions 646b as seen. Any shaped or sized central portion that can have utilitarian value can be utilized in at least some exemplary embodiments. FIG. 6R23 depicts another exemplary embodiment where the flanking portions can be bifurcated into separate components and fit about the central portion. In the embodiment depicted, each of the flanking portions 646b are divided into three sub-portions. FIG. 6R24 depicts another exemplary embodiment where the central portion vastly dominates the flanking portions, where the flanking portions are nonoverlapping. In this exemplary embodiment, the lateral sides of the central portion extend past the inside lateral sides of the flanking portions. Conversely, FIG. 6R25 is such that the lateral sides of the central portion do not extend past the inside lateral sides of the flanking portions.

In view of the above, it can be seen that in an exemplary embodiment, there is an implantable medical device, comprising a magnet and a body encompassing the magnet, wherein the magnet is racetrack shaped. In an exemplary embodiment, the racetrack shaped magnet is located in a racetrack shaped housing. In an exemplary embodiment, the racetrack shaped magnet is attached, either directly or indirectly, to flanking portions in the shape of partial moons on either side thereof. In an exemplary embodiment, the racetrack shaped magnet is located in a hermetic housing.

In an exemplary embodiment, the implantable medical device described above has a racetrack shaped magnet that has a magnetic axis that is offset from a vertical axis that is parallel to the skin of the recipient when the implantable medical devices implanted in the recipient. In an exemplary embodiment, the racetrack-shaped magnet has a magnetic axis that is offset by an amount that is 10 to 80 degrees from a vertical axis that is parallel to the skin of the recipient when the implantable medical devices implanted in the recipient. In an exemplary embodiment, the racetrack-shaped magnet has a magnetic axis that is offset by an amount that is 30 to 70 degrees from a vertical axis that is parallel to the skin of the recipient when the implantable medical devices implanted in the recipient.

Figure 6S:
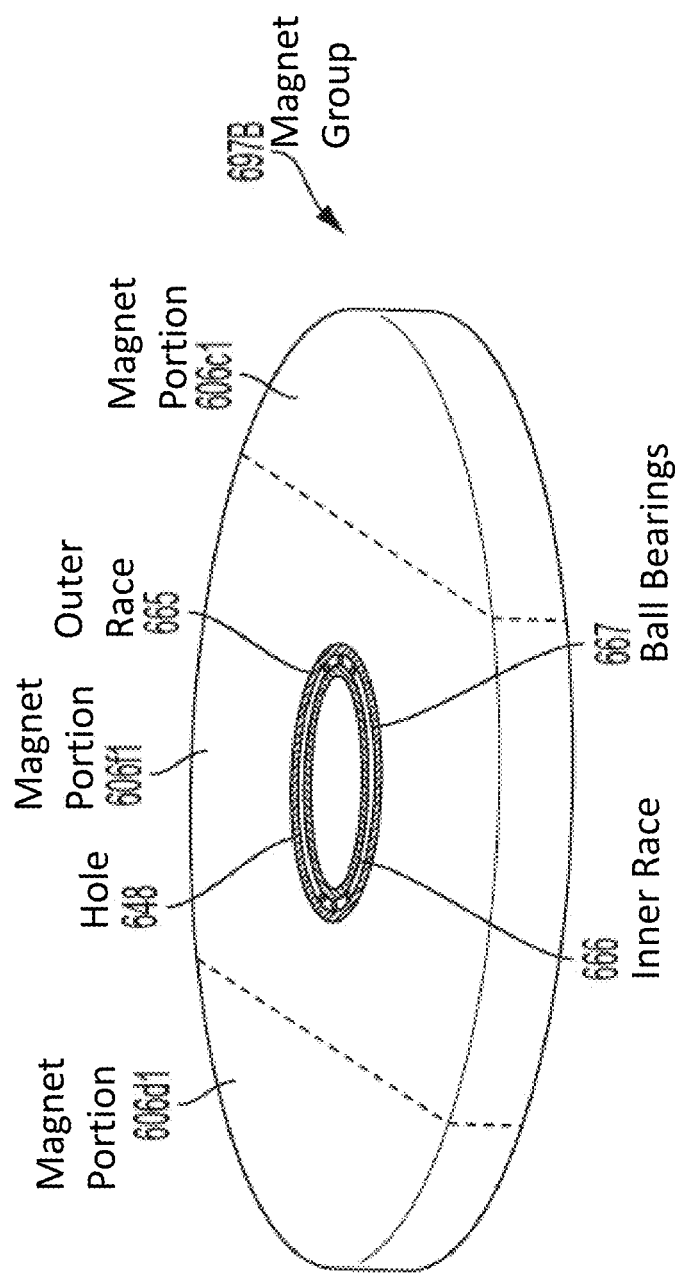

As noted above, some embodiments can utilize a bushing 655. The bushing 655 can be a bearing or part of a bearing that can enable the magnet group to spin/revolve. FIG. 6S depicts an exemplary embodiment of such. Here, there is an outer race 665 of a ball bearing apparatus that can be interference fitted or otherwise adhesively fitted or welded etc. into the hole through the magnet group. There is also an inner race 666 and ball bearings 667. The ball bearings permit the inner race, or, more accurately, the outer race (because the inner race is typically fixed —more on this below) to move relative to the inner race with relative ease, thus permitting the magnet group to rotate/revolve with greater ease than that which would otherwise be the case. In an exemplary embodiment, the bearings are lubricated and can be a thrust bearing apparatus so that the bearing supports the entire magnet group away from the housing wall in embodiments where the magnet is located in a housing.

FIG. 6T1 presents an exemplary embodiment of the utilization of the bushing 655. In this embodiment, the bushing 655 is a compound bushing that has a portion that accepts the head of the screw 222 that the top surface is generally flush. That said, in an alternate embodiment, a normal cylindrical bushing with constant inner and outer diameters can be used such as that seen in FIG. 6T2, where the bushing 655 is inside a housing 687, and the screw head of screw 222 or other components close the housing and hermetically seal or otherwise isolate in a utilitarian manner the magnet group 697B from the ambient environment. This as contrasted to the embodiment of FIG. 6T1, where the magnet group 697B is coated with a biocompatible coating that isolates the magnetic material of the magnet portions from the ambient environment.

With reference to the variation of the embodiment of using a bearing, such as a thrust bearing apparatus, instead of the mere utilization of a bushing, FIG. 6T3 depicts a side view of such an exemplary embodiment. Here, the bearing apparatus is inside a housing 687, where the inner race 666 is interference fitted or slipped fitted or welded or otherwise adhesively bonded to the inner wall of the housing 688 that extends from the bottom of the housing to the top of the housing (the central inner wall can be a cylindrical structure that extends from the bottom of the housing to the top of the housing and can be monolithic with one of those components and welded to the lid (or bottom) of the housing to establish the hermetic seal—the inner race 666 can be slipped over such—it is noted that this configuration can also be utilized with the bushing 655 above—the bushing can be slip fit or interference fitted or otherwise adhesively attached or not attached to the inner cylindrical wall of the housing, and the lid or bottom can be welded to the cylindrical wall to establish the hermetic seal). Here, a roller bearing 667 is utilized instead of a ball bearing as disclosed in the embodiment above—any bearing that can enable the teachings detailed herein can be utilized at least some exemplary embodiment. The outer race 665 is interference fitted or slipped fitted or otherwise attached to the magnet group in general, and the third magnet portion 606/1 or the group thereof in particular). The screw head of screw 222 extends to the cylindrical wall of the housing 668 so as to secure the housing 668, and thus the magnet group therein, to a bone fixture to bone of the recipient, etc. In an exemplary embodiment of this embodiment, the bearing apparatus provides an arrangement that permits the magnet group to rotate about the screw 222 or otherwise about the cylindrical inner wall of the housing in a low friction manner. In an exemplary embodiment, the area inside the housing can be filled with a low viscosity lubricant, such as a biocompatible oil or the like. The bearings can be lubricated or non-lubricated.

The above said, in at least some exemplary embodiments, the magnet group can rotate or otherwise spin about the bushing/the bushing can rotate or otherwise spin about the inner cylindrical housing wall and/or the screw. The bushing can be made of a low friction material that will result in low friction with respect to the inner and/or the outer surface thereof, thus permitting the magnet group to rotate with or without rotation of the bushing. In an exemplary embodiment, a lubricant can be located on the inner surface and/or the outer surface of the bushing to enhance rotation of the magnet.

Thus, in an exemplary embodiment, the implantable apparatus can be configured such that it enables the magnet group to rotate as a unit relative to the housing about an axial direction. In some exemplary embodiments, the magnet group has a hole extending through the group, and a bearing body is located in the hole, the bearing body being used to guide rotation of the magnet group.

Figure 20A:
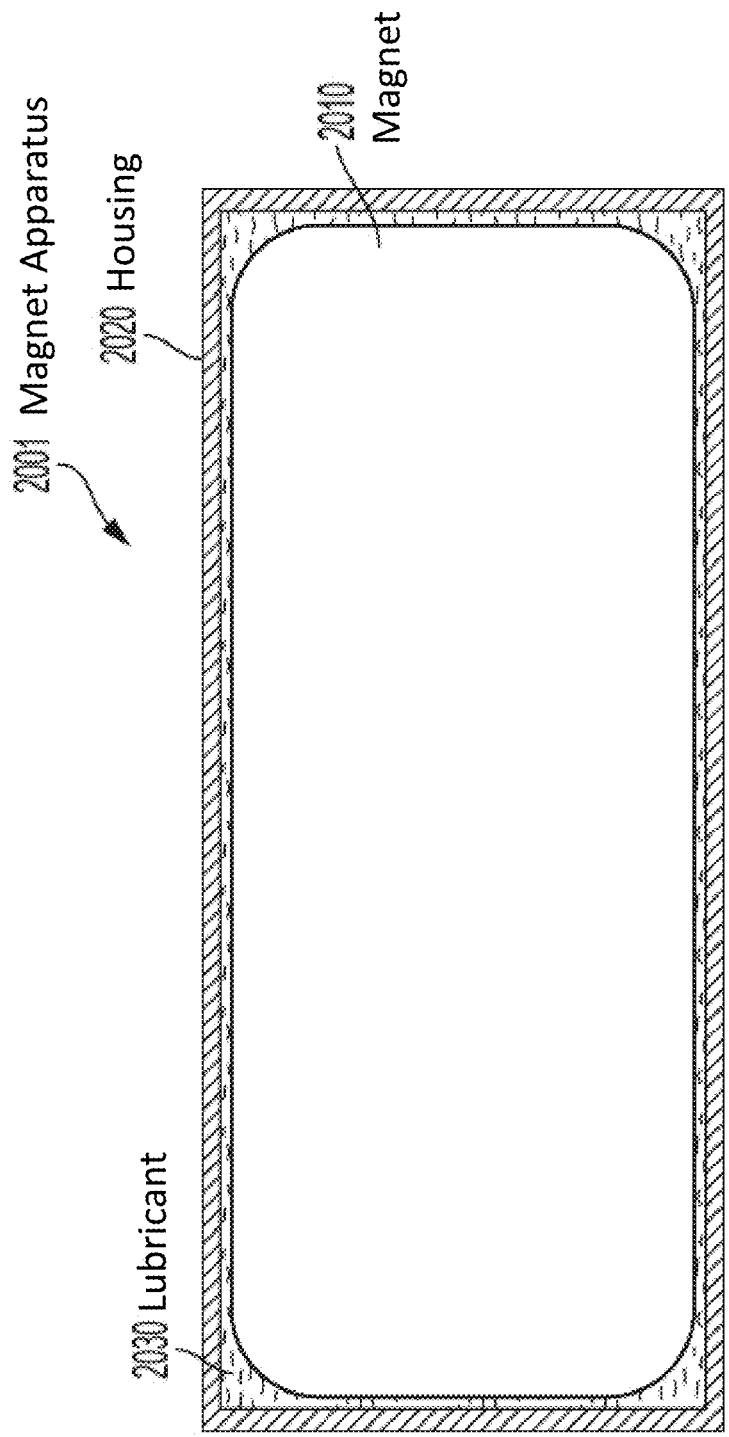
FIGS. 20A to 27 present cross-sections (partial and/or full) of some exemplary magnet apparatuses.
Figure 21:
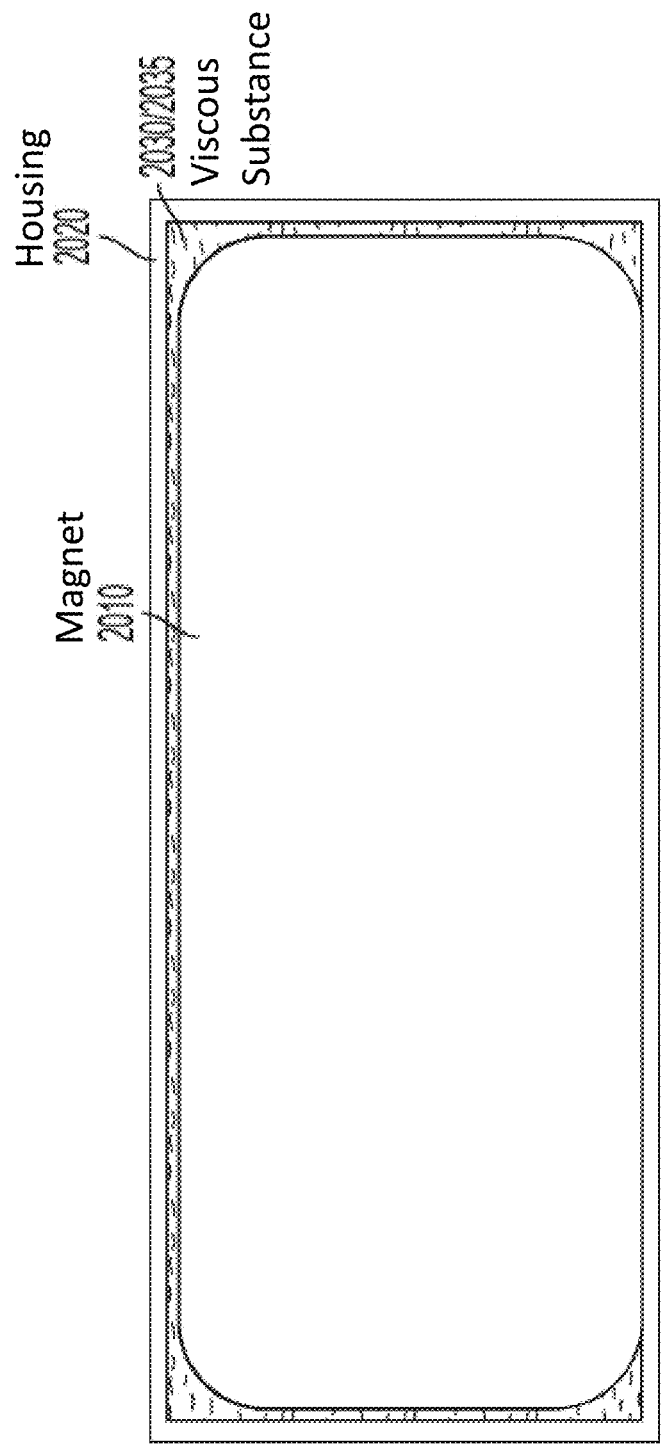

FIG. 20A presents an exemplary embodiment of a magnet apparatus 2001 that includes a magnet 2010 (which can be instead a magnet group and/or a magnet apparatus/magnet sub-assembly as describe above and/or below—any disclosure herein of a magnet and/or magnet group corresponds to a disclosure of an alternate embodiment where there is a magnet apparatus and/or a magnet group as disclosed herein, and vice versa, unless otherwise noted or unless the art does not enable such—more on this below) located in a housing 2020 that hermetically isolates the interior of the housing from the outside environment. The housing can be a titanium housing, or can be another type of metallic housing, and/or can be a ceramic housing and/or can be a plastic based housing, etc. Any housing that can enable the teachings herein can be utilized in some embodiments. In an exemplary embodiment, a lubricant 2030, such as a fluid lubricant, is located inside the housing, and otherwise, in combination with the magnet, fills the interior of the housing or otherwise substantially fills are effectively fills the interior of the housing. In an exemplary embodiment, this results in a design friction that is low. This enables the magnet 2010 (or magnet apparatus) to rotate within the housing relatively easily. In an exemplary embodiment, the magnet 2010 can instead be a magnet group according to any of the teachings detailed herein. In an exemplary embodiment, such as where there are three separate magnets, the magnet group can be encased in a second housing (not shown) or in a membrane or in a sealed environment to isolate the magnet components from the fluid inside the housing. Note also that in some embodiments, the extra-membrane or the sealing or the extra housing can also be utilized with the monolithic magnet as well.

In an exemplary embodiment, such as by way of example only and not by way of limitation, where the housing includes a fluid lubricant, there can be utilitarian value with respect to encasing the magnet apparatus in a secondary housing. In an exemplary embodiment, there is a housing that includes the center portions and the two flanking portions according to any of the embodiments detailed herein, and this housing can be sealed or the like, and then the housing including the center and flanking components can be placed into the outer housing (e.g., housing 2020), and then the inner housing can move relative to the outer housing. In an exemplary embodiment, the center and flanking portions can be interference fitted or slipped fitted or clearance fitted into the inner housing. The components can be secured in the inner housing any manner that can have utilitarian value with respect to implementing the teachings detailed herein. In an exemplary embodiment, an epoxy the like can be used to fill the inside of the interior housing and thus "lock" the center portions of the flanking portions in the inside of the housing.

The above said, in an alternate embodiment, the magnet apparatuses detailed herein can be placed inside the housing 2020 without those components being located in a separate housing.

In an exemplary embodiment, the components of the magnet apparatuses can be coated, either individually or collectively, with a substance, such as a polymer or the like, and then the coded components can be located in the housing 2020.

All of the above said, in some embodiments, there is utilitarian value with respect to preventing the magnet group (or magnet or magnet apparatus, etc., as noted above) from rotating within the housing 2020 (or any other housing disclosed herein, such as housing 688) where the housing does not rotate, either. This can be because, by way of example only and not by way of limitation, the orientation of the magnetic field relative to the skull is desired to be aligned in a consistent manner that is maintained for a long period of time, such as 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, or 35 or 40 or 45 or 50 or 55 or 60 years or more or any value or range of values therebetween in one day increments. The orientation could be desired to be maintained for the life of the recipient. The orientation could be designed to be maintained irrespective of the exposure of the recipient to a magnetic field, at least some magnetic fields of at least limited strengths, such as, for example, the magnetic field resulting from the external magnet of the external component. Still further, in an exemplary embodiment, the orientation could be maintained when subjected to a high strength magnetic field, such as, for example, the magnetic field of an MRI device, which can be 1, 1.5, 2, 2.5, 3, 3.5, 4, 4.5, 5, 5.5, 6, 6, 5, 7, 8, 9 T or more. Some exemplary scenarios of this will be described in detail below. The point is, in at least some exemplary embodiments, the arrangement is configured so as to provide friction or otherwise prevent or otherwise limit the rotation of the magnet group (or any magnet that is utilized, for that matter, whether it is a magnet group or a magnet having polarity that is uniform).

In an exemplary embodiment, the exposure to the magnetic field takes place at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, or 35 or 40 or 45 or 50 or 55 months or years after implantation of the magnet. In an exemplary embodiment, the magnet has at least never effectively never rotated relative to the implanted medical device prior the exposure to the magnetic field. That said, in an alternative embodiment, the magnet has rotated by at least X amount at least Y number of times during that period, were Y is a number that is equal to 5, 10, 15, 20, 25, 30, 35, 40, 45, 50, 55, 60, 65, 70, 75, 80, 85, 90 or 95 percent of the number of days since implantation. The variable X can be any of 1, 2, 3, 4, 5, 6, 7, 8, 9, 10, 11, 12, 13, 14, 15, 20, 25, 30, 35, 40 or 45 degrees or more or any value or range of values therebetween in 1% increments (and can be different for every occurrence and can be the same for some and different for others) again be positive or negative—this is simply a change from one change to the next.

Thus, in an exemplary embodiment, the orientation of the magnet group according to some methods has remained at least substantially constant and/or effectively constant from the time of implantation of the implanted device to the time at least just before exposure to the magnetic field.

It is noted that while the embodiments depicted in FIGS. 6T2 and 6T1 utilize the monolithic magnet group, other embodiments utilize the separate components according to the other teachings detailed herein where they are adhered otherwise supported are held together according to any of the teachings detailed herein or other variations.

Figure 6U:
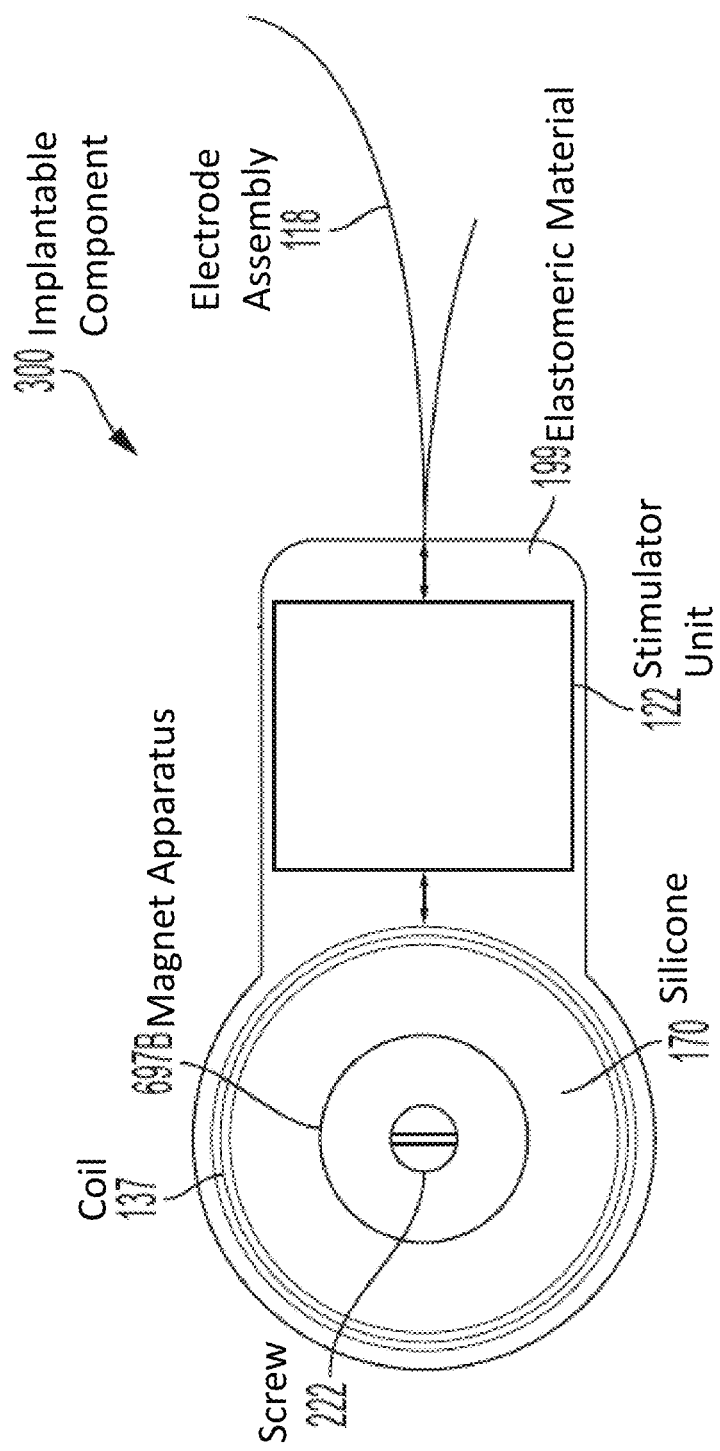

In accordance with the teachings above, it is noted that the embodiments disclosed herein that utilize the magnet groups and/or magnet apparatuses, etc., provide enhanced magnetic attraction relative to that which would otherwise be the case for a similarly situated magnet. In exemplary embodiments, this can result in the magnet on the outside being smaller than that which would otherwise be the case to achieve the same magnetic force. This is utilitarian in that the external component can be lighter and smaller than that which would otherwise be the case. Alternatively, and/or in addition to this, a stronger magnetic attraction can be established between the external component and the implant. In any event, there is the possibility that the implanted component can come into contact with a stronger magnet of an external component or otherwise experience a stronger magnetic field, such as in the case of an MRI, and this might dislodge the implanted component or otherwise impart a torque onto the implant that could cause discomfort to the recipient because skin tissue is resisting/counteracting the torque. Accordingly, the teachings detailed herein with respect to holding the magnet utilizing the screw 222 can be utilitarian. While the embodiments detailed above focused on utilizing a screw to hold the magnet group for a passive transcutaneous bone conduction device according to FIG. 2 above, it is noted that this embodiment can be utilized for the other types of implantable components, such as for example, the implantable portion of the cochlear implant and the implantable portion of the active change continues bone conduction device. For example, FIG. 6U presents the implantable component of the cochlear implant 300, where the magnet group/magnet apparatus/magnet 697B is located in the silicone body, and the magnet group/magnet apparatus/magnet 697B is held to the skull via screw 222 (directly or into a bone fixture). This embodiment can have utilitarian value with respect to maintaining the overall position of the implantable portion during both normal usage and with respect to exposure to high magnetic fields such as, for example, that which could result from the exposure of the recipient to an MRI. To be clear, element 697B can be any of the magnets/magnet groups/magnet apparatuses disclosed herein or variations thereof and can be utilized in conjunction with a housing as detailed above and/or below, or without a housing.

Accordingly, in an exemplary embodiment, the teachings detailed herein can be utilized to maintain a position of the magnet/magnet group/magnet apparatus relatively globally stationary when a magnetic field is applied to the magnet portion of the group/apparatus, etc., at issue, that results in a force that is normal to the longitudinal axis of the magnet group/magnet and away from the skull and/or that is parallel to the longitudinal axis of the magnet group/magnet and thus parallel with the skull of less than, greater than or equal to 1, 2, 3, 4, 5, 6, 7, 8, 9, 10, 11, 12, 13, 14, 15, 16, 17, 18, 19, or 20, or more Newtons or any value or range of values therebetween in 0.1 N increments. With respect to the phrase "globally stationary," it is noted that in at least some embodiments, the magnet group can spin or rotate, such as spin within the housing, and thus the magnet group will be locally movable but will not move relative to its overall position adjacent the skull, etc. Indeed, it is noted that the embodiments described above can be implemented with a housing that has a through hole for the bolt. In this regard, in an exemplary embodiment, there can be a donut-shaped housing or the like that houses the magnet group and/or the magnet apparatus, where the hole of the magnet apparatus extends about the cylindrical passageway through the center of the housing, such that the inside the housing can be hermetically sealed from the external environment while the bolt extends through the housing from one side to the other to attach to the fixture, and thus secure the magnet/magnet group/magnet apparatus.

The above said, embodiments include implant components, such as cochlear implant 300, or, for that matter, receiver stimulators of stimulating prostheses, such as middle ear implants, or bionic eye implants, passive transcutaneous bone conduction devices, etc. (teachings herein are applicable to any such devices or any implantable device unless otherwise noted or otherwise not enabled by the art), that are not affirmatively anchored to the skull of the recipient, or at least do not utilize the bone fixture arrangement detailed above (instead, less substantial screws might be utilized, for example). In some such embodiments, the receiver stimulator is simply located between the skull and the skin and the natural pressure of the skin on the skull holds the receiver stimulator relatively in place, or, in some embodiments, a shallow cavity or more than a shallow cavity is cut into the skull, and the receiver stimulator is located therein. In any event, in at least some exemplary embodiments, the magnet group or magnet apparatus, etc., is not bolted to the skull or otherwise directly attached to the skull.

FIGS. 6U1 and 6U2 presents some exemplary embodiments of such an exemplary embodiment. Here, magnet group 606, which can correspond to the arrangement of FIG. 6M above, by way of example only and not by way of limitation, or the magnet apparatus 636 of FIG. 6R10 can be utilized, again by way of example only and not by way of limitation (any magnet group or apparatus or magnet disclosed herein can be utilized in the embodiments of FIGS. 6U1 and 6U2—these are simply specific examples for purposes of discussion) as the implanted magnetic component. In this exemplary embodiment, the magnet apparatus 606/636 is held within the silicone body 170 by direct contact therewith by the silicone (or by direct contact with a housing housing the components of 606/636, in embodiments where the magnet components/portions of the groups/apparats are housed in a housing—again, any disclosure herein of a magnet group and or magnet apparatus and/or a magnet corresponds to a disclosure of an embodiment where that group/apparatus/magnet is housed in a housing, consistent with the fact that any teaching herein can be combined with any other teaching herein unless otherwise noted providing the art enable such) of the body 170. Note that this is not mutually exclusive with the embodiment of FIG. 6U, where the silicone of the body is also in direct contact with the magnet group/housing thereof—there is just also a bolt that extends through the magnet group as shown above. That said, in some embodiments of the teachings of FIG. 6U, the silicone body is purposely away from the magnet group/magnet apparatus, as seen in FIG. 6U3, where boundary 171 is present completely and circling the boundary of the magnet 697B, in an exemplary embodiment, this can enable easy removal of the magnet 697B without disturbing the overall receiver stimulator. Accordingly, embodiments include implants where the silicone of the silicone body is purposely not in contact with any portion of the magnet/magnet group/magnet apparatus and/or housing thereof.

The above said, in some embodiments, the arrangement of FIG. 6U3 can be such that the boundary 171 of the silicone abuts the outer circumference of the magnet group and/or housing thereof. In this exemplary embodiment, there is no silicone above and/or below the magnet group/housing. This can enable removal of the magnet 697B without disturbing the overall receiver stimulator, while still providing a maximum of silicone to support the coil 137.

In an exemplary embodiment, the boundary 171 is less than greater than or equal to 0.1, 0.2, 0.3, 0.4, 0.5, 0.6, 0.7, 0.8, 0.9, 1.0, 1.1, 1.2, 1.3, 1.4, 1.5, 1.75, 2.0, 2.25, 2.5, 2.75, 3, 3.5, 4, 4.5, or 5 mm or any range of values therebetween in 0.01 mm increments away from the outer circumference of the magnet group/housing thereof. Conversely, in an exemplary embodiment, the boundary 171 establishes an interference fit or a slip fit with the magnet apparatus/housing thereof.

It is noted that while the embodiment of FIG. 6U3 is presented in terms of the utilization of bolt 222, while in other embodiments, the arrangement of FIG. 6U three is combined otherwise utilized with the other embodiments without a bolt.

Still, with respect to the embodiments that utilize the silicone of the body 170 to support the magnet group in its entirety, in an exemplary embodiment, again, the only thing that is in contact with the magnet group/housing thereof is the silicone of the silicone body. In an exemplary embodiment, the implantable component 300 is configured so as to resist movement of the magnet apparatus/magnet group/magnet, housed or otherwise, about the longitudinal axis thereof (the axis extending in and out of the plane of FIG. 6U1, by way of example). Some additional teachings of this will be described in greater detail below. Briefly however, if the magnet is housed in a housing, in this exemplary embodiment, the magnet-housing combination is such that the magnet will not move relative to the housing, at least not without great difficulty or otherwise breaking a component thereof. In an exemplary embodiment, if the magnet is housed in a housing, any movement of the magnet will also correspond to an equal movement of the housing—that is, to the extent anything moves, it is the housing that moves with the magnet (e.g., in a one to one relationship), owing to a torque placed onto the magnet via a stronger magnetic field, such as an MRI field. If the housing is not present, it is the magnet that moves. The aforementioned movement can be rotation about the longitudinal axis just detailed. In these exemplary embodiments, to the extent there is movement, is movement that is due because the magnet group/magnet apparatus/magnet, or the housing thereof, experiences a torque that is high enough to overcome the friction forces between the silicone body and the pertinent components of the magnet group.

Accordingly, in an exemplary embodiment, there is an implant that is configured such that the magnet group/magnet apparatus/magnet, whether or not housed, thereof, will resist rotation about the longitudinal axis thereof/not rotate when subjected to a torque about the longitudinal axis of less than, greater than or equal to 0.1, 0.15, 0.2, 0.25, 0.5, 0.75, 1, 1.25, 1.5, 1.75, 2, 2.5, 2.75, 3, 3.5, 4., 4.5, 5, 5.5, 6, 7, 8, 9, 10, 11, 12, 13, 14, 15, 16, 17, 18, 19, 20, 21, 22, 23, 24, 25, 30, 35, 40, 45 or 50 or 60 or 70 or 80 or 90 or 100 or more inch-pounds or any value or range of values therebetween in 0.05 inch-pound increments. The above said, as with all structures, there is always a certain amount of flexure that exists. In this regard, a concrete block will flex even a limited amount when a person sits on such. Accordingly, it is to be understood that there will be some flexure of the silicone body when the aforementioned torques are applied, and thus some movement, such as rotation, of the magnet group/housing thereof. Accordingly, in an exemplary embodiment, there is an implant that is configured such that the magnet group/magnet apparatus/magnet, whether or not housed, does not rotate more than 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10, 11, 12, 13, 14 or 15 degrees or any value or range of values therebetween in 0.01° increments when exposed to a torque about the longitudinal axis of less than, greater than or equal to 0.1, 0.15, 0.2, 0.25, 0.5, 0.75, 1, 1.25, 1.5, 1.75, 2, 2.5, 2.75, 3, 3.5, 4, 4.5, 5, 5.5, 6, 7, 8, 9, 10, 11, 12, 13, 14, 15, 16, 17, 18, 19, 20, 21, 22, 23, 24, 25, 30, 35, 40, 45 or 50 or 60 or 70 or 80 or 90 or 100 or more inch-pounds or any value or range of values therebetween in 0.05 inch-pound increments. FIG. 6U4 presents another exemplary embodiment where the magnet apparatus includes arms 176 extending from the circumference of the housing of the magnet apparatus, which arms extended into the silicone body 170, and provide further reaction surfaces beyond that which would be the case with respect to the embodiments detailed above against rotation of the housing (or magnet group/magnet apparatus embodiments where there is no housing). In this regard, this embodiment provides additional antirotation features relative to that which is the case with respect to the silicone on the outer circumference of a cylindrical body such as the embodiments detailed above. Here, arms 176 extend greater than less than or equal to 0.25, 0.5, 0.75, 1, 1.5, 2, 2.5, 3, 3.5, 4, 4.5, 5, 6, 7, 8, 9 or 10 mm or more away from the circular wall of the outer circumference of the housing or magnet apparatus, an equivalent length into the body 170. The silicone body 170 envelops these arms and thus provides additional reaction against rotation. For arms are shown in this embodiment, but in other embodiments, fewer more arms can be utilized. By way of example only and not by way limitation, one, two, three, four, five, six, seven, eight, nine, 10, 11, 12, 13, 14, 15 or more arms can be utilized at least some embodiments. Also, it is noted that in at least some exemplary embodiments, the housing of the magnet apparatus and/or the magnet apparatus or group etc., can be rigidly connected to component 122, so as to provide additional antirotation features.

In at least some exemplary embodiments, the height of the arms 176 are about the same as the heights of the housing of the magnet apparatus and where the magnet apparatus, etc. In some embodiments, the height of the arms can be larger while in other embodiments, the height can be smaller. FIG. 6U5 presents an exemplary embodiment where the arms actually extend above and below the housing of the magnet apparatus. Here, arm 176' extends from one side of the housing to the other side of the housing, and has a component that extends over the housing as well (and below, but such cannot be seen). In an exemplary embodiment, the height of the arm 176' (or 176, for that matter) can be such that it is completely enveloped in the silicone body above and below, while in other embodiments, at least a portion of the arm may extend through the silicone body/not be enveloped by the silicone body.

It is noted that while the embodiments detailed above have been presented with the slit 180 present, in some embodiments, the slit 180 is not present.

In any event, it is noted that embodiments include any of the magnet apparatuses disclosed herein or variations thereof housed in a housing, where the magnet apparatus (group or single magnet, etc.) is configured to not rotate relative to the housing, when the magnet apparatus is subjected to a torque about the longitudinal axis of the magnet apparatus of less than, greater than or equal to 0.1, 0.15, 0.2, 0.25, 0.5, 0.75, 1, 1.25, 1.5, 1.75, 2, 2.5, 2.75, 3, 3.5, 4., 4.5, 5, 5.5, 6, 7, 8, 9, 10, 11, 12, 13, 14, 15, 16, 17, 18, 19, 20, 21, 22, 23, 24, 25, 30, 35, 40, 45 or 50 or 60 or 70 or 80 or 90 or 100 or more inch-pounds or any value or range of values therebetween in 0.05 inch-pound increments. Further, in an exemplary embodiment, there is an implant that is configured such that the magnet group/magnet apparatus/magnet does not rotate, relative to the housing more than 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10, 11, 12, 13, 14 or 15 degrees or any value or range of values therebetween in 0.01° increments when exposed to a torque about the longitudinal axis of less than, greater than or equal to 0.1, 0.15, 0.2, 0.25, 0.5, 0.75, 1, 1.25, 1.5, 1.75, 2, 2.5, 2.75, 3, 3.5, 4., 4.5, 5, 5.5, 6, 7, 8, 9, 10, 11, 12, 13, 14, 15, 16, 17, 18, 19, 20, 21, 22, 23, 24, 25, 30, 35, 40, 45 or 50 or 60 or 70 or 80 or 90 or 100 or more inch-pounds or any value or range of values therebetween in 0.05 inch-pound increments. Corollary to the above is that in some embodiments, there is a magnet apparatus/group that rotates in a one to one relationship with the housing relative to the rest of the implant when exposed to a sufficient torque that will cause the magnet apparatus and the housing to rotate relative to the implant.

It is briefly noted that the embodiment of FIG. 6U1 differs from the embodiment of FIG. 6U2 in the orientation of the magnet group 606/636. In the embodiment of FIG. 6U1, the central portion of the magnet group has its long axis parallel to the longitudinal axis of the implant, while in the embodiment of FIG. 6U2, central portion of the magnet group has its long axis perpendicular to the longitudinal axis of the implant. In an exemplary embodiment, the orientation of the central portion vis-à-vis the long axis thereof can be 0, 5, 10, 15, 20, 25, 30, 35, 40, 45, 50, 55, 60, 65, 70, 75, 80, 85 or 90 degrees any value or range of values therebetween in 1° increments from the longitudinal axis of the implant. It is also noted that these orientations can be applicable for any of the alternative embodiments associated with a multi-component magnet apparatus—any definable axis of the magnet apparatus can be aligned, relative to the longitudinal axis, according to the aforementioned values, and in some embodiments, this alignment can be intended to be permanent (i.e., the magnet apparatus is configured not rotate relative to the rest of the implant).

Figure 6V:
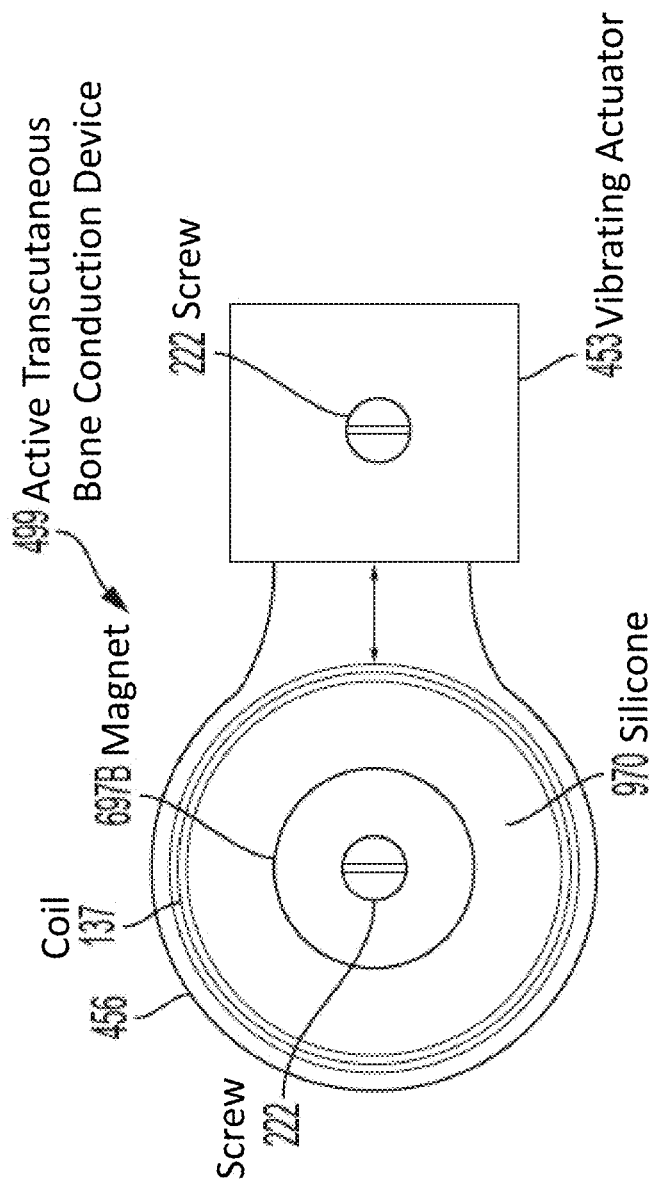

FIG. 6V presents another exemplary embodiment of an implantable component of a hearing prosthesis, the implantable component of an active transcutaneous bone conduction device 499. Here, the receiver assembly 456 includes an RF coil 137 that is supported by or otherwise encased in a silicone body 970, and magnet group 697B that is also encased in the silicone body 970. The magnet group 697B is bolted to the skull via screw 222. Because this embodiment utilizes a separate housing that contains the vibrating actuator (component 453), a second screw 222 is utilized to hold that component down against the skull. As can be seen as represented by the two-way arrow, the coil 137 is in signal communication with component 453, consistent with the teachings detailed above in regard to an active transcutaneous bone conduction device.

Still further, as can be seen, at least some exemplary embodiments are configured to be implanted into a recipient without intent to be removed. In some instances, there is intent to not remove the magnet group even when exposed to high strength MRI fields. In some embodiments, there are methods that include exposing the recipient's head to at least about (and including a 1.5, 2, 2.5, 3, 3.5, 4, 4.5, 5, 5, 5, 6, 7, 8 9 T or more MRI magnetic field without removing the magnet group from the recipient. In some embodiments, this is done without applying any additional restraints, such as a bandage and/or splint to hold the magnet in place. Indeed, in an exemplary embodiment, the screw 222 eliminates any need for such.

Accordingly, now with reference to FIG. 12, which presents an exemplary flowchart for an exemplary algorithm for an exemplary method, method 1200, there is an exemplary method in an exemplary embodiment, there is an exemplary method that includes method action 1210 which includes obtaining access to a recipient of a medical device including a magnet group implanted in the recipient. Method 1200 also includes method action 1220, which includes exposing the recipient and the magnet group to an MRI field of at least 2.5 T without removing the magnet group. In a variation of this method, the MRI field is at least 1, 1.5, 2, 2.25, 2.5, 2.75, 3, 3.25, 3.5, 3.75, 4, 4.25, 4.5, 4.75, or 5 T or any value or range of values therebetween in 0.1 T increments.

In an exemplary embodiment of this method, consistent with the teachings detailed above the magnet group is positively retained to the skull via a screw, such as screw 222. Also, as noted above, in at least some exemplary embodiments, there is no external component that applies pressure to the skin or otherwise holds the magnet in place, such as a bandage or a splint. In at least some exemplary embodiments, this is enabled via the utilization of the screw 222. In an exemplary embodiment, when the magnet group is subjected to the aforementioned fields, the global position of the magnet changes no more than 0.05, 0.06, 0.07, 0.08, 0.09, 0.1, 0.11, 0.12, 0.13, 0.14, 0.15, 0.175 0.2, 0.25, 0.3, 0.35, 0.4, 0.45, 0.5, 0.6, 0.7, 0.8, 0.9 or 1 mm measured at a given point relative to that which was the case prior to exposure to the aforementioned magnetic field. In an exemplary embodiment, the recipient is wearing nothing on his or her head during the entire time of exposure to the aforementioned MRI field strengths.

Accordingly, now with reference to FIG. 13, which presents an exemplary flowchart for an exemplary algorithm for an exemplary method, method 1300, there is an exemplary method in an exemplary embodiment, there is an exemplary method that includes method action 1310 which includes obtaining access to a recipient of a medical device including a magnet group implanted in the recipient. Method 1300 also includes method action 1320, which includes exposing the recipient and the magnet group to an MRI field of at least 2.5 T without removing the magnet group and without anything being worn on the recipient's head or attached to the recipient's head. In a variation of this method, the MRI field is at least 1, 1.5, 2, 2.25, 2.5, 2.75, 3, 3.25, 3.5, 3.75, 4, 4.25, 4.5, 4.75 or 5 T or more any value or range of values therebetween in 0.1 T increments.

An exemplary method also includes implanting the implantable component into the recipient. Accordingly, now with reference to FIG. 14, which presents an exemplary flowchart for an exemplary algorithm for an exemplary method, method 1400, there is an exemplary method in an exemplary embodiment, there is an exemplary method that includes method action 1410 which includes implanting a medical device with a magnet group in a head of the recipient. In an exemplary embodiment, this is executed by cutting into the recipient at a location above the mastoid bone or other skull bone and placing any of the implantable medical devices disclosed herein or variations thereof or other medical devices into the opening. In an exemplary embodiment where the magnet group is screwed to bone, an exemplary embodiment includes placing a torque applying device, such as a screwdriver an Allen wrench, etc. through a slit in the silicone that covers the magnet group. By way of example only and not by way of limitation, with respect to FIG. 6W1, it can be seen that in an exemplary embodiment of the implantable component 300 of the cochlear implant, there is a slit 180A that extends through the silicone body 170 that encases the magnet group 697B, in an exemplary embodiment, the implantable component 300 can be placed over a bone fixture and the screw 222 is aligned with the bone fixture, and the torque is applied to the screw 222 using the tool extending to the slit 180A to screw the screw 222 into the bone fixture and thus secure and otherwise fix the magnet group 697B to the skull. In an exemplary embodiment, the silicone body is formed around the magnet group (and a housing if the magnet group is located in the housing), such that the screw 222 extends through the bottom of the silicone body. In an exemplary embodiment, the slit is large enough so that the tool can pass through, but no more. This is because the magnet group 697B is not intended to be removed from the implantable component 300 during the life of the implantable component, at least not while the implantable component is implanted into the recipient. That is, to the extent that the magnet group 697B is to be removed from the head or otherwise body of the recipient, the screw 222 is unscrewed from the bone (bone fixture) and the entire implantable component is removed.

That said, in some alternate embodiments, the implantable component 300 is configured so that the magnet group 697B can be removed (along with a housing if the magnet group is located in a housing) from the implantable component 300 while the implantable component remains in the recipient's head or otherwise in the body. In this regard, in an exemplary embodiment, referring now to FIG. 6W2, there is a larger slit 180B that is large enough to enable the magnet group 697B and any housing associated there with to be removed from the silicone body 170 when the screw 222 is unscrewed. In an exemplary embodiment, the aforementioned slits are, in length less than, equal to or greater than 70, 75, 80, 85, 90, 95, 100, 105, 110, 115, 120, 125, 130, 135, 140, or 145 percent, or any value or range of values therebetween in 1% increments of the maximum and/or minimum diameter normal to the longitudinal axis of the screw and or the tool that is utilized to unscrew or screw the screw and/or the magnet group 697B and/or the housing that houses the magnet group 697B.

Continuing with reference to FIG. 14, method 1400 further includes method action 1420, which includes obtaining access to a recipient of a medical device including a magnet group implanted in the recipient. Method 1400 also includes method action 1430, which includes exposing the recipient and the magnet group to an MRI field of at least 2.5 T without removing the magnet group. In a variation of this method, the MRI field is at least 1, 1.5, 2, 2.25, 2.5, 2.75, 3, 3.25, 3.5, 3.75, 4, 4.25, 4.5, 4.75 or 5 T or any value or range of values therebetween in 0.1 T increments.

Superimposed onto the magnet group 697B of FIG. 6R are dimension values D3, D4 and D5. D3, D4, and/or D5 can be individually or collectively more than, less than or equal to 0.1, 0.2, 0.3, 0.4, 0.5, 0.6, 0.7, 0.8, 0.9, 1.0, 1.1, 1.2, 1.3, 1.4, 1.5. 1.6. 1.7, 1.8. 1.9, 2.0, 2.1, 2.2, 2.3, 2.4, 2.5, 2.6. 2.7, 2.8, 2.9, 3.0, 3.5, 4, 4.5, 5, 5.5, 6, 7, 8, 9 or 10 or 11 or 12 or 13 or 14 or 15 or 16 or 17 or 18 or more mm or any value or range of values therebetween in 0.01 mm increments (e.g., 1.12 mm to 4.44 mm, 3.55 mm, 5.44 mm, etc.). It is noted that the aforementioned values can be applicable to the other shaped magnets, such as the rectangular shape and square shape. In this regard, diameters normal to the distances of FIG. 6R can be less than, greater than or equal to 1.0, 1.1, 1.2, 1.3, 1.4, 1.5. 1.6. 1.7, 1.8. 1.9, 2.0, 2.1, 2.2, 2.3, 2.4, 2.5, 2.6. 2.7, 2.8, 2.9, 3.0, 3.5, 4, 4.5, 5, 5.5, 6, 7, 8, 9 or 10 or 11 or 12 or 13 or 14 or 15 or 16 or 17 or 18 or 19, or 20, or 21, or 22, or 23, or 24, or 25 or 26 or 27 or 28 or 29 or 30 or 31 or 32 or 33 or 34 or 35 or 36 or 37 or 38 or 39 or 40 or more mm or any value or range of values therebetween in 0.01 mm increments.

Consistent with the teachings detailed above, in at least some exemplary embodiments, the magnet group is configured to spin or otherwise rotate within the housing or otherwise relative to the other components of the implantable device when exposed to a magnetic field. In an exemplary embodiment, the spinning/rotation can be less than equal to or greater than 10, 15, 20, 25, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, or 360 degrees or more, or any value or range of values therebetween in 1° increments from the orientation that was present prior to the exposure to the magnetic field. This magnetic field to which the implanted magnet is exposed can be a magnetic field that is less than, greater than and/or equal to 0.5, 0.6, 0.7, 0.8, 0.9, 1, 1.1, 1.2, 1.3, 1.4, 1.5, 1.75, 2, 2.25, 2.5, 2.75, 3, 3.5, 4, 4.5, 5, 5.5, 6, 6.5, 7, 8, 9, 10, 11, 12, 13, 14, 15, 20, 25, 30, 35, 40, 45, 50, 60, 70, 80, 90, 100, 125, 150, 175, 200, 225, 250, 275, 300, 350, 400, 450, 500, 550, 600, 700, 800, 900, or 1000 times or more (or any value or range of values therebetween in 0.1 increments) stronger than the magnetic field generated by the implantable magnet group or magnet, and/or when exposed to a magnetic field that is less than, equal to and/or greater than 0.25, 0.5, 0.75, 1, 1.25, 1.5, 1.75, 2, 2.5, 2.75, 3, 3.5, 4., 4.5, 5, 5.5, 6 or more Tesla or any value or range of values therebetween in 0.05 increments) as measured at a location 0.5, 0.75, 1, 1.5, or 2 inches away from the implantable magnet/magnetic group. In an exemplary embodiment, the magnet will spin (or perhaps rotate is a better word, as the magnet will likely not complete a 360 degree rotation) when exposed to any of these magnetic fields, while in other embodiments the magnet will not rotate when exposed to any of those fields, while in other embodiments, the magnet will only rotate when exposed to a magnetic field that is the same as or stronger than one or more of those detailed and will not rotate when exposed to a lower strength field. In an exemplary embodiment, the bushing and/or the screw 222 can be splined or keyed such that it interfaces with the magnet group or the housing enclosing the magnet so that the magnet group will not rotate. In an alternate embodiment, it is the clamping force between the head of the screw and the magnet group/housing that houses the magnet group that prevents the magnet group from rotating.

In an exemplary embodiment, the bone fixture can have a spline or a key that interacts with the magnet group and/or the housing that prevents the magnet group and/or housing from rotating.

In an exemplary embodiment, the magnet group and/or the housing enclosing the magnet group is configured to resist rotation/not rotate when subjected to a torque about the longitudinal axis of the group of at least 0.1, 0.15, 0.2, 0.25, 0.5, 0.75, 1, 1.25, 1.5, 1.75, 2, 2.5, 2.75, 3, 3.5, 4., 4.5, 5, 5.5, 6, 7, 8, 9, 10, 11, 12, 13, 14, 15, 16, 17, 18, 19, 20, 21, 22, 23, 24, 25, 30, 35, 40, 45 or 50 or 60 or 70 or 80 or 90 or 100 or more inch-pounds or any value or range of values therebetween in 0.05 inch-pound increments. Thus, as can be seen from the above, in an exemplary embodiment, there is an apparatus that is configured such that the magnet group resists rotation as a unit relative to the housing about an axial direction with respect to a first torque range applied about the axial direction to the magnet group and enables rotation as a unit relative to the housing about the axial direction with respect to a second torque range that has components that are substantially larger than the components of the first torque range. The torque ranges can be any values within the above-noted ranges in 0.05 inch-pound increments.

Also, there is an implant that is configured such that the magnet group/magnet apparatus/magnet, does not rotate relative to the housing more than 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10, 11, 12, 13, 14 or 15 degrees or any value or range of values therebetween in 0.01° increments when exposed to a torque about the longitudinal axis of less than, greater than or equal to 0.1, 0.15, 0.2, 0.25, 0.5, 0.75, 1, 1.25, 1.5, 1.75, 2, 2.5, 2.75, 3, 3.5, 4., 4.5, 5, 5.5, 6, 7, 8, 9, 10, 11, 12, 13, 14, 15, 16, 17, 18, 19, 20, 21, 22, 23, 24, 25, 30, 35, 40, 45 or 50 or 60 or 70 or 80 or 90 or 100 or more inch-pounds or any value or range of values therebetween in 0.05 inch-pound increments.

Thus, as can be seen, in an exemplary embodiment, there is an implantable medical device, comprising a magnet (which can be a magnet portion of a magnet group, or a monolithic magnet disk, etc.) and a body encompassing the magnet. In an exemplary embodiment, the implantable medical device is configured to enable the magnet to rotate. In an exemplary embodiment, this rotation is enabled, with respect to exposure to a magnetic field, only under a magnetic field that is stronger than at least 1.1, 1.2, 1.3, 1.4, 1.5, 1.75, 2, 2.25, 2.5, 2.75, 3, 3.5, 4, 4.5, 5, 5.5, 6, 6.5, 7, 8, 9, 10, 11, 12, 13, 14, 15, 20, 25, 30, 35, 40, 45, 50, 60, 70, 80, 90, 100, 125, 150, 175, 200, 225, 250, 275, 300, 350, 400, 450, 500, 550, 600, 700, 800, 900, or 1000 or more, or any value or range of values in 0.01 increments times the magnetic field generated by the magnet. In an exemplary embodiment, the body is a case and the rotation is rotation relative to the case. In an exemplary embodiment, the case is a titanium case that has a rectangular cross-section that is slightly larger than the magnet that is located therein. An exemplary embodiment, this can be a plastic case such is made out of PEEK. In an exemplary embodiment, the case can have a nonrectangular cross-section and can be any shape that can enable utilitarian teachings detailed herein. In an exemplary embodiment, there is an apparatus, that includes the implantable medical device and an external component including a second magnet, wherein the external component is held proximate the implantable medical device via magnetic attraction between the magnet and the external magnet. In an exemplary embodiment, the implantable component is configured such that the external component can be rotated 90, 180, 270, or 360 degrees relative to the implantable medical device when the two components are within 1, 2, 3, 4, 5, 6, 7, 8, 9, 10, 11, 12, 13, 14, or 15 mm of each other or any value or range of values therebetween without the magnet in the implantable component rotating relative to the body and/or the remainder of the implantable medical device, the rate of rotation being no more than 5, 10, 15, 20, 25, 30, 35, 40, 45, 50, 55, or 60 degrees per second. In an exemplary embodiment, the implantable component is configured such that the external component can be rotated 90, 180, 270 or 360 degrees relative to the implantable medical device when the two components are within 1, 2, 3, 4, 5, 6, 7, 8, 9, 10, 11, 12, 13, 14, or 15 mm of each other with the magnet in the implantable component rotating relative to the body and/or the remainder of the implantable medical device no more than 1, 2, 3, 4, 5, 6, 7, 8, 9, or 10 degrees, the rate of rotation being no more than 5, 10, 15, 20, 25, 30, 35, 40, 45, 50, 55, or 60 degrees per second. In an exemplary embodiment, the implantable component is configured such that a magnet having a force at least 2, 3, 4, 5, 6, 7, 8, 9, 10, 11, 12, 13, 14, 15, 16, 17, 18, 19, 20, 25, 30, 35, 40, 50, 60, 70, 80, 90, 100, 125, 150, 175, 200, 300, 400, or 500 or more, or any value or range of values therebetween in integer increments of the implanted magnet can be rotated 90, 180, 270, or 360 degrees relative to the implantable medical device when the two components are within 1, 2, 3, 4, 5, 6, 7, 8, 9, 10, 11, 12, 13, 14, or 15 mm of each other or any value or range of values therebetween without the magnet in the implantable component rotating relative to the body and/or the remainder of the implantable medical device, the rate of rotation being no more than 5, 10, 15, 20, 25, 30, 35, 40, 45, 50, 55, or 60 degrees per second. In an exemplary embodiment, the implantable component is configured such that the aforementioned magnet can be rotated 90, 180, 270, or 360 degrees relative to the implantable medical device when the two components are within 1, 2, 3, 4, 5, 6, 7, 8, 9, 10, 11, 12, 13, 14, or 15 mm of each other with the magnet in the implantable component rotating relative to the body and/or the remainder of the implantable medical device no more than 1, 2, 3, 4, 5, 6, 7, 8, 9, or 10 degrees, the rate of rotation being no more than 5, 10, 15, 20, 25, 30, 35, 40, 45, 50, 55, or 60 degrees per second. It is noted that in some embodiments, the aforementioned magnet is generating a magnetic field that is aligned and results in a pulling force, including a maximum pulling force, towards the implantable magnet.

It is noted that in some embodiments, any of the above can also correspond to the features of the magnet of the external device.

In some embodiments, the implantable medical device and/or the external medical device is configured to enable the respective magnet to rotate only under very strong external magnetic fields.

In an exemplary embodiment, there is an implantable medical device, wherein the body is an enclosure that at least partially encloses the magnet. Also, designed friction between the body and/or a component within the body and the magnet prevents the magnet from rotating under a magnetic field that is not as strong as the magnetic field that causes the magnet to rotate. In an exemplary embodiment, pressure force exerted by the body directly and/or indirectly onto the magnet prevents the magnet from rotating under a magnetic field that is not as strong as the magnetic field that causes the magnet to rotate. By designed friction, it is meant friction that is clearly purposely imparted to increase the torque needed to begin rotation, as opposed to friction that exists simply because there is friction in everything.

Figure 20B:
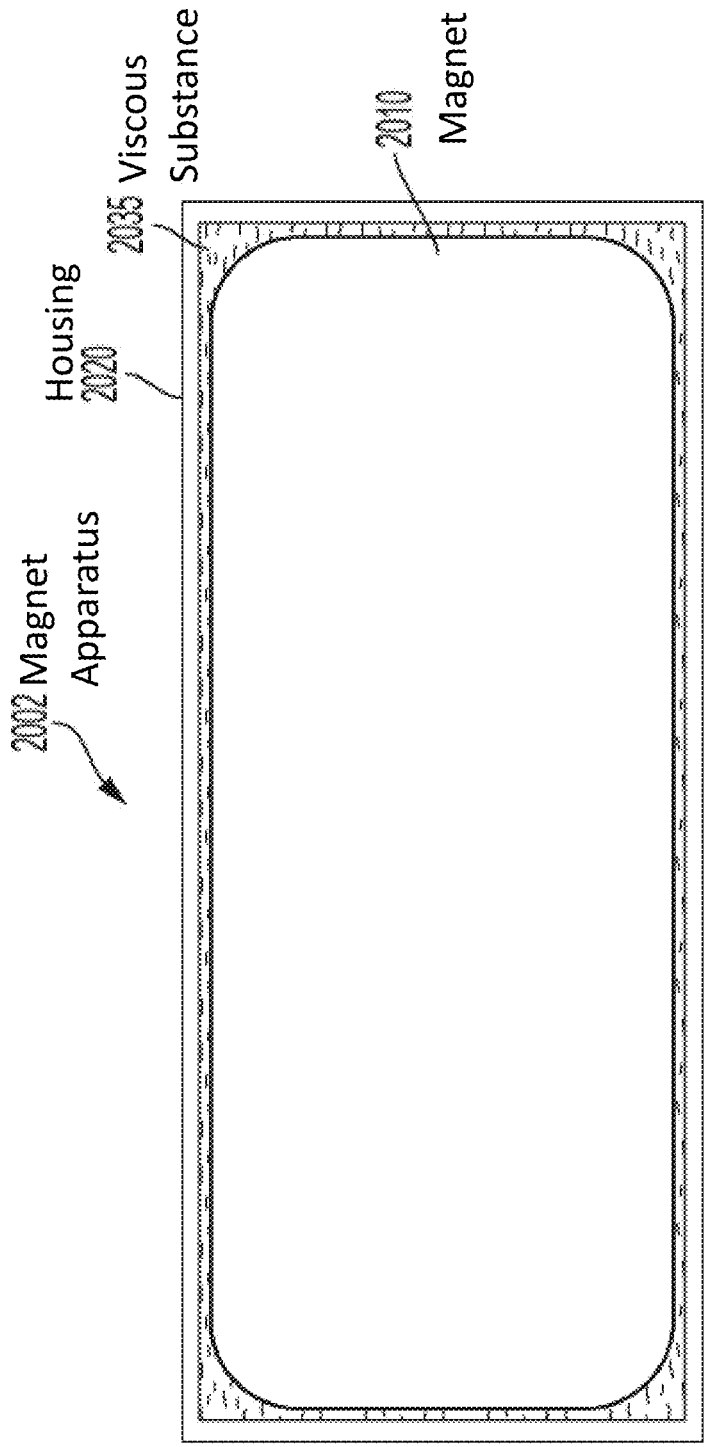

FIG. 20B presents an exemplary embodiment of a magnet apparatus 2001 that includes a magnet 2010 (which can be instead a magnet group—more on this below) located in a housing 2020 that hermetically isolates the interior of the housing from the outside environment. In an exemplary embodiment, a viscous substance 2035, such as a viscous fluid, is located inside the housing, and otherwise, in combination with the magnet, fills the interior of the housing or otherwise substantially fills are effectively fills the interior of the housing. In an exemplary embodiment, results in a design friction that is higher than that which would otherwise be the case. This enables the magnet 2010 to rotate within the housing with more difficulty. In an exemplary embodiment, the magnet 2010 can instead be a magnet group or magnet apparatus according to any of the teachings detailed herein. Again, in an exemplary embodiment, such as where there are three separate components, the magnet group can be encased in a second housing (not shown) or in a membrane or in a sealed environment to isolate the magnet components from the fluid inside the housing. Note also that in some embodiments, the extra-membrane or the sealing or the extra housing can also be utilized with the monolithic magnet as well.

In an exemplary embodiment, the substance 2035 can be a gel. In an exemplary embodiment, the substance 2035 can be a particulate matter, such as sand or a powder or a grit material that is "packed" into the spaces between the magnet in the housing (or the housing, for example, that houses the magnet inside the housing 2020) that otherwise increases the design friction and thus makes it more difficult for the magnet 2010 (or magnet group or magnet apparatus), with or without the additional housing, to rotate within the housing 2035.

FIG. 21 presents an alternative exemplary embodiment of the magnet apparatus where the magnet 2010 is resting on the bottom of the housing 2020. The embodiment of FIG. 21 can be utilized with a lubricant 2030 and/or a viscous substance 2035 or any other substance that can increase the friction between the two components. In an exemplary embodiment, the bottom surface of the housing can be a low friction surfaces while in other embodiments the bottom surface of the housing can be a high friction surface in an exemplary embodiment, the housing can press down upon the magnet to push the magnet down onto the bottom surface of the housing (the housing can be bowed downward, or can have a portion that extends down to the magnet). Alternatively, and/or in addition to this, a component can be located between the magnet and the housing that applies the force on to the magnet to push the magnet onto the bottom surface. In an exemplary embodiment, this component can be held in place by the magnet and/or by the housing. In an exemplary embodiment, it can be attached to one or both.

That said, in an exemplary embodiment, the position of the magnet is simply that which results from gravity or the like or otherwise as a result of meniscus forces.

FIG. 22 presents an exemplary embodiment that utilizes a bearing 2040 to enable rotation of the magnet 2010 in the housing 2020. In an exemplary variation of the embodiment of FIG. 22, a substance 2035 can be located in the housing, which substance increases the friction and otherwise resist rotation of the magnet 2010 in the housing 2020. Thus, by utilizing the bearing 2040 so that the magnet can rotate easily relative to the housing, the combination of the substance 2035 and the bearing permits the rotational features of the magnet relative to the housing to be controlled in a more defined manner relative to that which would otherwise be the case in the absence of the bearing 2040. Of course, in embodiments where it is desired to have low friction and thus enable the magnet to relatively rotate freely, the bearing itself can be utilized. The bearing can be a ball bearing or an oilite bearing (body impregnated with a lubricating substance) or can be a roller bearing, etc. Any bearing that can enable the magnet to rotate relatively easily can be utilized at least some exemplary embodiments. FIG. 23 presents an alternate exemplary embodiment utilizing a support structure 2045. The support structure is a high friction material and thus resists movement of the magnet 2010 relative to the housing 2020. In an exemplary embodiment, structure 2045 can be a rubber disk, rubber block, etc. Indeed, in some embodiments, structure 2045 can be a frangible body that breaks upon the application of a given torque indeed, in an exemplary embodiment, structure 2045 can be a clutch like mechanism that prevents rotation of the magnet relative to the housing up until a certain torque is applied, and then permits the rotation.

FIG. 24 presents an exemplary embodiment where there is no viscous or lubricant substance in the housing, and the only components other than gas located in the housing that create the link between the magnet 2010 and the housing 2020 is the bearing 2040, or the movement resisting structure 2045. In an exemplary embodiment, structure 2045 can be a gooey substance that permits some rotation of the magnet 2010 relative to the housing 2020 (e.g., no more than 1, 2, 3, 4, 5, 6, 7, 8, 9, 10 degrees, for example), when subjected to a torque/torque within a given range, and then permits more rotation (more than 10, 20, 30, 40, 50 degrees or more) when that torque is exceeded. By way of example, this can enable a little bit of give (rotation) for low torques, and then total rotation for the larger torques.

FIG. 25 presents an alternate exemplary embodiment of the magnet apparatus 2004, which utilizes fiction components 2050. In an exemplary embodiment, friction component 2050 is interference fitted between the outer circumference that rotates at the highest velocity of the magnet 2010 and the housing wall. Depending on the surface area of this component and/or the amount of friction fit (where the magnet 2010 is radially held in place so that the friction component 25 zero does not simply push the magnet to the side), a desired torque resistance regime can be achieved. In an exemplary embodiment, the friction component 2050 can be a cylindrical rod that can be fixed to the magnet and/or the housing by way of adhesive, welding, or a divot/detent in one of the housing of the magnet (or both—in an alternate embodiment, the divot/detent can be such that it requires a certain torque to be applied before the cylinder "pops out" of the divot/detent). In an exemplary embodiment the friction components 2050 can be arcuate bodies that are contrary to the inner surface of the housing and the outer surface of the magnet 2010 over a certain percentage of the overall 360° of the interior of the housing (like a drum brake assembly), the greater the extension in the axial and/or radial direction, the greater the friction and thus the higher torque that is required to commence rotation. In an exemplary embodiment, the friction component can be an asbestos component and/or can be a component that is the same as a brake pad in an automobile (this can also be the case with respect to the component 2045 detailed above). The friction component 2050 can be a rectangular cross-section beam that is interference fitted between the housing and the magnet. In an exemplary embodiment, a plurality of friction component 2050 can be interference fitted between the magnet and the housing.

Figure 26:
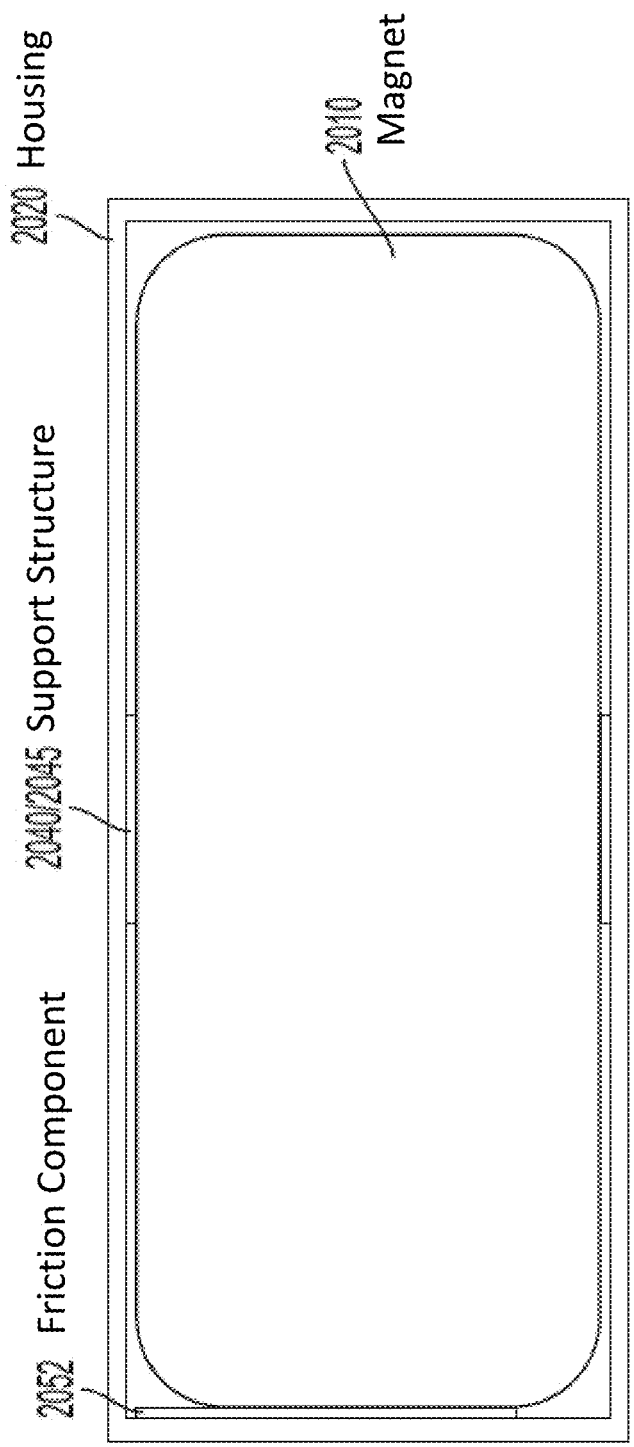
Figure 27:
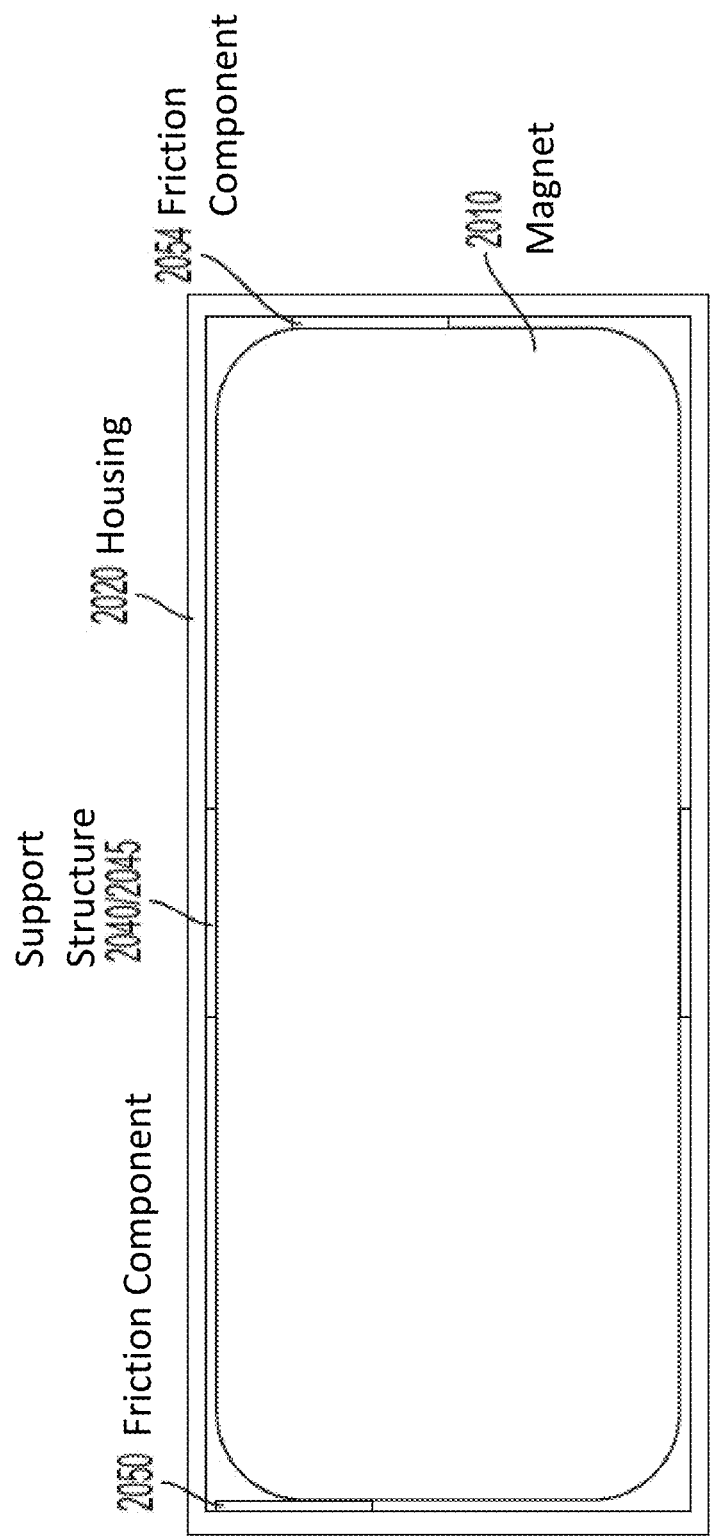

FIG. 26 presents an alternate exemplary embodiment where a longer friction component 2052 is located between the housing and the magnet 2010. Because the component is longer than that of the embodiment of FIG. 25, there will be more friction surface between the two components, and thus a larger torque will be required to commence rotation relative to that of FIG. 25. The embodiment of FIG. 27 presents yet alternate exemplary embodiment where there are two friction components 2050 and 2054 that are shown. Here, the lengths and the positions can be varied to vary the amount of torque that is required to commence rotation of the magnet. Any arrangement of section components that can enable the teachings detailed herein can be utilized at least some exemplary embodiments.

Figure 28:
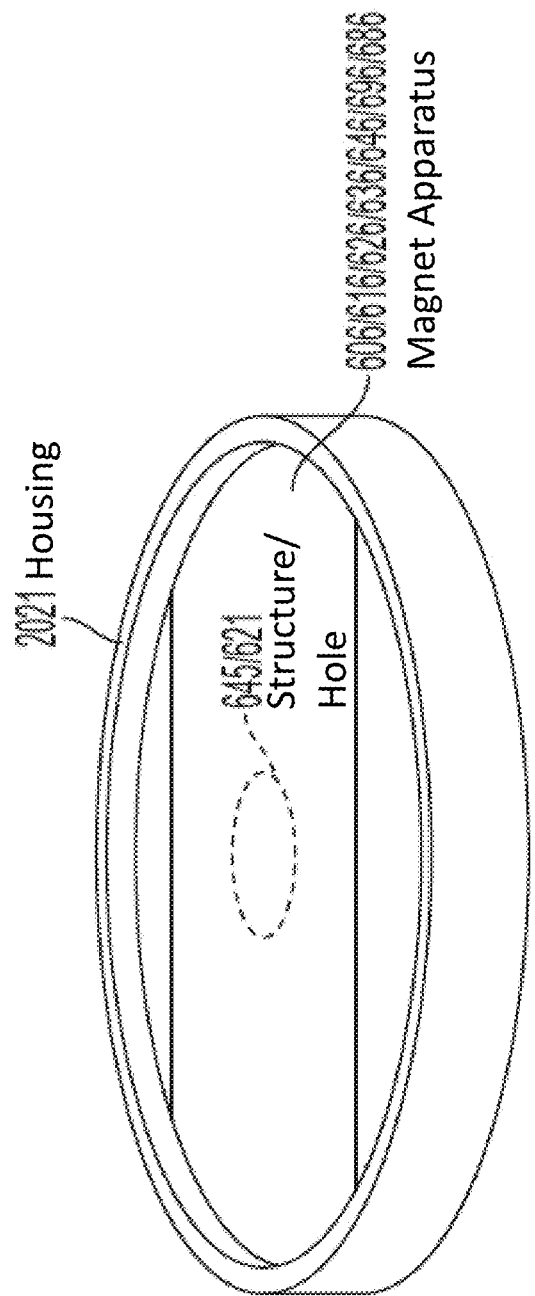
FIG. 28 presents an isometric view of an exemplary embodiment.

FIG. 28 depicts an isometric view of an exemplary embodiment of a magnet apparatus according to any of the embodiments above in a housing 2021, with the top of the housing removed/not shown, for clarity, where the housing 2021 can be any of the housing detailed herein and/or variations thereof.

In an exemplary embodiment, the magnet apparatuses located in the housing are configured, or, more accurately, the assembly is configured to enable the magnet apparatus inside the housing to rotate relative to the housing about the longitudinal axis of the apparatus/about an axis that is normal to the skin of the recipient when implanted therein. That said, in an alternate embodiment, the magnet apparatuses located in the housing, or, more accurately, the assembly is configured to prevent the magnet apparatus inside the housing from rotating relative to the housing about the longitudinal axis. In some embodiments, the assembly is configured to prevent the magnet apparatus inside the housing from rotating relative to the housing about the longitudinal axis for certain torques, but above a certain level or when exposed to other torques, the magnet apparatus can rotate relative to the housing (at least if the housing is held fixed or otherwise there is something that can resist rotation of the housing, such as, for example, the interaction of the silicone body of the implant with the outside of the housing).

In some exemplary embodiments, there is metal on metal contact between the magnet portion(s) and the housing. In an exemplary embodiment, a coating and/or a lubricant is provided so as to reduce the friction between the two components. In an exemplary embodiment, the magnet apparatuses can be interference fitted into the housing so as to create an assembly where the magnet apparatus will not rotate relative to the housing. In an exemplary embodiment, the magnet apparatuses can be interference fitted in the housing so as to create an assembly where the magnet apparatus will only rotate relative to the housing if a sufficient torque is applied. In an exemplary embodiment, the magnet apparatuses can be slipped fitted into the housing so as to create an assembly where the magnet apparatus will rotate relative to the housing, where, in some embodiments, only if a sufficient torque is applied, while in other embodiments, even if a relatively de minimis torque is applied that simply provides sufficient inertia to get the magnet apparatus to rotate (analogous to the minimum forces needed to have a car wheel rotate—it is designed to rotate, and, in fact, is designed to be as low friction as possible, but there is still a relatively de minimis amount of force that is needed to get the wheel to rotate).

In an exemplary embodiment, the maximum outer diameter of the magnet apparatus is less than the minimum inner diameter of the housing chamber. In an exemplary embodiment, this configuration can enable the magnet apparatus to rotate relative to the housing.

In an exemplary embodiment, the maximum outer diameter of the magnet apparatus can be Z % of the minimum diameter of the chamber of the housing in which the magnet apparatus is located, in a plane normal to the longitudinal axis of the apparatus, where Z can be 90, 91, 92, 93, 94, 95, 96, 97, 98, 99, 100, 101, 102, 103, 104, 105, 106, 107, 108, 109, 110, or any value or range of values therebetween in 0.01 increments.

Figure 29:
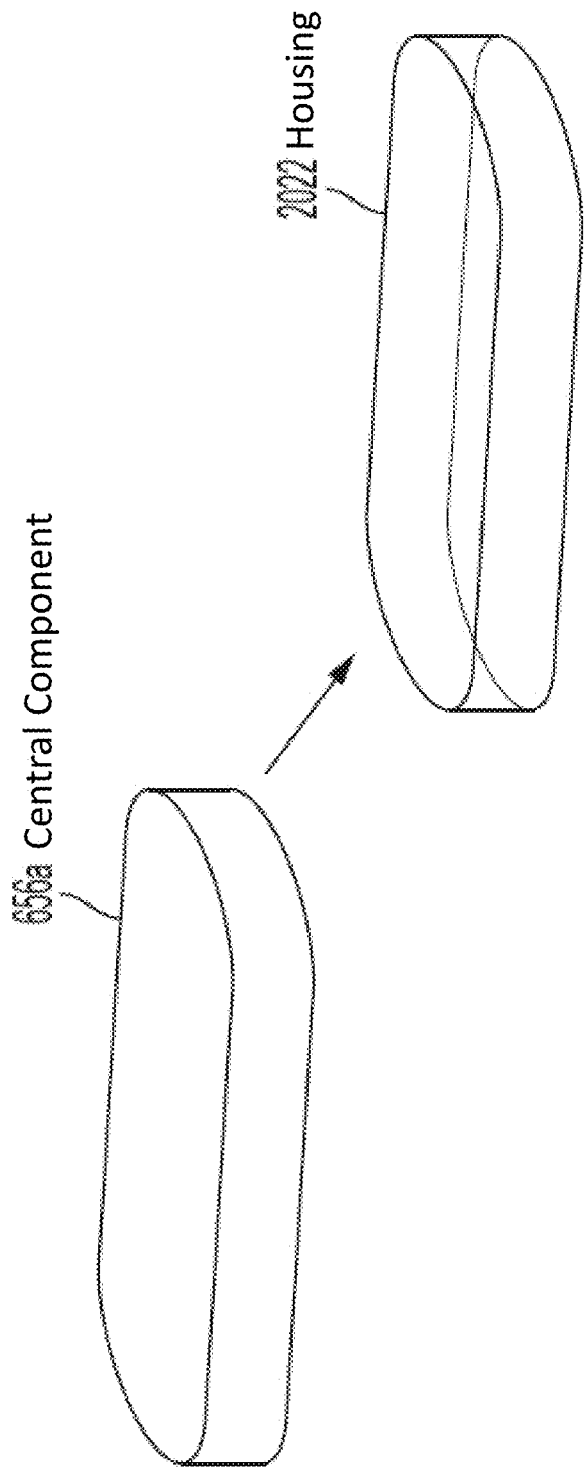
FIGS. 29-32 present some graphics associated with some exemplary embodiments.

FIG. 29 presents an exemplary embodiment that utilizes a racetrack shaped housing that houses only the central portion. Here, the racetrack shaped central portion 656*a* or otherwise any utilitarianly shaped central portion (the central portion can be a bar shaped element—this is also the case with the embodiments above) can be placed into a hermetic housing 2022 that is in the shape of a racetrack (cross-section). The fit can be interference, slip or clearance, and an adhesive and/or a filler material can be located between the central portion and the walls of the housing, if such is utilitarian, such as to prevent the central portion from rattling or otherwise moving relative to the housing 2022 (other embodiments that provide anti-rattling are described below). Then, with respect to FIG. 30, the racetrack shaped housing 2022 is combined with the flanking portions 636*b*, and then is placed into a housing 2023, which can be plastic, metal, etc., and may or may not be hermetically sealed. Any of the connection techniques between the flanking portions and the central portion detailed herein can be utilized in at least some exemplary embodiments. While the racetrack shaped housing is disclosed, in an exemplary embodiment, any shape housing that can have utilitarian value can be utilized in at least some exemplary embodiments. In an exemplary embodiment, the embodiments of FIGS. 29 and 30 reduce the metal footprint inside the coil (e.g., where implemented in a cochlear implant, or an active transcutaneous bone conduction device) to reduce the impact on the RF link. In an exemplary embodiment, the strength of the RF link is at least 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 350, 400, 450, or 500% in the absence of these teachings, all other things being equal. The housing can be metallic or can be on the other material that can have utilitarian value. The hermetic housing can be metallic, and the housing that is utilized to encase the sub-assembly with the moons can be non-metallic.

Figure 31:
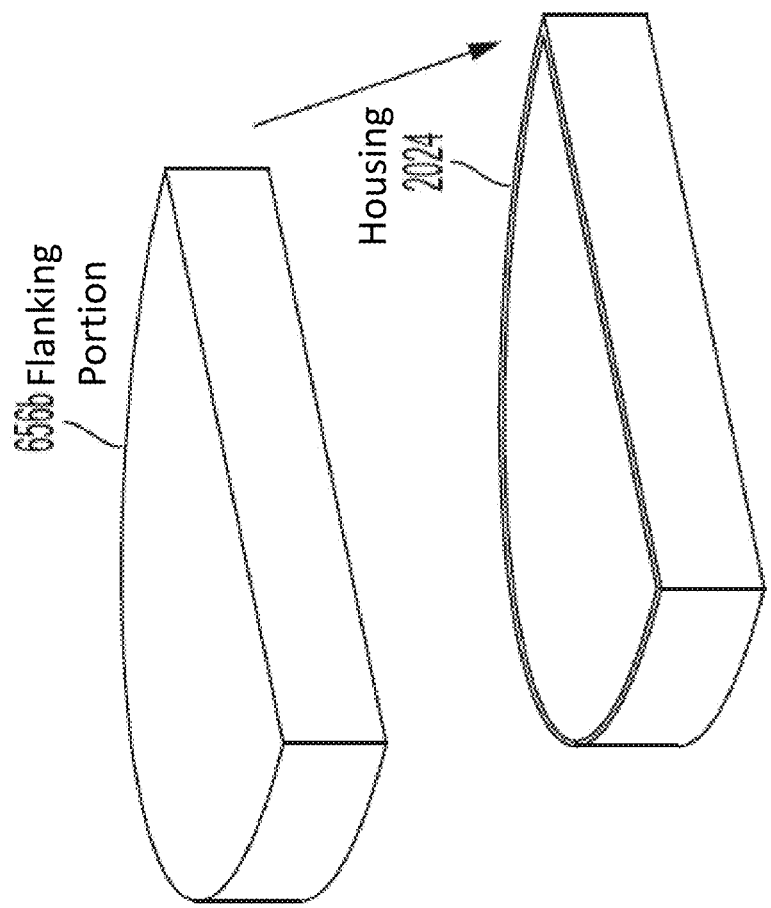

FIG. 31 presents an exemplary embodiment that utilizes moon-shaped housings that respectively houses only the flanking portions. Here, the moon shaped flanking portions 656b otherwise any utilitarianly shaped central portions can be placed into a hermetic housing 2024 that is in the shape of half-moon (cross-section). The fit can be interference, slip or clearance, and an adhesive and/or a filler material can be located between the flanking portion and the walls of the housing, if such is utilitarian, such as to prevent the central portion from rattling or otherwise moving relative to the housing 2024. Then, with respect to FIG. 32, the racetrack shaped housing 2024 is combined with the central portion 656a, and then is placed into a housing 2023, which can be plastic, metal, etc., and may or may not be hermetically sealed. Any of the connection techniques between the flanking portions and the central portion detailed herein can be utilized in at least some exemplary embodiments. While the moon-shaped housings are disclosed, in an exemplary embodiment, any shape housing that can have utilitarian value can be utilized in at least some exemplary embodiments. In an exemplary embodiment, the embodiments of FIGS. 31 and 32 reduce the metal footprint inside the coil.

Figure 30:
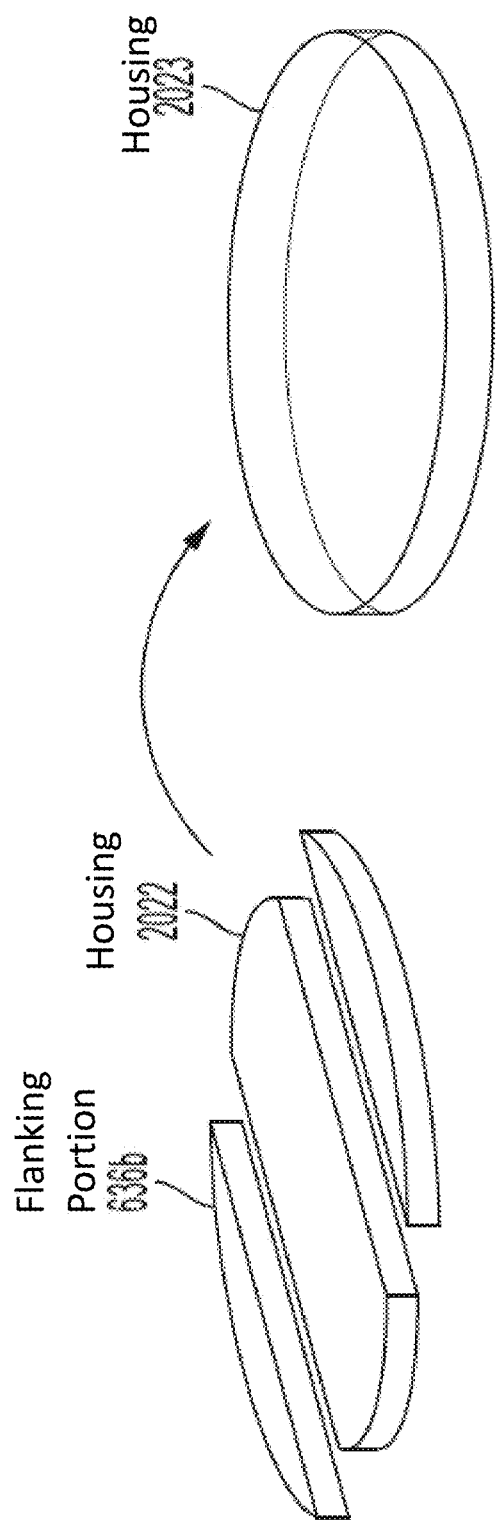
Figure 32:
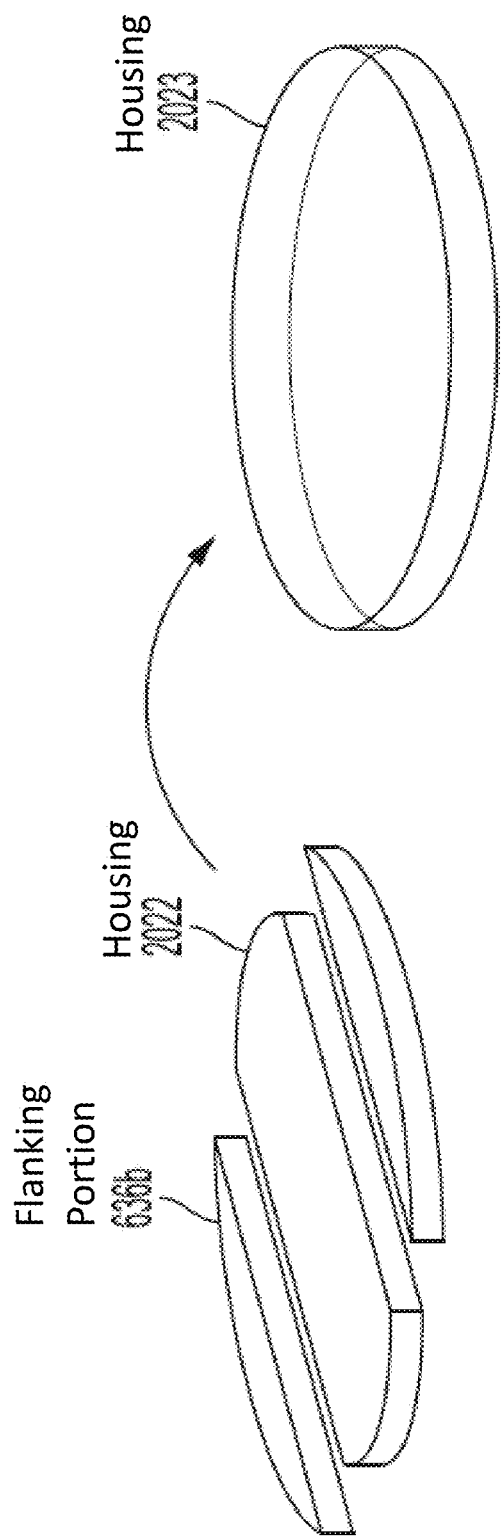

In an exemplary embodiment, the techniques of the embodiment of FIGS. 29 and 30 can be combined with those of FIGS. 31 and 32, consistent with the fact that any embodiment feature can be combined with any other embodiment feature unless otherwise specifically noted or otherwise not enabled by the art.

Figure 33:
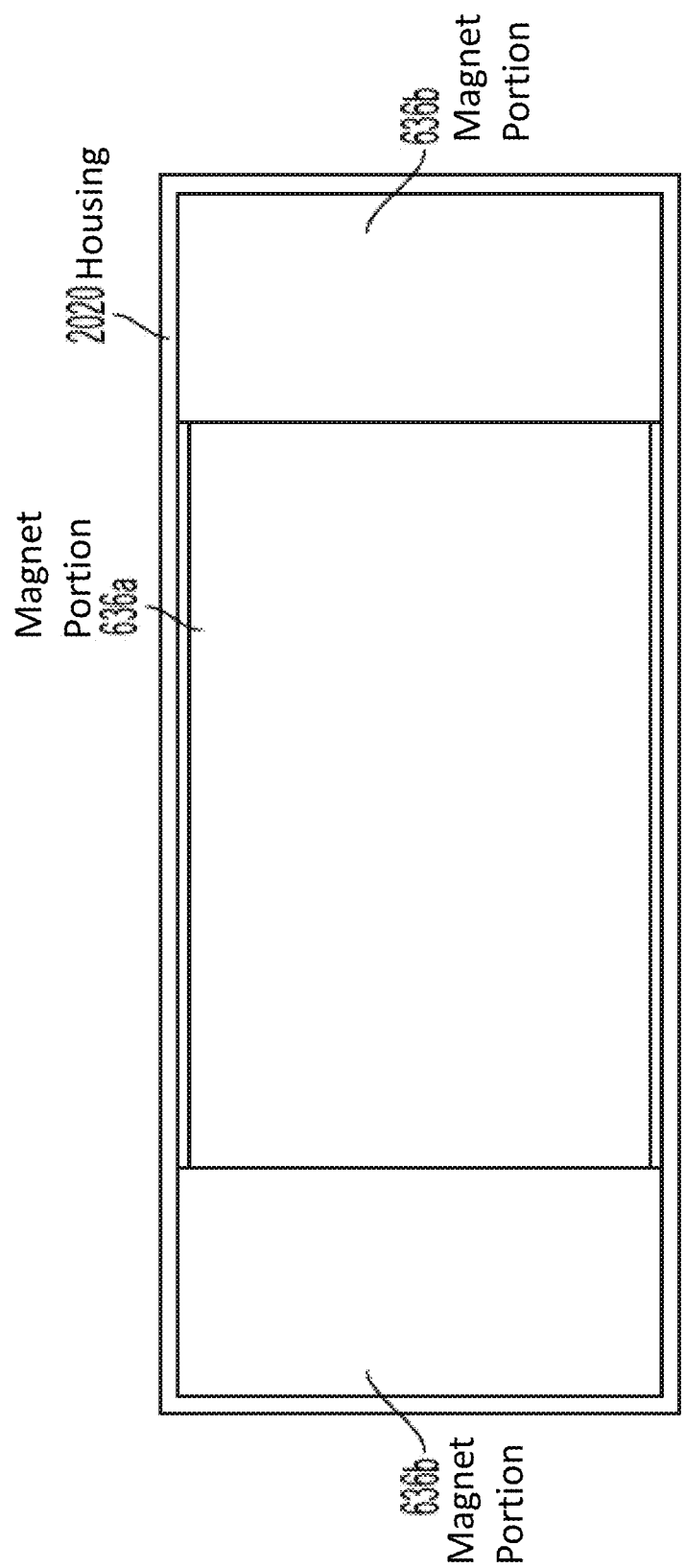
FIGS. 33 to 37 present cross-sections (partial and/or full) of some exemplary magnet apparatuses.

FIG. 33 depicts an exemplary embodiment of an anti-rattling implementation that utilizes the above exemplary embodiments where the central portion and/or the flanking portions is/are made of a nonmagnetic indoor nonmetallic material. In this exemplary embodiment, flanking portions 636b extended outwards and outwards beyond the central portion 636a, as seen. In this exemplary embodiment, the central portion can be a magnetic material, such as a magnet, and the flanking portions can be the polymer-based material or nonmagnetic materials, etc., according to the teachings detailed herein and/or variations thereof. In this exemplary embodiment, the flanking portions 636B are interference fitted into the housing 2020, while in other embodiments, the flanking portions 636B are slipped fitted. In any event, the tolerances are such that the magnet apparatus that is located in the housing 2020 will not rattle or otherwise rattle less than that which would otherwise be the case in the absence of the teachings detailed herein. In an exemplary embodiment, a measured noise resulting from a given vibratory regime is reduced by at least 0.1, 0.2, 0.3, 0.4, 0.5, 0.6, 0.7, 0.8, 0.9, 1.0, 1.25, 1.5, 1.75, 2.0, 2.25, 2.5, 2.75, 3, 3.5, 4, 4.5, 5, 5.5, 6, 6.5, 7, 8, 9, or 10 dB or more, or any value or range of values therebetween in 0.01 dB increments relative to that which be the case if the entire component was made of metallic components/magnetic components. (It is noted that in at least some other exemplary embodiments detailed herein, these performance features are also present.)

Figure 34:
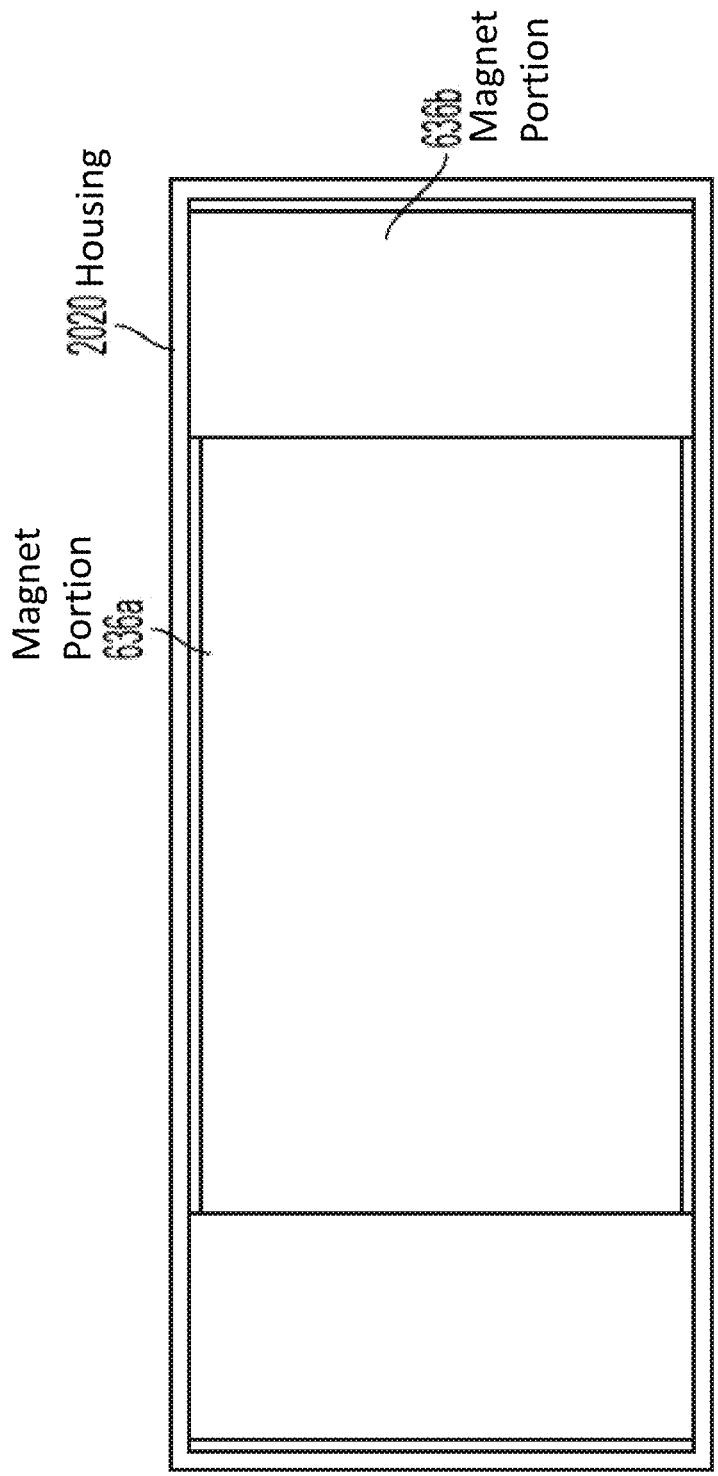

FIG. 34 presents an alternate exemplary embodiment where the flanking portions 636b are non-magnetic/nonmetallic, and the lateral sides are spaced away from the side walls of the housing 2020, as can be seen. In this exemplary embodiment, the flanking portions 636b are interference fitted into the housing 2020 in the longitudinal direction and/or slipped fitted in that longitudinal direction. In this embodiment, the center portion 636a is a permanent magnet, and the flanking portions are made of a nonmagnetic material according the teachings herein.

Figure 35:
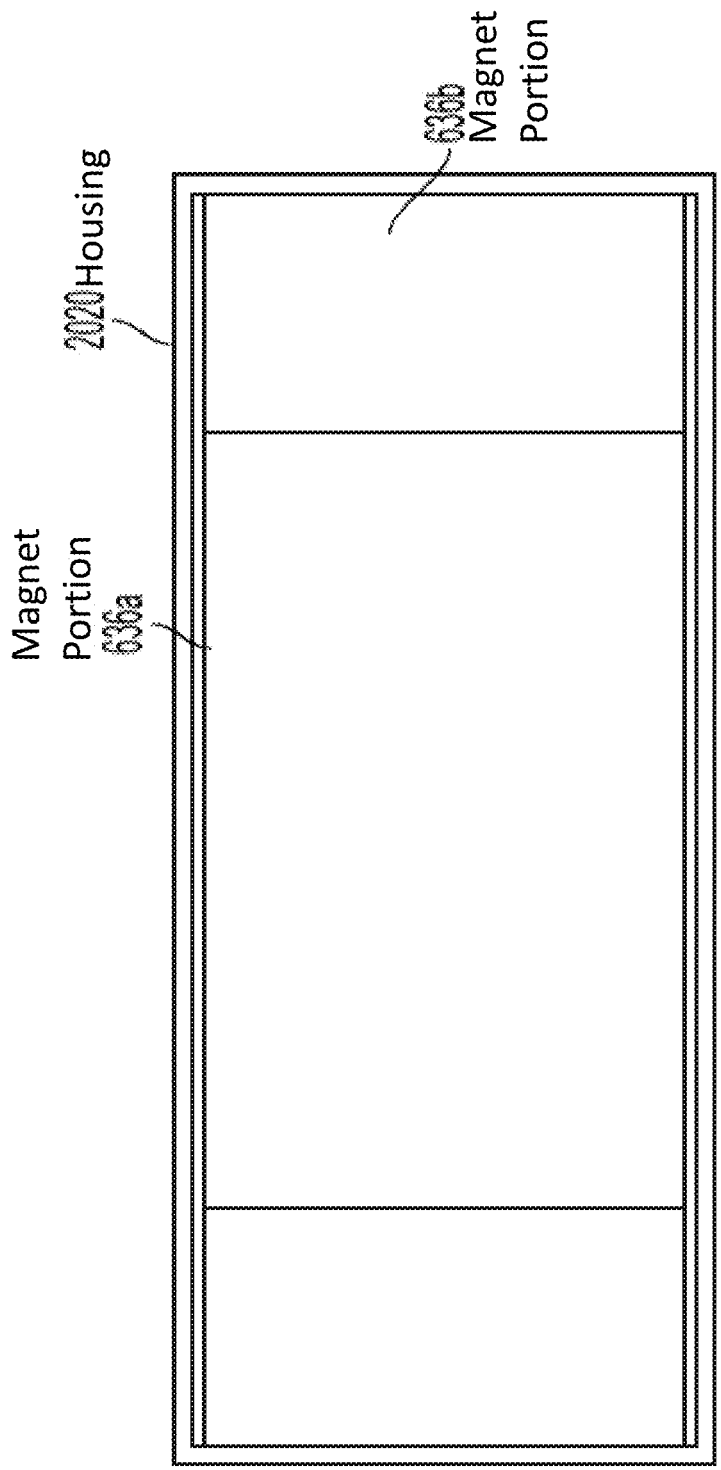

FIG. 35 presents an alternate exemplary embodiment, where the flanking portions 636b are nonmagnetic/nonmetallic, and the lateral sides are spaced away from the top walls and bottom walls of the housing 2020, as can be seen. In this exemplary embodiment, the flanking portions 636b are interference fitted into the housing 2020 in the lateral direction and/or slipped fitted in that lateral direction. In this embodiment, the central portion 636a is a permanent magnet, and the flanking portions are made of a nonmagnetic material according to the teachings herein.

Figure 36:
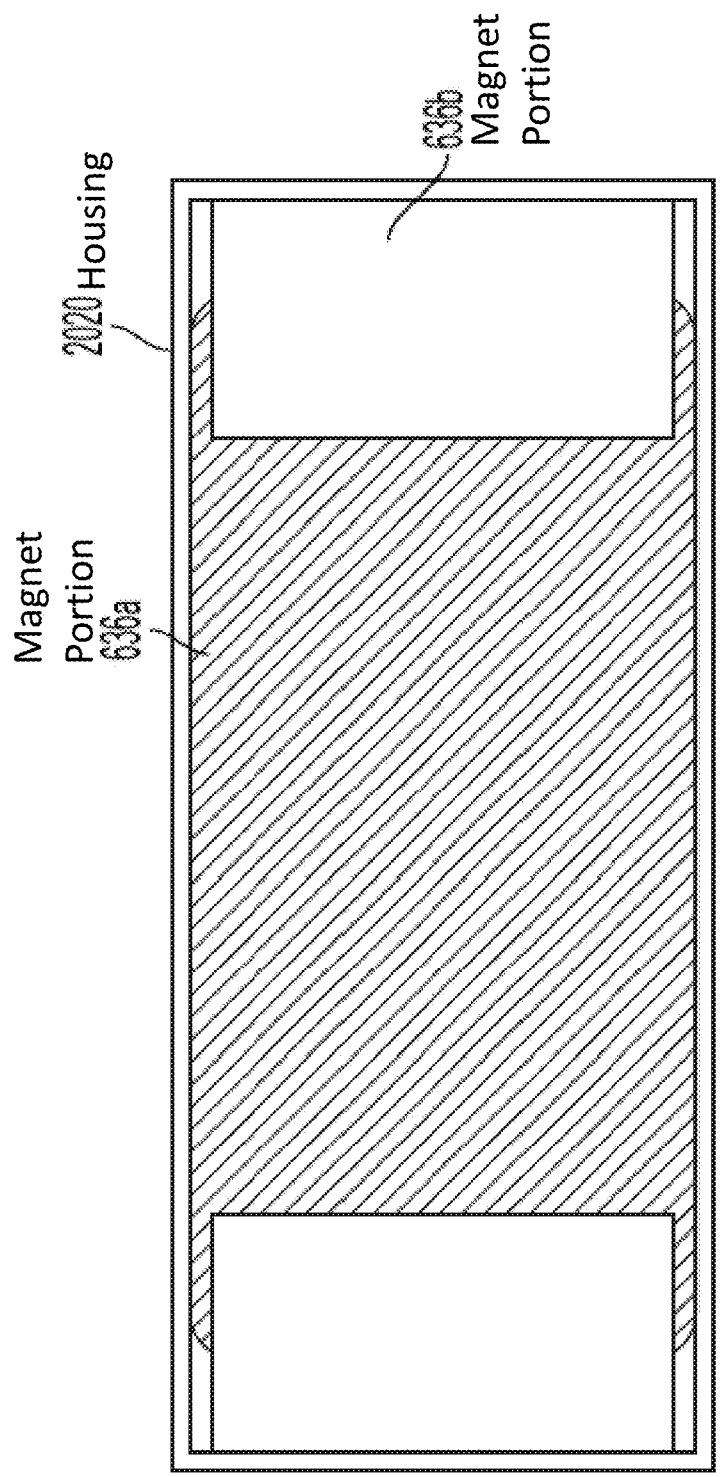

FIG. 36 presents yet an alternate exemplary embodiment, where instead of the flanking portions being utilized to support the central portion away from the housing 2020 such that the housing does not contact the central portion/the central portion does not contact the housing, here, the central portion 636a is in contact with the housing 2020, and the flanking portions 636b also contact the housing 2020 and the lateral direction. Thus, the two separate components collectively provide the preventive movement in two directions.

Figure 37:
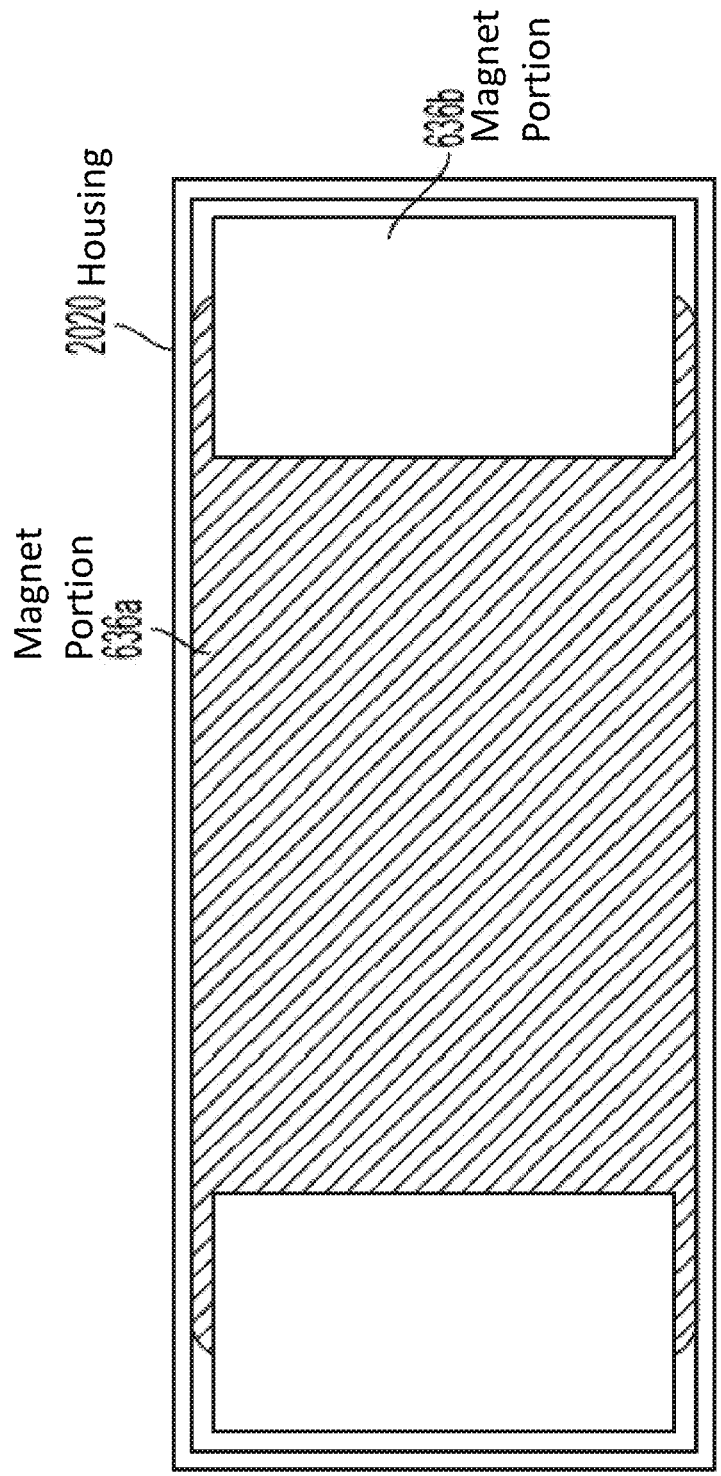

FIG. 37 presents yet another exemplary embodiment, where instead of the flanking portions being utilized to support the central portion away from the housing 2020 such that the housing does not contact the central portion/the central portion does not contact the housing, here, the central portion 636a is in contact with the housing 2020, but the flanking portions 636b are spaced away from the walls of the housing 2020. In this exemplary embodiment, as in the embodiment of FIG. 36, the central portion 636a can be interference fitted and/or slipped fitted into the housing 2020.

In at least some exemplary embodiments, the embodiments described above reduce and/or prevents and/or eliminate the aforementioned rattling according to any of the aforementioned performance regimes. In an exemplary embodiment, this can have utilitarian value with respect to scenarios where the recipient undergoes an MRI scan and/or during normal use of the implant that might cause rattling, and the teachings detailed herein reduce and/or eliminate that rattling.

In some embodiments, the flanking portions and/or the central portions are arranged relative to the housing 2020 such that the magnet apparatus can rotate, while in other embodiments, those components are arranged such that the magnet apparatus cannot rotate within the housing, while in other embodiments, consistent with the teachings detailed herein, these components are arranged such that the magnet apparatus can rotate within the housing only after a given torque is imparted onto the magnet apparatus relative to the housing. Some additional details of this will be described in greater detail below. First however, some embodiments will be described with respect to the rotating magnet apparatus which is a single magnet.

Figure 38:
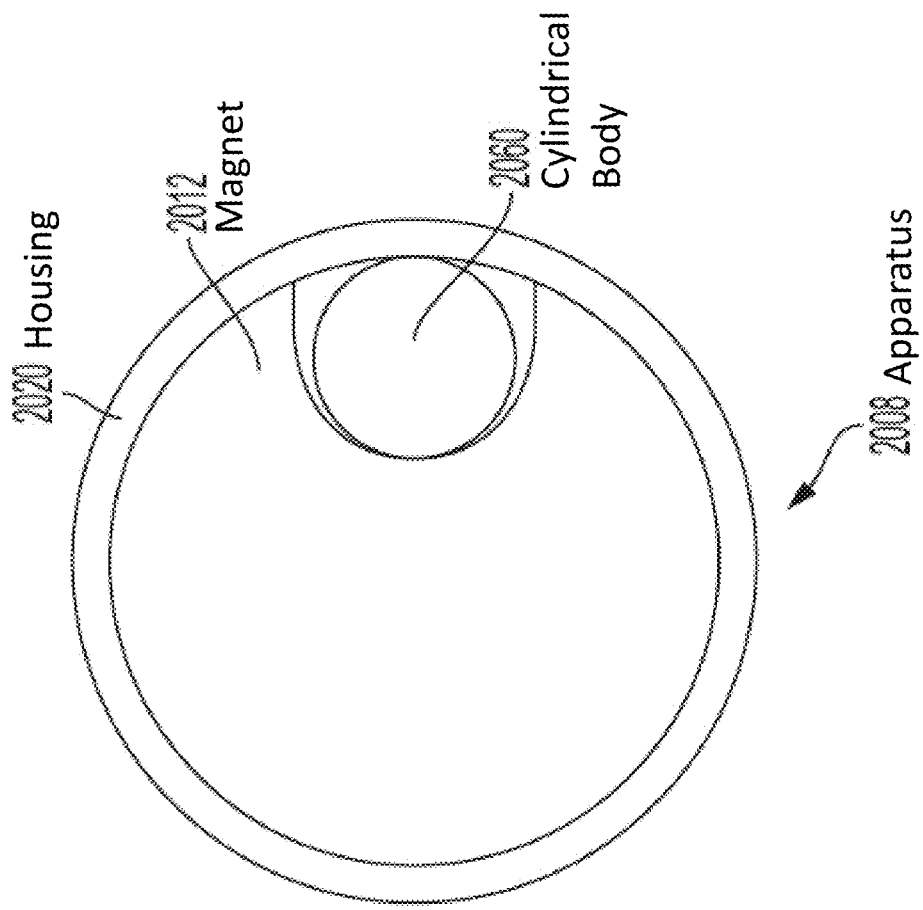
FIG. 38 presents a top view of an exemplary embodiment.
Figure 39:
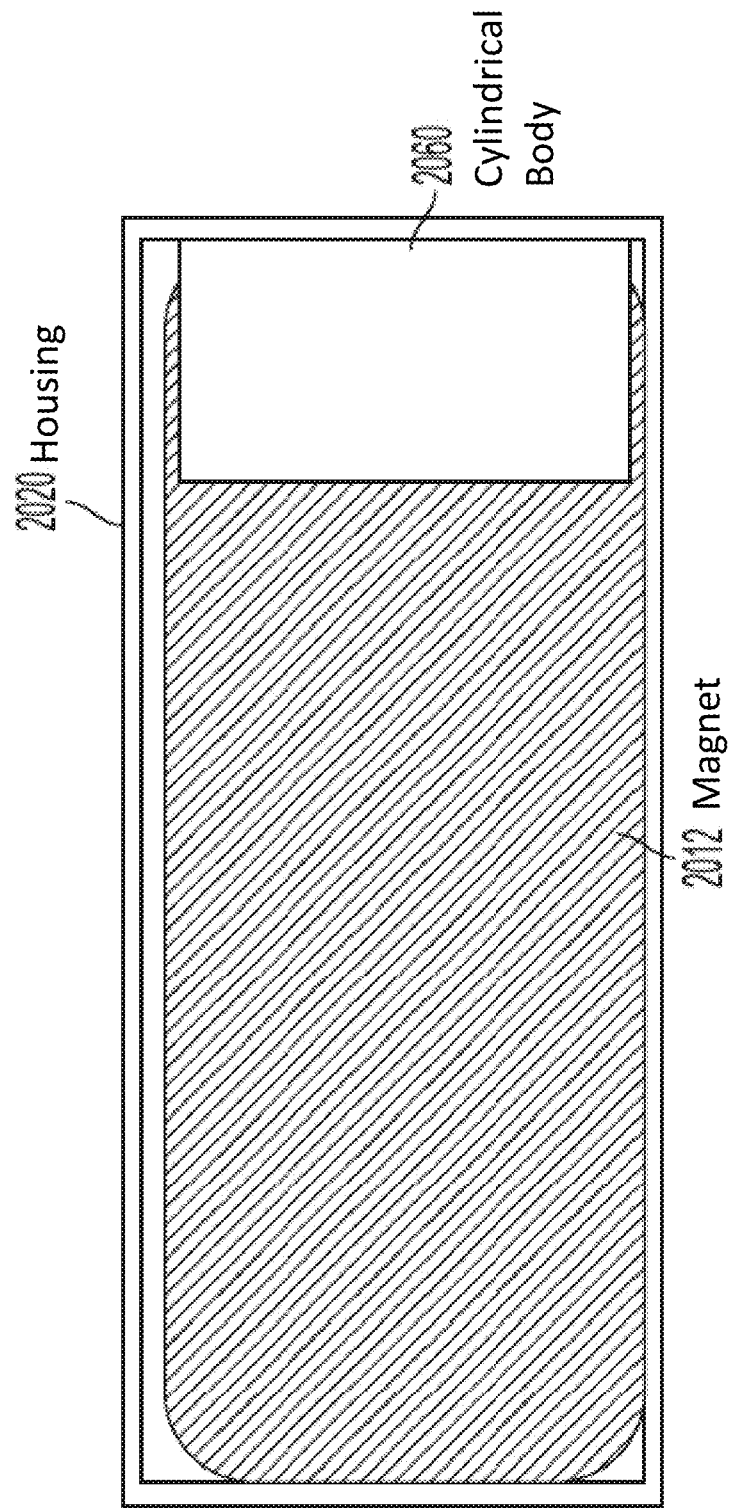
FIG. 39 presents a side view of an exemplary embodiment.
Figure 40:
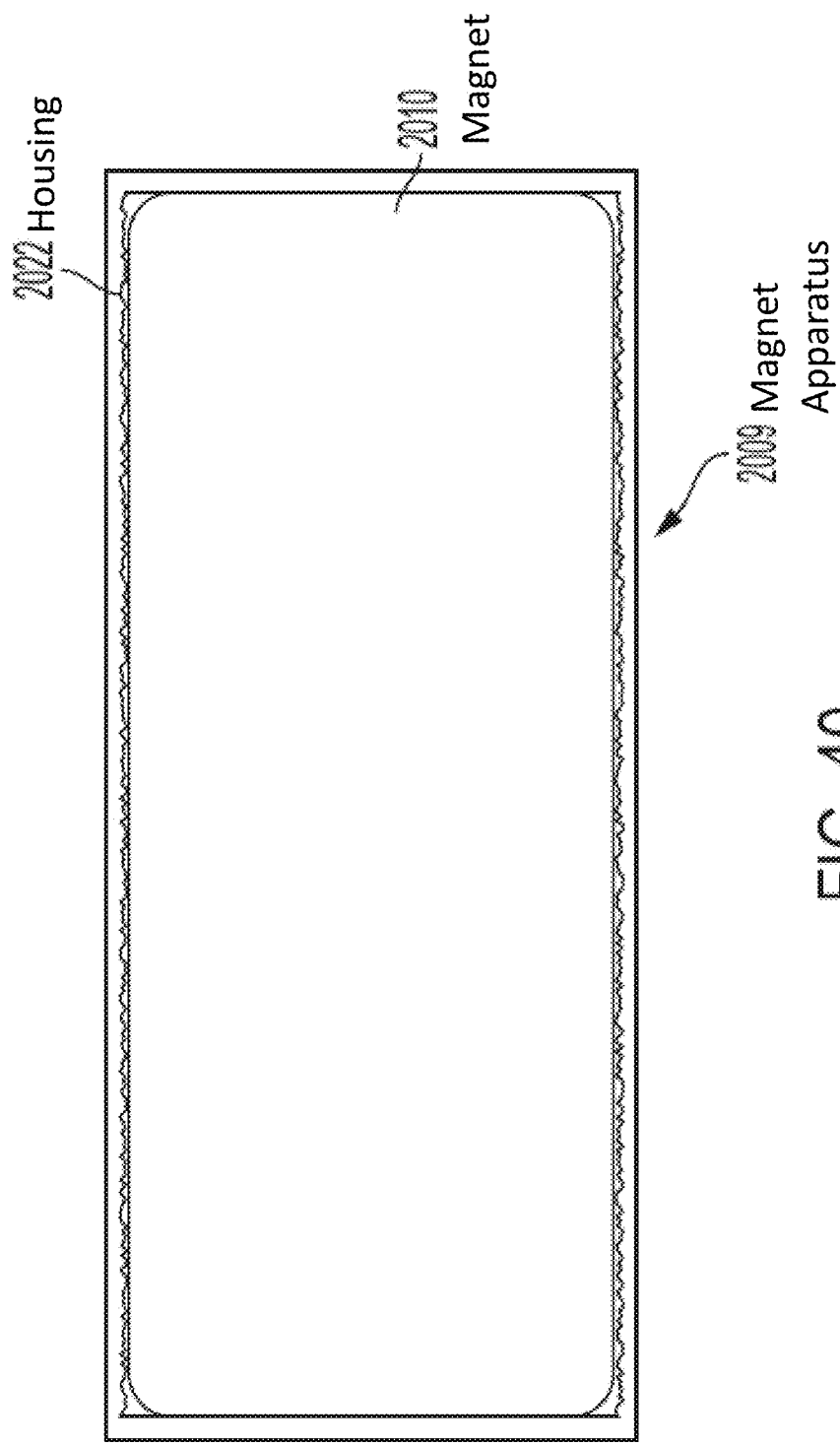
FIGS. 40 to 44 present cross-sections (partial and/or full) of some exemplary magnet apparatuses.
Figure 41:
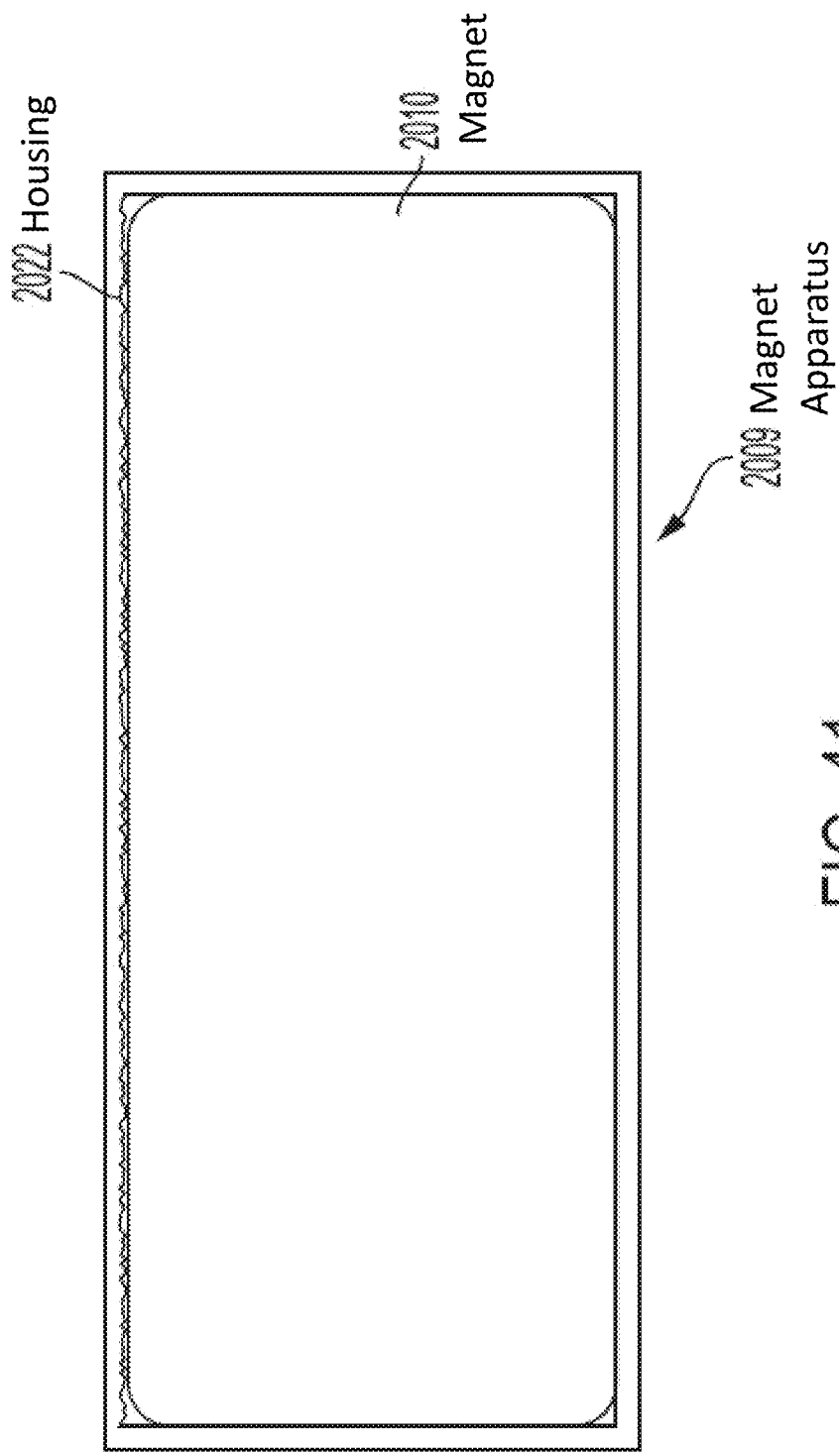

FIG. 38 depicts another exemplary embodiment of an apparatus 2008. Here, there is a large cutout within the magnet 2012. A cylindrical body 2060 is located in the cutout. FIG. 39 presents a cross-section through the embodiment of FIG. 38 in a direction perpendicular to the plane shown in FIG. 38. In this exemplary embodiment, the cylindrical body 2060 does not extend the full height of the magnet, while in other embodiments, it can extend the full height of the magnet. In an exemplary embodiment, the cylindrical body 2060 can be a rubber body (as can be the friction components of the embodiments above) that is interference fitted between the housing wall and the magnet 2012. In an exemplary embodiment, the body can be a metallic body or a plastic body (as can be any of the friction components detailed herein). Any arrangement that can prevent the magnet from rotating until a certain torque is applied thereto can be utilized at least some exemplary embodiments. 2009 presents yet another exemplary embodiment of a magnet apparatus that includes a housing 2022 and a magnet 2010. In this exemplary embodiment, the housing walls are rough surface walls that impart higher friction than that which would be the case if a smoother wall was utilized. In an exemplary embodiment, the location/distance of extension of the roughened surface can be varied to vary the friction forces. In an exemplary embodiment, the roughened surface can extend completely across from one side to the other on both sides, whereas in another exemplary embodiment, the roughened surface only exist on one side, as can be seen in FIG. 41. In an exemplary embodiment, the roughened surface can be limited to the locations only at the geometric center of the housing while in other embodiments, the roughened surfaces can be limited to locations only at the outboard locations. Combinations of the two can be utilized. It is to be understood that the further out that the roughened surfaces are from the geometric center, the more friction force will be generated for a given surface area, all other things being equal. By varying the positions, the torque that is required to initiate rotation can be varied.

Figure 42:
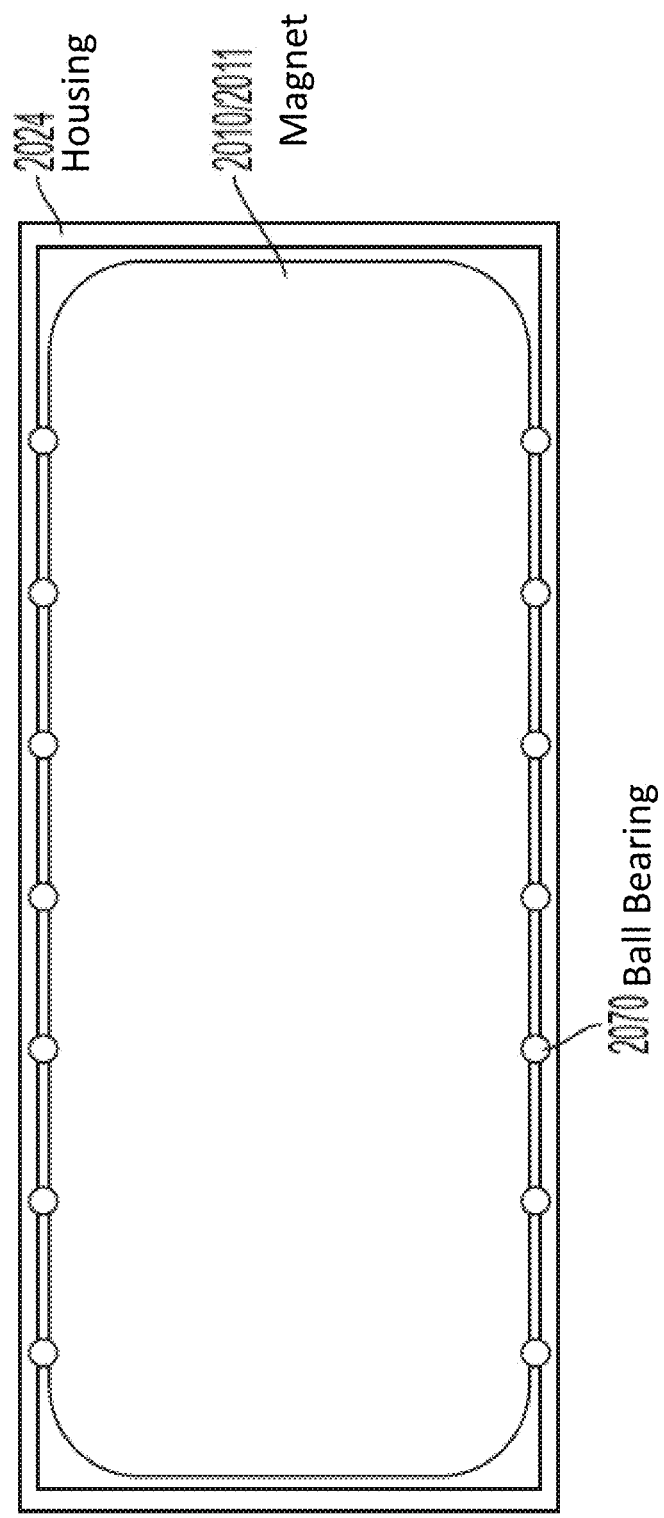

FIG. 42 presents another exemplary embodiment where ball bearings 2070 are located in detents in the housing 2024 and/or in the magnet 2010/2011. In an exemplary embodiment, these ball bearings can be rubber and can be compressed to vary the amount of torque that is required to begin rotation of the magnet. In an exemplary embodiment, the bearings can be metal or can be plastic, etc. That said, in an exemplary embodiment, the bearings can be low friction components that actually enhance rotation. In this regard, in an exemplary embodiment, the bearings could be located therein in a manner where the bearings are not substantially compressed, as opposed to the other embodiments where the bearings are compressed or otherwise there is a relatively large downward force/pressure between the two components to increase the friction and thus increase the amount of torque that is required to begin rotation.

In some embodiments, there is a disk shaped, diametrically polarized implant magnet (in other embodiments, it is a combination polarized magnet, such as in FIG. 4A) enclosed in a case/shell/cassette. A mechanism is located inside the housing/cassette to sufficiently secure the magnet so that it shall remain fixed during normal operation, such as when paired with the external sound processor magnet or similarly low strength magnetic fields. Conversely, under the influence of a high strength magnetic field (such as an MRI field, the mechanism will allow the implant magnet to reorient itself to align with the field, reducing the experienced torque and ensuing pain/damage. The orientation will remain until exposed to another high strength field. The viscous substance/friction enhancing substances within the cassette can coat the magnet and/or the inside of the housing and/or the intentionally roughened internal surfaces (relative to the normal surface/that which exists from manufacturing without roughening) can be located on any of the components.

Figure 43:
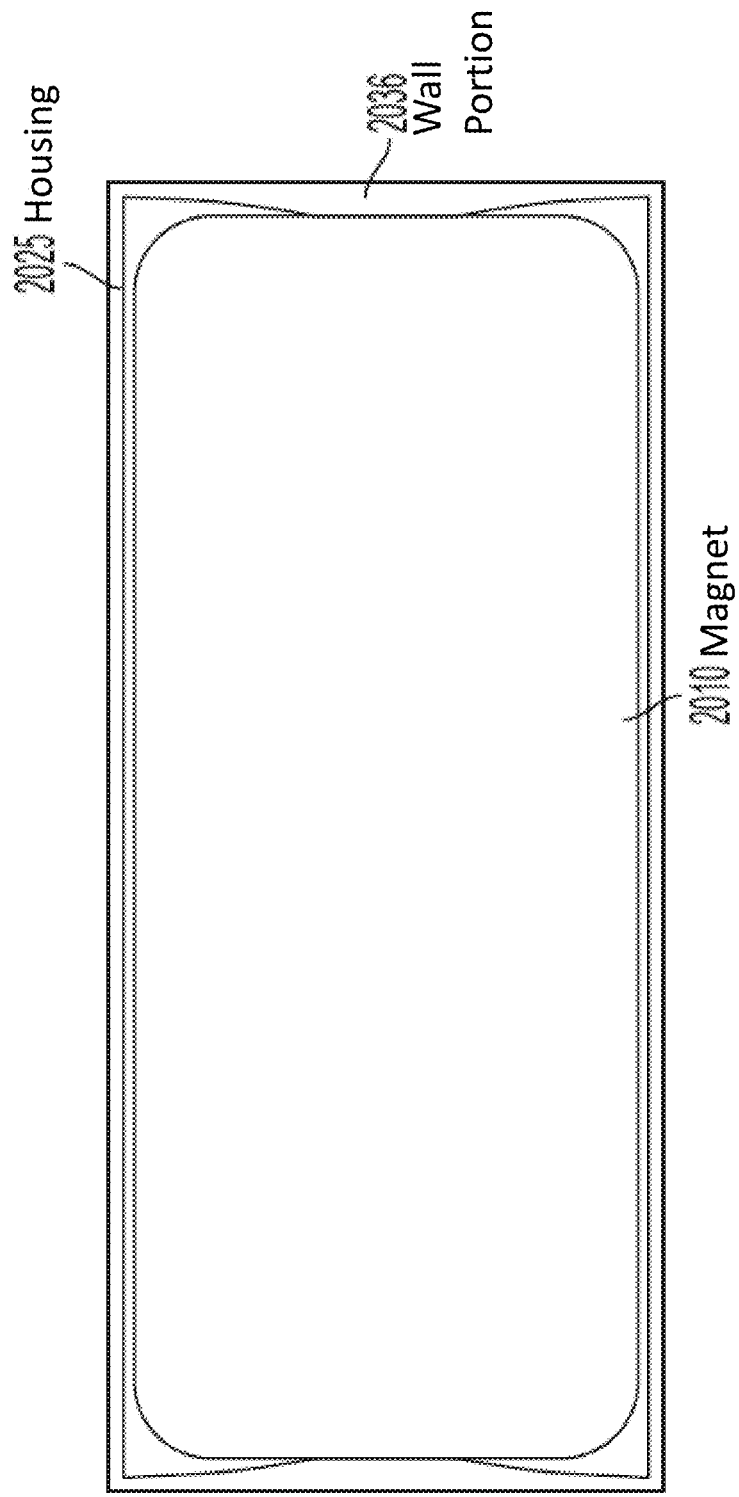
Figure 44:
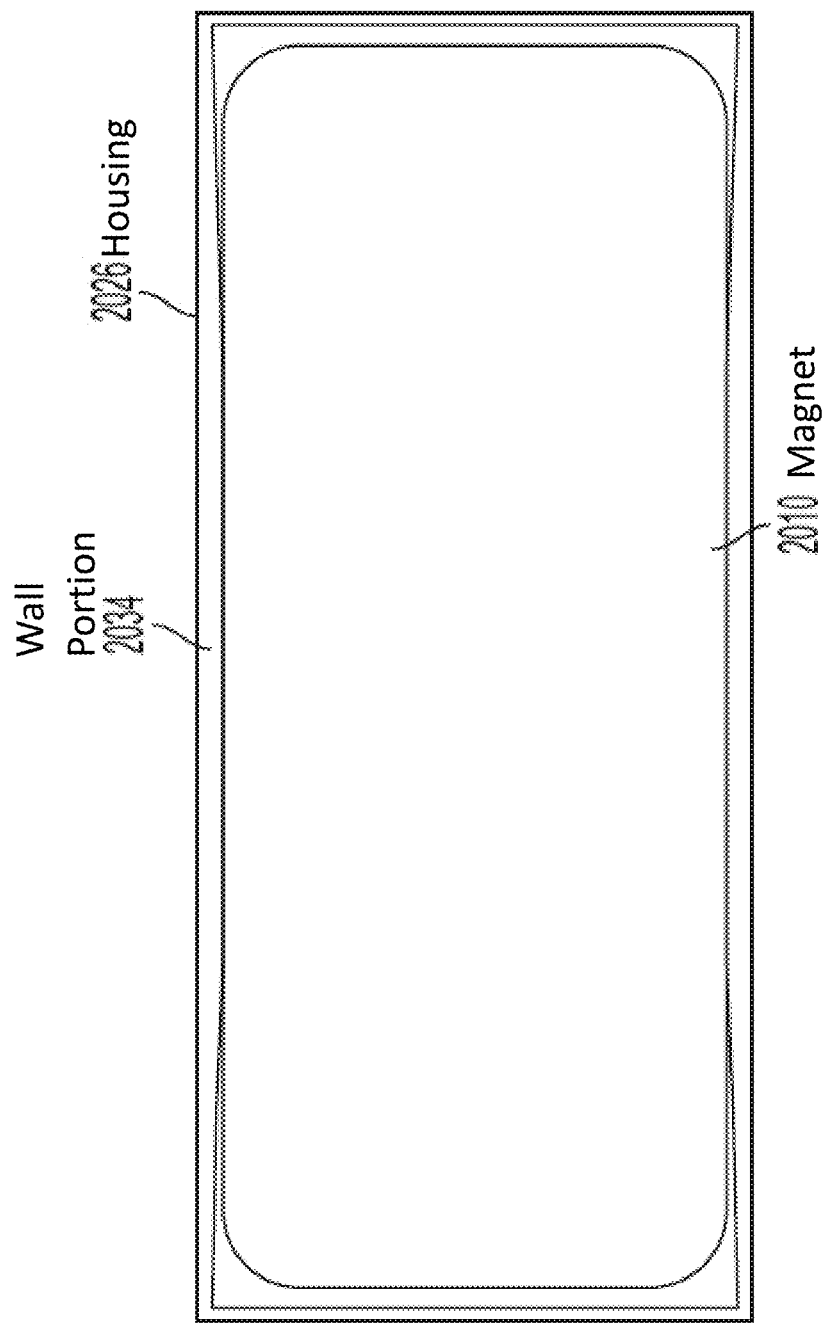

Further, a convex cassette interior can result in specific points of contact with the magnet in the housing can increase the torque required to begin rotation of the magnet. By way of example only and not by way limitation, FIG. 43 depicts an exemplary housing 2025 that houses magnet 2010. As seen, the interior side walls of the housing 2025 are convexly shaped inside so as to compress against the magnet 2010 at wall potion 2036. FIG. 44 presents an alternate embodiment of a housing 2026 where the top and bottom walls include convex portions 2037 that compress upon the magnet 2010 at wall potion 2034. These configurations increase the torque that is required to begin rotation of the magnet relative to that which would otherwise be the case in the absence of these components.

It is noted that while the embodiments shown in FIGS. 43 and 44 depict the outer surfaces of the walls of the housing as being flat or otherwise parallel to each other, in an alternate embodiment, the walls can be bow shaped so that the walls extend in towards the magnet apparatus forming a convex shape on the inside in a concave shape on the outside. Indeed, in an exemplary embodiment, the case/housing can be deformed utilizing a press or the like with the magnet insider prior to the magnet being placed inside, and then the lid can be forced onto the rest of the housing such that the lid must deformed to fully close the lid, and the resulting interference causes the force that resists the magnet from rotating until a certain torque is achieved.

In view of the above, it can be seen that in at least some exemplary embodiments include a magnet and housing combination that does not generate heat due to kinetic energy associated with one of the parts moving relative to the other. Thus, in an exemplary embodiment, there is the action of attaching and detaching an external component to a recipient's head at a location above implanted component that has the magnet apparatus as detailed herein or variations thereof wherein the action of attaching does not result in heat generation. Still further, in at least some exemplary embodiments, there are exemplary methods where the recipient does not have an external component attached to himself or herself but where the implantable component includes the magnet apparatuses as detailed herein at least in some embodiments or variations thereof, and the period of time where there is no external component that is attached at least for 1, 2, 3, 4, 5, 6, 7, 8, 9, 10, 11, 12, 13, 14, 15, 16, 17, 18, 19 or 20 hours at a time or any value or range of values therebetween in 0.1 hour increments but where the internal magnet does not move or otherwise rotate relative to the housing. Thus, there is no heat generation or effectively no heat generation as a result of kinetic energy associated with the magnet relative to the housing for at least any of the aforementioned periods of time.

Further, at least some exemplary embodiments according to the teachings detailed herein that utilize the compression features or the higher friction features can also result in the prevention of unintentional or undesirable vibrational rattling of the magnet within the housing, such as that which can occur when the external component is not paired with the implantable component or otherwise when there is no external magnet that is generating a field that interacts with the implanted magnet. Accordingly, in an exemplary embodiment, there are exemplary methods where the recipient does not have an external component attached to himself or herself but where the implantable component includes the magnet apparatuses as detailed herein at least in some embodiments or variations thereof, and the period of time where there is no external component that is attached at least for 1, 2, 3, 4, 5, 6, 7, 8, 9, 10, 11, 12, 13, 14, 15, 16, 17, 18, 19, or 20 hours at a time or any value or range of values therebetween in 0.1 hour increments but where the internal magnet does not move or otherwise rotate relative to the housing. Thus, there is no noise or energy or effectively no noise or energy generated by the implanted magnet for at least any of the aforementioned periods of time.

In an exemplary embodiment, this can have utilitarian value with respect to avoiding rattling or otherwise noise or tactical sensation resulting from a moving component within a body of the recipient.

In an exemplary embodiment, there is an implantable (or external) medical device, wherein the body is an enclosure that at least partially encloses the magnet, and a pressure force exerted by the body directly and/or indirectly onto the magnet prevents the magnet from rotating under a magnetic field that is not as strong as the magnetic field that causes the magnet to rotate. In an exemplary embodiment, a force of 0.1, 0.2, 0.3, 0.4, 0.5, 0.6, 0.7. 0.8, 0.9, 1.0, 1.1, 1.2, 1.3, 1.4, 1.5, 1.75, 2, 2.25, 2.5, 2.75, 3, 3.25, 3.5, 3.75, 4, 4.5, 5, 5.5, 6, 6.5, 7, 7.5, 8, 8.5, 9, 10, 11, 12, 13, 14, 15, 16, 17, 18, 19, 20, 21, 22, 23, 24, 25 or more pounds of force are applied onto the magnet.

In an exemplary embodiment, the body is an enclosure that at least partially encloses the magnet (e.g., a housing as disclosed above). As seen, in some embodiments, high friction element(s) between and/or part of the body directly and/or indirectly in contact with the magnet prevent(s) the magnet from rotating under a magnetic field that is not as strong as the magnetic field that causes the magnet to rotate. In an exemplary embodiment, the external component including a second magnet and the second magnet is rotatable within the external component (along with or instead of the magnet in the implantable component). In an exemplary embodiment, the external component includes a second magnet and the second magnet is rotatable within the external component (in addition to or instead of the magnet in the implant). Further, the external component is configured to enable the second magnet to rotate under the magnetic field generated by the magnet in the implant when the external component is held proximate the implantable medical device. It is noted that in some embodiments, the external component has an identical magnet apparatus as the implant, and in other embodiments, it is different from that of the implant. Any disclosure herein of an implanted magnet/magnet apparatus/magnet group corresponds to a disclosure of an external device that has such, and vice versa.

By does not rotate, it is meant that the magnet group only moves an amount that would be consistent with deformation/flexure of the components of the system when a force is applied (by analogy, a cinder block will compress when a force is applied, but the block does not move in any meaningful way). That said, in some embodiments, the aforementioned features can be classified in terms of a magnet group that does not rotate more than 2, 3, 4, 5, 6, 7, 8 9 or 10 degrees from its initial orientation.

It is noted that while teachings detailed above have been directed towards a magnet group that has magnet portions with different axes of magnetic flux, in an alternate embodiment, the teachings detailed herein can be applicable to a magnet apparatus where all of the flux axes are aligned the same (diametrically, radially, obliquely, etc.). Accordingly, any disclosure herein to a magnet group corresponds to a disclosure of an alternate embodiment where the magnet group is a magnet (or a group) that has a single magnetic flux and/or the generated magnetic flux of the various components are all aligned or otherwise substantially aligned with each other.

In the embodiments described above, it is a screw thread that ultimately provides the resistance against the rotation (whether it be the screw thread of the screw that fits into the bone fixture, or the screw thread of the bone fixture that interfaces with the bone—actually, a combination of the two can be also the case). Accordingly, in an exemplary embodiment, the threat alignment can be adopted such that any torque that is likely to be experienced owing to the exposure of magnetic field result in a tightening effect (analogous to the direction of threads of wheel lugs—the thread (right hand vs. left hand) is selected based on the rotation of the wheels so that the rotation tightens the lug nuts). In this regard, the torque applied to the magnet group that results from the exposure of the magnetic field is transferred into the screw in a manner that actually further tightens the screw.

The above performance features associated with the rotations and non-rotations and resistance to rotation until a certain torque is achieved of the magnet/magnet group/magnet apparatus can also be applicable to the embodiments detailed above where a non-magnetic material/nonmetallic material is utilized to support the magnet portions of the magnet apparatus and/or or otherwise included in the magnet apparatus (the nonmagnetic portions need not necessarily be utilized for support—in other embodiments, these are simply utilized to center at least partially the magnet apparatus—in this regard, while some embodiments are directed towards anti-rattling/limited rattling embodiments, other embodiments are not necessarily so directed). In this regard, in an exemplary embodiment, the embodiments that utilize, for example, flanking components made of a polymer or a nonmagnetic material or a non-metallic material can, in some embodiments, be utilized so that there is a modicum of resistance to rotation until a certain torque is achieved. In some embodiments, the flanking components guide the magnet component with respect to rotation within the housing. That said, in alternative embodiments, such as where the flanking portions of the magnetic materials, in some embodiments, the central portion is the component that guides the flanking portions within the housing during rotation.

In the embodiments where the magnet is made of a discorectangle or racetrack configuration, and is shaped magnetized along its length, such can be utilized in combination with the flanking portions, in some embodiments, to enable the magnet to rotate within the disk-shaped housings detailed herein. Further, as noted above, the discorectangular configuration of the magnet can be housed in a discorectangular shaped housing which rotates within a non-conducting housing, made of PEEK or PTFE, etc. In the embodiments where the magnet is made of half-moon shapes and the magnets are magnetized along their length, such can be utilized in combination with the central portion, in some embodiments, to enable the magnets to rotate within the disk-shaped housings detailed herein. Further, as noted above, the moon shaped magnets can be housed in a moon shaped housing which rotates within a non-conducting housing, made of PEEK or PTFE, etc. In an exemplary embodiment, the outer housing can be made of a metallic material as well.

In at least some embodiments, the flanking portions and/or the central portion is made of low friction material such as PTFE or PEEK, while in other embodiments, the flanking portions under the central portion is made of high friction material. In an exemplary embodiment, as will be understood, some embodiments will provide for much freer rotation relative to that which would otherwise be the case, all other things being equal, while in other exemplary embodiments, as will be understood, some other embodiments provide for much less/more restricted rotation relative to that which would otherwise be the case all other things being equal.

In an exemplary embodiment, a torque of 0.01, 0.02, 0.03, 0.04, 0.05, 0.06, 0.07, 0.08, 0.09, 0.1, 0.11, 0.12, 0.13, 0.14, 0.15, 0.16, 0.17, 0.18. 0.19, 0.20, 0.25, 0.3, 0.35, 0.4, 0.45, 0.5, 0.55, 0.6, 0.65, 0.7, 0.8, 0.9, 1.0, 1.2, 1.5, 1.75, 2, 2.25, 2.5, 2.75, 3, 3.25, 3.5, 3.75, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 60, 70, 80, 90, or 100 or more inch-pounds, or any value or range of values therebetween in 0.005 inch-pound increments, will cause the magnet apparatus within the housing to rotate relative to the housing. That said, in an exemplary embodiment, the application of any one or more the aforementioned torques will cause the magnet apparatus to break. In an exemplary embodiment, the application of any one or more the aforementioned torques will still not cause the magnet apparatus to rotate relative to the housing.

In an exemplary embodiment, the magnet apparatus can move, relative to the interior of the housing, no more than or more than 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18. 0.19, 0.20, 0.25, 0.3, 0.35, 0.4, 0.45, 0.5, 0.55, 0.6, 0.65, 0.7, 0.8, 0.9, or 1.0 millimeters or any value or range of values therebetween in 0.001 mm increments in one or two or three directions of the Cartesian coordinate system with one axis aligned with the longitudinal axis of the magnet apparatus, at least without effectively deforming the housing/relative to an ideally perfectly rigid housing. In an exemplary embodiment, the largest diameter of the magnet apparatus and/or of any of the components of the magnet apparatus is/are no more than or more than 4, 5, 6, 7, 8, 9, 10, 11, 12, 13, 14, 15, 16, 17, 18, 19, 20, 21, 22, 23, 24, 25, 26, 27, 28, 29, or 30 mm or any value or range of values therebetween in 0.001 mm increments. In an exemplary embodiment, the largest diameter of the interior cavity of the housing can be larger than or less than or equal to 4, 5, 6, 7, 8, 9, 10, 11, 12, 13, 14, 15, 16, 17, 18, 19, 20, 21, 22, 23, 24, 25, 26, 27, 28, 29, or 30 mm, or any value or range of values therebetween in 0.001 mm increments.

In an exemplary embodiment, the racetrack shaped central portions have flat sides, as opposed to curved sides. That said, in an alternate embodiment, the central portions can have a body that has different radiuses of curvature about the periphery, such as, for example, instead of having flat sides as shown in the figures above, the sides are curved, just with a lower radius of curvature than that of the ends of the central portion. In an exemplary embodiment, the ratio of the radius of curvature of the ends of the central portion to the sides of the central portion is 1, 1.1, 1.2, 1.3, 1.4, 1.5, 1.6. 1.7, 1.8, 1.9, 2, 2.25, 2.5. 2, 75, 3, 4, 5, 6, 7, 8, 9, 10, 11, 12, 13, 14, 15, 20, 25, 30, 35, 40, 45, 50, 60, 70, 80, 90, or 100 or more, or any value or range of values therebetween in 0.1 increments. In an exemplary embodiment, the radius of curvature of the ends of the central portion can be 2, 3, 4, 5, 6, 7, 8, 9, 10, 11, 12, 13, 14, 15, 16, 17, 18, 19, or 20 mm, or any value or range of values therebetween in 0.001 mm increments. In an exemplary embodiment, the radius of curvature of the flanking portions can also be any of these values just detailed.

In an exemplary embodiment, the distance from one side of the center portion of the other side of the center portion and/or the distance from one side of the flanking portion to the other side of the flanking portion (from the curved side to the flat side (maximum distance) can be 1, 2, 3, 4, 5, 6, 7, 8, 9, 10, 11, 12, 13, 14, 15, 16, 17, 18, 19, or 20 mm, or any value or range of values therebetween in 0.001 mm increments.

While the embodiments detailed herein have frequently been described in terms of components that have smoothly curved surfaces, in other embodiments, faceted surfaces can be utilized that can approximate a curved surface. By way of example only and not by way of limitation, any one or more of the curves detailed herein can be replaced by 2, 3, 4, 5, 6, 7, 8, 9, 10, 11, 12, 13, 14, 15, 16, 17, 18, 19, or 20 flat surfaces that are contiguous with one another, save for, potentially, edged broken surfaces which could be curved or chamfered surfaces between the two.

In an exemplary embodiment, the thickness of any of the components of the magnet apparatus can be 1, 1.1, 1.2, 1.3, 1.4, 1.5, 1.6. 1.7, 1.8, 1.9, 2, 2.1, 2.2, 2.3, 2.4, 2.5, 2.6. 2.7, 2.8, 2.9, 3, 3.25, 3.5, 3.75 or 4 mm or any value or range of values therebetween in 0.001 mm increments. In an exemplary embodiment, the height of the cavity of the housing can be 1, 1.1, 1.2, 1.3, 1.4, 1.5, 1.6. 1.7, 1.8, 1.9, 2, 2.1, 2.2, 2.3, 2.4, 2.5, 2.6. 2.7, 2.8, 2.9, 3, 3.25, 3.5, 3.75 or 4 mm or any value or range of values therebetween in 0.001 mm increments.

In an exemplary embodiment, the portions of the magnet apparatus are flat on the top and the bottom and are parallel to one another, while in other embodiments, as will be described in greater detail herein, the portions on the top and bottom are not necessarily flat and/or not necessarily parallel to one another.

Figure 45:
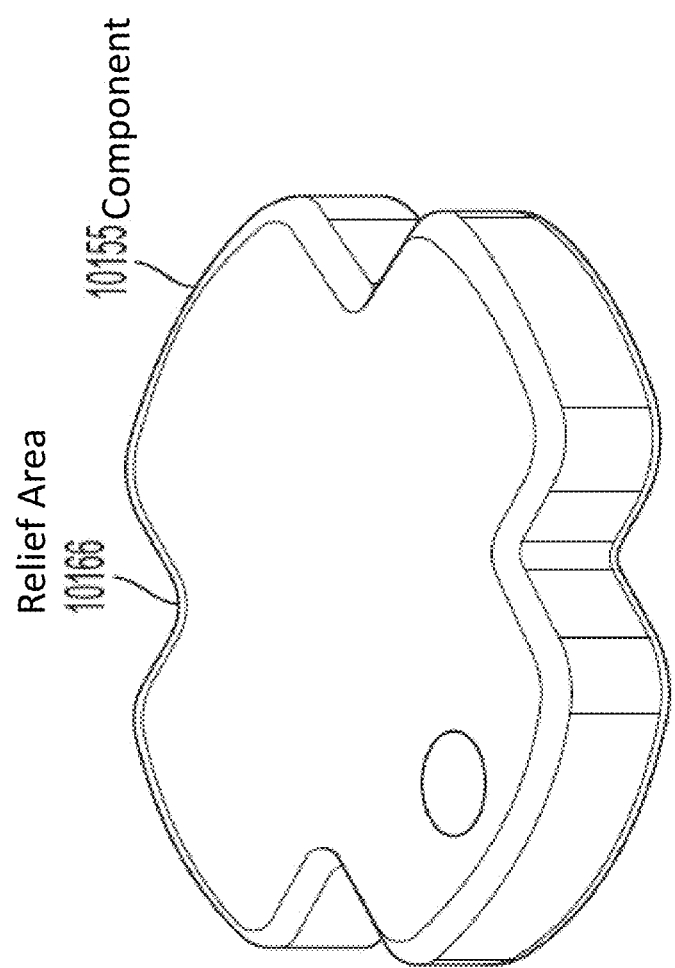
FIGS. 45 and 46 present isometric views of exemplary embodiments.
Figure 46:
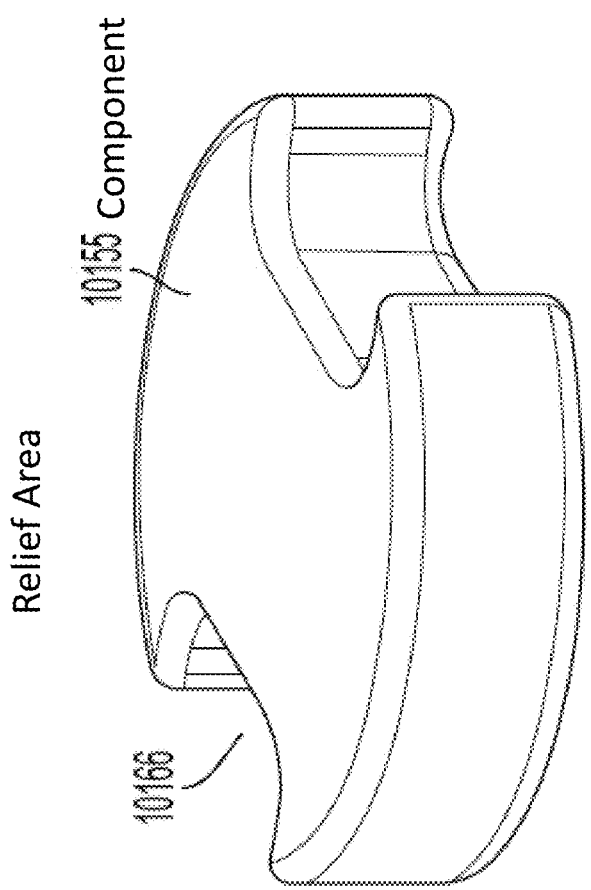
Figure 47:
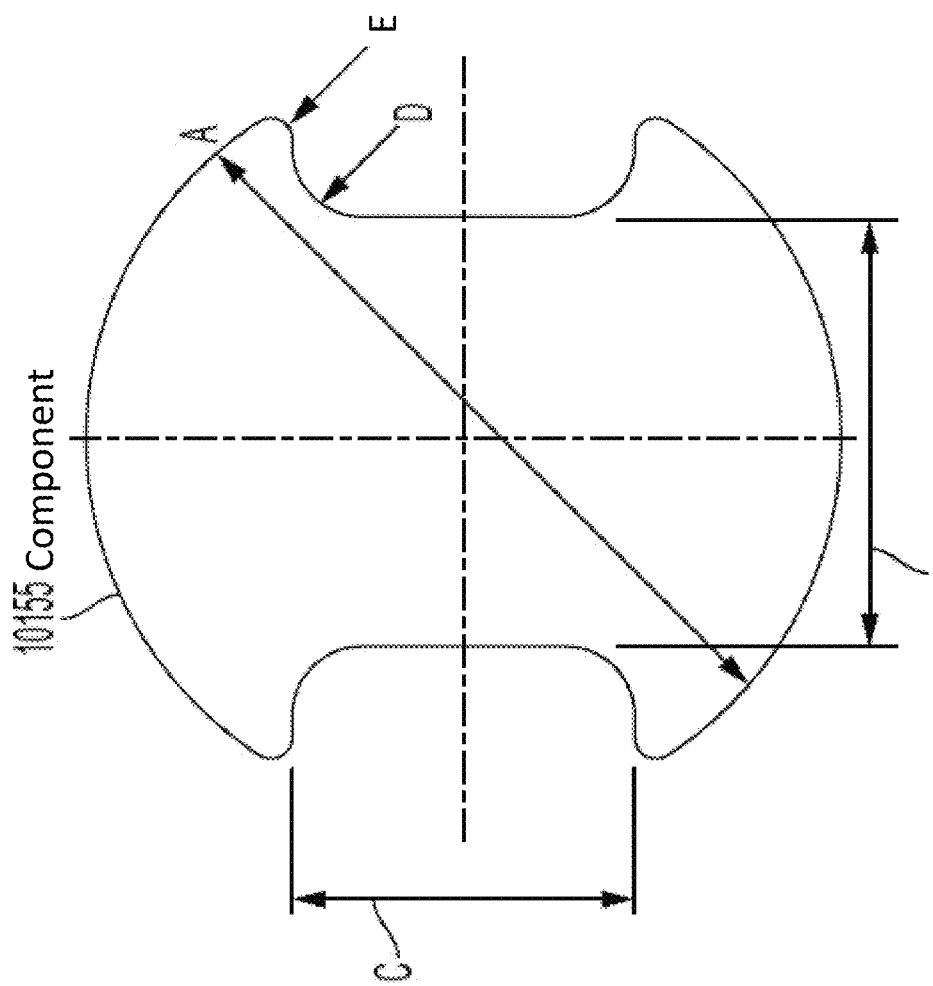
FIGS. 47-51 present top views of some exemplary embodiments.

FIGS. 45, 46, and 47 present alternate embodiments of some components that can be utilized with some embodiments herein. These can be magnet components or non-magnet components. The components can be monolithic, as is the case with all of the components herein in some embodiments, or can be made up of separate sub-components. In an exemplary embodiment, any apparatus or component herein can be a monolithic apparatus or component unless otherwise proscribed or unless the art does not enable such.

As can be seen, one embodiment is a cross-shape, the other is a "battle axe" shape. The component's if magnets, can have a diametric polarity or an axial polarity (e.g., in and out of the page with respect to the view of FIG. 103). Thus, for example, the north pole of the magnet is at one blade of the 'battle axe', and the south pole of the magnet is at the other end of the 'battle axe,' with respect to the diametrically opposed polarity.

In FIG. 45, component 10155 can be a magnet. In an exemplary embodiment, the relief areas 10166 between the arms of the cross provide for the aforementioned rotational features detailed herein and/or anti-rotational features detailed herein. In this regard, in an exemplary embodiment, the relief areas reduce the surface that interfaces with the interior surface of the housing, and thus reduces the friction forces, thus making it easier for the component to rotate. In an alternate embodiment, the arms of the cross can be such that they deform the housing ever so slightly in a manner that effectively locks the component 10155 within the housing and thus effectively prevents the component from rotating or otherwise makes it more difficult for the component to rotate.

Figure 48:
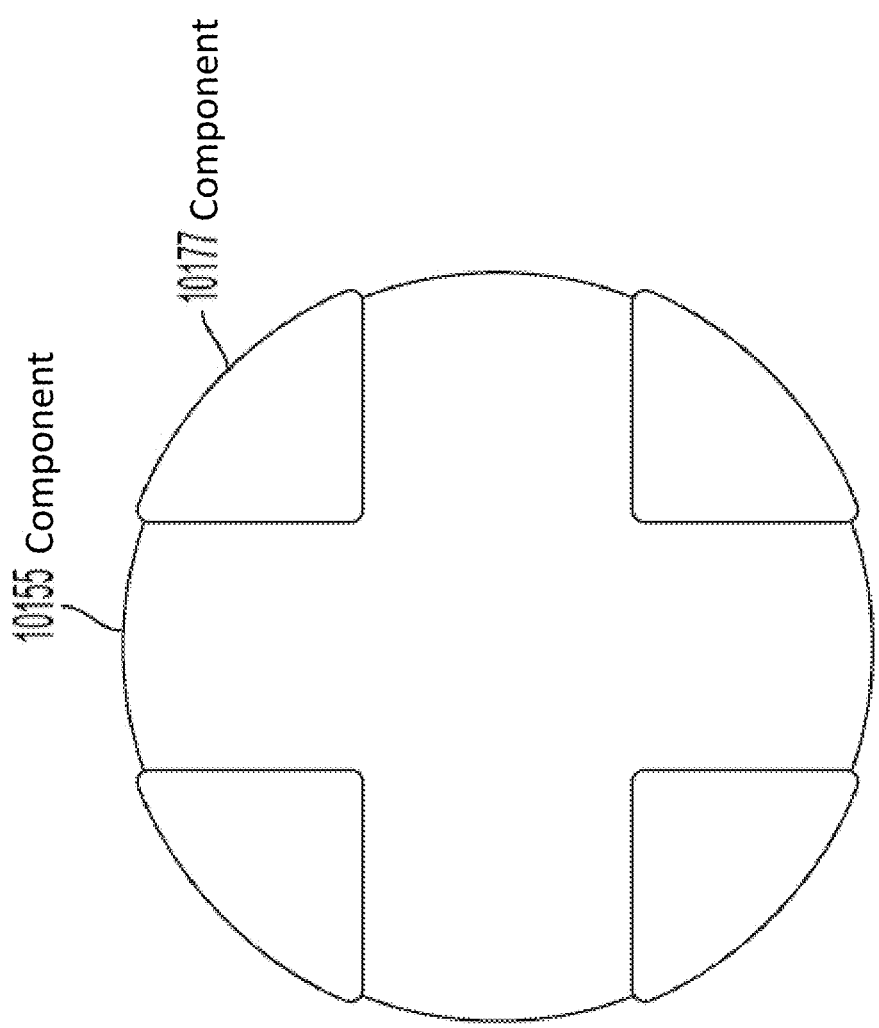
Figure 49:
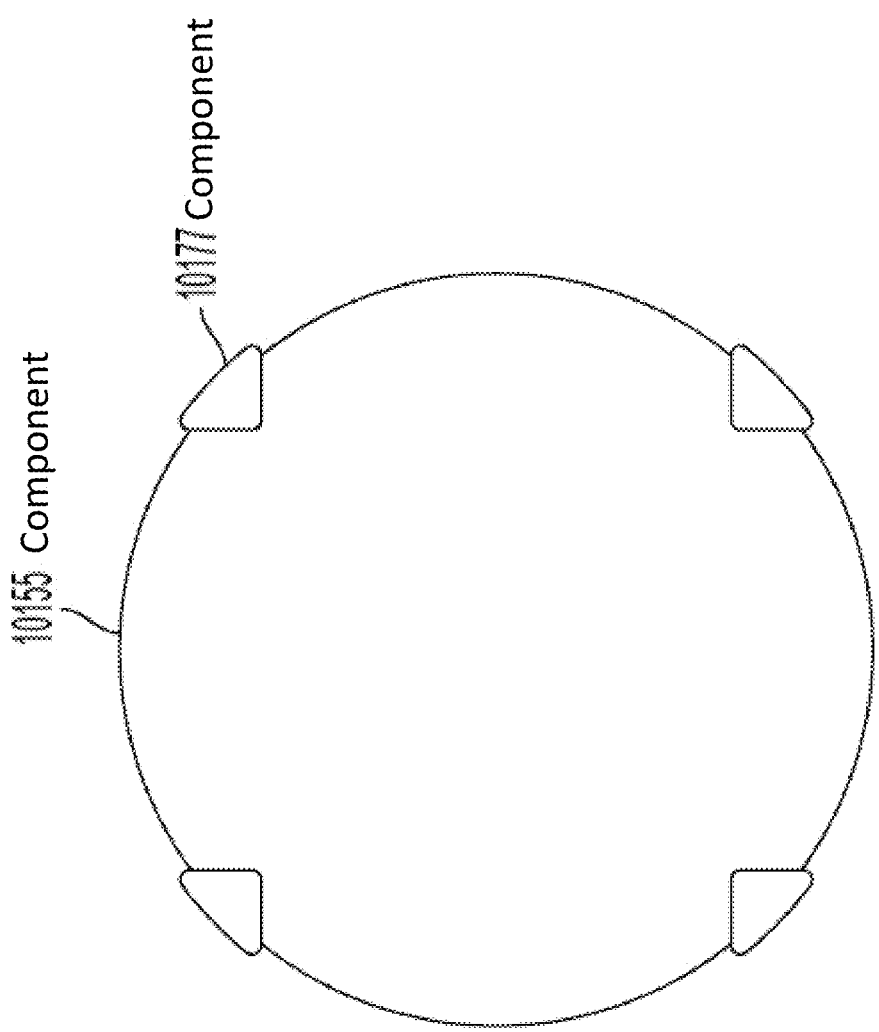

In an exemplary embodiment, the relief areas 10166 between the arms of the cross can be filled with a material that is of a low friction material, while in other embodiments, the relief areas can be filled with a material that is a high friction material, these materials can interact with the inside surfaces of the housing to make rotation easier and/or harder. In an exemplary embodiment, quarter pie shaped components 10177, as seen in FIG. 48, can be located within each of the relief areas, where the curved area of the pie shaped portions has a larger overall outer diameter than the arms of the cross of the component 10155. (These can correspond to the low friction or high friction materials.) In this regard, these pie shaped components can serve the function of the flanking portion detailed above than the other embodiments. Various shapes can be utilized or otherwise implemented, such as seen in FIG. 49, where the outer diameter of the component 10155 is the same as that of FIG. 104, but there is more of the 10155 than in FIG. 48.

Figure 50:
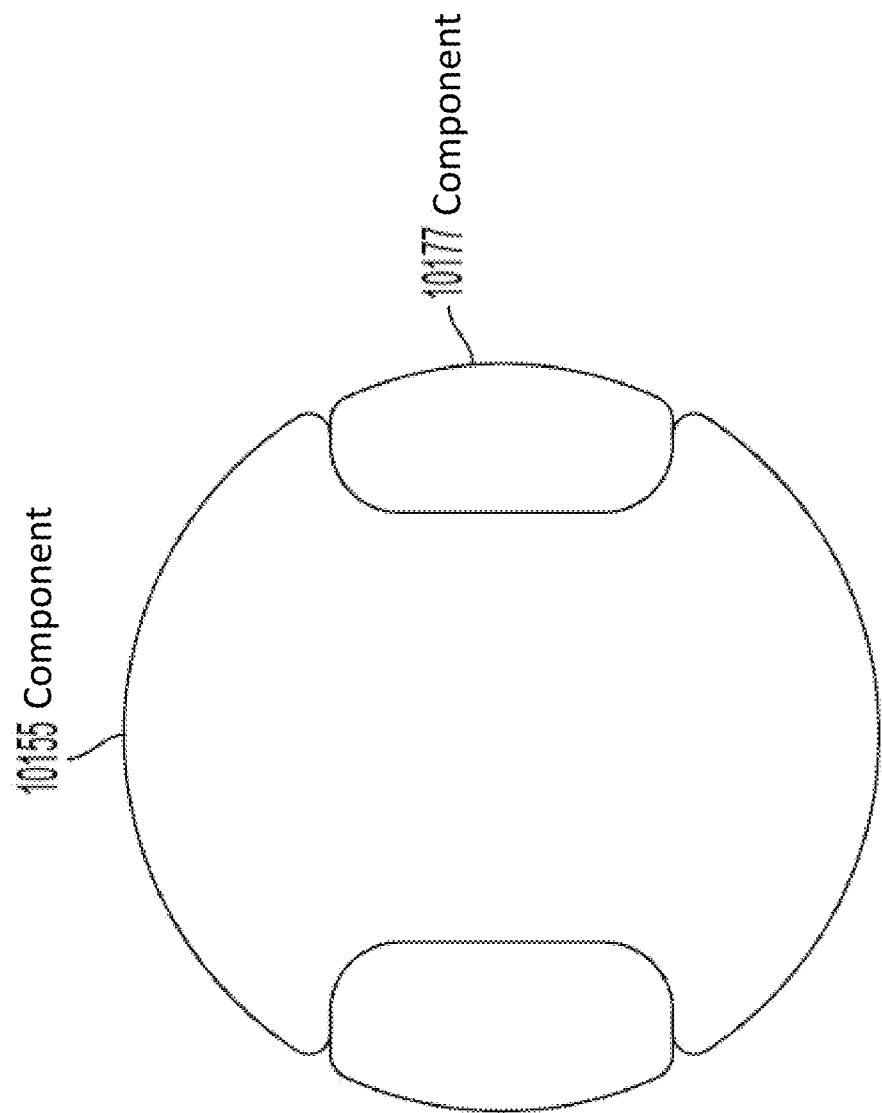

FIG. 46 and FIG. 47 and FIG. 50 depict the aforementioned battle axe configuration. In this exemplary embodiment, as with the cross embodiment, low friction or high friction materials can be located in the recesses 10166. In an exemplary embodiment, truncated half-moons 10177 can be located in the recesses 10166, where the outer curved surface extends past the outer surfaces of the component 10155 as seen.

With respect to the dimensions of FIG. 47, A can be 4, 5, 6, 7, 8, 9, 10, 11, 12, 13, 14, 15, 16, 17, 18, 19, 20, 21, 22, 23, 24, 25, 26, 27, 28, 29, or 30 mm or any value or range of values therebetween in 0.001 mm increments, B can be 1, 2, 3, 4, 5, 6, 7, 8, 9, 10, 11, 12, 13, 14, 15 mm or any value or range of values therebetween in 0.001 mm increments, C can be 1, 2, 3, 4, 5, 6, 7, 8, 9, 10, 11, 12, 13 mm or any value or range of values therebetween in 0.001 mm increments, D can be 0.1, 0.2, 0.3, 0.4, 0.5, 0.6, 0.7, 0.8, 0.9, 1, 2, 3, 4, 5, 6, 7, 8 mm or any value or range of values therebetween in 0.001 mm increments and E can be 0.1, 0.2, 0.3, 0.4, 0.5, 0.6, 0.7, 0.8, 0.9, 1, 2, 3, 4, 5, 6, 7, 8 mm or any value or range of values therebetween in 0.001 mm increments.

The embodiments of FIGS. 45-50 can have any of the dimensions detailed herein if those dimensions are applicable (e.g., radius of curvature, maximum diameter, thickness, etc.).

(The embodiment of FIG. 45 is labeled with magnetic pole markings. This is related to another embodiment which is described above with the angled pole. Briefly, in an embodiment, the polarity of the magnet components, for such embodiments where the components are magnets, are aligned longitudinally and/or diametrically, while in other embodiments, the polarity is different, as described herein.)

It is noted that components 10177 can be used to support the component 10155 or otherwise guide the component in a manner analogous to/the same way as the teachings above with respect to the flanking components. Thus, the anti-rattling features as well as the torque/rotation features can exists in these embodiments as well.

Figure 51:
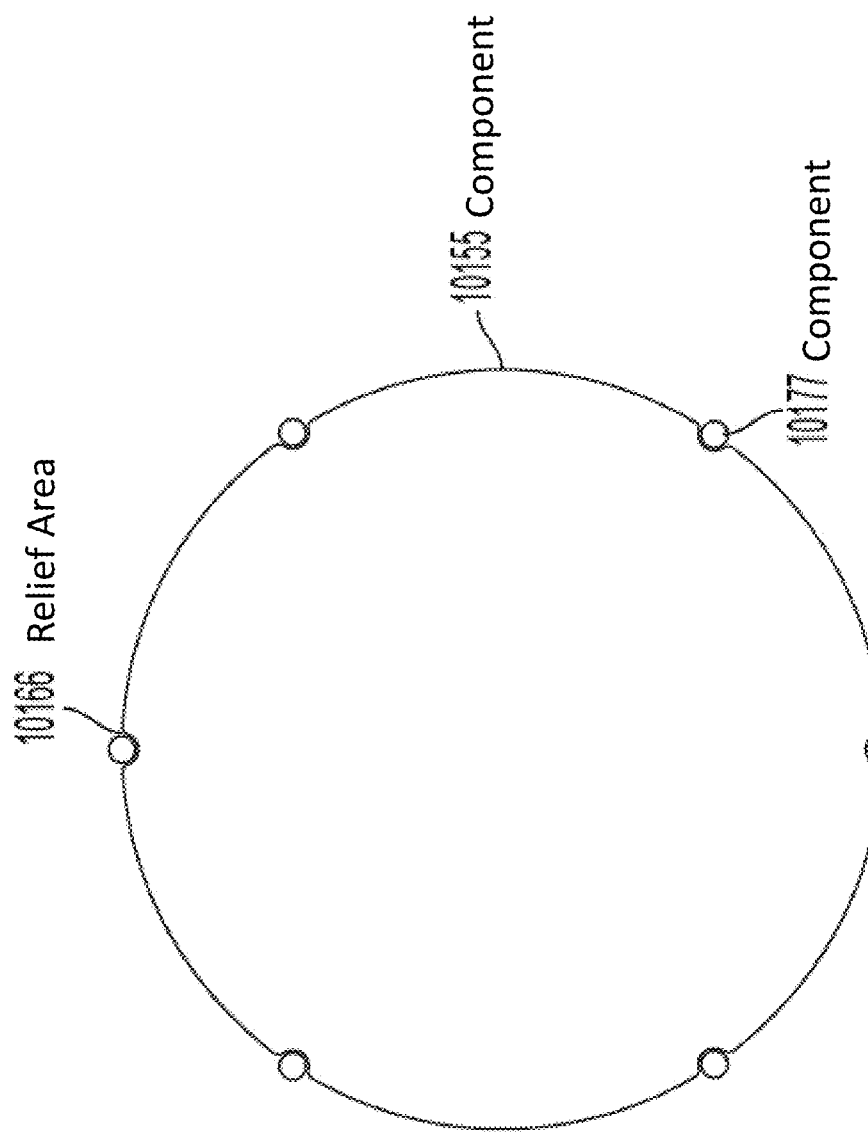

It is further noted that component 10155 can exist in other shapes than detailed above (as is the case with respect to the central portion of the magnet apparatus detailed above and the flanking portions detailed above). Indeed, the embodiment of FIG. 45 can instead be a circle where there are three recesses equally spaced about the periphery at 120-degree increments where support components of the like are located in those recesses. Alternatively, and/or in addition to this, 5, 6, 7, 8, 9, 10, 11, 12, 13, 14, 15 or more recesses can be located about a periphery of a component. In this regard, FIG. 51 presents another exemplary embodiment where there is a magnet component that includes 6 recesses, but can instead be 2, 3, 4, 5, 6, 7, 8, 9, 10, 11, 12, 13, 14, 15 or more recesses arrayed about the perimeter in a symmetrical manner, while in other embodiments these need not necessarily be symmetric. In this exemplary embodiment, cylindrical rollers are located in the recesses, which are sized and dimensioned so that the interfaces between the rollers and the component and the interfaces between the rollers and the sidewall of the housing controls the torque needed to have the component rotate. Particularly, component 10155 can include the 6 recesses 10166, in which rollers (or ball bearings) 10177 are located, as seen in FIG. 51.

It is noted that while the rollers 10177 and the associated recesses 10166 are presented such that the rollers are proud of the outer circumference by about 50% of the diameter of the rollers, in an alternate embodiment, the recesses and the rollers are sized and dimensioned such that only about 1, 2, 3, 4, 5, 6, 7, 8, 9, 10, 11, 12, 13, 14, 15, 16, 17, 18, 19, 20, 21, 22, 23, 24, 25, 30, 35 or 40 percent or more of the roller diameter extends proud of the outer circumference. In an alternate embodiment, the opposite is the case: a majority of the roller diameter extends proud of the outer periphery, and thus the aforementioned percentages can correspond to the amounts of the diameter that is below the outer periphery. (All of the above is with respect to a roller/ball bearing that is pressed against the bottom of the recess/against the component 10155.)

Depending on how much interference exists between the component 10155, the roller 10166/ball bearing 10166, and the inside of the housing, the amount of torque that is required to cause the component 10155 to rotate can be varied.

In an alternate embodiment, the flexibility of the housing can be used to control the amount of torque that is required to cause the component 10155 to rotate. In this regard, and oil canning effect with respect to the sidewalls can be relied upon to impart a resistance that can be overcome upon a sufficient amount of torque to have the component rotate. In an exemplary embodiment, the rollers or ball bearings could be fixed relative to the component 10155. Indeed, in an exemplary embodiment, simple protrusions of the like can be located about the outer periphery of the component 10155. The ideas that as the protrusions interfere with the sidewalls of the housing, the protrusions cause the housing to flex outward, and thus provide resistance against the rotation but permit the rotation.

Figure 52:
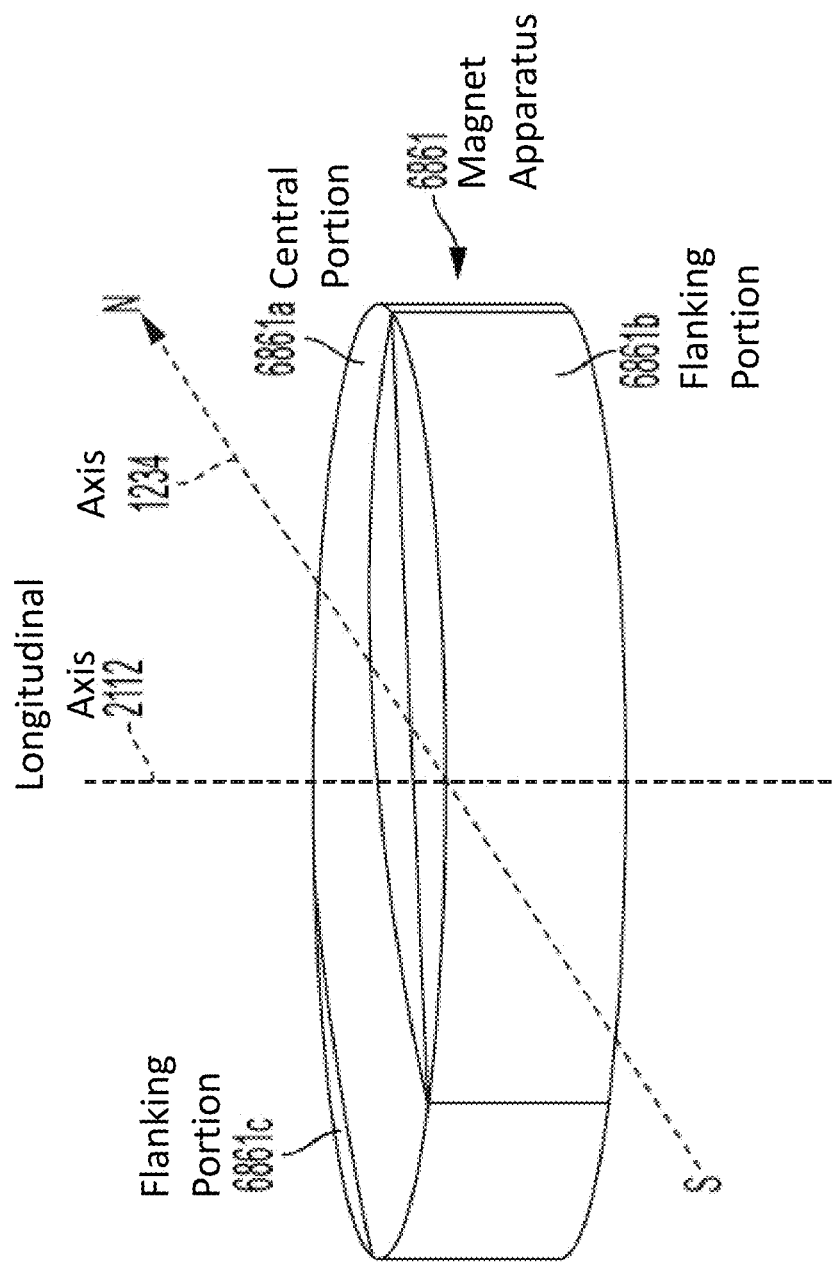
FIG. 52 presents an isometric view of an exemplary embodiment.

An exemplary embodiment includes increasing the amount of magnet material by doming the upper surface of the magnet (e.g., the central portion, the entire magnet apparatus, etc.). In an exemplary embodiment, the doming can be such that it matches the curvature of the outer surface of the implant in that region. This is seen in FIG. 52, which depicts a magnet apparatus 6861 that includes a central portion 6861*a* and flanking portions 6861*b* and 6861*c*. in this exemplary embodiment, the overall polarity of the magnet apparatus 6861 is aligned along axis 1234 as seen. That said, in an exemplary embodiment, a non-angled polar axis can be utilized (aligned with the longitudinal axis 2112 or diametrically aligned). In this exemplary embodiment, all three of the magnet apparatus are magnetic and they are magnetized in the same direction. In this is that at least some exemplary embodiments, the magnet apparatus 6861 can be a monolithic structure. Conversely, in an exemplary embodiment, one or more of the flanking portions need not be a magnetic component/a permanent magnet and/or the central portion 6861a may not be a permanent magnet. Any one or more these components can be a nonmagnetic material such as that disclosed above.

Figure 53:
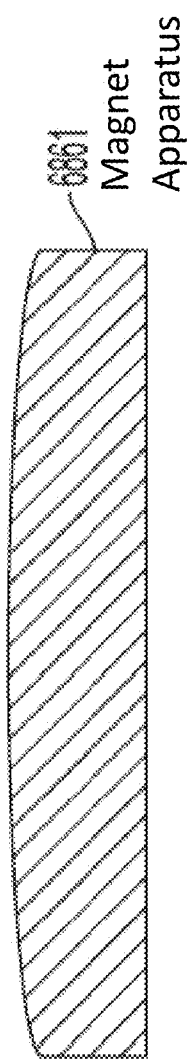
FIGS. 53-55 present cross-sections of some exemplary embodiments.
Figure 54:
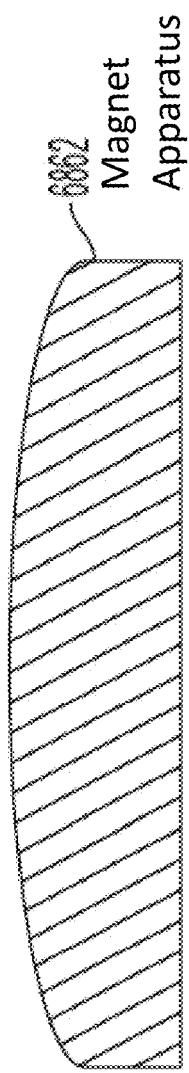
Figure 55:
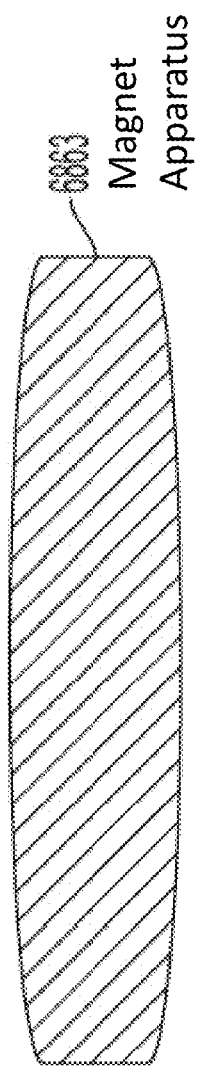

FIG. 53 depicts a cross-sectional view of the magnet apparatus 6861, depicting how the upper surface is curved, corresponding to the domed surface of FIG. 52. In an exemplary embodiment, the dome surface is rotationally symmetric about axis 2112, while in other embodiments, the dome is not rotationally symmetric about axis 2112 or. In an exemplary embodiment, when viewed from above, the overall magnet apparatus is circular. Moreover, the dome can be a surface that has a constant radius of curvature and/or has a varying radius of curvature from one side to the other. In an exemplary embodiment, the dome surface is elliptical (e.g., half of an ellipse) while in other embodiments the dome surface is circular (can be, for example, a tenth or a $20^{th}$ or a $30^{th}$ or a $50^{th}$, etc., of a circle. Any arrangement that can enable the teachings detailed herein can be utilized at least some exemplary embodiments. FIG. 54 depicts an alternate exemplary embodiment of a magnet apparatus 6862 that has a domed top surface that has a lower radius of curvature than that of the embodiment of FIG. 53. FIG. 55 depicts an exemplary embodiment of a magnet apparatus 6863 where both the top and bottom are domed.

In an exemplary embodiment, the external component retention force can be increased by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 40 or 50% or any value or range of values therebetween in 0.1% increments, relative to that which would be the case with a flat surface, all other things being equal. In an exemplary embodiment, there can be thus an increased retention force which can mean that the external coil is less likely to fall off during daily activities. In an exemplary embodiment, the dome can have a maximum height above an extrapolated flat surface (if the magnet apparatus was disk shaped) of 0.1, 0.15, 0.2, 0.25, 0.3, 0.35, 0.4, 0.45, 0.5, 0.55, 0.6, 0.65, 0.7, 0.75, 0.8, 0.85, 0.9. 0.95, 1, 1.1, 1.2, 1.3, 1.4, 1.5, 1.6. 1.7, 1.8, 1.9 or 2 mm or any value or range of values therebetween in 0.01 mm increments. In an exemplary embodiment, the aforementioned values are the maximum height of the dome relative to a flat/disk shaped magnet, and/or the radius of curvature of the dome (at least in some locations), etc. An exemplary embodiment has a radius of curvature at at least one location of 1, 1.5, 2, 2.5, 3, 3.5, 4, 4.5, 5, 5.5, 6, 6.5, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 450 or 500 mm or more or any value or range of values therebetween in 0.1 mm increments.

In view of the above, it can be seen that embodiments include an implantable medical device, comprising a magnet apparatus, which can be a monolithic body or made up of a plurality of components, and a body encompassing the magnet, wherein the magnet apparatus has a circular cross-section on a plane normal to a longitudinal axis of the magnet apparatus with a dome shape on top. In an exemplary embodiment, the dome is a 0.1 to 1.0 mm dome, 0.2 to 0.7 mm dome, a 0.3 to 0.6 mm dome, etc.

In an exemplary embodiment, the implantable medical device described above and/or below has a dome located only on one side of the magnet apparatus, while in other embodiments, the dome is located on both sides of the magnet apparatus (and the domes need not be identical—the domes can have different configurations.

In an exemplary embodiment, there is an implantable medical device as described above and/or below, wherein the dome is located only on both sides of the magnet apparatus and the magnet apparatus is not symmetrical about a plane that bisects the circular portion in half that does not extend through the dome.

In an exemplary embodiment, as compared to a disk, where the tops and bottoms are flat and parallel to each other, the magnet apparatus 6861 is such that the amount of magnetic material is greater than at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 40 or 50% or more or any value or range of values therebetween in 0.1% increments, relative to that which would be the case with a flat surface, all other things being equal. The dome/portions above the flat section would be located if the magnet apparatus was a disk, can constitute at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 40 or 50% or more or any value or range of values therebetween in 0.1% increments of the amount of the magnetic material of the magnet apparatus.

Some additional features of devices and systems and methods that prevent the magnet group from rotating in some embodiments, and enhance rotation in other embodiments, will be described in greater detail below. First however, some exemplary methods will now be described.

Accordingly, now with reference to FIG. 15, which presents an exemplary flowchart for an exemplary algorithm for an exemplary method, method 1500, there is an exemplary method in an exemplary embodiment, there is an exemplary method that includes method action 1510 which includes obtaining access to a recipient of a medical device including a magnet group implanted in the recipient. Method 1500 also includes method action 1520, which includes exposing the recipient and the magnet group to an MRI field of at least 1 T without removing the magnet group and without the magnet rotating. Any disclosure herein of exposure of the implantable component to an MRI magnetic field or otherwise to a magnetic field corresponds to a disclosure of an exemplary embodiment where that magnetic field is applied in a direction that imparts maximum torque onto the magnet/magnet apparatus/magnet group, etc. Accordingly, the aforementioned MRI field of at least 1 T can, in some embodiments, but not in others, the exposing the direction that imparts the maximum torque onto the implanted magnet. Further, any disclosure herein of exposure of the implantable component to an MRI magnetic field or otherwise to a magnetic field corresponds to a disclosure of an exemplary embodiment where that magnetic field is applied in a direction that is parallel to and aligned with the longitudinal axis of the implant (e.g., with respect to the cochlear implant 300 above, parallel to the line from the point where the array 118 enters the body 199 to the center point of the screw 222 in the view of FIG. 6U.) and also corresponds to an alternate disclosure of an exemplary embodiment where the magnetic field is applied in a direction that is perpendicular to the longitudinal axis of the implant. In an exemplary embodiment, any of these aforementioned magnetic fields can be applied in a direction that is parallel to the tangent surface of the skin immediately above the implant and/or perpendicular to the tangent surface of the skin immediately above the implant. In an exemplary embodiment, any of these aforementioned magnetic fields can be applied in a direction that is 0, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175 or 180 degrees or any value or range of values therebetween in 1° increments about the longitudinal axis as measured from a location that is perpendicular to the bottom surface of the implant (either direction) and/or angled relative to the longitudinal axis (as measure from the longitudinal axis), and/or about an axis that is normal to the longitudinal axis that is also normal to the bottom surface of the implant.

Still with respect to FIG. 15, in an exemplary embodiment, method action 1520 can include exposing the recipient and the magnet group to an MRI field of at least 1.5, 2, 2.5, 3, 3.5, 4, 4.5, 5, 5.5, 6, 6.5, 7, 7.5 or 8 T or any value or range of values therebetween in 0.1 T increments without removing the magnet group and without the magnet rotating. In an alternate embodiment of this exemplary embodiment, the magnet group rotates but only a limited amount, such as any of the amounts detailed above. In an exemplary embodiment, the aforementioned magnetic fields are applied in any one or more of the aforementioned regimes, including, for example, some regimes that results in maximum torque being applied to the magnet apparatus.

Corollary with the teachings detailed above, it is noted that in some embodiments, any rotation can include rotation of the overall housing in which the magnet group is located/magnet apparatus is located, if such is applicable. Again, in some embodiments, it is possible that the housing rotates with the magnets upon the application of a sufficient torque onto the magnets, and that rotation can be in a one-to-one relationship.

FIG. 16 presents another exemplary flowchart for an exemplary algorithm for an exemplary method, method 1600, where there is an exemplary method action 1610 which includes obtaining access to a recipient of a medical device including a magnet group implanted in the recipient. Method 1500 also includes method action 1620, which includes exposing the recipient and the magnet group to an MRI field of at least 1 T without removing the magnet group and with the magnet rotating.

The aforementioned values of 1 T can be replaced with any of the values detailed herein in alternative embodiments. Thus, as with the embodiment of FIG. 15, in an exemplary embodiment, Still with respect to FIG. 16, in an exemplary embodiment, method action 1620 can include exposing the recipient and the magnet group to an MRI field of at least 1.5, 2, 2.5, 3, 3.5, 4, 4.5, 5, 5.5, 6, 6.5, 7, 7.5 or 8 T or any value or range of values therebetween in 0.1 T increments without removing the magnet group and with the magnet rotating.

In an exemplary embodiment of some of the methods, prevention of rotation of the magnet group/magnet apparatus that occurs results in the magnet having an orientation that is maintained for at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, or 35 or 40 or 45 or 50 or 55 or 60 years or more or any value or range of values therebetween in one day increments. This can be the case irrespective of whether or not the magnet rotates upon the exposure to the magnetic field. In the embodiment where the magnet rotates, that can be the first time that the magnet group was rotated since implantation (if there was rotation during implantation). That said, in some embodiments, the magnet group will never rotate the life of the implant a long as the implant is implanted into the recipient, irrespective of the magnetic field applied thereto (or at least one or more of the magnetic fields detailed herein).

Orientation of the magnet group can be determined by taking a predetermined arbitrary point on the magnet group (e.g., one or both of the locations on the circumference where the first magnet portion ends and the second portion begins) and/or can be determined based on the magnetic field (which can be determined using a device that can measure a magnetic field and/or determine a direction of the magnetic field—low tech could be to put a compass at a fixed location from the magnet and see how the compass changed). The field might not shift at all (other than the normal flexure) or may shift no more than 1, 2, 3, 4, 5, 6, 7, 8, 9, or 10 degrees or any value or range of values therebetween in 0.1° increments.

FIG. 17 presents an exemplary algorithm for an exemplary method, method 1700, according to an exemplary embodiment. Method 1700 includes method action 1710, which includes subjecting a magnet implanted in an implanted medical device implanted in a head of a recipient to a magnetic field. Note that the magnet can be the monolithic magnet group or can be one of the three magnets—this could entail subjecting all three of the magnets to the magnetic field, and thus method action 1710 is met—method action 1710 can be executed by only subjecting one magnet to the field as well. Method 1700 also includes method action 1720, which includes rotating the magnet of the implanted medical device as a result of exposure to the magnetic field. In this exemplary embodiment, the implanted medical device resists rotation of the magnet, but the magnetic field overcomes the resistance. In an exemplary embodiment, the bushing arrangement in a variation of FIG. 6T2 is utilized, where the bushing is interference fitted into the hole through the magnet group and also interference fitted around the cylindrical housing wall that extends from the bottom to the top of the housing so that there is a high friction force between the various components. Indeed, in an exemplary embodiment, a torque of more than 100 inch-pounds is required to be applied to the magnet group to turn the magnet group. In an alternate exemplary embodiment, the implanted medical device does not resist rotation of the magnet. Indeed, in an exemplary embodiment, the implanted medical device has a housing and magnet group apparatus that is lubricated and utilizes the bearings apparatus of FIG. 6T3. In an exemplary embodiment, a torque of 0.1 inch-pounds is sufficient to turn the magnet group. In an exemplary embodiment where the magnet rotates by overcoming resistance to rotation, this is the first time that the magnet rotates since implantation and/or since the last time that the recipient was exposed to an MRI field. In an exemplary embodiment, the magnetic field of at least 1, 1.5, 2, 2.5, 3, 3.5, 4, 4.5, 5, 5.5, 6, 6.5, 7, 7.5, 8, 8.5, 9 T or any value or range of values therebetween in 0.1 T increments that is required to be applied in the method to achieve the rotation of the magnet in method action 1720, which rotation can be any of the rotations detailed herein. This magnetic field can be applied at any of the directions detailed herein and/or variations thereof.

FIG. 18 presents an exemplary algorithm for an exemplary method, method 1800, according to an exemplary embodiment. Method 1800 includes method action 1810, which includes subjecting a magnet implanted in an implanted medical device implanted in a head of a recipient to a magnetic field. Note that the magnet can be the monolithic magnet group or can be one of the three magnets—this could entail subjecting all three of the magnets to the magnetic field, and thus method action 1810 is met—method action 1810 can be executed by only subjecting one magnet to the field as well. Method 1800 also includes method action 1820, which includes rotating the magnet of the implanted medical device as a result of exposure to the magnetic field. In this exemplary embodiment, the implanted medical device resists rotation of the magnet, but the magnetic field overcomes the resistance. In other embodiments, there is no resistance. Still further, in other embodiments, there is residence, and such is substantial. Method 1800 also includes method action 1830, which includes removing the recipient from the magnetic field, wherein after removing the recipient from the magnetic field, an orientation of a magnetic field of the magnet has changed to a second orientation relative to that which was the case when the external medical device was las held against the recipient prior to exposure to the magnetic field and/or the orientation right before application of the magnetic field. In an exemplary embodiment, change in the orientation is rotation about the longitudinal axis of the magnet group of more than or less than or equal to 5, 10, 15, 20, 25, 30, 35, 40, 45, 50, 55, 60, 65, 70, 75, 80, 90, 100, 110, 120, 130, 140, 150, 160, 170, 180, 190, 200, 210, 220, 230, 240, 250, 260, 270, 280, 290, 300, 310, 320, 330, 340, or 350 degrees, or any value or range of values therebetween in 1° increments. In an exemplary embodiment, the implanted medical device maintains that second orientation after removal from the magnetic field due to the resistance to the rotation. In an exemplary embodiment, the orientation is maintained within at least 0.5, 1, 1.5, 2, 2.5, 3, 3.5, 4, 4.5, 5, 6, 7, 8, 9, or 10 degrees or any value or range of values therebetween in 0.1° increments due to the resistance to the rotation. The aforementioned maintenance of the orientation occurs even after a method action that includes replacing the external component onto the recipient such that the implanted magnet group retains the external component against the skin of the recipient as a result of magnetic attraction between the implanted magnet group and a ferromagnetic material the external component.

In an exemplary embodiment, the magnetic field of the methods above are an MRI magnetic field. The MRI field can have any of the strengths herein. In an exemplary embodiment, the magnetic field is the magnetic field of another magnet, such as the external device. The magnet of the external device can be any of the strengths detailed herein.

Figure 19:
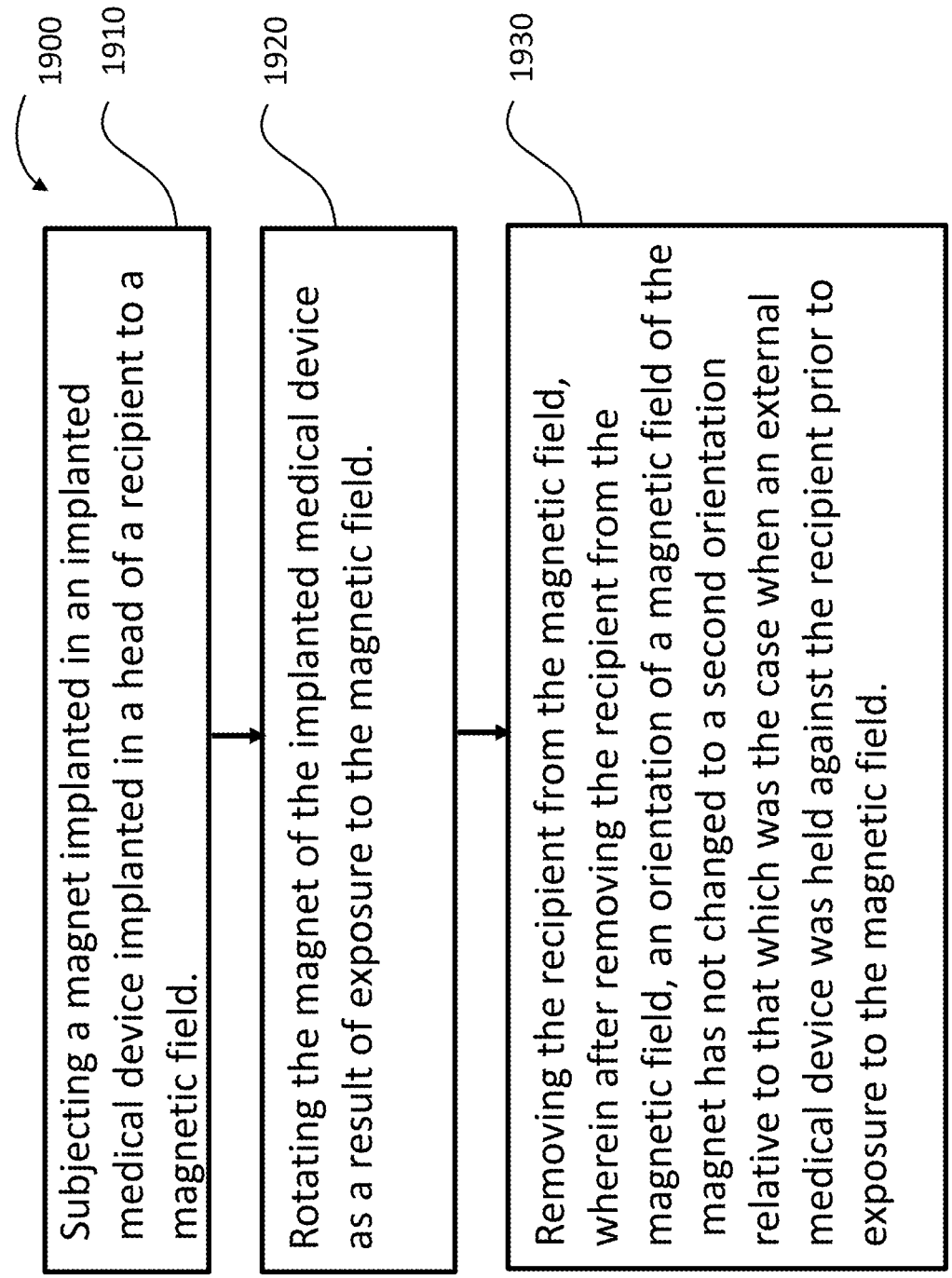

FIG. 19 presents an exemplary algorithm for an exemplary method, method 1900, according to an exemplary embodiment. Method 1900 includes method action 1910, which includes subjecting a magnet implanted in an implanted medical device implanted in a head of a recipient to a magnetic field. Note that the magnet can be the monolithic magnet group or can be one of the three magnets—this could entail subjecting all three of the magnets to the magnetic field, and thus method action 1910 is met—method action 1910 can be executed by only subjecting one magnet to the field as well. Method 1900 also includes method action 1920, which includes rotating the magnet of the implanted medical device as a result of exposure to the magnetic field. In this exemplary embodiment, the implanted medical device resists rotation of the magnet, but the magnetic field overcomes the resistance. Method 1900 also includes method action 1930, which includes removing the recipient from the magnetic field, wherein after removing the recipient from the magnetic field, an orientation of a magnetic field of the magnet has changed to a second orientation relative to that which was the case when the external medical device was held against the recipient prior to exposure to the magnetic field. In an exemplary embodiment, change in the orientation is rotation about the longitudinal axis of the magnet group of more than or equal to 5, 10, 15, 20, 25, 30, 35, 40, 45, 50, 55, 60, 65, 70, 75, 80, 90, 100, 110, 120, 130, 140, 150, 160, 170, 180, 190, 200, 210, 220, 230, 240, 250, 260, 270, 280, 290, 300, 310, 320, 330, 340, or 350 degrees or any value or range of values therebetween in 1° increments. In an exemplary embodiment, the implanted medical device does not maintain the second orientation after removal from the magnetic field. In an exemplary embodiment, there is no resistance to the rotation (the bearing apparatus of FIG. 6T3 can be used in some embodiments). In an exemplary embodiment, within a day or two or three or four or five or the next time that the recipient attaches the external medical device, the orientation changes by at least 0.5, 1, 1.5, 2, 2.5, 3, 3.5, 4, 4.5, 5, 6, 7, 8, 9, 10, 11, 12, 13, 14, 15, 20, 25, 30, 35, 40, 45, 50, 55, or 60 degrees or more, or any value or range of values therebetween in 0.1° increments due to the lack of resistance to rotation. The change can be a result of a method action that includes replacing the external component onto the recipient such that the implanted magnet group retains the external component against the skin of the recipient as a result of magnetic attraction between the implanted magnet group and a ferromagnetic material the external component.

In this regard, in an exemplary embodiment, the magnet of the implanted medical device becomes automatically reoriented to be aligned with the magnet of the external device upon reattachment of the external medical device to the recipient. That said, in an alternate embodiment, this does not happen.

Consistent with the teachings above, in an exemplary embodiment, there is a method according to any of the teachings herein that further includes the action of reattaching the external medical device to the recipient by reestablishing a magnetic connection between the external medical device and the magnet of the implanted medical device. In some embodiments as noted above, the second orientation is maintained while the external medical device is attached to the recipient and afterwards, while in other embodiments, the second orientation changes to another orientation, such as that prior to the second orientation, or another orientation, while the external medical device is attached to the recipient.

It is also noted that, in some embodiments, such as where there is a modicum of flexure associated with the components in, the device limits any change from the new orientation to no more than 1, 2, 3, 4, 5, 6, 7, 8, 9, or 10 degrees.

In some embodiments, the orientation of the external medical device when reattached and subsequently attached is the same as that which was the case when the external medical device was attached to the recipient prior to the action of removing the external medical device from the recipient. In some embodiments, the orientation of the external medical device when reattached and subsequently attached is within 1, 2, 3, 4, 5, 6, 7, 8, 9, 10, 11, 12, 13, 14, 15, 16, 17, 18, 19, or 20 degrees, or any value or range of values therebetween in 0.1 degree increments of that which was the case when the external medical device was attached to the recipient prior to the action of removing the external medical device from the recipient. In an exemplary embodiment, the orientations of the external device are controlled by the orientation of the magnet/magnet group of the implanted device having the new orientation. In an exemplary embodiment, the orientations the external device are independent of the orientation of the implanted magnet. The implanted magnet orientation does not affect the orientation of the external component. In an exemplary embodiment, the orientation of the external component is controlled by or otherwise more influenced at least by a wire that extends from the antenna component of the external component to a behind the ear device, which wire, while flexible, imparts a force however minimal onto the coil component of the external component. In this regard, in an exemplary embodiment, when the external component is reattached, the orientation of the external device is the same as it was prior to the orientation of the implanted magnet changing.

In an exemplary embodiment of the methods detailed above, such as where the orientation of the magnetic field has shifted at least 10, 15, 20, 25, 30, 35, 40, 45, 50, 55, 60, 65, 70, 75, 80, 85, or 90 degrees or more about the longitudinal axis of the magnet group (direction normal to the skin)/the longitudinal axis between the magnet group that is implanted in the recipient and a magnet group of the external medical device with respect to the second orientation relative to the orientation prior to exposure to the magnetic field and/or that which is the case prior to removing the external component prior to exposure to the magnetic field, the aforementioned orientations of the external component are achieved.

In at least some exemplary embodiments, the magnetic field of the methods above can be a magnetic field that is less than, greater than and/or equal to 0.5, 0.6, 0.7, 0.8, 0.9, 1, 1.1, 1.2, 1.3, 1.4, 1.5, 1.75, 2, 2.25, 2.5, 2.75, 3, 3.5, 4, 4.5, 5, 5.5, 6, 6.5, 7, 8, 9, 10, 11, 12, 13, 14, 15, 20, 25, 30, 35, 40, 45, 50, 60, 70, 80, 90, 100, 125, 150, 175, 200, 225, 250, 275, 300, 350, 400, 450, 500, 550, 600, 700, 800, 900, or 1000 times or more (or any value or range of values therebetween in 0.1 increments) stronger than the magnetic field generated by the magnet(s) of the external medical device that is held against the skin by the implantable magnets when that device was held against the person via the magnetic connection between the two.

In an exemplary embodiment, the magnet of the implanted medical device becomes automatically reoriented to be aligned with the orientation of the external magnet upon reattachment of the external medical device to the recipient. Alternatively, in an exemplary embodiment, the magnet of the external medical device becomes automatically reoriented to be aligned with the second orientation upon reattachment of the external medical device to the recipient. That is, the external magnet can rotate in some embodiments. In an exemplary embodiment, one or more of the configurations or features detailed herein associated with the implanted magnet group and/or implanted magnet can be present in the external component as well. Indeed, in an exemplary embodiment, the magnet apparatus of the external component is effectively a duplicate of the magnet apparatus in the implant, while in other embodiments, the tube can have differences. In an exemplary embodiment, the magnet apparatus of the external component can have any one or more or all of the functionalities of the magnet group/magnet of the implanted component. (Also, any method action detailed herein associated with the implanted magnet components can be executed or otherwise associated with the external magnet components providing that the art enables such unless otherwise noted.) In this regard, in an exemplary embodiment, there is a method action that includes replacing the external component against the skin of the recipient such that the external component is magnetically held to the skin by a magnetic attraction between the implant and the external component, wherein the magnet/magnet group of the external component rotates at least 5, 10, 15, 20, 25, 30, 35, 40, 45, 50, 55, 60, 65, 70, 75, 80, 90, 100, 110, 120, 130, 140, 150, 160, 170, 180, 190, 200, 210, 220, 230, 240, 250, 260, 270, 280, 290, 300, 310, 320, 330, 340, or 350 degrees or any value or range of values therebetween in 1° increments. In an exemplary embodiment, the rotation is equal to or at least about equal to the amount of change to the orientation of the magnetic field/implanted magnet that results from exposure to the magnetic field in the methods detailed herein. In an exemplary embodiment, the rotation is an amount that is less than, equal to or greater than 70, 75, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 125, or 130% the amount of change in orientation that resulted in the second orientation or any value or range of values therebetween in 1% increments.

An exemplary embodiment includes an exemplary method, comprising the action of subjecting a magnet located in a housing implanted in an implanted medical device implanted in a head of a recipient to a magnetic field of an MRI machine of at least 1.5 T, or any of the values detailed herein. In this method, there is further the action of maintaining an orientation of the magnet (apparatus or magnet group, etc.) relative to the housing while the magnet is exposed to the magnetic field, wherein the magnetic field imparts a torque onto the magnet, and wherein the magnet is diametrically magnetized. In this embodiment, it is possible for the housing and the magnet to rotate. In an alternate embodiment, neither the magnet nor the housing rotates, or at least the rotation is limited in accordance with the teachings herein.

In an exemplary embodiment, the magnet is part of a magnet group that includes two flanking magnets that are axially magnetized. In an exemplary embodiment, the the magnet is part of a magnet apparats that includes two flanking components that are non-magnetic components and are also located in the housing. In an alternate embodiment, the two flanking components are located outside the housing.

In an exemplary embodiment of this method, there is the action of removing the recipient from the magnetic field, wherein after removing the recipient from the magnetic field, an orientation of a magnetic field of the magnet has not changed. An exemplary embodiment of this method includes the action of reattaching an external medical device to the recipient by reestablishing a magnetic connection between the external medical device and the magnet of the implanted medical device, wherein the attachment force between the external medical device and the implant is the same as that which was the case prior to the exposure to the 1.5 T magnetic field or whatever field that is the subject of this method.

An exemplary embodiment of this method also is such that as a result of the method, the orientation of the external medical device when reattached and subsequently attached is effectively the same as that which was the case when the external medical device was attached to the recipient prior to the action of removing the external medical device from the recipient. Also, in an exemplary embodiment, as a result of the method, the exposure to the magnetic field takes place at least 6 months after implantation of the magnet and the magnet has effectively never rotated relative to the implanted medical device prior the exposure to the magnetic field.

Figure 6X:
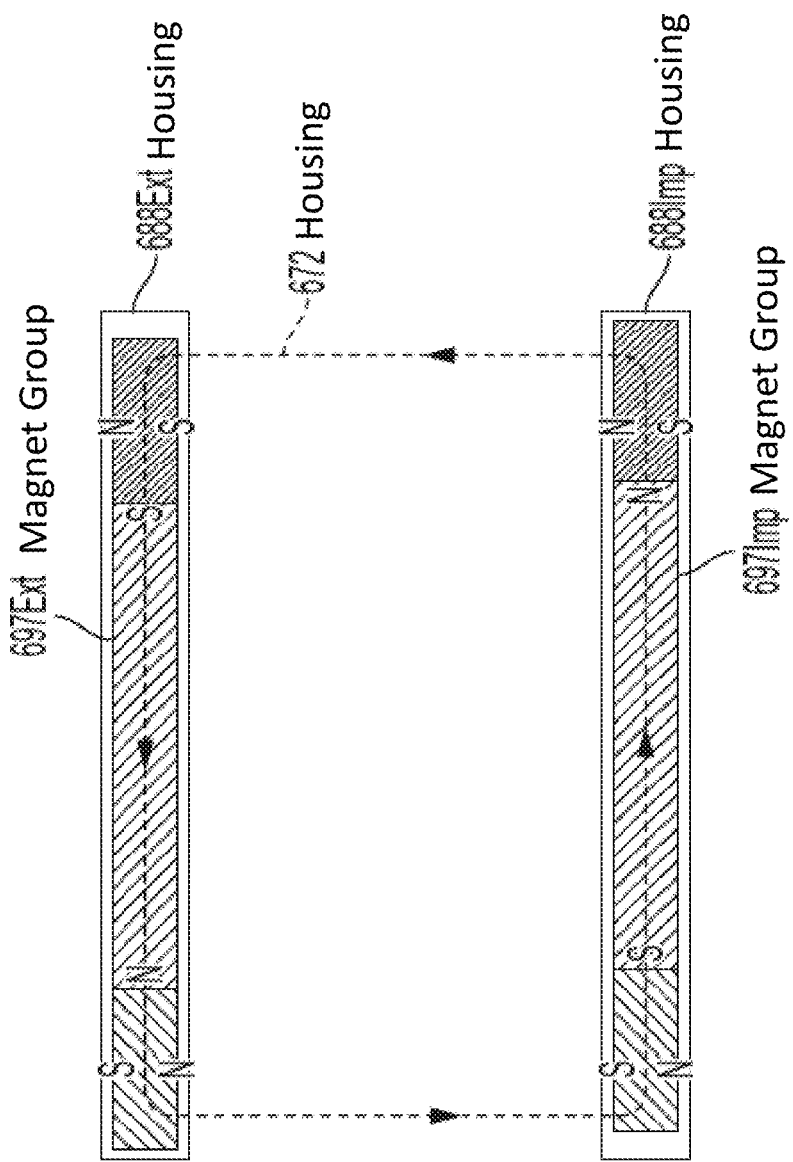
FIG. 6X presents an exemplary magnet arrangement.

Embodiments include an assembly, comprising a housing, such as any of the housings detailed herein, and a magnet apparatus (e.g., any of the magnet groups disclosed herein, or a single magnet/magnet that is a single portion) in the housing. In an exemplary embodiment, the magnet apparatus is configured to provide an axial magnetic flux outside the housing as the strongest magnetic force relative to a diametrical flux and/or a non-axial magnetic flux, if present, existing outside the housing. In an exemplary embodiment, the magnet apparatus has a substantial portion thereof that generates a diametrical flux. In this regard, FIG. 6X depicts a magnet group 679Imp and a magnet group 697Ext, the groups of the respective implanted and external components. Both groups are housed in housings 688Imp and 688Ext, respectively. As can be seen, the magnet groups generate a magnetic flux 672 that has an axial portion (the vertical portion—it is axial because it is parallel with the axial direction of the magnet group/the longitudinal direction) that is located outside the housing and a diametrical portion (the horizontal portion—it is diametrical because it is in the direction of the diameter of the magnet group). The axial flux is at least 1.05, 1.1, 1.15, 1.2, 1.25, 1.3, 1.35, 1.4, 1.45, 1.5, 1.6, 1.7, 1.8, 1.9, 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4 times or more, or any value or range of values therebetween in 0.05 increments stronger than the other flux and/or diametrical flux. It is noted that in some alternate embodiments, as detailed above, the flanking magnets and/or the central magnet may not be present, and otherwise may be a non-magnetic component, in which case the magnetic fields will be difference as would be understood than that depicted in FIG. 6X. Still further, it is noted that in some alternate embodiments, as detailed above, the flanking magnets will have sides that are aligned with the central magnet, and in other alternate embodiments, the magnets can all have polar alignments that are arrayed in the vertical direction. In an exemplary embodiment, the resulting fluxes can still be any of the values detailed herein and/or variations thereof, if such is applicable.

Embodiments include an assembly, comprising a housing, such as any of the housings detailed herein, and a magnet apparatus (e.g., any of the magnet groups disclosed herein, or a single magnet/magnet that is a single portion) in the housing. In an exemplary embodiment, the magnet apparatus is configured to provide an axial magnetic flux outside the housing as the strongest magnetic force relative to a diametrical flux and/or a non-axial magnetic flux, if present, existing outside the housing. In an exemplary embodiment, the magnet apparatus has a substantial portion thereof that generates a diametrical flux. In an exemplary embodiment, the magnet apparatus generates a magnetic field as measured at 2, 3, 4, 5, 6, 7, and/or 8 mm away from the apparatus that is at least 1.05, 1.1, 1.15, 1.2, 1.25, 1.3, 1.35, 1.4, 1.45, 1.5, 1.6, 1.7, 1.8, 1.9, 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4 times or more, or any value or range of values therebetween in 0.05 increments stronger than the flux that would result if the magnet apparatus had all portions generating only respective fluxes that are more aligned with the axial direction (e.g., a single monolithic magnet, such as a disc-shaped magnet, with the N-S axis aligned vertically, or a magnet group having a plurality of portions, all of which have the north south and/or south north axis aligned vertically) or if the apparatus had all portions generating only respective fluxes that are more aligned with the radial direction (e.g., a single monolithic magnet, such as a disk-shaped magnet, within a N-S axis aligned horizontally, or a magnet group having a plurality of portions, all of which have the north south and/or south north axis aligned horizontally), as measured at the same relative location, all other things being equal. In an exemplary embodiment, the location of measurement is at a location that is normal to a face of the magnet apparatus at one of the aforementioned distances as measured above a location that is 0, 5, 10, 15, 20, 25, 30, 35, 40, 45, 50, 55, 60, 65, 70, 75, 80, 85, 90, 95, or 100% of the way across the face of the magnet apparatus as measured at one of its longest or shortest dimension on the skin facing face thereof.

Figure 6Y:
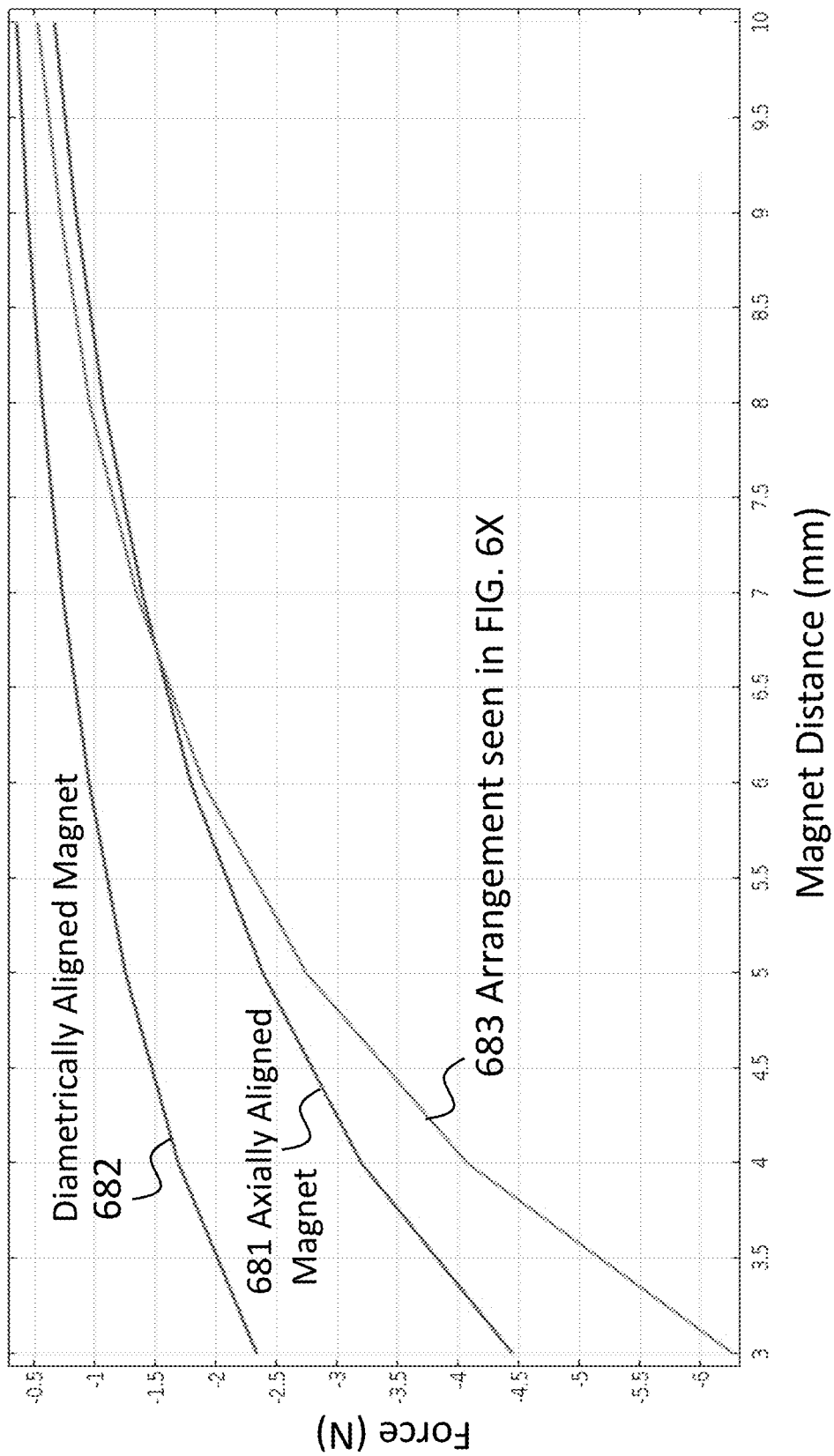
FIG. 6Y presents a chart of data.

Further, in an exemplary embodiment, there is a medical device, comprising an implantable component including a first magnet apparatus (e.g., magnet apparatus 697Imp), and an external component including a second magnet apparatus (e.g., magnet apparatus 967Ext). The first magnet apparatus includes a first portion that generates a first flux that is more aligned with an axial direction of the device (e.g., one of the portions that have the N-S axis aligned in the vertical) and a second portion that generates a second flux that is more aligned with a direction normal to the axial direction (e.g., the portion in the center, having the S-N axis aligned horizontally). In this embodiment, the magnetic force between the implantable component and an external component is stronger than that which would be the case if the first magnet apparatus had all portions generating only respective fluxes that are more aligned with the axial direction (e.g., a single monolithic magnet, such as a disc-shaped magnet, with the N-S axis aligned vertically, or a magnet group having a plurality of portions, all of which have the north south and/or south north axis aligned vertically) or if the first magnet apparatus had all portions generating only respective fluxes that are more aligned with the radial direction (e.g., a single monolithic magnet, such as a disk-shaped magnet, within an N-S axis aligned horizontally, or a magnet group having a plurality of portions, all of which have the north-south and/or south-north axis aligned horizontally). All of this is based on the qualifier that all other things are equal. That is, for example, the material that makes up the magnet apparatuses are the same, the volumes and densities and shapes are all the same, any spacing associated with the components of the same, the housing in which the magnets might be located are the same, etc. This as opposed to, for example, a magnet that has a larger or smaller diameter or larger or smaller thickness or is made up of a different type of magnetic material or is not as "aggressively" magnetized as the comparison or is more "aggressively" magnetized, etc. FIG. 6Y presents an exemplary chart presenting exemplary data for force versus magnet distances for magnet apparatuses that are aligned with one another in a manner akin to that of FIG. 6X but spaced away from one another (the distance is being from the closest surfaces and/or from the centers of gravity and/or the geometric centers of the magnet apparatuses), where 681 is for an axial aligned arrangement (both external and internal magnet apparatuses), 682 is for a diametrically aligned arrangement (both external and internal magnet apparatuses) and 683 is for the arrangement seen in FIG. 6X. It is noted that in the above-described embodiment, only qualifiers have been applied to the magnet apparatus of the implant (other than the all things being equal qualifier which applies to everything), and thus the magnet apparatus of the external component can be a same type or a different type of magnet than that detailed. In this regard, the magnet apparatus of the external component can be a magnet apparatus that has all portions thereof (it can be a monolithic component or separate components—it can also have only one portion) having magnetization in the same direction (axial, diametric, etc.). In an exemplary embodiment, the external component can have a magnet apparatus that is a monolithic disc magnet (working the magnet group) or a cylindrical magnet that has the north-south axis (or the group of axes) aligned in the axial direction. In an exemplary embodiment, the external component can have a magnet apparatus that is a monolithic disc magnet or a cylindrical magnet that has a north-south axis (or group of axes) aligned in the diametric direction. In an exemplary embodiment, for one or both of these alternate arrangements, the force curves for a given distance can be greater than, less than or equal to 1, 1.05, 1.1, 1.15, 1.2, 1.25, 1.3, 1.35, 1.4, 1.45, or 1.5 times or more, or any value or range of values therebetween in 0.01 increments of that shown in FIG. 6Y (e.g., the force can be increased by 1.06 times or decreased by 1.06 times at the 5 mm separation, and be increased or decreased 1.08 times at the 5.25 separation, etc.). Note also that the axes can be offset from perfectly axial and perfectly diametrical. In an exemplary embodiment, the flux for an external axially aligned magnet can have the flux that flows through a center of the magnet (where there is a north-south alignment with the north pole facing the implant) to the south pole of the axially aligned implanted magnet and in the flux flows through the diametrically aligned magnet to the magnet on the end with the north pole facing the external magnet, and then the flux flows from the north pole of that magnet around the external magnet to the south pole which faces away from the implanted magnet, and so on.

In an exemplary embodiment, the magnet apparatus is disk shaped, while in other embodiments, the magnet apparatus is rectangular shaped, and in other embodiments, it is cylindrical shaped (anything where the diameter is less than half the height shall be considered cylindrical as that is used herein). In an exemplary embodiment, as seen in FIG. 6X, the magnet apparatus has a component thereof that generates a diametrically aligned magnetic flux at a geometric center of the magnet apparatus. This as opposed to the embodiments where there is a hole at the center, and thus do not generate such a flux at the geometric center.

In an exemplary embodiment, consistent with the teachings above, the housing and magnet apparatus are parts of an implantable component of the medical prosthesis, the medical prosthesis includes an external component that includes a respective magnet apparatus, and the medical prosthesis is configured to hold the external component against skin of the recipient via the axial magnetic flux.

In an exemplary embodiment, there is a medical prosthesis, comprising a housing and a magnet apparatus in the housing, wherein the magnet apparatus is configured to provide an axial magnetic flux outside the housing as the strongest magnetic force relative to a diametrical flux, if present, outside the housing and the magnet apparatus is configured to rotate about the axial direction, wherein the axial direction is at least generally normal to skin of a recipient when the medical prosthesis is used with a recipient.

In an exemplary embodiment, the magnetic force between the magnet apparatus of the implantable component and the magnet apparatus of the external component, when positioned as would be positioned when used on a recipient at a distance of ABC mm away from each other, is at least and/or equal to and/or no greater than XYZ times that which would be the case with respect to purely axial polarity magnets of the same size and same mass and same material magnetized at a maximum magnetism while still being usable as a medical prosthesis. ABC can be any value or range of values shown on the chart on FIG. 6Y, in 0.1 mm increments, and can be smaller or larger (e.g., 0 mm to 20 mm, all in 0.1 mm increments. YZX can be 1.05, 1.1, 1.15, 1.2, 1.25, 1.3, 1.35, 1.4, 1.45, 1.5, 1.6, 1.65, 1.7, 1.75, 1.8, 1.85, 1.9, 2, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8. 3.9, 4, 4.25, 4.5, 4.75, 5, 5.5, 6, 6.5, 7. 7.5, 8 or any value or range of values therebetween in 0.01 increments. XYZ can also be converted to a percentage (e.g., 1.05 times would be 5% greater, etc.). These values can be for the arrangement of FIG. 6X, or for the variation thereof where the external magnet apparatus has the different configurations detailed above.

In an exemplary embodiment, there is an apparatus as detailed herein wherein the magnetic force between the magnet apparatus of the implantable component and the magnet apparatus of the external component, when positioned as would be positioned when used on a recipient at a distance of three mm away from each other, is at least 100% greater than that which would be the case with respect to purely diametrical polarity magnets of the same size and same mass and same material magnetized at a maximum magnetism while still being usable as a medical prosthesis. In this regard, it is noted that at least some embodiments herein associated with comparisons to other designs are at comparisons where the magnets are magnetized to their maximum magnetization capacity.

In some embodiments, the implanted and/or the external magnet apparatus is configured to rotate relative to the remainder of the respective internal and/or external component (which includes the embodiments where a minimum torque is needed to start the rotation (initially resists, and then rotates). In some embodiments, the implanted and/or the external magnet apparatus is configured to not rotate relative to the remainder of the respective internal and/or external component (different from the embodiments where a minimum torque is needed to start the rotation (initially resists, and then rotates). In some embodiments, one rotates and the other does not. In some embodiments, both rotate. In some embodiments, no magnet apparatus rotates. Thus, in some embodiments, the magnet apparatus of the external component is configured to rotate relative to the remainder of the external component, and the magnet apparatus of the implantable component drives the orientation of the magnet apparatus of the external component (this can be a result of the implantable component not rotating at all, and also a result of the implantable component having rotated but then being fixed because a torque is not applied that is strong enough to have the magnet rotate more). Thus also, in some embodiments, the magnet apparatus of the implanted component is configured to rotate relative to the remainder of the implanted component, and the magnet apparatus of the external component drives the orientation of the magnet apparatus of the implantable component (this can be a result of the external component not rotating at all, and also a result of the external component having rotated but then being fixed because a torque is not applied that is strong enough to have the magnet rotate more). In an exemplary embodiment, the housing and the magnet apparatus establish a housing-magnet apparatus assembly (of the internal component or the external component, respectively—both can have such as well). The (respective) housing-magnet apparatus assembly is configured to resist rotation of the magnet apparatus within the housing for magnet fields below ZKW Tesla, where ZKW can be 0.25, 0.5, 0.75, 1, 1.25, 1.5, 1.75, 2, 2.25, 2.5, 2.75, 3, 3.25, 3.5, 3.75, 4, 4.25, 4.5, 4.75, or 5 or more, or any value or range of values therebetween in 0.05 increments, where these fields are aligned, in some embodiments, and not others, to impart at least about maximum torque onto the magnet apparatus. The (respective) housing-magnet apparatus assembly is configured to enable rotation of the magnet apparatus within the housing for magnet fields only larger than ZKW Tesla (so aligned as detailed above), in some other embodiments.

In an exemplary embodiment, the implant is configured such that the magnet group or magnet apparatus or magnet resists rotation as a unit relative to the housing (here, there is a housing containing the magnet) about an axial direction with respect to a first torque range applied about the axial direction to the magnet group/apparatus/magnet, wherein the first range is a range that includes a torque that causes the housing and the magnet group to rotate relative to a remainder of the apparatus. Here, the housing and the magnet are such that any rotation that occurs will be one to one rotation, and will result in the torque overcoming the friction between the silicone body and the housing, for example. Also, in an exemplary embodiment, the implant is configured such that the magnet group, etc., resists rotation as a unit relative to the housing about an axial direction with respect to a first torque range applied about the axial direction to the magnet group, wherein the first range is a range that includes a torque that causes the apparatus to fail due to the torque. For example, the housing will pop out of the silicone body 170, the silicone body will rip apart, or otherwise plastically deform, etc. In an exemplary embodiment, the first torque range can be a range of torques according to any of the ranges herein, and can be a range that includes zero to 0.1, 0.15, 0.2, 0.25, 0.5, 0.75, 1, 1.25, 1.5, 1.75, 2, 2.5, 2.75, 3, 3.5, 4., 4.5, 5, 5.5, 6, 7, 8, 9, 10, 11, 12, 13, 14, 15, 16, 17, 18, 19, 20, 21, 22, 23, 24, 25, 30, 35, 40, 45 or 50 or 60 or 70 or 80 or 90 or 100 or more inch-pounds or any value or range of values therebetween in 0.05 inch-pound increments.

It is noted that any disclosure of a device and/or system herein corresponds to a disclosure of a method of utilizing such device and/or system. It is further noted that any disclosure of a device and/or system herein corresponds to a disclosure of a method of manufacturing such device and/or system. It is further noted that any disclosure of a method action detailed herein corresponds to a disclosure of a device and/or system for executing that method action/a device and/or system having such functionality corresponding to the method action. It is also noted that any disclosure of a functionality of a device herein corresponds to a method including a method action corresponding to such functionality. Also, any disclosure of any manufacturing methods detailed herein corresponds to a disclosure of a device and/or system resulting from such manufacturing methods and/or a disclosure of a method of utilizing the resulting device and/or system.

Unless otherwise specified or otherwise not enabled by the art, any one or more teachings detailed herein with respect to one embodiment can be combined with one or more teachings of any other teaching detailed herein with respect to other embodiments. Also, unless otherwise specified or otherwise not enabled, any one or more teachings detailed herein can be excluded from combination with one or more other teachings, in some embodiments.

Figure 7A:
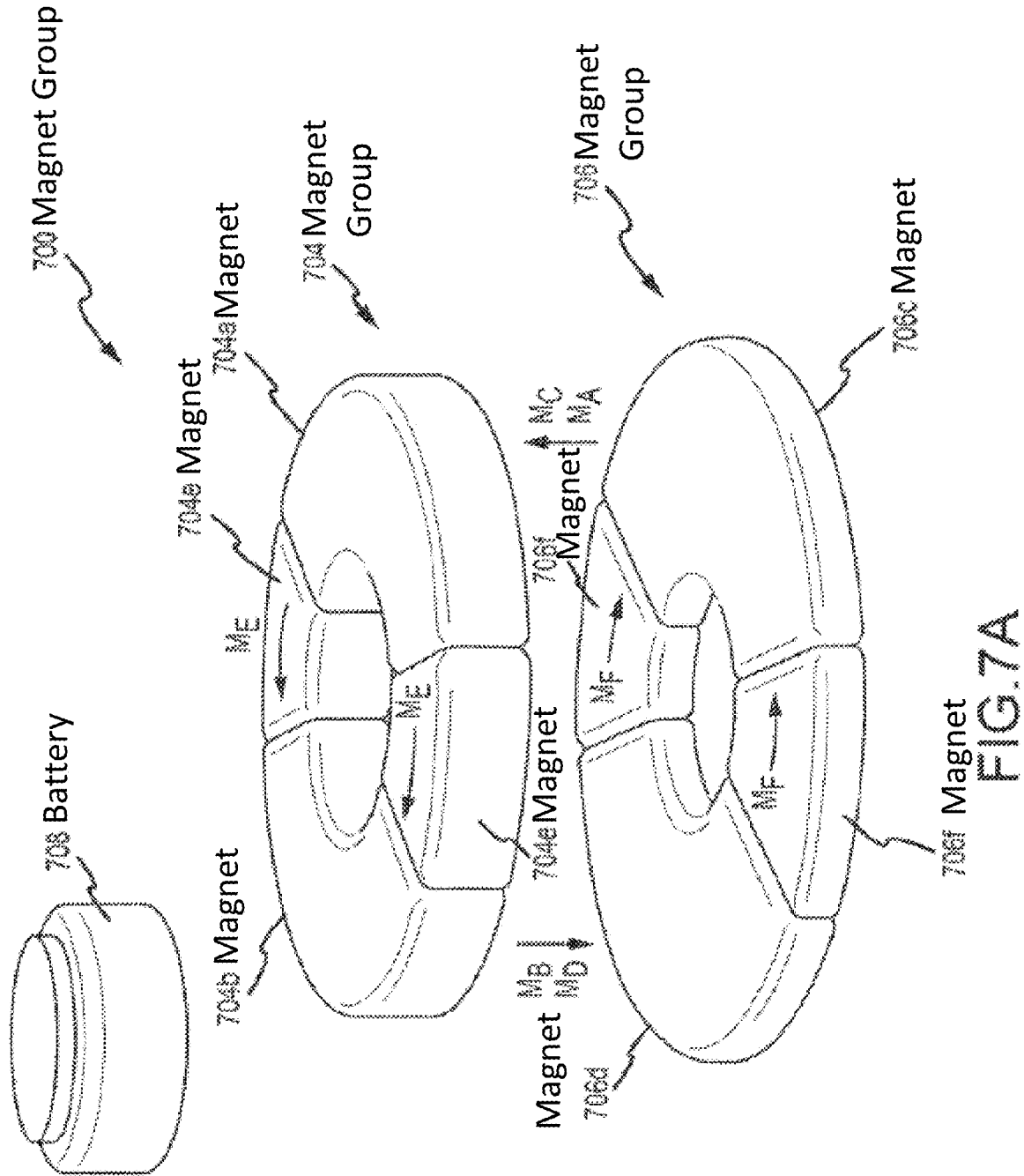
FIG. 7A is a perspective view of a magnet group in accordance with another example of the technology.

Thus, any of the magnet portion arrangements disclosed herein can be used anywhere (internal and/or external) and any of the features described with respect to the magnet arrangement of FIG. 6A for example, can be used with that of FIG. 7A, etc., and vice versa.

While various embodiments have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments but should be defined only in accordance with the following claims and their equivalents.

FIG. 7A is a perspective view of a magnet group 700 in accordance with another example of the technology. Many of the components are generally numbered consistently with the components of FIG. 6A, but beginning with 700, and not all elements thereof are necessarily described further. Magnet group 704 also includes a third magnet 704e that includes two discrete magnets, disposed between magnets 704a and 704b. Similarly, magnet group 706 also includes a third magnet 706f, disposed between magnets 706c and 706d. Here, magnets 704e and 706f are substantially wedge-shaped. FIG. 7B is a plot showing retention force versus magnet separation for the magnet group 700 of FIG. 7A. FIG. 7C is a plot showing battery force versus magnet separation for the magnet group 700 of FIG. 7A. The forces plotted in both are based on a separation distance of the external and implantable magnet groups 704, 706, and are compared to plots depicted in FIGS. 8B and 8C below in an exemplary embodiment, bushing 655 is interference fitted.

Figure 8A:
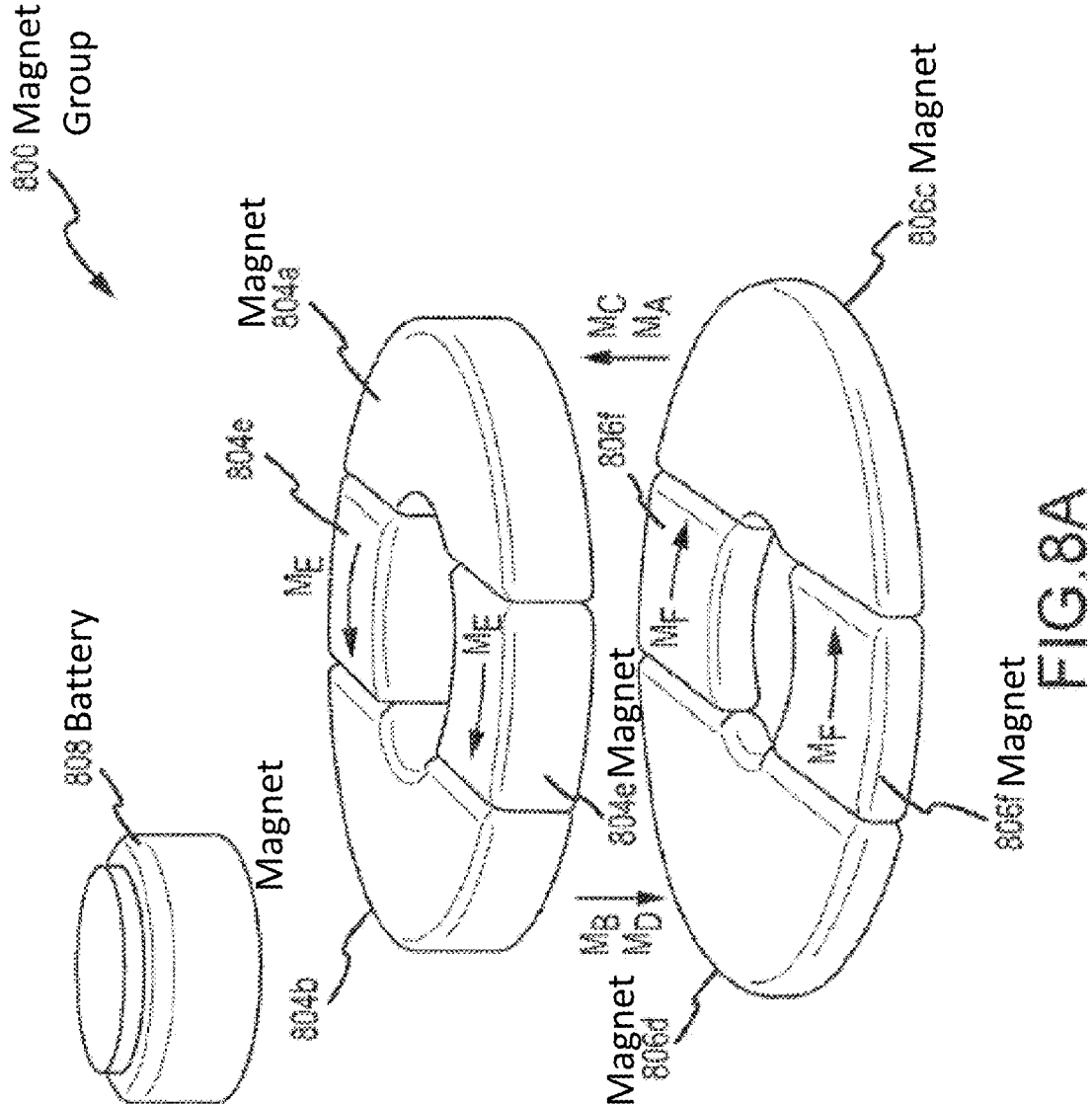
FIG. 8A is a perspective view of a magnet group in accordance with another example of the technology.
Figure 8C:
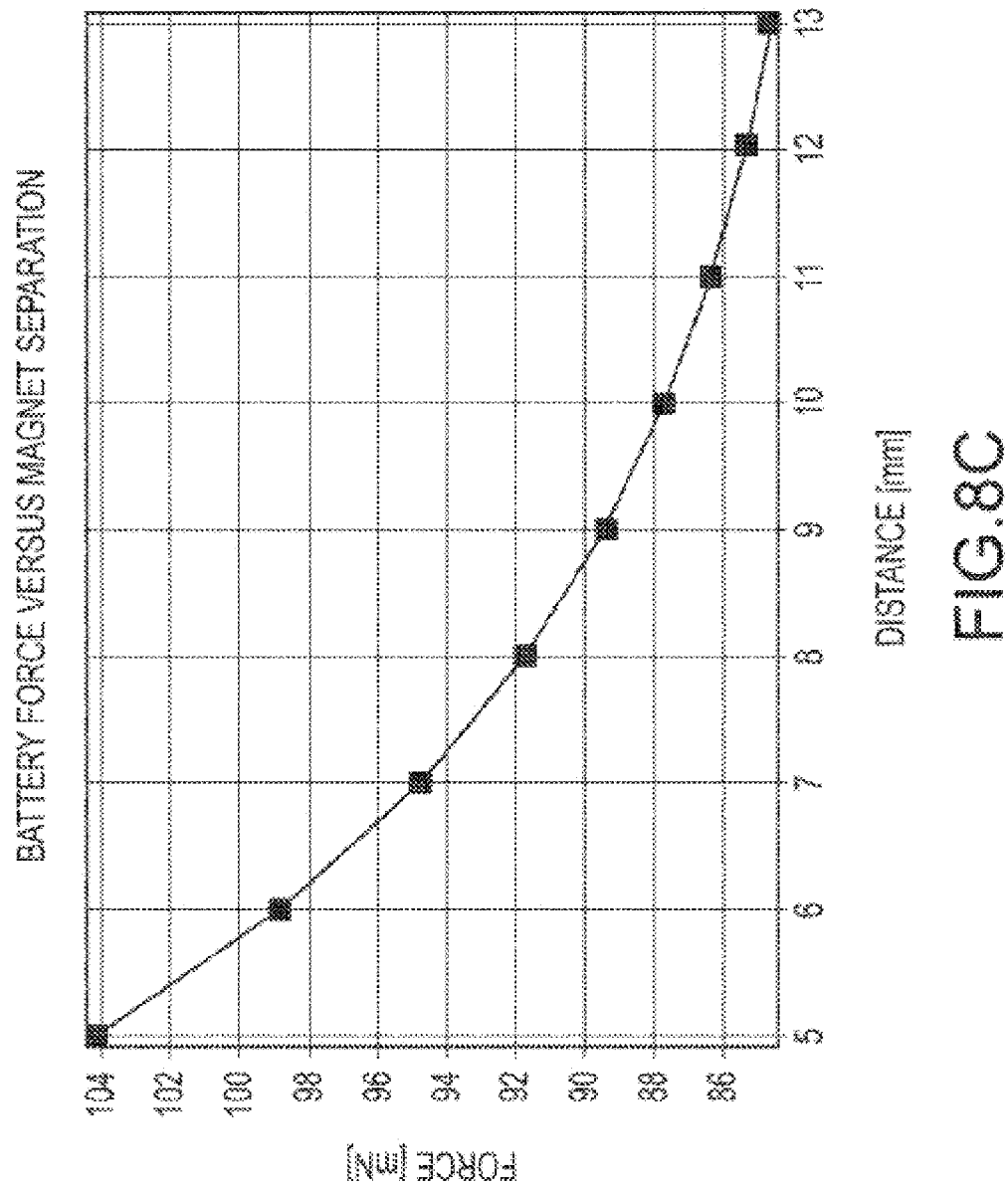
FIG. 8C is a plot showing battery force versus magnet separation for the magnet group of FIG. 8A.

FIG. 8A is a perspective view of a magnet group 800 in accordance with another example of the technology. This magnet group 800 is identical to the magnet group 600 depicted FIG. 6A and thus not all elements thereof are necessarily described further. Here, magnets 804e and 806f are substantially trapezoidal. FIG. 8B is a plot showing retention force versus magnet separation for the magnet group 800 of FIG. 8A. This plot presents the same information as the plot of retention force versus magnet separation for the magnet group 600, as depicted in FIG. 6A. As compared to the plots of FIGS. 7B and 7C, it can be concluded that the shapes of the diametrically magnetized third magnets (e.g., 704e, 706f in FIG. 7A; and 804e, 806f in FIG. 8A) are not critical. FIG. 8C is a plot showing battery force versus magnet separation for the magnet group 800 of FIG. 8A. This plot presents the same information as the plot of battery force versus magnet separation for the magnet group 600, as depicted in FIG. 6A. The reduced battery force depicted in FIG. 8C indicates that the configuration of magnet group 800 might be slightly more desirable than that of magnet group 700.

Figure 9A:
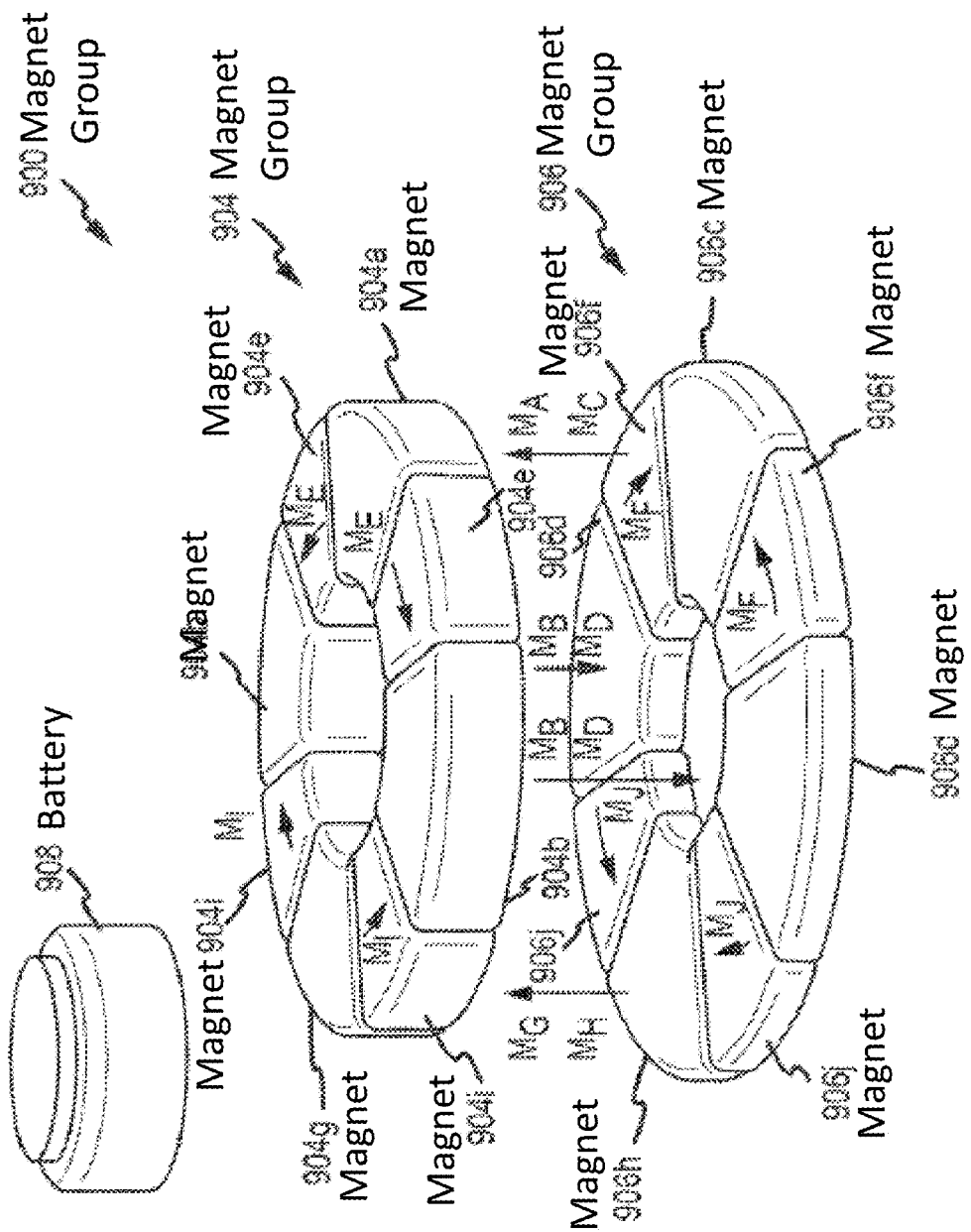
FIG. 9A is a perspective view of a magnet group in accordance with another example of the technology.
Figure 9C:
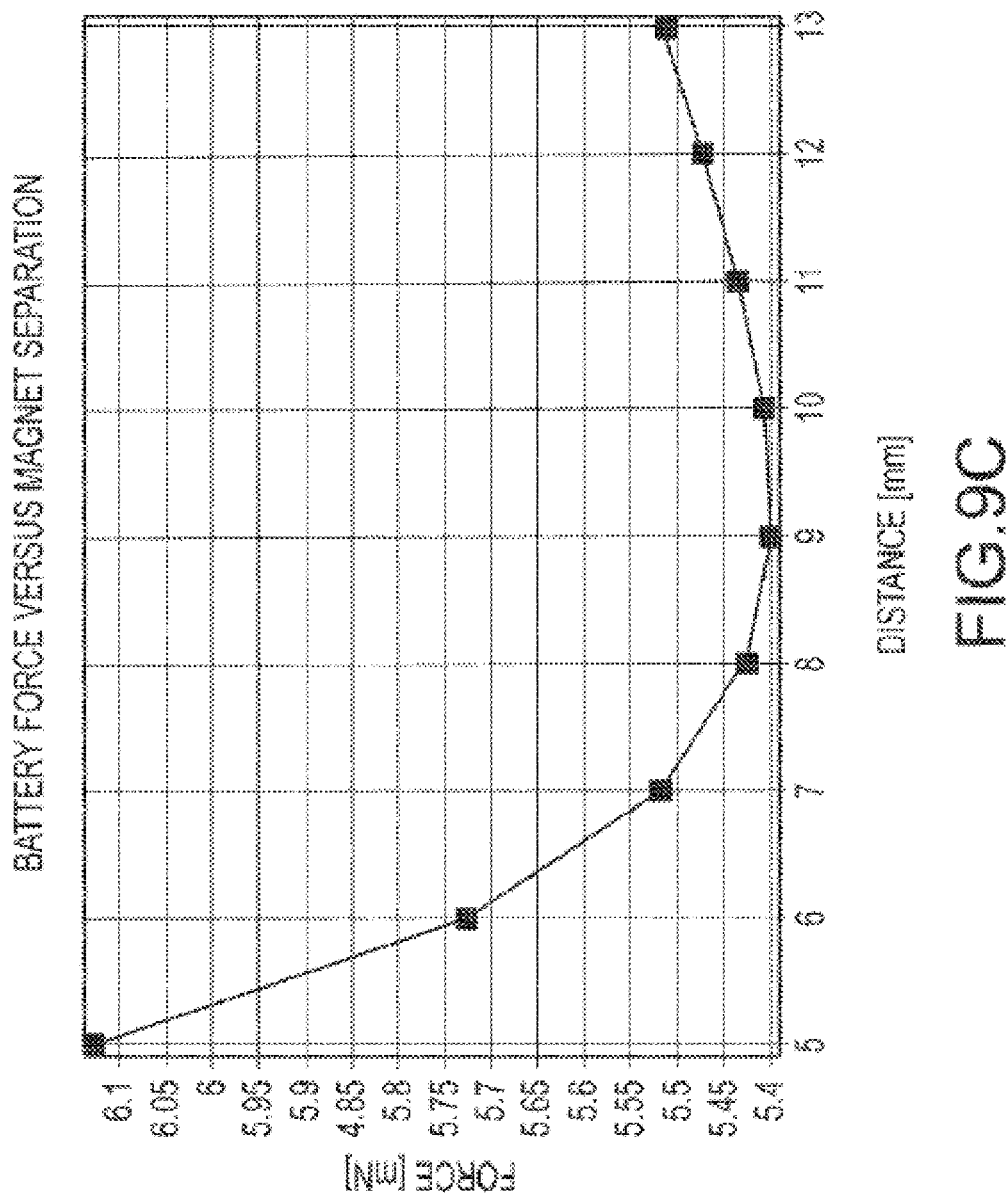
FIG. 9C is a plot showing battery force versus magnet separation for the magnet group of FIG. 9A.

FIG. 9A is a perspective view of a magnet group 900 in accordance with another example of the technology. External magnet group 904 includes axially magnetized magnets 904a, 904b (in two parts), and 904g. Additionally, diametrically magnetized magnets 904e and 904i (both in two parts) are depicted. Implantable magnet group 906 includes axially magnetized magnets 906c, 906d (in two parts), and 906h. Additionally, diametrically magnetized magnets 906f and 906j (both in two parts) are depicted. Similarly referenced magnetization directions are also indicated. FIG. 9B is a plot showing retention force versus magnet separation for the magnet group 900 of FIG. 9A. As compared to the retention force plots of FIGS. 7B and 8B, the increased number of magnets depicted in FIG. 9A results in only slight improvement to retention force at shorter separation distances. Retention force at greater separation distances is worse. FIG. 9C is a plot showing battery force versus magnet separation for the magnet group 900 of FIG. 9A. Notably, battery force shows a significant overall decrease, as compared to the battery forces depicted in FIGS. 7C and 8C of magnet group 900. This indicates that the use of more magnets leads to a marked decrease in battery force.

Figure 10A:
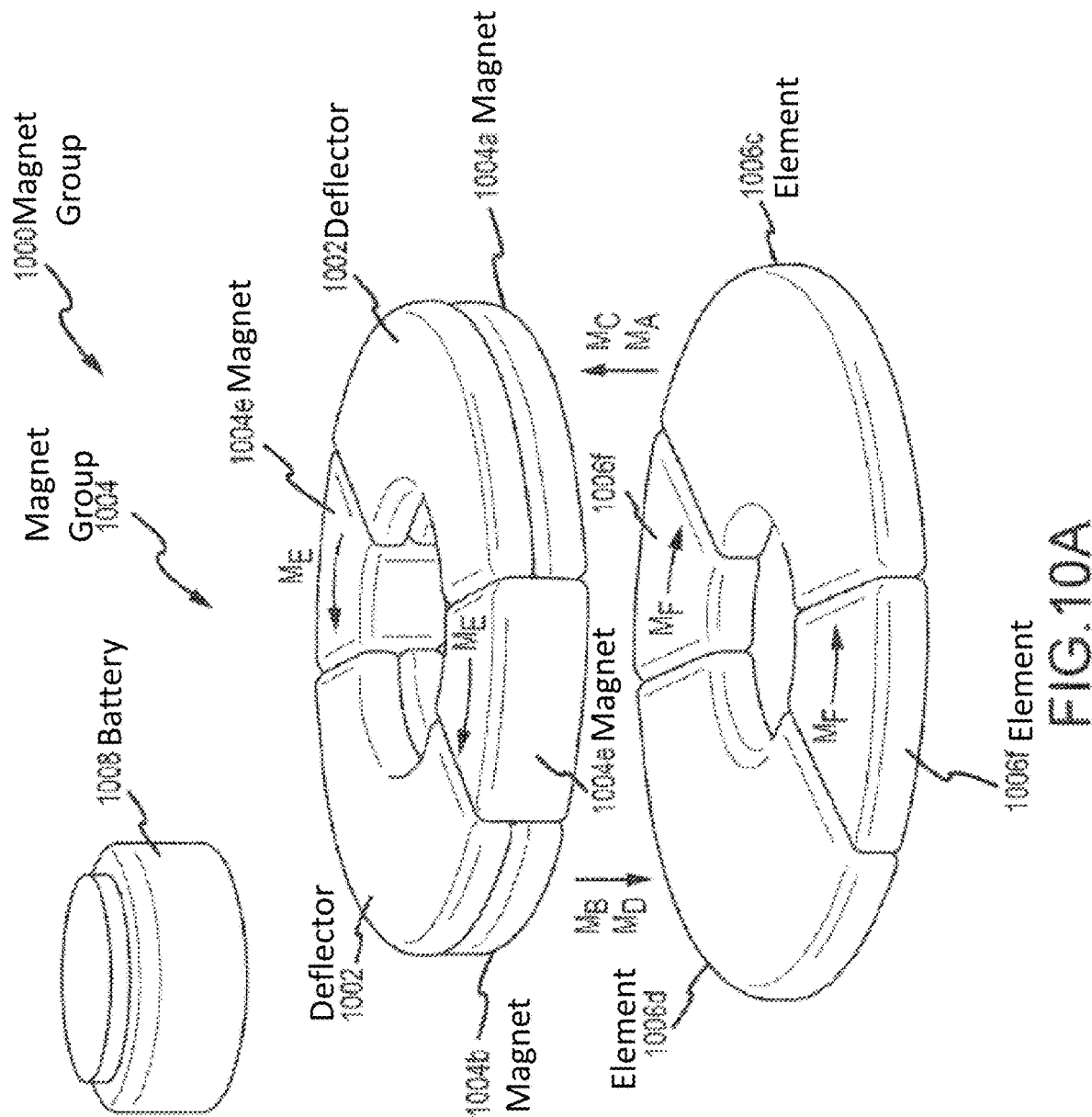
FIG. 10A is a perspective view of a magnet group in accordance with another example of the technology.
Figure 10C:
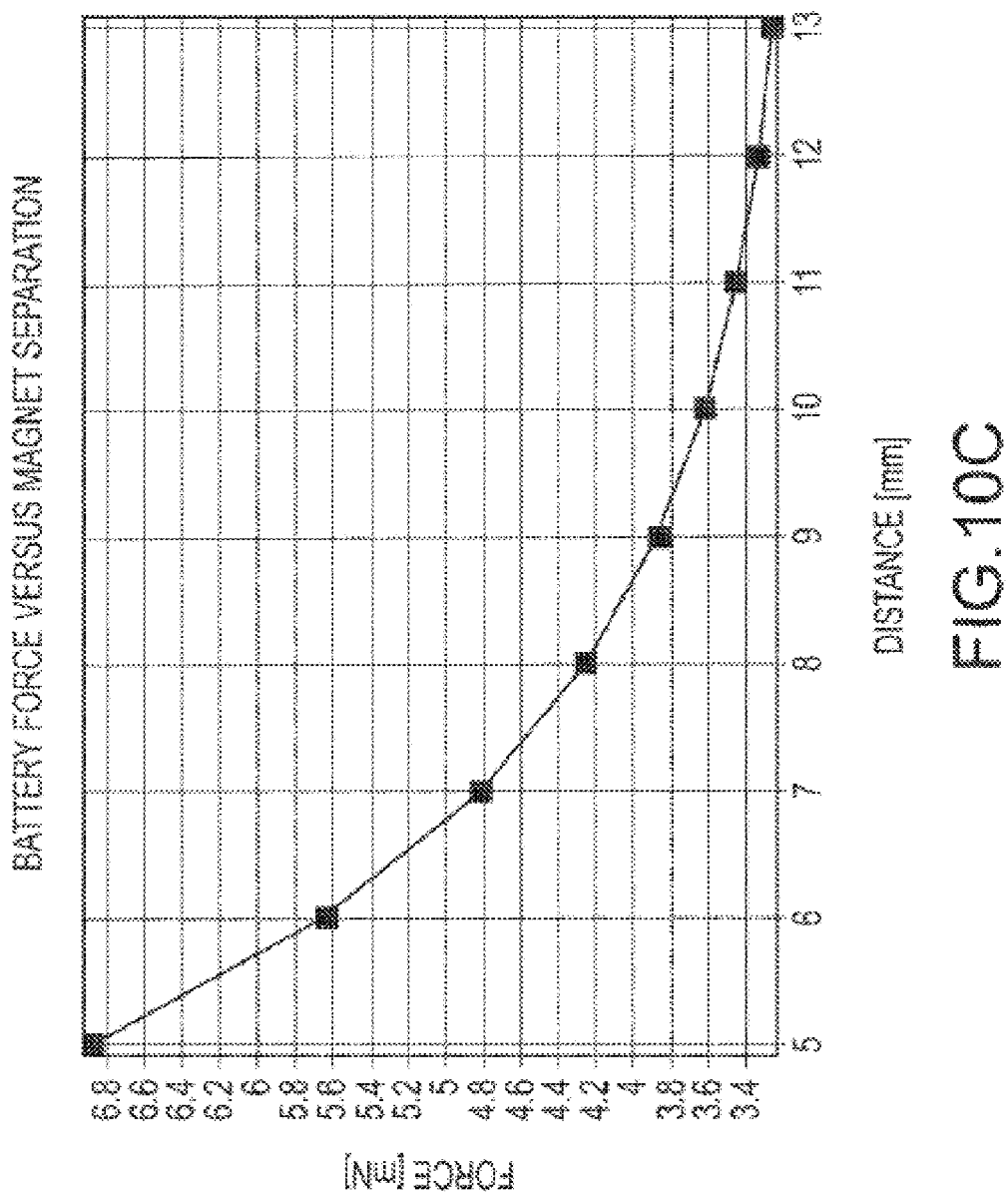
FIG. 10C is a plot showing battery force versus magnet separation for the magnet group of FIG. 10A.

FIG. 10A is a perspective view of a magnet group 1000 in accordance with another example of the technology. Many of the components are generally numbered consistently with the components of FIG. 7A, but beginning with 1000, and not all elements thereof are necessarily described further. Notably here, a deflector 1002 is disposed above magnets 1004*a* and 1004*b*. Also shown are elements 1006*d*, 1006*f* and 1006*e*. FIG. 10B is a plot showing retention force versus magnet separation for the magnet group 1000 of FIG. 10A. As compared to the retention force plots of FIGS. 7B and 8B, use of a deflector somewhat lowers retention force, mostly for a small separation distance. FIG. 10C is a plot showing battery force versus magnet separation for the magnet group 1000 of FIG. 10A. As compared to the battery force plots of FIGS. 7C and 8C, use of a deflector significantly lowers the battery force, to values even lower than the reference magnet group 400 incorporating a deflector. Thus, use of the deflector may be desirable for cases where it is not possible to locate the battery at a favorable position as in FIG. 6B.

Figure 11A:
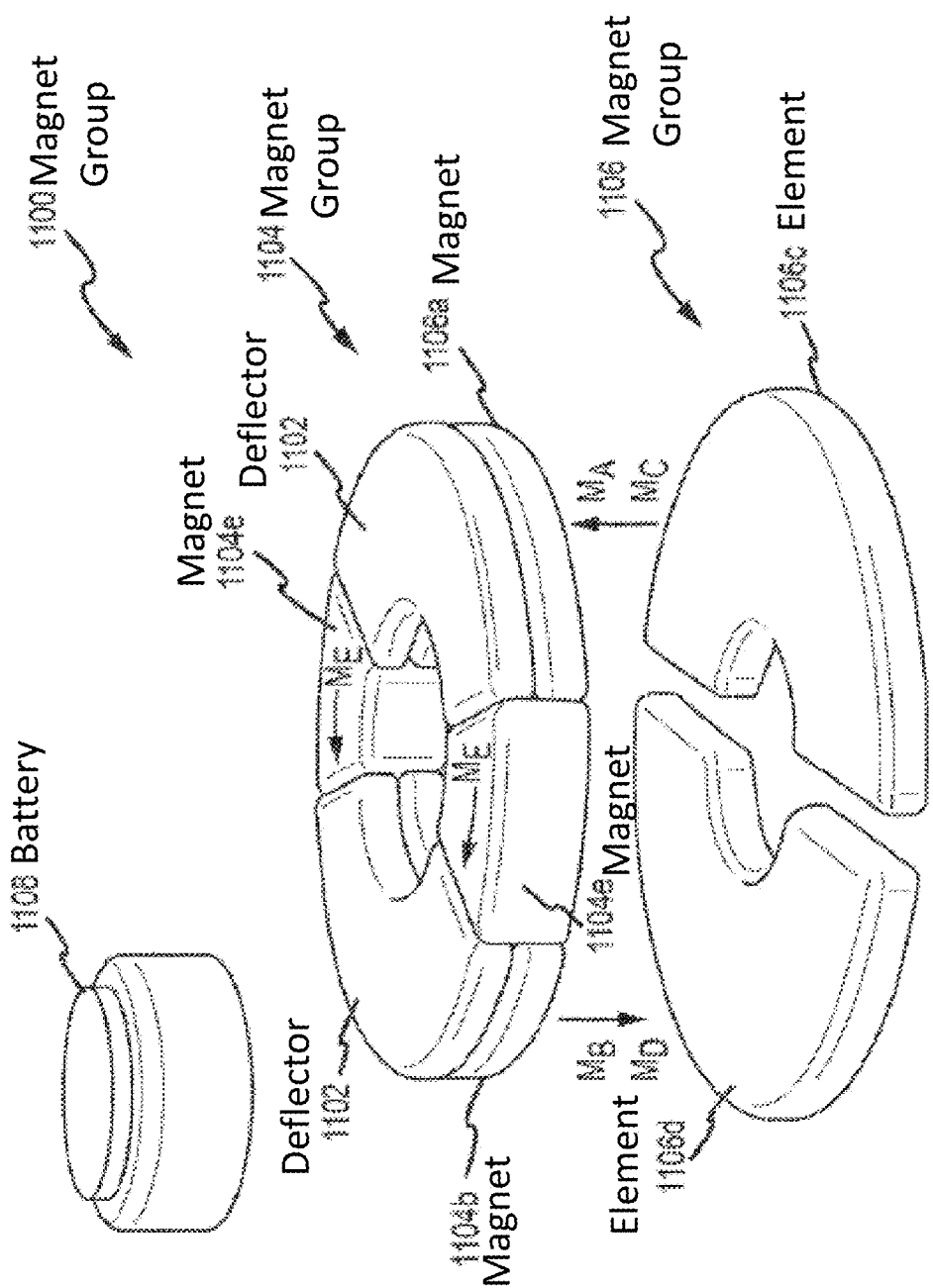
FIG. 11A is a perspective view of a magnet group in accordance with another example of the technology.
Figure 11C:
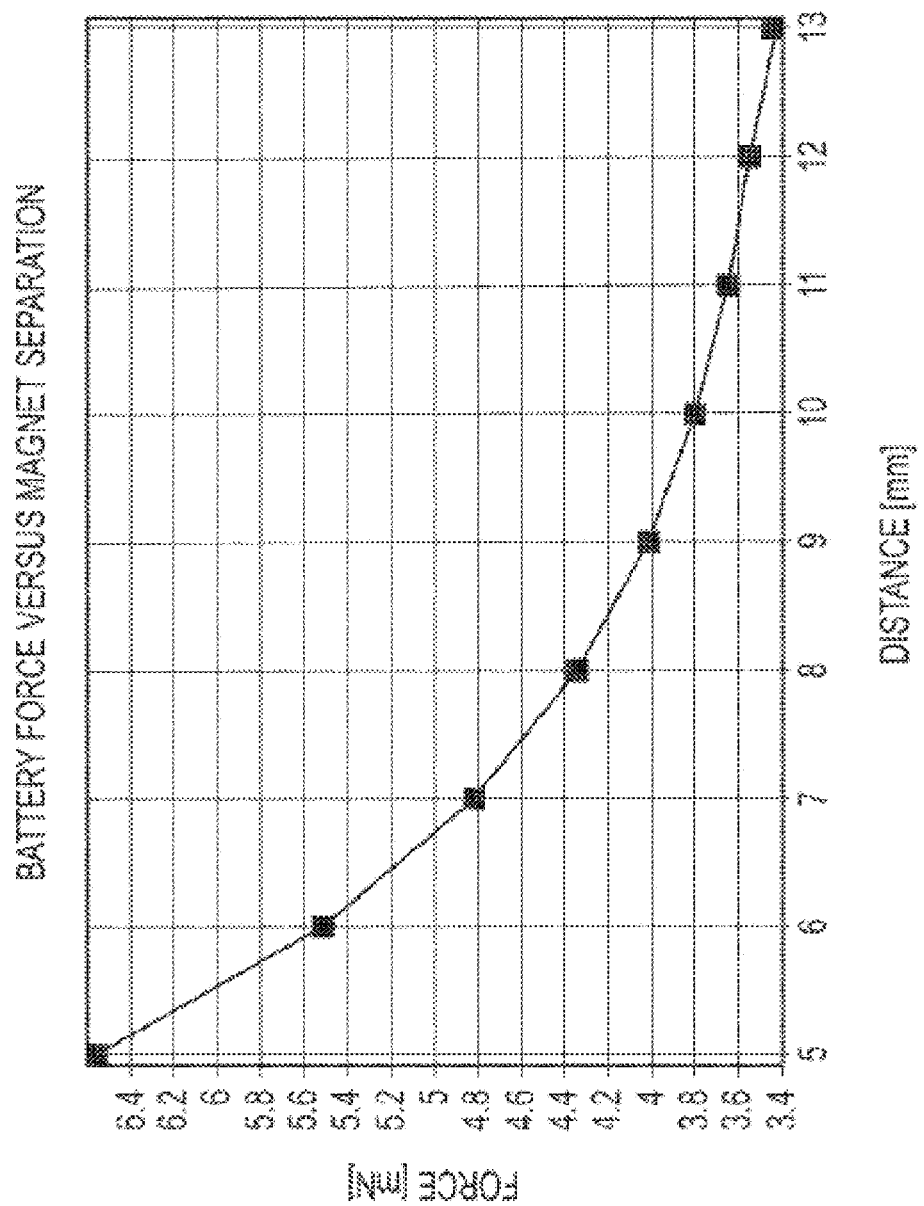
FIG. 11C is a plot showing battery force versus magnet separation for the magnet group of FIG. 11A.

FIG. 11A is a perspective view of a magnet group 1100 in accordance with another example of the technology. In this example, external magnet group 1104 is identical to the magnet group 1004 depicted FIG. 10A and thus not all elements thereof are necessarily described further. Shown in FIG. 11A are deflector 1102, magnet 1104*e*, magnet 1104*b*, magnet 1106*a* and elements 1006*d* and 1006*c*. Implantable magnet group 1106 is identical to implantable magnet group 406 depicted in FIG. 4 and thus not all elements thereof are necessarily described further. FIG. 11B is a plot showing retention force versus magnet separation for the magnet group 1100 of FIG. 11A. Here, retention force is lowered significantly, indicating that the benefits of magnet groups having greater numbers of magnets can be lost unless such groups are utilized in both the external and implantable magnet groups. Nevertheless, the magnet groups having a greater number of magnets are compatible with currently existing implantable magnet groups having a magnet configuration as 1106 in FIG. 11A. FIG. 11C is a plot showing battery force versus magnet separation for the magnet group 1100 of FIG. 11A. This indicates that battery force is lower than that of the implantable magnet group 400 of FIG. 4.

In an exemplary embodiment, there is an implantable medical device, comprising: a magnet; and a body encompassing the magnet, wherein the implantable medical device is configured to enable the magnet to rotate, with respect to exposure to a magnetic field, only under a magnetic field that is stronger than at least twice a magnetic field generated by the magnet. In an exemplary embodiment, there is an implantable medical device as described above and/or below, wherein the body is a case; and the rotation is rotation relative to the case. In an exemplary embodiment, there is an apparatus comprising the implantable medical device as described above and/or below, an external component including a second magnet, wherein the external component is held proximate the implantable medical device via magnetic attraction between the magnet and the external magnet, and the implantable component is configured such that the external component can be rotated 360 degrees relative to the implantable medical device when the two components are within 10 mm of each other without the magnet rotating relative to the body and/or the remainder of the implantable medical device, the rate of rotation being no more than 20 degrees per second. In an exemplary embodiment, there is an apparatus as described above and/or below, wherein the implantable component is configured such that a magnet at least 10 times the strength of the magnet can be rotated 360 degrees relative to the implantable medical device relative to a plane that is parallel to a skin surface facing side of the implantable component when the two components are within 5 mm of each other without the magnet rotating relative to the body and/or relative to the remainder of the implantable medical device, the rate of rotation being no more than 20 degrees per second.

In an exemplary embodiment, there is an implantable medical device as described above and/or below, wherein: the implantable medical device is configured to enable the magnet to rotate only under very strong external magnetic fields. In an exemplary embodiment, there is an implantable medical device as described above and/or below, wherein: the body is an enclosure that at least partially encloses the magnet; and designed friction between the body and/or a component within the body and the magnet prevents the magnet from rotating under a magnetic field that is not as strong as the magnetic field that causes the magnet to rotate. In an exemplary embodiment, there is an implantable medical device as described above and/or below, wherein: the body is an enclosure that at least partially encloses the magnet; and pressure force exerted by the body directly and/or indirectly onto the magnet prevents the magnet from rotating under a magnetic field that is not as strong as the magnetic field that causes the magnet to rotate. In an exemplary embodiment, there is an implantable medical device as described above and/or below, wherein: the body is an enclosure that at least partially encloses the magnet; and high friction element(s) between and/or part of the body directly and/or indirectly in contact with the magnet prevent(s) the magnet from rotating under a magnetic field that is not as strong as the magnetic field that causes the magnet to rotate.

In an exemplary embodiment, there is an apparatus comprising the implantable medical device as described above and/or below, an external component including a second magnet, wherein the second magnet is rotatable within the external component. In an exemplary embodiment, there is an apparatus comprising an implantable medical device as described above and/or below, and an external component including a second magnet, wherein the second magnet is rotatable within the external component, and the external component is configured to enable the second magnet to rotate under the magnetic field generated by the magnet when the external component is held proximate the implantable medical device.

In an exemplary embodiment, there is a method, comprising: subjecting a magnet implanted in an implanted medical device implanted in a head of a recipient to a magnetic field; and rotating the magnet of the implanted medical device as a result of exposure to the magnetic field, wherein the implanted medical device resists rotation of the magnet, but the magnetic field overcomes the resistance. In an exemplary embodiment, there is a method as described above and/or below, further comprising: removing the recipient from the magnetic field, wherein after removing the recipient from the magnetic field, an orientation of a magnetic field of the magnet has changed to a second orientation relative to that which was the case when an external medical device was last held against the recipient prior to exposure to the magnetic field, the implanted medical device maintaining that second orientation after removal from the magnetic field due to the resistance to the rotation. In an exemplary embodiment, there is a method as described above and/or below, further comprising: reattaching the external medical device to the recipient by reestablishing a magnetic connection between the external medical device and the magnet of the implanted medical device, wherein the second orientation is maintained while the external medical device is attached to the recipient and afterwards. In an exemplary embodiment, there is a method as described above and/or below, wherein: the orientation of the external medical device when reattached and subsequently attached is effectively the same as that which was the case when the external medical device was attached to the recipient prior to the action of removing the external medical device from the recipient.

In an exemplary embodiment, there is a method as described above and/or below, wherein: the orientation of the magnetic field shifted at least 30 degrees about a longitudinal axis between the magnet and a magnet of the external medical device with respect to the second orientation relative to the orientation prior to exposure to the magnetic field. In an exemplary embodiment, there is a method as described above and/or below, wherein: the orientation of the magnet has remained at least substantially constant from the time of implantation of the implanted device to the time at least just before exposure to the magnetic field. In an exemplary embodiment, there is a method as described above and/or below, wherein: the action of subjecting the person to the magnetic field is such that the magnetic field is at least one of five (5) times greater than the magnet or at least greater than 0.5 T. In an exemplary embodiment, there is a method as described above and/or below, wherein: the action of subjecting the person to the magnetic field is such that the magnetic field is at least one of five (5) times greater than that created by the external medical device when the external medical device was held against the person via the magnetic connection or at least greater than 0.5 T. In an exemplary embodiment, there is a method as described above and/or below, wherein: a magnet of the external medical device becomes automatically reoriented to be aligned with the second orientation upon reattachment of the external medical device to the recipient. In an exemplary embodiment, there is a method as described above and/or below, wherein: the exposure to the magnetic field takes place at least 6 months after implantation of the magnet; and the magnet has effectively never rotated relative to the implanted medical device prior the exposure to the magnetic field.

In an exemplary embodiment, there is a medical prosthesis, comprising: a housing; and a magnet apparatus in the housing, wherein the magnet apparatus is configured to provide an axial magnetic flux outside the housing as the strongest magnetic force relative to a diametrical flux, if present, outside the housing; and the magnet apparatus is configured to rotate about the axial direction, wherein the axial direction is at least generally normal to skin of a recipient when the medical prosthesis is used with a recipient. In an exemplary embodiment, there is a medical prosthesis as described above and/or below, wherein: the magnet apparatus is disk shaped. In an exemplary embodiment, there is a medical prosthesis as described above and/or below, wherein: the magnet apparatus has a component thereof that generates a diametrically aligned magnetic flux at a geometric center of the magnet apparatus. In an exemplary embodiment, there is a medical prosthesis as described above and/or below, wherein: the housing and magnet apparatus are parts of an implantable component of the medical prosthesis; the medical prosthesis includes an external component that includes a respective magnet apparatus; and the medical prosthesis is configured to hold the external component against skin of the recipient via the axial magnetic flux. In an exemplary embodiment, there is a medical prosthesis as described above and/or below, wherein: the magnetic force between the magnet apparatus of the implantable component and the magnet apparatus of the external component, when positioned as would be positioned when used on a recipient at a distance of three mm away from each other, is at least 10% greater than that which would be the case with respect to purely axial polarity magnets of the same size and same mass and same material magnetized at a maximum magnetism while still being usable as a medical prosthesis.

In an exemplary embodiment, there is a medical prosthesis as described above and/or below, wherein: the magnetic force between the magnet apparatus of the implantable component and the magnet apparatus of the external component, when positioned as would be positioned when used on a recipient at a distance of three mm away from each other, is at least 25% greater than that which would be the case with respect to purely axial polarity magnets of the same size and same mass and same material magnetized at a maximum magnetism while still being usable as a medical prosthesis. In an exemplary embodiment, there is a medical prosthesis as described above and/or below, wherein: the magnetic force between the magnet apparatus of the implantable component and the magnet apparatus of the external component, when positioned as would be positioned when used on a recipient at a distance of three mm away from each other, is at least 100% greater than that which would be the case with respect to purely diametrical polarity magnets of the same size and same mass and same material magnetized at a maximum magnetism while still being usable as a medical prosthesis. In an exemplary embodiment, there is a medical prosthesis as described above and/or below, wherein: the magnet apparatus of the external component is configured to rotate relative to the remainder of the external component.

In an exemplary embodiment, there is a medical prosthesis as described above and/or below, wherein: the magnet apparatus of the external component is configured to rotate relative to the remainder of the external component; and the magnet apparatus of the implantable component drives the orientation of the magnet apparatus of the external component. In an exemplary embodiment, there is a medical prosthesis as described above and/or below, wherein: the housing and magnet apparatus establish a housing-magnet apparatus assembly; and the housing-magnet apparatus assembly is configured to resist rotation of the magnet apparatus within the housing for magnet fields below 0.5 T.

In an exemplary embodiment, there is a medical prosthesis, comprising: a housing; and a magnet apparatus in the housing, wherein the magnet apparatus is configured to provide an axial magnetic flux outside the housing as the strongest magnetic force relative to a diametrical flux, if present, outside the housing; and the magnet apparatus is configured to resist rotation about the axial direction, wherein the axial direction is at least generally normal to skin of a recipient when the medical prosthesis is used with a recipient. In an exemplary embodiment, there is a medical prosthesis as detailed above and/or below, wherein the magnet apparatus is disk shaped. In an exemplary embodiment, there is a medical prosthesis as detailed above and/or below, wherein the magnet apparatus has a component thereof that generates a diametrically aligned magnetic flux at a geometric center of the magnet apparatus. In an exemplary embodiment, there is a medical prosthesis as detailed above and/or below, wherein: the housing and magnet apparatus are parts of an implantable component of the medical prosthesis; the medical prosthesis includes an external component that includes a respective magnet apparatus; and the medical prosthesis is configured to hold the external component against skin of the recipient via the axial magnetic flux. In an exemplary embodiment, there is a medical prosthesis as detailed above and/or below, wherein: the magnetic force between the magnet apparatus of the implantable component and the magnet apparatus of the external component, when positioned as would be positioned when used on a recipient at a distance of three mm away from each other, is at least 10% greater than that which would be the case with respect to purely axial polarity magnets of the same size and same mass and same material magnetized at a maximum magnetism while still being usable as a medical prosthesis. In an exemplary embodiment, there is a medical prosthesis as detailed above and/or below, wherein: the magnetic force between the magnet apparatus of the implantable component and the magnet apparatus of the external component, when positioned as would be positioned when used on a recipient at a distance of three mm away from each other, is at least 25% greater than that which would be the case with respect to purely axial polarity magnets of the same size and same mass and same material magnetized at a maximum magnetism while still being usable as a medical prosthesis. In an exemplary embodiment, there is a medical prosthesis as detailed above and/or below, wherein: the magnetic force between the magnet apparatus of the implantable component and the magnet apparatus of the external component, when positioned as would be positioned when used on a recipient at a distance of 3 mm away from each other, is at least 100% greater than that which would be the case with respect to purely diametrical polarity magnets of the same size and same mass and same material magnetized at a maximum magnetism while still being usable as a medical prosthesis. In an exemplary embodiment, there is a medical prosthesis as detailed above and/or below, wherein: the magnet apparatus of the external component is configured to not rotate relative to the remainder of the external component. In an exemplary embodiment, there is a medical prosthesis as detailed above and/or below, wherein: the housing and magnet apparatus establish a housing-magnet apparatus assembly; and the housing-magnet apparatus assembly is configured to resist rotation of the magnet apparatus within the housing for magnet fields below 0.5 T. In an exemplary embodiment, there is a medical prosthesis as detailed above and/or below, wherein the prosthesis is configured such that the magnet apparatus is fixed within the prosthesis such that it does not rotate relative to the prosthesis, such as when exposed to one or more or all of the magnetic fields detailed herein.

In an exemplary embodiment, there is a method, comprising: subjecting a magnet located in a housing implanted in an implanted medical device implanted in a head of a recipient to a magnetic field of an MRI machine of at least 1.5 T; and maintaining an orientation of the magnet relative to the housing while the magnet is exposed to the magnetic field, wherein the magnetic field imparts a torque onto the magnet, and wherein the magnet is diametrically magnetized. In an exemplary embodiment, there is the method described above and/or below wherein: the magnet is part of a magnet group that includes two flanking magnets that are axially magnetized. In an exemplary embodiment, there is the method described above and/or below wherein: the magnet is part of a magnet apparats that includes two flanking components that are non-magnetic components and are also located in the housing. In an exemplary embodiment, there is the method described above and/or below wherein: removing the recipient from the magnetic field, wherein after removing the recipient from the magnetic field, an orientation of a magnetic field of the magnet has not changed. In an exemplary embodiment, there is the method described above and/or below wherein: the magnet is part of a magnet apparats that includes two flanking components that are non-magnetic components and are located outside the housing. In an exemplary embodiment, there is the method described above and/or below further comprising reattaching an external medical device to the recipient by reestablishing a magnetic connection between the external medical device and the magnet of the implanted medical device, wherein the attachment force between the external medical device and the implant is the same as that which was the case prior to the exposure to the 1.5 T magnetic field. In an exemplary embodiment, there is the method described above and/or below wherein: the orientation of the external medical device when reattached and subsequently attached is effectively the same as that which was the case when the external medical device was attached to the recipient prior to the action of removing the external medical device from the recipient. In an exemplary embodiment, there is the method described above and/or below wherein: the exposure to the magnetic field takes place at least 6 months after implantation of the magnet; and the magnet has effectively never rotated relative to the implanted medical device prior the exposure to the magnetic field.

This disclosure described some embodiments of the present technology with reference to the accompanying drawings, in which only some of the possible embodiments were shown. Other aspects, however, can be embodied in many different forms and should not be construed as limited to the embodiments set forth herein. Rather, these embodiments were provided so that this disclosure was thorough and complete and fully conveyed the scope of the possible embodiments to those skilled in the art.

Any disclosure of a device and/or system detailed herein also corresponds to a disclosure of otherwise providing that device and/or system and/or utilizing that device and/or system.

It is also noted that any disclosure herein of any process of manufacturing other providing a device corresponds to a disclosure of a device and/or system that results there from. Is also noted that any disclosure herein of any device and/or system corresponds to a disclosure of a method of producing or otherwise providing or otherwise making such. Any disclosure of an embodiment that has a functionally corresponds to a device configured to have that functionality, and also corresponds to a method that results in the functionality/ includes the actions associated with the functionality, and vice versa.

Any embodiment or any feature disclosed herein can be combined with any one or more or other embodiments and/or other features disclosed herein, unless explicitly indicated and/or unless the art does not enable such. Any embodiment or any feature disclosed herein can be explicitly excluded from use with any one or more other embodiments and/or other features disclosed herein, unless explicitly indicated that such is combined and/or unless the art does not enable such exclusion.

Any function or method action detailed herein corresponds to a disclosure of doing so an automated or semi-automated manner.

Although specific embodiments were described herein, the scope of the technology is not limited to those specific embodiments. One skilled in the art will recognize other embodiments or improvements that are within the scope of the present technology. Therefore, the specific structure, acts, or media are disclosed only as illustrative embodiments. The scope of the technology is defined by the following claims and any equivalents therein.

Any disclosure herein of any component and/or feature can be combined with any one or more of any other component and/or feature disclosure herein unless otherwise noted. Providing that the art enables such. Any disclosure herein of any component and/or feature can be explicitly excluded from combination with any one or more or any other component and/or feature disclosed herein unless otherwise noted, providing that the art enables such. Any disclosure herein of any method action includes a disclosure of a device and/or system configured to implement that method action. Any disclosure herein of a device and/or system corresponds to a disclosure of a method of utilizing that device and/or system. Any disclosure herein of a manufacturing method corresponds to a disclosure of a device and/or system that results from the manufacturing method. Any disclosure of a device and/or system corresponds to a disclosure of a method of making a device and/or system.

While various embodiments of the present invention have been described above, it should be understood that they have been presented by way of example only, and not limitation. It will be apparent to persons skilled in the relevant art that various changes in form and detail can be made therein without departing from the spirit and scope of the invention.

The invention claimed is:

1. A device, comprising:
  a housing; and
  a magnet group disposed in the housing, the magnet group generating a group magnetic field, the magnet group including:
    a first magnet portion that produces a first magnetic field; and
    a second magnet portion that produces a second magnetic field, wherein
      the first magnetic field and the second magnetic field contribute to the group magnetic field, wherein
    the device is a medical device,
    the magnet group is a disk-like magnet group,
    the first magnet portion has a first magnetization direction that is different from a longitudinal axis of the magnet group,
    the second magnet portion has a second magnetization direction that is different from the longitudinal axis of the magnet group,
    the magnet group is configured so that the first magnetization direction and the second magnetization direction are fixed relative to each other,
    the magnetization direction of the first magnet portion is oblique relative to the longitudinal axis, and
    the magnetization direction of the second magnet portion is oblique relative to the longitudinal axis.

2. The device of claim 1, wherein:
  the disk-like magnet group is a disk having a circular outer profile.

3. The device of claim 1, wherein:
  the first magnetization direction has a first axis, and the second magnetization direction has a second axis, and the first axis is a mirror of the second axis about a plane parallel to and lying on the longitudinal axis.

4. A system, comprising:
  the device of claim 1; and
  a second device, wherein
    one of the device or the second device is an external component of the medical device,
    the other of the device or the second device is an implantable portion of the medical device, and
    the medical device is a hearing prosthesis.

5. The device of claim 1, wherein:
  the device is an implantable portion of a medical device.

6. The device of claim 1, further comprising:
  a sound processor.

7. The device of claim 1, wherein:
  the device includes a third magnet portion that produces a third magnetic field, wherein the first magnetic field, the second magnetic field, and the third magnetic field contribute to the group magnetic field, and
  the third magnet portion is located between the first magnet portion and the second magnet portion and is part of the magnet group.

8. The device of claim 7, wherein the third magnet portion has a third magnetization direction that is transverse relative to the longitudinal axis.

9. A device, comprising:
  a housing; and
  a magnet group disposed in the housing, the magnet group generating a group magnetic field, the magnet group including:
    a first magnet portion that produces a first magnetic field; and
    a second magnet portion that produces a second magnetic field, wherein
      the first magnetic field and the second magnetic field contribute to the group magnetic field, wherein
    the device is a medical device,
    the magnet group is a disk-like magnet group,
    the first magnet portion has a first magnetization direction that is different from a longitudinal axis of the magnet group,
    the second magnet portion has a second magnetization direction that is different from the longitudinal axis of the magnet group,
    the magnet group is configured so that the first magnetization direction and the second magnetization direction are fixed relative to each other,
    the first magnetization direction is angled at a first non-zero angle from the longitudinal axis and the second magnetization direction is angled at a second non-zero-angle from the longitudinal axis, and
    the value of the first non-zero angle is the same as the value of the second non-zero angle.

10. The device of claim 9, wherein:
  the longitudinal axis is an axis of rotational symmetry of the magnet group.

11. The device of claim 9, wherein:
  the device includes a third magnet portion that produces a third magnetic field, wherein the first magnetic field, the second magnetic field, and the third magnetic field contribute to the group magnetic field, and
  the third magnet portion is located between the first magnet portion and the second magnet portion and is part of the magnet group.

12. The device of claim 11, wherein the third magnet portion has a third magnetization direction that is transverse relative to the longitudinal axis.

13. The device of claim 12, wherein the first magnet portion abuts the third magnet portion and the second magnet portion abuts the third magnet portion.

14. The device of claim 9, wherein:
  the magnetization direction of the first magnet portion is between 5 and 85 degrees relative to the longitudinal axis; and the magnetization direction of the second magnet portion is between 5 and 85 degrees relative to the longitudinal axis.

15. The device of claim 9, wherein:
the medical device is one of a cochlear implant, a transcutaneous bone conduction device or a direct acoustic stimulator.

16. The device of claim 9, wherein:
the device is an implantable portion of a medical device.

17. A device, comprising:
a housing; and
a magnet group disposed in the housing, the magnet group generating a group magnetic field, the magnet group including:
　a first magnet portion that produces a first magnetic field; and
　a second magnet portion that produces a second magnetic field, wherein
　　the first magnetic field and the second magnetic field contribute to the group magnetic field, wherein
the device is a medical device,
the magnet group is a disk-like magnet group,
the first magnet portion has a first magnetization direction that is different from a longitudinal axis of the magnet group,
the second magnet portion has a second magnetization direction that is different from the longitudinal axis of the magnet group,
the magnet group is configured so that the first magnetization direction and the second magnetization direction are fixed relative to each other, and
the first magnetization direction has a first axis, and the second magnetization direction has a second axis and the first axis is a mirror image of the second axis.

18. The device of claim 17, wherein:
the first magnetization direction is different from an axis of rotational symmetry of the magnet group.

19. The device of claim 17, wherein:
the disk-like magnet group is a disk having a circular outer profile.

20. The device of claim 17, wherein:
the first magnetization direction of the first magnet portion is between 5 and 85 degrees relative to the longitudinal axis.

21. The device of claim 17, wherein:
the device is an implantable portion of a medical device.

22. The device of claim 17, further comprising:
a sound processor.

23. A system, comprising:
the device of claim 17; and
a second device, wherein
one of the device or the second device is an external component of the medical device,
the other of the device or the second device is an implantable portion of the medical device, and
the medical device is a hearing prosthesis.

24. A device, comprising:
a housing; and
a magnet group disposed in the housing, the magnet group generating a group magnetic field, the magnet group including:
　a first magnet portion that produces a first magnetic field; and
　a second magnet portion that produces a second magnetic field, wherein
　　the first magnetic field and the second magnetic field contribute to the group magnetic field, wherein
the device is a medical device,
the magnet group is a disk-like magnet group,
the first magnet portion has a first magnetization direction that is different from a longitudinal axis of the magnet group,
the second magnet portion has a second magnetization direction that is different from the longitudinal axis of the magnet group,
the magnet group is configured so that the first magnetization direction and the second magnetization direction are fixed relative to each other,
the device includes a third magnet portion that produces a third magnetic field, wherein the first magnetic field, the second magnetic field, and the third magnetic field contribute to the group magnetic field, and
the third magnet portion is located between the first magnet portion and the second magnet portion and is part of the magnet group.

25. The device of claim 24, wherein the third magnet portion is disposed so as to divert the magnetic flux of the first magnet portion to the second magnet portion.

26. The device of claim 25, wherein the third magnet portion has a third magnetization direction that is transverse relative to the longitudinal axis.

27. The device of claim 26, wherein the first magnet portion abuts the third magnet portion and the second magnet portion abuts the third magnet portion.

28. A system, comprising:
the device of claim 24; and
a second device, wherein
one of the device or the second device is an external component of the medical device,
the other of the device or the second device is an implantable portion of the medical device, and
the medical device is a hearing prosthesis.

29. The device of claim 24, wherein:
the device is an implantable portion of a medical device.

30. The device of claim 24, further comprising:
a sound processor.

31. The device of claim 24, wherein:
the medical device is one of a cochlear implant, a transcutaneous bone conduction device or a direct acoustic stimulator.

32. A device, comprising:
a housing; and
a magnet group disposed in the housing, the magnet group generating a group magnetic field, the magnet group including:
　a first magnet portion that produces a first magnetic field; and
　a second magnet portion that produces a second magnetic field, wherein
　　the first magnetic field and the second magnetic field contribute to the group magnetic field, wherein
the device is a medical device,
the first magnet portion has a first magnetization direction that is different from a longitudinal axis of the magnet group,
the second magnet portion has a second magnetization direction that is different from the longitudinal axis of the magnet group,
the device is configured so that the first magnetization direction remains extended toward a first side of the magnet group,
the device is configured so that the second magnetization direction remains extended toward a second side of the magnet group, wherein the first and second sides are opposing sides of the magnet group, and the device includes a sound processor.

33. The device of claim 32, wherein:

the first magnetization direction is different from an axis of rotational symmetry of the magnet group.

34. The device of claim 33, wherein:

the second magnetization direction is different from the axis of rotational symmetry of the magnet group.

35. The device of claim 32, wherein:

the device is configured to enable the magnet group to rotate as a unit relative to the housing about an axial direction.

36. The device of claim 35, wherein:

the device is an implantable portion of the medical device.

37. The device of claim 35, wherein:

the first magnetization direction of the first magnet portion is oblique relative to the longitudinal axis; and the second magnetization direction of the second magnet portion is oblique relative to the longitudinal axis.

38. The device of claim 32, wherein:

the first magnetization direction of the first magnet portion is between 5 and 85 degrees relative to the longitudinal axis; and the second magnetization direction of the second magnet portion is between 5 and 85 degrees relative to the longitudinal axis.

39. The device of claim 32, further comprising:

a third magnet portion that produces a third magnetic field, wherein the first magnetic field, the second magnetic field, and the third magnetic field contribute to the group magnetic field; and the third magnet portion is located between the first magnet portion and the second magnet portion and is part of the magnet group.

40. The device of claim 39, wherein:

the device is an external portion of the medical device.

41. The device of claim 39, wherein:

third magnet portion is disposed so as to divert a magnetic flux of the first magnet portion to the second magnet portion.

42. A system, comprising:

the device of claim 32; and a second device, wherein one of the device or the second device is an external component of the medical device, the other of the device or the second device is an implantable portion of the medical device, and the medical device is a hearing prosthesis.

43. The device of claim 32, wherein:

the medical device is one of a cochlear implant, transcutaneous bone conduction device or a direct acoustic stimulator.

44. The device of claim 32, wherein:

the device is an implantable portion of the medical device.

* * * * *